US006642389B2

(12) United States Patent
Binggeli et al.

(10) Patent No.: US 6,642,389 B2
(45) Date of Patent: Nov. 4, 2003

(54) OXAZOLE DERIVATIVES

(75) Inventors: Alfred Binggeli, Binningen (CH); Markus Boehringer, Moehlin (CH); Uwe Grether, Loerrach (DE); Hans Hilpert, Reinach (CH); Hans-Peter Maerki, Basel (CH); Markus Meyer, Neuenburg (DE); Peter Mohr, Basel (CH); Fabienne Ricklin, Hombourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/142,567

(22) Filed: May 9, 2002

(65) Prior Publication Data

US 2003/0055265 A1 Mar. 20, 2003

(30) Foreign Application Priority Data

May 15, 2001 (EP) ............................................. 01111745

(51) Int. Cl.⁷ ......................................... C07D 263/32
(52) U.S. Cl. ..................................................... 548/236
(58) Field of Search ......................................... 548/236

(56) References Cited

U.S. PATENT DOCUMENTS

| 5,089,514 A | 2/1992 | Hulin |
| 5,856,529 A | 1/1999 | Catt et al. |
| 6,121,397 A | 9/2000 | MacLeod et al. |

FOREIGN PATENT DOCUMENTS

| DE | 2633905 | 2/1977 |
| EP | 0903343 | 3/1999 |
| EP | 1 078 923 | 2/2001 |
| JP | 2001048876 | 2/2001 |
| WO | WO 91/19702 | 12/1991 |
| WO | WO 94/01420 | 1/1994 |
| WO | WO 94/13650 | 6/1994 |
| WO | WO 94/27995 | 12/1994 |
| WO | WO 95/17394 | 6/1995 |
| WO | WO 97/25042 | 7/1997 |
| WO | WO 98/42704 | 10/1998 |
| WO | WO 99/08501 | 2/1999 |
| WO | WO 99/10339 | 3/1999 |
| WO | WO 00 08002 | 2/2000 |
| WO | WO 02 16331 | 2/2002 |

OTHER PUBLICATIONS

STN International® CAPLUS Database, Accession No. 2000:117035; Collins et al., WO 2000008002, abstract.*
Malamas, M.S. et al., Eur. J. Med. Chem., vol. 36, No. 1, pp. 31–42 (2001).
Hulin B. et al., Current Pharmaceutical Design, vol. 2 pp. 85–102 (1996).
Haigh et al., Tetrahedron: Asymmetry, 10, pp. 1353–1367 (1999).
Gotteland et al., Synlett., 9, pp. 931–932 (1995).
Hulin et al., J. Med. Chem., 39, pp. 3897–3907 (1996).
Nicolaou et al., J. Am. Chem. Soc., 122, pp. 3830–3838 (2000).
Nichols et al., Anal. Biochem., 257, pp. 112–119 (1998).
Einsiedel et al., Bioorg. Med. Chem. Lett., 10, pp. 2041–2044 (2000).
Goto et al., Chem. Pharm. Bull., 19, pp. 2050–2057 (1971).
Reichstein et al., Helvetica Chimica Acta, 16, pp. 121–129 (1933).
Diels et al., Chem. Ber., 48, pp. 897–905 (1915).
Wightman et al., J. Org. Chem., 43, pp. 2167–2170 (1978).
Musser et al., J. Med. Chem. 30, pp. 62–67 (1987).
Rahman et al., J. Chem. Soc. Perkin Trans. 1, 12, pp. 2973–2977 (1983).
Kelly et al., J. Am. Chem. Soc., 110, pp. 6471–6480 (1988).
Kneen et al., Synthetic Communications, 16, pp. 1635–1640 (1986).
Kim et al., Can. J. Chem., 60, pp. 2093–2098 (1982).
Párkányi et al., Monatsh. Chem., 123, pp. 637–645 (1992).
McDougald et al., Current Biology, 5, pp. 618–621 (1995).
Keller et al., Trends Endocrin. Metab., 4, pp. 291–296 (1993).
Oplinger, et al., ACS National Meeting, San Diego, Apr. 1–5, 2001, Poster 238, Division of Medicinal Chemistry, Section C.

* cited by examiner

*Primary Examiner*—Deborah C. Lambkin
*Assistant Examiner*—Sonya Wright
(74) *Attorney, Agent, or Firm*—George W. Johnston; Dennis P. Tramaloni; Eileen M. Ebel

(57) ABSTRACT

The present invention relates to novel oxazole compounds which act as PPARα and PPARγ agonists and are accordingly useful for the treatment of diseases modulated by PPARα and PPARγ such as diabetes.

27 Claims, No Drawings

OXAZOLE DERIVATIVES

BACKGROUND OF THE INVENTION

Peroxisome Proliferator Activated Receptors (PPAR's) are members of the nuclear hormone receptor super family, which are ligand-activated transcription factors regulating gene expression. Various subtypes thereof have been identified and cloned. These include PPARα, PPARβ (also known as PPARδ), and PPARγ. There exist at least two major isoforms of PPARγ. While PPARγ1 is ubiquitously expressed in most tissues, the longer isoform PPARγ2 is almost exclusively found in adipocytes. In contrast, PPARα is predominantly expressed in the liver, kidney and heart. PPAR's modulate a variety of body responses including glucose- and lipid-homeostasis, cell differentiation, inflammatory responses and cardiovascular events.

Diabetes is a disease in which a patient's ability to control glucose levels in blood is impaired, because he has partially lost the ability to respond properly to the action of insulin. In type II diabetes (T2D), often referred to as non-insulin dependent diabetes mellitus (NIDDM), which afflicts 80–90% of all diabetic patients in developed countries, the Isles of Langerhans in the pancreas still produce insulin. However, the target organs, mainly muscle, liver and adipose tissue, exhibit a profound resistance to insulin stimulation, and the body compensates by producing unphysiologically high levels of insulin. In later stage of disease, however, insulin secretion decreases due to exhaustion of the pancreas. In addition to that T2D is a metabolic-cardiovascular disease sysndrome. Among the comorbidities associated with T2D are for example insulin resistance, dyslipidemia, hypertension, endothelial dysfunction and inflammatory atherosclerosis.

Current first line treatment for diabetes generally involves low fat—and glucose—diet and exercise. However, compliance can be moderate and as the disease progresses, treatment with hypoglycemic drugs, e.g. sulfonylureas or metformin, becomes necessary. A promising new class of drugs has recently been introduced that resensitizes patients to their own insulin (insulin sensitizers), thereby reverting blood glucose and triglyceride levels to normal, and thus abolishing, or at least reducing, the requirement for exogenous insulin. Pioglitazone (Actos™) and rosiglitazone (Avandia™) belong to the thiazolidinediones (TZD) class of PPARγ-agonists and were the first representatives who had been approved for NIDDM in several countries. These compounds, however, suffer from side effects including rare but severe liver toxicity (as seen with troglitazone), and they increase body weight in humans. Therefore, new, better and more efficacious drugs for the treatment of NIDDM are urgently needed. Recent studies provide evidence that a coagonism on PPARα and PPARγ would result in compounds with enhanced therapeutic potential, i.e. with an improved lipid profile effect on top of the normalization of glucose- and insulin-levels (Keller and Wahli: Trends Endocrin. Metab. 1993; 4:291–296, Macdonald and Lane: Current Biology Vol.5 pp.618–621 (1995)).

SUMMARY OF THE INVENTION

The present invention comprises novel oxazole derivatives, their manufacture and their use as medicaments. In particular, the invention relates to compounds of the formula (I)

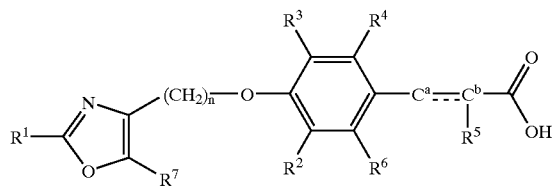

and pharmaceutically acceptable salts and esters thereof.

DETAILED DESCRIPTION OF THE INVENTION

The present invention comprises compounds of the formula

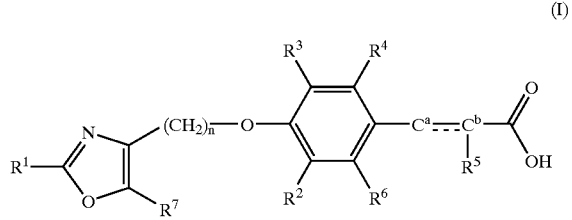

and pharmaceutically acceptable salts and esters thereof, wherein $R^1$ is aryl or heteroaryl;

$R^2$, $R^3$, $R^4$ and $R^6$ are independently selected from the group consisting of hydrogen, hydroxy, lower-alkenyl, halogen, lower-alkyl and lower-alkoxy, wherein at least one of $R^2$, $R^3$, $R^4$ and $R^6$ is not hydrogen, or $R^2$ and $R^6$ are independently selected from the group consisting of hydrogen, hydroxy, lower-alkenyl, halogen, lower-alkyl and lower-alkoxy, and $R^3$ and $R^4$ are bonded to each other to form a ring together with the carbon atoms to which they are attached, and $R^3$ and $R^4$ together are —CH═CH—S—, —S—CH═CH—, —CH═CH—O—, —O—CH═CH—, —CH═CH—CH═CH—, —(CH$_2$)$_{3-5}$—, —O—(CH$_2$)$_{2-3}$— or —(CH$_2$)$_{2-3}$—O—;

$R^5$ is lower-alkoxy, lower-alkenyloxy,

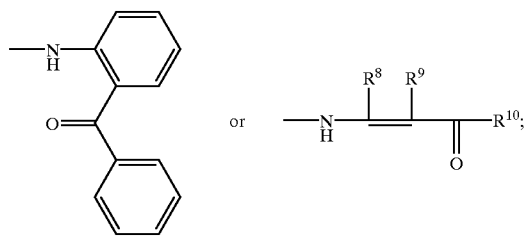

$R^7$ is hydrogen or lower-alkyl;
$R^8$ is hydrogen or lower-alkyl;
$R^9$ is hydrogen or lower-alkyl;
$R^{10}$ is aryl;
n is 1, 2 or 3;
wherein the bond between the carbon atom $C^a$ and the carbon atom $C^b$ is a carbon carbon single or double bond.

The novel compounds of the present bind to and activate both, PPARα and PPARγ, simultaneously and very efficiently. Therefore, these compounds combine the antigylcemic effect of PPARγ activation with the antidyslipidemic effect of PPARα activation. Consequently, plasma glucose and insulin are reduced (=insulin sensitization), triglycerides lowered and HDL cholesterol increased (=improved lipid profile). In addition, such compounds may also lower LDL cholesterol, decrease blood pressure and counteract inflammatory atherosclerosis. Since multiple facets of the T2D disease syndrome are addressed by PPARα and γ coagonists, they are expected to have an enhanced therapeutic potential compared to the compounds already known in the art.

The compounds of the present invention further exhibit improved pharmacological properties compared to known compounds.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine.

The term "protecting group" refers to groups such as e.g. acyl, alkoxycarbonyl, aryloxycarbonyl, silyl, or iminederivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Alkyl groups can be substituted e.g. with halogen, hydroxy, lower-alkoxy, lower-alkoxy-carbonyl, $NH_2$, N(H, lower-alkyl) and/or N(lower-alkyl)$_2$.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may have a substitution pattern as described earlier in connection with the term "alkyl".

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy.

The term "lower-alkenyl", alone or in combination signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower-alkenyloxy" means a group R"—O—, wherein R" is lower-alkenyl. Examples of lower-alkenyloxy groups are butenyloxy, particularly but-3-enyloxy.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower-alkoxy, aryl and/or aryloxy. Preferred substituents are halogen, $CF_3$, lower-alkyl and/or lower-alkoxy.

The term "heteroaryl" refers to an aromatic 5- or 6-membered ring which can comprise 1,2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts with acids are formates, maleates, citrates, hydrochlorides, hydrobromides and methanesulfonic acid salts. The compounds of formula I further form salts with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes pharmaceutically acceptable solvates.

The term pharmaceutically acceptable esters of the compounds of formula I means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH group of compounds according to formula I can be esterified. Alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein e.g. a hydroxy group is esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

Preferred compounds of formula I are compounds according to formula Ib

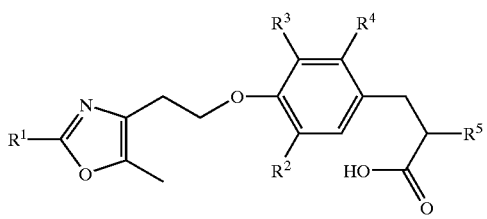
(Ib)

wherein
R$^1$ is aryl or heteroaryl,
R$^2$, R$^3$ and R$^4$ independently from each other are hydrogen, halogen, lower-alkyl, or lower-alkoxy, wherein at least one of R$^2$, R$^3$ and R$^4$ is not hydrogen, or
R$^3$ and R$^4$ are bonded to each other to form a ring together with the carbon atoms to which they are attached, and R$^3$ and R$^4$ together are —CH═CH—S—, —S—CH═CH—, —CH═CH—O—, —O—CH═CH—, —CH═CH—CH═CH—, or —(CH$_2$)$_{3-5}$—, and R$^2$ is as defined above,
R$^5$ is lower-alkoxy or

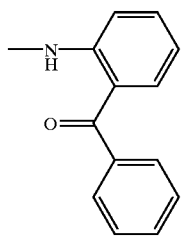

and pharmaceutically acceptable salts thereof.

In a particularly preferred embodiment, the present invention relates to compounds of formula (I), characterized by formula (Ibb)

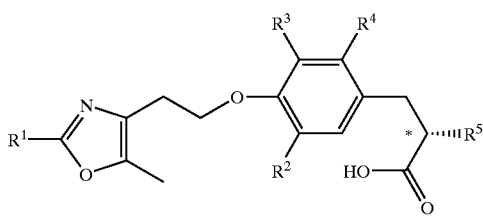
(Ibb)

wherein R$^1$, R$^2$, R$^3$, R$^4$ and R$^5$ are as defined above, and pharmaceutically acceptable salts thereof Formula (Ibb) means that the asymmetric carbon atom C* has the S configuration according to the Cahn-Ingold-Prelog-Convention.

In addition, compounds as defined above in which R$^1$ is phenyl optionally substituted with 1 to 3 substituents independently selected from the group consisting of halogen, CF$_3$, lower-alkyl and lower-alkoxy are preferred, with unsubstituted phenyl being particularly preferred. Furthermore, compounds as defined above in which R$^1$ is thienyl optionally substituted with 1 to 3 substituents independently selected from the group consisting of halogen, CF$_3$, lower-alkyl and lower-alkoxy are preferred, with unsubstituted thienyl being particularly preferred.

Compounds of formula (I), wherein R$^3$ and R$^4$ are bonded to each other to form a ring together with the carbon atoms to which they are attached, and R$^3$ and R$^4$ together are —CH═CH—CH═CH—, and R$^2$ and R$^6$ are hydrogen, are also preferred. Such compounds consequently comprise the following moiety

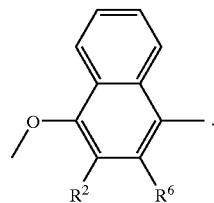

Further, compounds of formula (I), wherein R$^3$ and R$^4$ are bonded to each other to form a ring together with the carbon atoms to which they are attached, and R$^3$ and R$^4$ together are —CH═CH—S—, and R$^2$ and R$^6$ are hydrogen, are preferred. Such compounds consequently comprise the following moiety

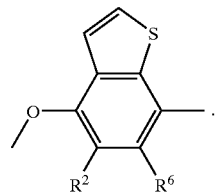

In addition, compounds as defined above, wherein R$^2$, R$^3$ and R$^4$ independently from each other are hydrogen or lower-alkyl are preferred, with those wherein R$^2$ and R$^3$ are methyl and R$^4$ is hydrogen being particularly preferred. Other particularly preferred compounds of formula (I) are those wherein R$^2$ is methyl and R$^3$ and R$^4$ are hydrogen. Further particularly preferred compounds of formula (I) are those wherein R$^4$ is methyl and R$^2$ and R$^3$ are hydrogen. Particularly preferred are those compounds of formula I, wherein R$^6$ is hydrogen.

Compounds of formula (I) wherein R$^5$ is lower-alkoxy represent a preferred embodiment of the present invention, with those compounds wherein R$^5$ is methoxy, ethoxy, propoxy, butoxy, isobutoxy, or hexyloxy representing a particularly preferred embodiment. Other preferred compounds are those wherein R$^5$ is

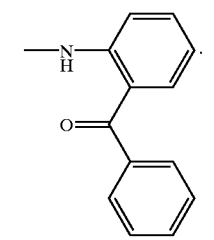

Preferred are compounds according to formula I and the pharmaceutically acceptable salts thereof. Particularly preferred are compounds of formula I.

A preferred aspect of the present invention are compounds according to formula I, wherein
R$^2$, R$^3$ and R$^4$ independently from each other are hydrogen, halogen, lower-alkyl or lower-alkoxy, wherein at least one of R$^2$, R$^3$ and R$^4$ is not hydrogen, or
R$^3$ and R$^4$ are bonded to each other to form a ring together with the carbon atoms to which they are attached, and $R^3$ and $R^4$ together are —CH=CH—S—, —S—CH=CH—, —CH=CH—O—, —O—CH=CH—, —CH=CH—CH=CH— or —(CH$_2$)$_{3-5}$— and, wherein $R^2$ is as defined above;

$R^5$ is lower-alkoxy or

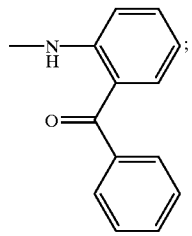

$R^6$ is hydrogen;

$R^7$ is methyl;

n is 2;

wherein the bond between the carbon atom $C^a$ and the carbon atom $C^b$ is a carbon carbon single bond;

and pharmaceutically acceptable salts thereof.

Preferred are compounds of formula I, wherein $R^1$ is phenyl or thienyl, optionally substituted with one or more, particularly one to three substituents, independently selected from trifluoromethyl, aryl, alkyl, alkoxy and halogen. Particularly preferred are compounds according to formula I, wherein $R^1$ is phenyl or phenyl substituted with 1 to 3 substituents independently selected from alkoxy and trifluoromethyl.

Another preferred aspect of the present invention are compounds of formula I, wherein $R^2$, $R^3$, $R^4$ and $R^6$ independently from each other are hydrogen, hydroxy, lower-alkyl or lower-alkoxy, wherein at least one of $R^2$, $R^3$, $R^4$ and $R^6$ is not hydrogen, or $R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH—, or —CH=CH—CH=CH—, and, wherein $R^2$ and $R^6$ are as defined above.

Particularly preferred are compounds according to formula I, wherein $R^2$, $R^3$, $R^4$ and $R^6$ independently from each other are hydrogen, hydroxy, lower-alkyl or lower-alkoxy and wherein at least one of $R^2$, $R^3$, $R^4$ and $R^6$ is not hydrogen. Further particularly preferred are compounds of formula I, wherein $R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH— or —CH=CH—CH=CH—, and, wherein $R^2$ and $R^6$ are defined as before. Likewise particularly preferred are those compounds of formula I, wherein $R^6$ is hydrogen.

Further preferred are compounds according to formula I, wherein $R^2$ and $R^6$ are hydrogen and $R^3$ and $R^4$ are bonded to each other to form a ring together with the carbon atoms to which they are attached, and $R^3$ and $R^4$ together are —CH=CH—S— or —S—CH=CH—.

Particularly preferred are compounds according to formula I, wherein $R^3$ and $R^4$ together are —CH=CH—S—. Such compounds consequently are of the following formula

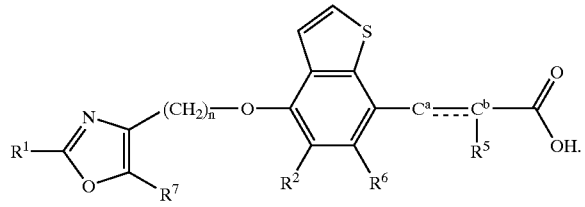

Another preferred aspect of the present invention are compounds according to formula I, wherein $R^5$ is lower-alkoxy or

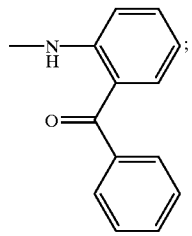

Particularly preferred are those compounds of formula I, wherein $R^5$ is lower-alkoxy. Further particularly preferred are compounds according to formula I, wherein $R^5$ is methoxy, ethoxy or propoxy.

A further preferred aspect of the present application are compounds of formula I, wherein $R^7$ is alkyl. Particularly preferred are those compounds according to formula I, wherein $R^7$ is methyl.

Also preferred are compounds of formula I, wherein $R^8$ is lower-alkyl particularly methyl.

Also preferred are compounds of formula I, wherein $R^9$ is hydrogen. Further preferred are compounds of formula I, wherein $R^9$ is lower-alkyl.

Further preferred are compounds of formula I, wherein $R^{10}$ is phenyl or phenyl substituted with lower-alkyl. Particularly preferred are those compounds of formula I, wherein $R^{10}$ is phenyl.

Preferred are compounds of formula I, wherein n is 1. Further preferred are compounds of formula I, wherein n is 2 or 3. Particularly preferred are those compounds of formula I, wherein n is 2.

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom" (C*) means a carbon atom with four different substituents. According to the Cahn-Ingold-Prelog-Convention the asymmetric carbon atom can be of the "R" or "S" configuration.

Preferred are chiral compounds of formula (I), characterized by formula (Ia)

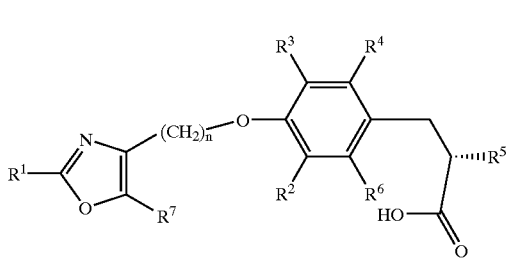

(Ia)

wherein $R^1$, $R^2$, $R^3$, $R^4$, $R^5$, $R^6$, $R^7$ and n are defined as before. Formula (Ia) means that the asymmetric carbon atom $C^*$

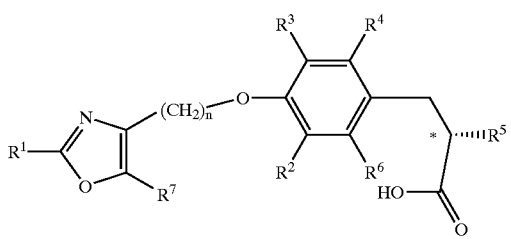

(Ia)

is of the S configuration. Particularly preferred are compounds according to formula (Ia), wherein $R^1$, $R^2$, $R^3$, $R^4$, $R^6$, $R^7$ and n are defined as before and, wherein $R^5$ means lower-alkoxy.

Preferred are compounds of formula I, wherein the bond between the carbon atom $C^a$ and the carbon atom $C^b$ is a carbon carbon double bond (either E- or Z-configuration according to the Cahn-Ingold-Prelog-Convention). Consequently, those compounds are of the following formula (Ic)

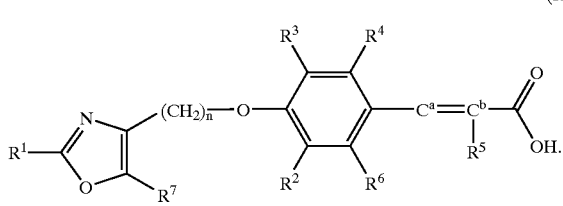

(Ic)

Preferred is the E-configuration. Particularly preferred is the Z-configuration.

Further, particularly preferred are compounds of formula I, wherein the bond between the carbon atom $C^a$ and the carbon atom $C^b$ is a carbon carbon single bond. Consequently, those compounds are of the following formula (Id)

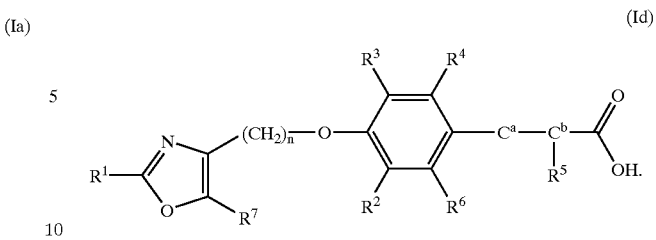

(Id)

Preferred compounds of general formula (I) are those selected from the following group:

1. 2-Methoxy-3-{4-[2-(5-methyl-2-phenyl-oxazol-4-yl)-ethoxy]-benzo[b]thiophen-7-yl}-propionic acid;
2. 2-Ethoxy-3-{4-[2-(5-methyl-2-phenyl-oxazol-4-yl)-ethoxy]-benzo[b]thiophen-7yl }-propionic acid;
3. 3-{4-[2-(5-Methyl-2-phenyl-oxazol-4-yl)-ethoxy]-benzo[b]thiophen-7-yl}-2-propoxy-propionic acid;
4. 2-Butoxy-3-{4-[2-(5-methyl-2-phenyl-oxazol-4-yl)-ethoxy]-benzo[b]thiophen-7-yl}-propionic acid;
5. 2-Isobutoxy-3-{4-[2-(5-methyl-2-phenyl-oxazol-4-yl)-ethoxy]-benzo[b]thiophen-7-yl}-propionic acid;
6. 2-Hexyloxy-3-{4-[2-(5-methyl-2-phenyl-oxazol-4-yl)-ethoxy]-benzo [b]thiophen-7-yl}-propionic acid;
7. 2-Methoxy-3-{4-[2-(5-methyl-2-phenyl-oxazol-4-yl)-ethoxy]-naphthalen-1-yl}-propionic acid;
8. 2-Ethoxy-3-{4-[2-(5-methyl-2-phenyl-oxazol-4-yl)-ethoxy]-naphthalen-1-yl}-propionic acid;
9. 3-{4-[2-(5-Methyl-2-phenyl-oxazol-4-yl)-ethoxy]-naphthalen-1-yl}-2-propoxy -propionic acid;
10. 2-Butoxy-3-{4-[2-(5-methyl-2-phenyl-oxazol-4-yl)-ethoxy]-naphthalen-1-yl}-propionic acid;
11. (S)-2-Methoxy-3-{4-[2-(5-methyl-2-phenyl-oxazol-4-yl)-ethoxy]-benzo[b]thiophen-7-yl}-propionic acid;
12. (S)-2-Ethoxy-3-{4-[2-(5-methyl-2-phenyl-oxazol-4-yl)-ethoxy]-benzo[b]thiophen-7-yl}-propionic acid;
13. (S)-2-Methoxy-3-{4-[2-(5-methyl-2-phenyl-oxazol-4-yl)-ethoxy]-naphthalen-1-yl}-propionic acid;
14. (S)-2-Ethoxy-3-{4-[2-(5-methyl-2-phenyl-oxazol-4-yl)-ethoxy]-naphthalen-1-yl}-propionic acid;
15. 2-(2-Benzoyl-phenylamino)-3-{4-[2-(5-methyl-2-phenyl-oxazol-4-yl)-ethoxy]-naphthalen-1-yl}-propionic acid;
16. 2-(2-Benzoyl-phenylamino)-3-{4-[2-(5-methyl-2-phenyl-oxazol-4-yl)-ethoxy]-benzo[b]thiophen-7-yl}-propionic acid;
17. 3-{3,5-Dimethyl-4-[2-(5-methyl-2-phenyl-oxazol-4-yl)-ethoxy]-phenyl}-2-ethoxy-propionic acid;
18. 2-Ethoxy-3-{3-methyl-4-[2-(5-methyl-2-phenyl-oxazol-4-yl)-ethoxy]-phenyl}-propionic acid;
19. 2-(2-Benzoyl-phenylamino)-3-{3,5-dimethyl-4-[2-(5-methyl-2-phenyl-oxazol-4-yl)-ethoxy]-phenyl}-propionic acid;
20. 2-(2-Benzoyl-phenylamino)-3-{3-methyl-4-[2-(5-methyl-2-phenyl-oxazol-4-yl)-ethoxy]-phenyl}-propionic acid;
21. (S)-2-Methoxy-3-(4-{2-[5-methyl-2-(4-trifluoromethyl-phenyl)-oxazol-4-yl]-ethoxy}-naphthalen-1-yl)-propionic acid;
22. (S)-2-Ethoxy-3-(4-{2-[5-methyl-2-(4-trifluoromethyl-phenyl)-oxazol-4-yl]-ethoxy}-naphthalen-1-yl)-propionic acid;
23. (S)-2-Methoxy-3-(4-{2-[5-methyl-2-(4-trifluoromethyl-phenyl)-oxazol-4-yl]-ethoxy}-benzo[b]thiophen-7-yl)-propionic acid;
24. (S)-2-Ethoxy-3-(4-{2-[5-methyl-2-(4-trifluoromethyl-phenyl)-oxazol-4-yl]-ethoxy}-benzo[b]thiophen-7-yl)-propionic acid;

25. (S)-3-{4-[2-(2-Biphenyl-4-yl-5-methyl-oxazol-4-yl)-ethoxy]-naphthalen-1-yl}-2-ethoxy-propionic acid;
26. (S)-3-{4-[2-(2-Biphenyl-4-yl-5-methyl-oxazol-4-yl)-ethoxy]-naphthalen-1-yl}-2-propoxy-propionic acid;
27. (S)-3-{4-[2-(2-Biphenyl-4-yl-5-methyl-oxazol-4-yl)-ethoxy]-benzo[b]thiophen-7-yl}-2-propoxy-propionic acid;
28. (S)-3-{4-[2-(2-Biphenyl-4-yl-5-methyl-oxazol-4-yl)-ethoxy]-naphthalen-1-yl}-2-methoxy-propionic acid;
29. (S)-3-{4-[2-(2-Biphenyl-4-yl-5-methyl-oxazol-4-yl)-ethoxy]-naphthalen-1-yl}-2-(2,2,2-trifluoro-ethoxy)-propionic acid;
30. (S)-3-{4-[2-(2-Biphenyl-4-yl-5-methyl-oxazol-4-yl)-ethoxy]-benzo[b]thiophen-7-yl}-2-ethoxy-propionic acid;
31. (S)-3-(4-{2-[2-(4-Isopropyl-phenyl)-5-methyl-oxazol-4-yl]-ethoxy}-benzo[b]thiophen-7-yl)-2-methoxy-propionic acid;
32. (S)-3-(4-{2-[2-(4-Isopropyl-phenyl)-5-methyl-oxazol-4-yl]-ethoxy}-benzo[b]thiophen-7-yl)-2-(2,2,2-trifluoro-ethoxy)-propionic acid;
33. (S)-3-(4-{2-[2-(3,5-Dimethyl-phenyl)-5-methyl-oxazol-4-yl]-ethoxy}-benzo[b]thiophen-7-yl)-2-methoxy-propionic acid;
34. (S)-3-(4-{2-[2-(3,5-Dimethoxy-phenyl)-5-methyl-oxazol-4-yl]-ethoxy}-benzo[b]thiophen-7-yl)-2-methoxy-propionic acid;
35. (S)-3-(4-{2-[2-(3,5-Dimethoxy-phenyl)-5-methyl-oxazol-4-yl]-ethoxy}-naphthalen-1-yl)-2-methoxy-propionic acid;
36. [rac]-3-(4-{2-[2-(3,5-Dichloro-phenyl)-5-methyl-oxazol-4-yl]-ethoxy}-benzo[b]thiophen-7-yl)-2-methoxy-propionic acid;
37. [rac]-3-(4-{2-[2-(3,5-Difluoro-phenyl)-5-methyl-oxazol-4-yl]-ethoxy}-benzo[b]thiophen-7-yl)-2-methoxy-propionic acid;
38. [rac]-2-Butoxy-3-(4-{2-[2-(3,5-difluoro-phenyl)-5-methyl-oxazol-4-yl}-benzo[b]thiophen-7-yl)-propionic acid;
39. [rac]-2-Butoxy-3-(4-{2-[2-(3,5-dimethoxy-phenyl)-5-methyl-oxazol-4-yl]-ethoxy}-benzo[b]thiophen-7-yl)-propionic acid;
40. [rac]-2-Butoxy-3-(4-{2-[2-(3,5-dimethyl-phenyl)-5-methyl-oxazol-4-yl]-ethoxy}-benzo[b]thiophen-7-yl)-propionic acid;
41. [rac]-3-(4-{2-[2-(3,5-Difluoro-phenyl)-5-methyl-oxazol-4-yl]-ethoxy}-benzo[b]thiophen-7-yl)-2-ethoxy-propionic acid;
42. [rac]-2-Methoxy-3-(4-{3-[2-(4-methoxy-phenyl)-5-methyl-oxazol-4-yl]-propoxy}-naphthalen-1-yl)-propionic acid;
43. [rac]-3-(4-{3-[2-(4-Chloro-phenyl)-5-methyl-oxazol-4-yl]-propoxy}-naphthalen-1-yl)-2-methoxy-propionic acid;
44. [rac]-2-Methoxy-3-(4-{3-[5-methyl-2-(4-trifluoromethyl-phenyl)-oxazol-4-propoxy}-benzo[b]thiophen-7-yl)-propionic acid;
45. [rac]-2-Ethoxy-3-(4-{3-[5-methyl-2-(4-trifluoromethyl-phenyl)-oxazol-4-yl]-propoxy}-benzo[b]thiophen-7-yl)-propionic acid;
46. [rac]-3-(4-{3-[2-(4-Chloro-phenyl)-5-methyl-oxazol-4-yl]-propoxy}-naphthalen-1-yl)-2-isopropoxy-propionic acid;
47. (S)-2-Methoxy-3-(4-{3-[5-methyl-2-(4-trifluoromethyl-phenyl)-oxazol-4-yl]-propoxy}-naphthalen-1-yl)-propionic acid;
48. [rac]-3-(4-{3-[2-(4-Chloro-phenyl)-5-methyl-oxazol-4-yl]-propoxy}-benzo[b]thiophen-7-yl)-2-methoxy-propionic acid;
49. [rac]-2-Ethoxy-3-(4-{3-[2-(4-methoxy-phenyl)-5-methyl-oxazol-4-yl]-propoxy}-naphthalen-1-yl)-propionic acid;
50. [rac]-2-Ethoxy-3-(4-{3-[2-(4-isopropyl-phenyl)-5-methyl-oxazol-4-yl]-propoxy}-naphthalen-1-yl)-propionic acid;
51. [rac]-3-(4-{3-[2-(4-Chloro-phenyl)-5-methyl-oxazol-4-yl]-propoxy}-naphthalen-1-yl)-2-ethoxy-propionic acid;
52. [rac]-3-(4-{3-[2-(4-Isopropyl-phenyl)-5-methyl-oxazol-4-yl]-propoxy}-naphthalen-1-yl)-2-methoxy-propionic acid;
53. [rac]-3-(4-{2-[2-(3,5-Dimethyl-phenyl)-5-methyl-oxazol-4-yl]-ethoxy}-benzo[b]thiophen-7-yl)-2-ethoxy-propionic acid;
54. [rac]-3-(4-{2-[2-(3,5-Dimethoxy-phenyl)-5-methyl-oxazol-4-yl]-ethoxy}-benzo[b]thiophen-7-yl)-2-ethoxy-propionic acid;
55. [rac]-2-Ethoxy-3-(4-{3-[2-(4-methoxy-phenyl)-5-methyl-oxazol-4-yl]-propoxy}-benzo[b]thiophen-7-yl)-propionic acid;
56. [rac]-2-Methoxy-3-(4-{3-[2-(4-methoxy-phenyl)-5-methyl-oxazol-4-yl]-propoxy}-benzo[b]thiophen-7-yl)-propionic acid;
57. [rac]-2-Ethoxy-3-(4-{3-[2-(4-isopropyl-phenyl)-5-methyl-oxazol-4-yl]-propoxy}-benzo[b]thiophen-7-yl)-propionic acid;
58. [rac]-3-(4-{3-[2-(4-Isopropyl-phenyl)-5-methyl-oxazol-4-yl]-propoxy}-benzo[b]thiophen-7-yl)-2-methoxy-propionic acid;
59. [rac]-3-(4-{3-[2-(4-Chloro-phenyl)-5-methyl-oxazol-4-yl]-propoxy}-benzo[b]thiophen-7-yl)-2-ethoxy-propionic acid;
60. [rac]-3-(4-{3-[2-(4-Chloro-phenyl)-5-methyl-oxazol-4-yl]-propoxy}-benzo[b]thiophen-7-yl)-2-methoxy-propionic acid
61. [rac]-2-Ethoxy-3-(4-{3-[2-(4-methoxy-phenyl)-5-methyl-oxazol-4-yl]-propoxy}-naphthalen-1-yl)-propionic acid;
62. [rac]-2-Ethoxy-3-(4-{3-[2-(4-isopropyl-phenyl)-5-methyl-oxazol-4-yl]-propoxy}-naphthalen-1-yl)-propionic acid;
63. [rac]-3-(4-{3-[2-(4-Chloro-phenyl)-5-methyl-oxazol-4-yl]-propoxy}-naphthalen-1-yl)-2-ethoxy-propionic acid;
64. [rac]-2-Ethoxy-3-(4-{2-[2-(4-isopropyl-phenyl)-5-methyl-oxazol-4-yl]-ethoxy}-benzo[b]thiophen-7-yl)-propionic acid;
65. (S)-2-But-3-enyloxy-3-(4-{2-[2-(4-isopropyl-phenyl)-5-methyl-oxazol-4-yl]-ethoxy}-benzo[b]thiophen-7-yl)-propionic acid;
66. [rac]-3-(4-{2-[2-(4-Isopropyl-phenyl)-5-methyl-oxazol-4-yl]-ethoxy}-naphthalen-1-yl)-2-propoxy-propionic acid;
67. [rac]-2-Ethoxy-3-(4-{2-[2-(4-isopropyl-phenyl)-5-methyl-oxazol-4-yl]-ethoxy}-naphthalen-1-yl)-propionic acid;
68. [rac]-3-(4-{2-[2-(3,5-Dimethoxy-phenyl)-5-methyl-oxazol-4-yl]-ethoxy}-benzo[b]thiophen-7-yl)-2-isopropoxy-propionic acid;
69. (S)-3-(4-{2-[2-(3,5-Dimethoxy-phenyl)-5-methyl-oxazol-4-yl]-ethoxy}-benzo[b]thiophen-7-yl)-2-isopropoxy-propionic acid;
70. [rac]-3-(4-{3-[2-(4-Isopropyl-phenyl)-5-methyl-oxazol-4-yl]-propoxy}-benzo[b]thiophen-7-yl)-2-propoxy-propionic acid;
71. [rac]-3-(4-{2-[2-(3,5-Dimethoxy-phenyl)-5-methyl-oxazol-4-yl]-ethoxy}-naphthalen-1-yl)-2-ethoxy-propionic acid;

72. [rac]-3-(4-{2-[2-(3,5-Dimethoxy-phenyl)-5-methyl-oxazol-4-yl]-ethoxy}-naphthalen-1-yl)-2-propoxy-propionic acid;
73. [rac]-3-(4-{2-[2-(3,5-Dimethoxy-phenyl)-5-methyl-oxazol-4-yl]-ethoxy}-naphthalen-1-yl)-2-isopropoxy-propionic acid;
74. [rac]-2-Isopropoxy-3-(4-{2-[2-(4-isopropyl-phenyl)-5-methyl-oxazol-4-yl]-ethoxy}-naphthalen-1-yl)-propionic acid;
75. 2Z-Ethoxy-3-{2-methyl-4-[2-(5-methyl-2-phenyl-oxazol-4-yl)-ethoxy]-phenyl}-acrylic acid;
76. [rac]-2-Ethoxy-3-{2-methyl-4-[2-(5-methyl-2-phenyl-oxazol-4-yl)-ethoxy]-phenyl}-propionic acid;
77. 2(S)-Ethoxy-3-{2-methyl-4-[2-(5-methyl-2-phenyl-oxazol-4-yl)-ethoxy]-phenyl}-propionic acid;
78. 2(R)-Ethoxy-3-{2-methyl-4-[2-(5-methyl-2-phenyl-oxazol-4-yl)-ethoxy]-phenyl}-propionic acid;
79. 3-{2,3-Dimethyl-4-[2-(5-methyl-2-phenyl-oxazol-4-yl)-ethoxy]-phenyl}-2Z-ethoxy-acrylic acid;
80. [rac]-3-{2,3-Dimethyl-4-[2-(5-methyl-2-phenyl-oxazol-4-yl)-ethoxy]-phenyl}-2-ethoxy-propionic acid;
81. 3-{2,6-Dimethyl-4-[2-(5-methyl-2-phenyl-oxazol-4-yl)-ethoxy]-phenyl}-2Z-ethoxy-acrylic acid;
82. [rac]-3-{2,6-Dimethyl-4-[2-(5-methyl-2-phenyl-oxazol-4-yl)-ethoxy]-phenyl}-2-ethoxy-propionic acid;
83. 2Z-Ethoxy-3-{4-[2-(5-methyl-2-phenyl-oxazol-4-yl)-ethoxy]-benzofuran-7-yl}-acrylic acid;
84. 2E-Ethoxy-3-{4-[2-(5-methyl-2-phenyl-oxazol-4-yl)-ethoxy]-benzofuran-7-yl}-acrylic acid;
85. [rac]-2-Ethoxy-3-{4-[2-(5-methyl-2-phenyl-oxazol-4-yl)-ethoxy]-benzofuran-7-yl}-propionic acid;
86. [rac]-2-Ethoxy-3-{4-[2-(5-methyl-2-phenyl-oxazol-4-yl)-ethoxy]-2,3-dihydro-benzofuran-7-yl}-propionic acid;
87. 2Z-Ethoxy-3-{7-[2-(5-methyl-2-phenyl-oxazol-4-yl)-ethoxy]-benzofuran-4-yl}-acrylic acid;
88. 2E-Ethoxy-3-{7-[2-(5-methyl-2-phenyl-oxazol-4-yl)-ethoxy]-benzofuran-4-yl}-acrylic acid;
89. [rac]-2-Ethoxy-3-{7-[2-(5-methyl-2-phenyl-oxazol-4-yl)-ethoxy]-benzofuran-4-yl}-propionic acid;
90. [rac]-2-Ethoxy-3-{7-[2-(5-methyl-2-phenyl-oxazol-4-yl)-ethoxy]-2,3-dihydro-benzofuran-4-yl}-propionic acid;
91. [rac]-2-Ethoxy-3-{7-[2-(5-methyl-2-phenyl-oxazol-4-yl)-ethoxy]-indan-4-yl}-propionic acid;
92. [rac]-2-Ethoxy-3-{4-[2-(5-methyl-2-phenyl-oxazol-4-yl)-ethoxy]-5,6,7,8-tetrahydro-naphthalen-1-yl}-propionic acid;
93. [rac]-3-(4-{2-[2-(4-Chloro-phenyl)-5-methyl-oxazol-4-yl]-ethoxy}-benzo[b]thiophen-7-yl)-2-ethoxy-propionic acid;
94. [rac]-2-Ethoxy-3-(4-{2-[2-(4-fluoro-phenyl)-5-methyl-oxazol-4-yl]-ethoxy}-benzob]thiophen-7-yl)-propionic acid;
95. [rac]-2-Ethoxy-3-(4-{2-[2-(2-ethoxy-4-fluoro-phenyl)-5-methyl-oxazol-4-yl]-ethoxy}-benzo[b]thiophen-7-yl)-propionic acid;
96. [rac]-2-Ethoxy-3-(4-{2-[2-(4-methoxy-phenyl)-5-methyl-oxazol-4-yl]-ethoxy}-benzo[b]thiophen-7-yl)-propionic acid;
97. [rac]-2-Ethoxy-3-(4-{2-[2-(4-isopropoxy-phenyl)-5-methyl-oxazol-4-yl]-ethoxy }-benzo[b]thiophen-7-yl)-propionic acid;
98. (S)-2-Methoxy-3-{7-[2-(5-methyl-2-phenyl-oxazol-4-yl)-ethoxy]-benzo[b]thiophen-4-yl}-propionic acid;
99. 2Z-Ethoxy-3-{7-[2-(5-methyl-2-phenyl-oxazol-4-yl)-ethoxy]-indan-4-yl}-acrylic acid; (S)-2-Methoxy-3-{7-[2-(5-methyl-2-phenyl-oxazol-4-yl)-ethoxy]-indan-4-yl}-propionic acid;
100. [rac]-3-(4-{2-[2-(2-Ethoxy-4-fluoro-phenyl)-5-methyl-oxazol-4-yl]-ethoxy}-naphthalen-1-yl)-2-methoxy-propionic acid;
101. [rac]-2-Methoxy-3-(4-{2-[2-(4-methoxy-phenyl)-5-methyl-oxazol-4-yl]-ethoxy}-naphthalen-1-yl)-propionic acid;
102. 2Z-Ethoxy-3-{7-[2-(5-methyl-2-phenyl- oxazol-4-yl)-ethoxy]-benzo[b]thiophen-4-yl}-acrylic acid;
103. [rac]-2-Ethoxy-3-{7-[2-(5-methyl-2-phenyl-oxazol-4-yl)-ethoxy]-benzo[b]thiophen-4-yl}-propionic acid;
104. [rac]-2-[1-Methyl-3-oxo-3-phenyl-(Z)-propenylamino]-3-{4-[2-(5-methyl-2-phenyl-oxazol-4-yl)-ethoxy]-benzo[b]thiophen-7-yl}-propionic acid;
105. [rac]-2-[1-Methyl-3-oxo-3-(4-trifluoromethyl-phenyl)-(Z)-propenylamino]-3-{4-[2-(5-methyl-2-phenyl-oxazol-4-yl)-ethoxy]-benzo[b]thiophen-7-yl}-propionic acid;
106. [rac]-3-{4-[2-(5-Methyl-2-phenyl-oxazol-4-yl)-ethoxy]-benzo[b]thiophen-7-yl}-2-[3-oxo-3-phenyl-1-trifluoromethyl-(Z)-propenylamino]-propionic acid;
107. [rac]-2-Ethoxy-3-{4-[2-(4-isopropyl-phenyl)-5-methyl-oxazol-4-ylmethoxy]-5,6,7,8-tetrahydro-naphthalen-1-yl}-propionic acid;
108. [rac]-2-Ethoxy-3-[4-(5-methyl-2-phenyl-oxazol-4-ylmethoxy)-5,6,7,8-tetrahydro-naphthalen-1-yl]-propionic acid;
109. [rac]-2-Ethoxy-3-(4-{2-[2-(2-ethoxy-4-fluoro-phenyl)-5-methyl-oxazol-4-yl]-ethoxy}-5,6,7,8-tetrahydro-naphthalen-1-yl)-propionic acid;
110. [rac]-2-Ethoxy-3-(4-{2-[2-(4-fluoro-phenyl)-5-methyl-oxazol-4-yl]-ethoxy}-5,6,7,8-tetrahydro-naphthalen-1-yl)-propionic acid;
111. [rac]-2-Ethoxy-3-(4-{3-[2-(4-methoxy-phenyl)-5-methyl-oxazol-4-yl]-propoxy}-5,6,7,8-tetrahydro-naphthalen-1-yl)-propionic acid;
112. [rac]-2-Ethoxy-3-(4-{2-[5-methyl-2-(4-trifluoromethyl-phenyl)-oxazol-4-yl]-ethoxy}-5,6,7,8-tetrahydro-naphthalen-1-yl)-propionic acid;
113. [rac]-2-Methoxy-3-{3-methyl-4-[2-(5-methyl-2-phenyl-oxazol-4-yl)-ethoxy]-phenyl}-propionic acid;
114. [rac]-2-Methoxy-3-{3-methoxy-4-[2-(5-methyl-2-phenyl-oxazol-4-yl)-ethoxy]-phenyl}-propionic acid;
115. [rac]-Lithium 2-ethoxy-3-{3-methoxy-4-[2-(5-methyl-2-phenyl-oxazol-4-yl)-ethoxy]-phenyl}-propionate
116. [rac]-3-{3,5-Dimethyl-4-[2-(5-methyl-2-phenyl-oxazol-4-yl)-ethoxy]-phenyl}-2-methoxy-propionic acid;
117. [rac]-3-{2-Hydroxy-4-[2-(5-methyl-2-phenyl-oxazol-4-yl)-ethoxy]-phenyl}-2-methoxy-propionic acid;
118. [rac]-3-{3-Methyl-4-[2-(5-methyl-2-phenyl-oxazol-4-yl)-ethoxy]-phenyl}-2-(1-methyl-3-oxo-3-phenyl-(Z)-propenylamino)-propionic acid;
119. [rac]-2-Ethoxy-3-[4-(5-methyl-2-phenyl-oxazol-4-ylmethoxy)-benzofuran-7-yl]-propionic acid;
120. [rac]-2-Ethoxy-3-[4-(5-methyl-2-thiophen-2-yl-oxazol-4-ylmethoxy)-benzofuran-7-yl]-propionic acid;
121. [rac]-2-Ethoxy-3-{4-[2-(4-ethyl-phenyl)-5-methyl-oxazol-4-ylmethoxy]-benzofuran-7-yl}-propionic acid;
122. [rac]-3-{4-[2-(4-tert-Butyl-phenyl)-5-methyl-oxazol-4-ylmethoxy-benzofuran-7-yl}-2-ethoxy-propionic acid;
123. [rac]-2-Ethoxy-3-{4-[2-(4-isopropoxy-phenyl)-5-methyl-oxazol-4-ylmethoxy-benzofuran-7-yl}-propionic acid;
124. [rac]-2-Ethoxy-3-[4-(5-methyl-2-phenyl-oxazol-4-ylmethoxy)-2,3-dihydro-benzofuran-7-yl]-propionic acid;
125. [rac]-2-Ethoxy-3-{4-[2-(4-ethyl-phenyl)-5-methyl-oxazol-4-ylmethoxy]-2,3-dihydro-benzofuran-7-yl}-propionic acid;

126. [rac]-3-{4-[2-(4-tert-Butyl-phenyl)-5-methyl-oxazol-4-ylmethoxy]-2,3-dihydro-benzofuran-7-yl}-2-ethoxy-propionic acid;
127. [rac]-2-Ethoxy-3-{4-[2-(4-isopropoxy-phenyl)-5-methyl-oxazol-4-ylmethoxy]-2,3-dihydro-benzofuran-7-yl}-propionic acid;
128. [rac]-2-Ethoxy-3-[2-methyl-4-(5-methyl-2-phenyl-oxazol-4-ylmethoxy)-phenyl]-propionic acid;
129. [rac]-2-Ethoxy-3-[2-methyl-4-(5-methyl-2-thiophen-2-yl-oxazol-4-ylmethoxy)-phenyl]-propionic acid;
130. [rac]-2-Ethoxy-3-{4-[2-(4-ethyl-phenyl)-5-methyl-oxazol-4-ylmethoxy]-2-methyl-phenyl}-propionic acid;
131. [rac]-3-{4-[2-(4-tert-Butyl-phenyl)-5-methyl-oxazol-4-ylmethoxy]-2-methyl-phenyl}-2-ethoxy-propionic acid;
132. [rac]-2-Ethoxy-3-{4-[2-(4-isopropoxy-phenyl)-5-methyl-oxazol-4-ylmethoxy]-2-methyl-phenyl}-propionic acid;
133. (S)-2-But-3-enyloxy-3-{3,5-dimethyl-4-[2-(5-methyl-2-phenyl-oxazol-4-yl)-ethoxy]-phenyl}-propionic acid;
134. 3-{3,5-Dimethyl-4-[2-(5-methyl-2-phenyl-oxazol-4-yl)-ethoxy]-phenyl}-2Z-ethoxy-acrylic acid;
135. [rac]-3-{4-[2-(4-Chloro-phenyl)-5-methyl-oxazol-4-ylmethoxy]-benzofuran-7-yl}-2-ethoxy-propionic acid;
136. [rac]-3-{4-[2-(4-Chloro-phenyl)-5-methyl-oxazol-4-ylmethoxy]-2-methyl-phenyl}-2-ethoxy-propionic acid;
137. [rac]-3-{4-[2-(3,5-Dimethoxy-phenyl)-5-methyl-oxazol-4-ylmethoxy]-benzofuran-7-yl}-2-ethoxy-propionic acid;
138. 2Z-Ethoxy-3-{4-[2-(4-isopropyl-phenyl)-5-methyl-oxazol-4-ylmethoxy]-2-methyl-phenyl}-acrylic acid;
139. [rac]-2-Ethoxy-3-[3-methyl-4-(2-phenyl-oxazol-4-ylmethoxy)-phenyl]-propionic acid;
140. (S)-3-{3,5-Dimethyl-4-[2-(5-methyl-2-phenyl-oxazol-4-yl)-ethoxy]-phenyl}-2-propoxy-propionic acid;
141. 2Z-But-3-enyloxy-3-{3,5-dimethyl-4-[2-(5-methyl-2-phenyl-oxazol-4-yl)-ethoxy]-phenyl}-acrylic acid;
142. 2E-But-3-enyloxy-3-{3,5-dimethyl-4-[2-(5-methyl-2-phenyl-oxazol-4-yl)-ethoxy]-phenyl}-acrylic acid;
143. [rac]-3-{4-[2-(2-Chloro-phenyl)-5-methyl-oxazol-4-ylmethoxy]-2-methyl-phenyl}-2-ethoxy-propionic acid;
144. [rac]-3-{4-[2-(3-Chloro-phenyl)-5-methyl-oxazol-4-ylmethoxy]-2-methyl-phenyl}-2-ethoxy-propionic acid;
145. [rac]-2-Ethoxy-3-{2-methyl-4-[3-(5-methyl-2-phenyl-oxazol-4-yl)-propoxy]-phenyl}-propionic acid;
146. [rac]-2-Ethoxy-3-{4-[2-(4-fluoro-3-methyl-phenyl)-5-methyl-oxazol-4-ylmethoxy]-2-methyl-phenyl}-propionic acid;
147. [rac]-2-Ethoxy-3-{4-[2-(2-methoxy-phenyl)-5-methyl-oxazol-4-ylmethoxy]-2-methyl-phenyl}-propionic acid;
148. [rac]-3-(4-{2-[2-(4-Chloro-phenyl)-5-methyl-oxazol-4-yl]-ethoxy}-5,6,7,8-tetrahydro-naphthalen-1-yl)-2-ethoxy-propionic acid;
149. [rac]-2-Ethoxy-3-[4-(5- methyl-2-phenyl-oxazol-4-ylmethoxy)-naphthalen-1-yl]-propionic acid;
150. [rac]-2-Ethoxy-3-[7-(5-methyl-2-phenyl-oxazol-4-ylmethoxy)-benzo[b]thiophen-4-yl]-propionic acid;
151. [rac]-2-Ethoxy-3-{7-[2-(4-isopropoxy-phenyl)-5-methyl-oxazol-4-ylmethoxy]-benzo[b]thiophen-4-yl}-propionic acid;
152. [rac]-2-Ethoxy-3-(7-{2-[2-(2-ethoxy-4-fluoro-phenyl)-5-methyl-oxazol-4-yl]-ethoxy}-benzo[b]thiophen-4-yl)-propionic acid;
153. [rac]-3-(7-{2-[2-(4-Chloro-phenyl)-5-methyl-oxazol-4-yl]-ethoxy}-benzo[]thiophen-4-yl)-2-ethoxy-propionic acid;
154. [rac]-3-{7-[2-(4-tert-Butyl-phenyl)-5-methyl-oxazol-4-ylmethoxy]-benzo[b]thiophen-4-yl}-2-ethoxy-propionic acid;
155. (S)-2-Ethoxy-3-{3-methyl-4-[2-(5-methyl-2-phenyl-oxazol-4-yl)-ethoxy]-phenyl}-propionic acid;
156. (2S)-3-{3,5-Dimethyl-4-[2-(5-methyl-2-phenyl-oxazol-4-yl)-ethoxy]-phenyl}-2-ethoxy-propionic acid;
157. [rac]-2-Ethoxy-3-{3-fluoro-4-[2-(5-methyl-2-phenyl-oxazol-4-yl)-ethoxy]-phenyl}-propionic acid;
158. [rac]-2-Ethoxy-3-{4-[2-(5-methyl-2-phenyl-oxazol-4-yl)-ethoxy]-3-propyl-phenyl}-propionic acid;
159. (2S)-2-Ethoxy-3-{3-methoxy-4-[2-(5-methyl-2-phenyl-oxazol-4-yl)-ethoxy]-phenyl}-propionic acid;
160. (2S)-2-Ethoxy-3-{2-methoxy-4-[2-(5-methyl-2-phenyl-oxazol-4-yl)-ethoxy]-phenyl}-propionic acid;
161. [rac]-2-Isopropoxy-3-{4-[2-(5-methyl-2-phenyl-oxazol-4-yl)-ethoxy]-benzo[b]thiophen-7-yl}-propionic acid;
162. (S)-2-Isopropoxy-3-{4-[2-(5-methyl-2-phenyl-oxazol-4-yl)-ethoxy]-benzo[b]thiophen-7-yl}-propionic acid;
163. [rac]-3-{3-Allyl-4-[2-(5-methyl-2-phenyl-oxazol-4-yl)-ethoxy]-naphthalen-1-yl}-2-ethoxy-propionic acid.

Particularly preferred compounds of formula I are selected from the following group:

2-Methoxy-3-{4-[2-(5-methyl-2-phenyl-oxazol-4-yl)-ethoxy]-benzo[b]thiophen-7-yl}-propionic acid;
3-{4-[2-(5-Methyl-2-phenyl-oxazol-4-yl)-ethoxy]-benzo[b]thiophen-7-yl}-2-propoxy-propionic acid;
(S)-2-Methoxy-3-{4-[2-(5-methyl-2-phenyl-oxazol-4-yl)-ethoxy]-benzo[b]thiophen-7-yl}-propionic acid;
(S)-3-(4-{2-[2-(3,5-Dimethoxy-phenyl)-5-methyl-oxazol-4-yl]-ethoxy}-benzo[b]thiophen-7-yl) -2-methoxy-propionic acid;
(S)-2-Methoxy-3-(4-{3-[5-methyl-2-(4-trifluoromethyl-phenyl)-oxazol-4-yl]-propoxy}-naphthalen-1-yl)-propionic acid;
2Z- Ethoxy-3-{2-methyl-4-[2-(5-methyl-2-phenyl-oxazol-4-yl)-ethoxy]-phenyl}-acrylic acid;
2(S)-Ethoxy-3-{2-methyl-4-[2-(5-methyl-2-phenyl-oxazol-4-yl)-ethoxy]-phenyl}-propionic acid;
2Z-Ethoxy-3-{4-[2-(5-methyl-2-phenyl-oxazol-4-yl)-ethoxy]-benzofuran-7-yl}-acrylic acid;
[rac]-2-[1-Methyl-3-oxo-3-phenyl-(Z)-propenylamino]-3-{4-[2-(5-methyl-2-phenyl-oxazol-4-yl)-ethoxy]-benzo[b]thiophen-7-yl}-propionic acid;
[rac]-3-{2-Hydroxy-4-[2-(5-methyl-2-phenyl-oxazol-4-yl)-ethoxy]-phenyl}-2-methoxy-propionic acid;
[rac]-3-{3-Methyl-4-[2-(5-methyl-2-phenyl-oxazol-4-yl)-ethoxy]-phenyl}-2-(1-methyl-3-oxo-3-phenyl-(Z)-propenylamino)-propionic acid;
[rac]-2-Ethoxy-3-[2-methyl-4-(5-methyl-2-phenyl-oxazol-4-ylmethoxy)-phenyl]-propionic acid;
[rac]-2-Ethoxy-3-{4-[2-(4-isopropoxy-phenyl)-5-methyl-oxazol-4-ylmethoxy]-2-methyl-phenyl}-propionic acid;
(2S)-3-{3,5-Dimethyl-4-[2-(5-methyl-2-phenyl-oxazol-4-yl)-ethoxy]-phenyl}-2-ethoxy-propionic acid; and
(2S)-2-Ethoxy-3-{3-methoxy-4-[2-(5-methyl-2-phenyl-oxazol-4-yl)-ethoxy]-phenyl}-propionic acid.

Further particularly preferred is (S)-2-methoxy-3-{4-[2-(5-methyl-2-phenyl-oxazol-4-yl)-ethoxy]-benzo[b]thiophen-7-yl}-propionic acid and pharmaceutically acceptable salts and esters thereof. Most preferred is (S)-2-methoxy-3-{4-[2-(5-methyl-2-phenyl-oxazol-4-yl)-ethoxy]-benzo[b]thiophen-7-yl}-propionic acid.

Compounds of formula (I) can have one or more asymmetric carbon atoms and can exist in the form of optically pure enantiomers or as racemates. The invention embraces all of these forms.

It will be appreciated, that the compounds of general formula (I) in this invention may be derivatised at functional groups to provide derivatives which are capable of conversion back to the parent compound in vivo.

A further aspect of the present invention is the process for the manufacture of compounds of formula I, comprising the deprotection of a compound of formula II

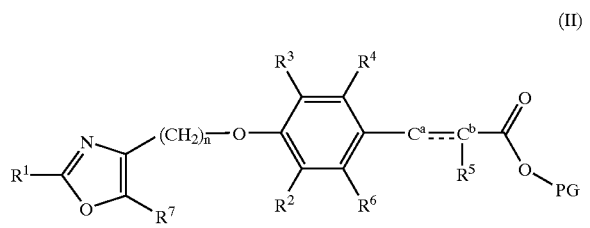

(II)

wherein $R^1$, $R^2$, $R^3$, $R^4$, $R^5$, $R^6$, $R^7$ and n are as defined as before and PG is a protecting group.

The present invention also relates to a process for the manufacture of compounds of formula (I) as defined above, which process comprises removing a protecting group in a compound of formula (IIa)

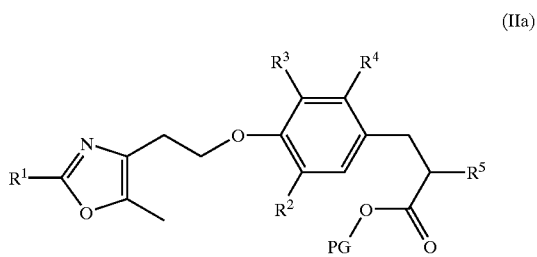

(IIa)

wherein $R^1$, $R^2$, $R^3$, $R^4$ and $R^5$ are as defined above and PG is a protecting group, and optionally converting the resulting compound of formula (I) to a pharmaceutically acceptable salt.

Possible protecting groups PG in compounds of formula (II) are e.g. lower-alkyl-, β-trimethylsilylethyl- and β-trichloroethyl-esters, which can be used for the protection of the corresponding carboxy group. Lower-alkyl-ester protecting groups can be removed in the presence of a base such as e.g. LiOH or NaOH in a solvent such as e.g. $H_2O$, ethanol, tetrahydrofuran, or dioxan, or in a mixture of such solvents, e.g. in a temperature range of 10–50° C. The β-trichloroethyl-ester protecting group can be removed in the presence of Zn in acetic acid, e.g. in a temperature range of 10–50° C. The β-trimethylsilylethyl-ester protecting group can be removed in the presence of tetrabutylammonium fluoride in tetrahydrofuran, e.g. in a temperature range of 20–65° C. Methods for converting a compound of formula (I) as defined above to a pharmaceutically acceptable salt are known in the art.

The invention further relates to compounds of formula (I) as defined above, when manufactured according to a process as defined above.

As described above, the compounds of formula (I) of the present invention can be used as medicaments for the treatment and/or prophylaxis of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases and metabolic syndrome. The use as medicament for the treatment and/or prophylaxis of non-insulin dependent diabetes mellitus is preferred.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases and metabolic syndrome, preferably non-insulin dependent diabetes mellitus.

In another embodiment, the invention relates to a method for the treatment and/or prophylaxis of diseases which are modulated by PPARα and/or PPARγ agonists, which method comprises administering a compound of formula I to a human or animal. Preferred examples of such diseases are diabetes, particularly non-insulin dependent diabetes mellitus, elevated blood pressure, increased lipid and cholesterol levels, atherosclerotic diseases and metabolic syndrome, preferably for the treatment and/or prophylaxis of non-insulin dependent diabetes mellitus.

The invention further relates to the use of compounds as defined above for the treatment and/or prophylaxis of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases and metabolic syndrome, preferably non-insulin dependent diabetes mellitus.

In addition, the invention relates to the use of compounds as defined above for the preparation of medicaments for the treatment and/or prophylaxis of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases and metabolic syndrome, preferably non-insulin dependent diabetes mellitus. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art.

Starting materials are either commercially available or can be prepared by methods analogous to the methods given below or in the examples or by methods known in the art, e.g. from WO 94/27995, WO 98/42704 and EP 1078923 and references cited therein and from references cited in the following text.

Racemates of compounds of formula (I), (compounds 11 in scheme 1, compounds 8 in scheme 2, compounds rac-6 in scheme 3) as well as achiral olefinic compounds of formula (I) with alkoxy substituents $R^5$ (compounds 11 in scheme 1) can e.g. be synthesized according to the methods depicted in scheme 1, scheme 2 and scheme 3 or by analogous methods.

Racemates and optically pure analogues of compounds of formula (I) with amino substituents $R^5$ (compounds 6 in scheme 3) can e.g. be synthesized according to the methods depicted in scheme 3 or by analogous methods.

Homochiral compounds of formula (I) with alkoxy substituents $R^5$, (compound 8 in scheme 4) can be prepared according to the method depicted in scheme 4 or by analogous methods.

Scheme I, part I
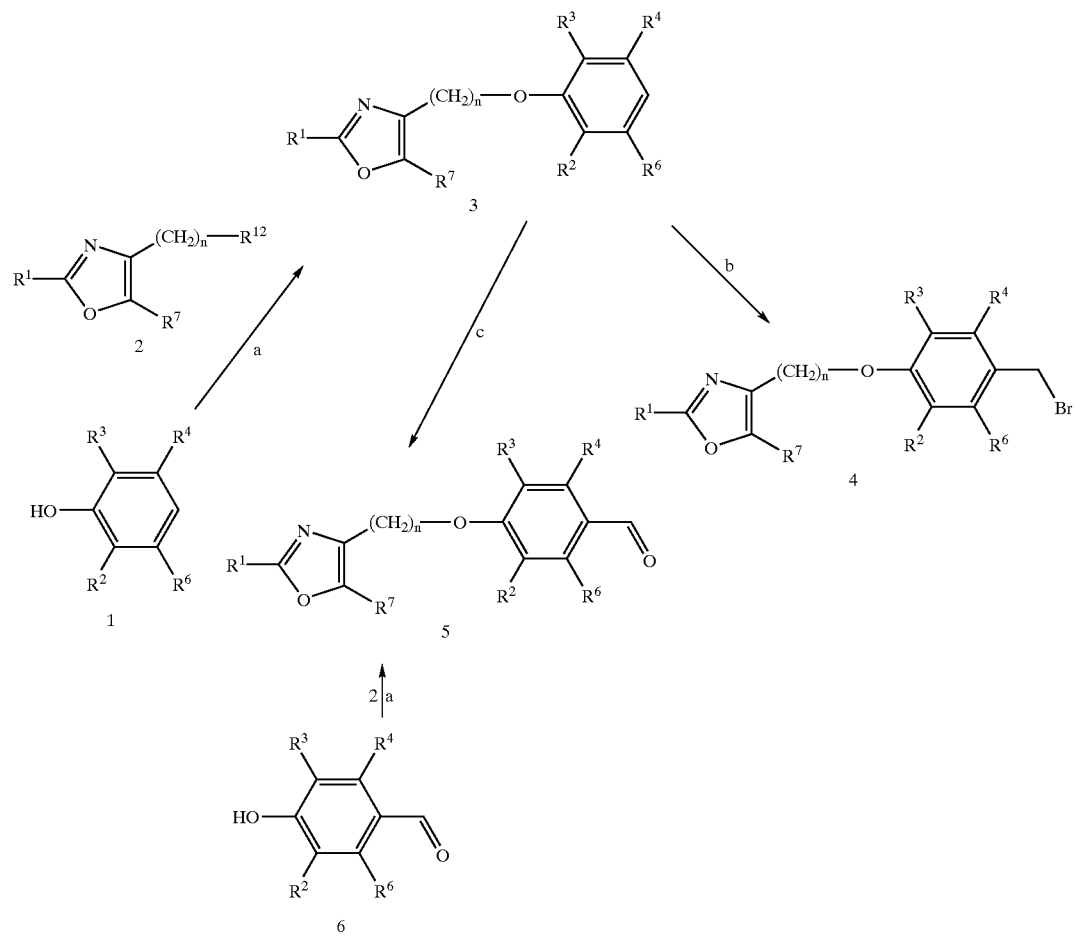
Scheme I, part II
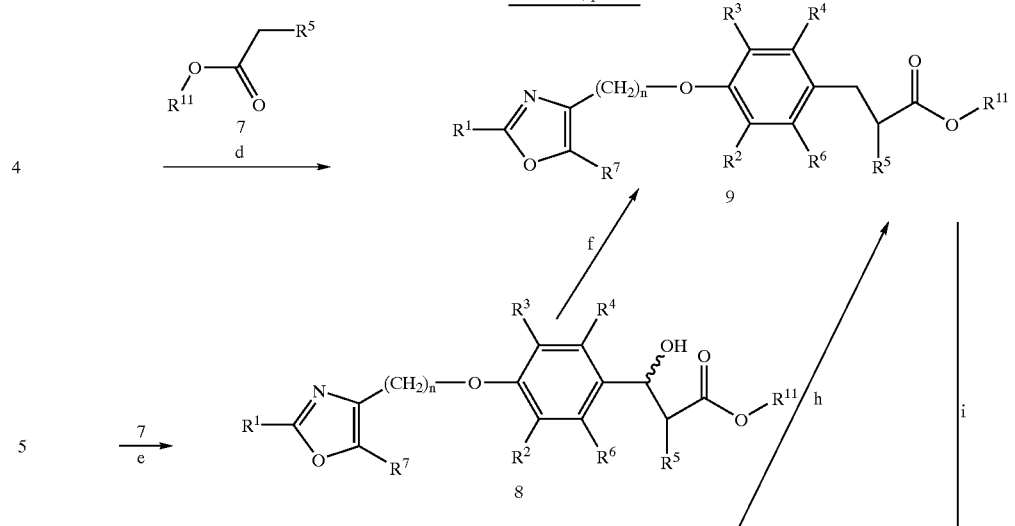

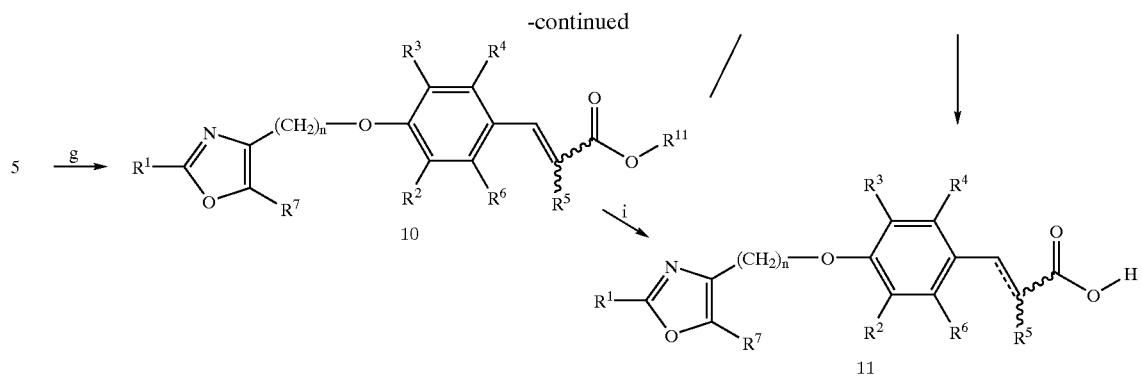

Phenols 1 and/or aldehydes 6 are known or can be synthesized by methods known in the art. Examples for possible syntheses of such phenols and aldehydes are given in schemes 5–10. Aryl-oxazole compounds 2 (prepared as outlined in schemes 11–12) are condensed with phenols 1 or aldehydes 6 according to well known procedures: if $R^{12}$ represents a hydroxy group e.g. via a Mitsunobu-reaction, with triphenylphosphine and di-tert-butyl-, diisopropyl- or diethyl-azodicarboxylate as reagents; the Mitsunobu-reaction is preferably carried out in a solvent like toluene or tetrahydrofuran at ambient temperature. Alternatively, if $R^{12}$ represents a halide, mesylate or tosylate moiety, the aryl-oxazole compounds 2 can be reacted with phenols 1 or aldehydes 6 in solvents like N,N-dimethylformamide, acetone or methyl-ethyl ketone in the presence of a weak base like cesium or potassium carbonate at a temperature ranging from room temperature to 140° C., preferably around 50° C.; thus ether compounds 3 or aldehydes 5 are obtained (step a). The former are then subjected to bromomethylation, e.g. by treatment with trioxane and HBr, preferably 62% aq. HBr, in an inert solvent, preferably dichloromethane, preferably at 0° C. giving a highly reactive, often quite unstable electrophile 4 (step b). The electrophile 4 is suitable to alkylate an enolate of alkoxy-acetic acid esters 7 ($R^{11}$=lower alkyl), preferably the lithium-enolate, prepared at −78° C. by treatment of 7 with a strong, non-nucleophilic base like lithium diisopropyla-mide in an inert solvent like tetrahydrofuran. To increase the reactivity of the enolate nucleophile, the reaction is preferably performed in the presence of a cosolvent like hexam-ethylphosphoramide (HMPA) or 1,3-dimethyl-3,4,5,6-tetrahydro-2(1H)-pyrimidinone (DMPU) to give esters 9 (step d). Alternatively, aldehyde compounds 5, which are also available by Vilsmeier formylation or through formy-lation with dichloromethyl methyl ether in the presence of titanium tetrachloride, preferably in dichloromethane at temperatures between −78° C. and the reflux temperature of the solvent (step c), are reacted with an enolate of alkoxy-acetic acid esters 7 (preferably the lithium-enolate, prepared at −78° C. by treatment of 7 with a strong, non-nucleophilic base like lithium diisopropylamide in an inert solvent like tetrahydrofuran), preferably at temperatures around −78° C., in solvents like tetrahydrofuran giving the aldol product 8 as a mixture of diasteromers (step e). Removal of the benzylic hydroxy group in 8 with a reducing agent like e.g. triethyl-silane in the presence of a Lewis acid, like boron-trifluoride, or a protic acid, like trifluoroacetic acid, in a suitable solvent like trifluoroacetic acid itself or dichloromethane between 0° C. and 60° C. gives racemic esters 9 (step f). Alternatively, aldehydes 5 can be reacted with a Wittig salt such as (ethoxy-ethoxycarbonyl-methyl)-triphenyl-phosphonium chloride or (methoxy-methoxycarbonyl-methyl)-triphenyl-phosphonium bromide in solvents like isopropanol, dichloromethane or tetrahydrofuran or mixtures thereof in the presence of a base like potassium carbonate or 1,8-diazabicyclo[5.4.0]undec-7-ene (DBU), preferably between 0° C. and the reflux temperature of the solvents, giving acrylic esters 10 as E and/or Z isomers (step g). Hydrogenation of acrylic esters 10 using palladium on charcoal as catalyst, preferably at room temperature and 1 atm. pressure of hydrogen, in solvents like methanol, tetrahydrofuran, acetic acid, dichloromethane and mixtures thereof, affords racemic esters 9 (step h). Hydrogenation of compounds in which $R^3$–$R^4$ together with the attached benzene ring form a benzofuran moiety can be performed using extended reaction times to provide the corresponding benzo-dihydrofuran analogues. In compounds, in which $R^3$–$R^4$ together with the attached benzene ring form a ben-zothiophene moiety, the double bond reduction is preferably performed with magnesium in solvent mixtures like tetrahydrofuran/methanol between room temperature and the reflux temperature of the solvents. The esters 9 and 10 can optionally be hydrolyzed according to standard procedures, e.g. by treatment with an alkali hydroxide like LiOH or NaOH in a polar solvent mixture like tetrahydrofuran/ethanol/water leading to carboxylic acids 11 (step i).

Scheme 2

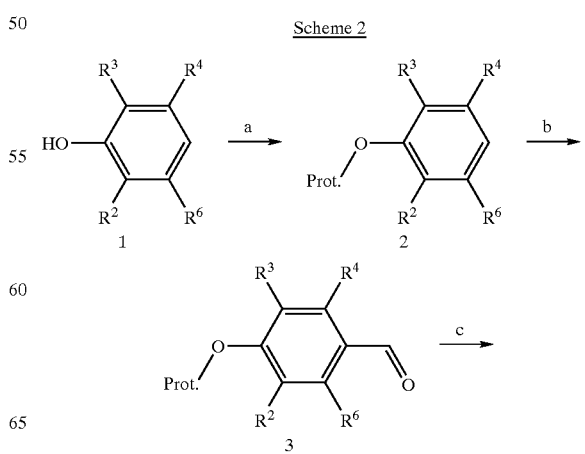

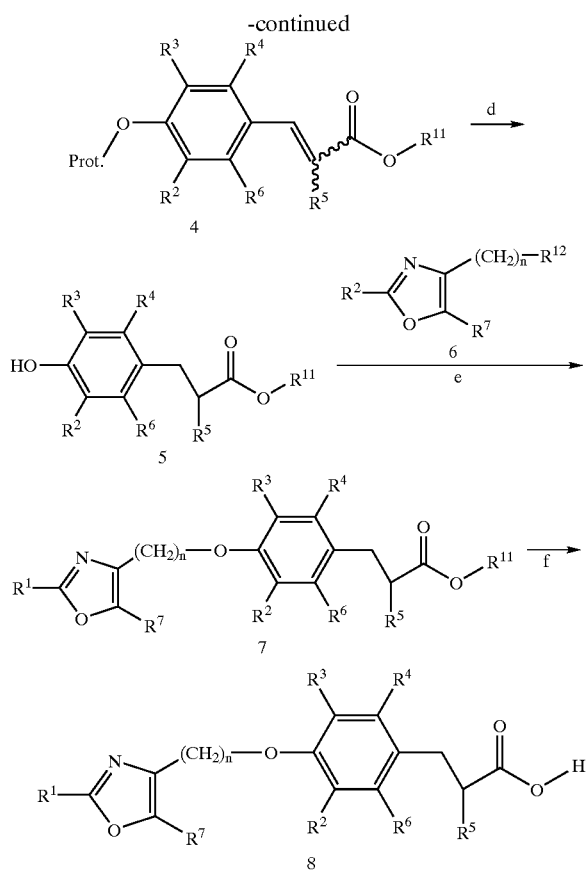

Aldehydes 3 (optionally carrying a protective function) can be obtained from phenols 1 or protected phenols 2 (introduction of protective function, preferably a benzyl ether: step a), by known formylation reactions such as the Vilsmeier formylation or formylation by dichloromethyl methyl ether in the presence of titanium tetrachloride, preferably in dichloromethane at temperatures between −78° C. and the reflux temperature of the solvent (step b). Aldehydes 3 can then be reacted with a Wittig salt such as (ethoxy-ethoxycarbonyl-methyl)-triphenyl-phosphonium chloride or (methoxy-methoxycarbonyl-methyl)-triphenyl-phosphonium bromide in solvents like isopropanol, dichloromethane or tetrahydrofuran or mixtures thereof in the presence of a base like potassium carbonate or 1,8-diazabicyclo[5.4.0]undec-7-ene (DBU), preferably between 0° C. and the reflux temperature of the solvents, giving acrylic esters 4 as E and/or Z isomers (step c). Catalytic hydrogenation of acrylic esters 4 with palladium on charcoal in solvents like methanol, ethanol or tetrahydrofuran leads to phenols 5 (step d). In cases, where $R^3$ and $R^4$ form together with the attached benzene ring a benzothiophene or a benzofuran moiety, a two step procedure is preferred: in a first reaction, the double bond of the acrylic ester moiety is reduced using magnesium in a mixture of methanol and tetrahydrofuran between room temperature and the reflux temperature of the solvents. Subsequently, the protecting group like a benzyl ether is cleaved, e.g. by using dimethyl sulfide and boron trifluoride diethyl etherate in a solvent like dichloromethane between room temperature and the reflux temperature of the solvent to give phenolic compounds 5. Those are then condensed with aryloxazoles 6 to ether compounds 7 (step e) using well known procedures described in scheme 1 for the condensation of phenols 1 or 4-hydroxy-benzaldehydes 6 with arlyoxazoles. Esters 7 can optionally be saponified to acids 8 using standard conditions of alkaline hydrolysis (step f)

Scheme 3

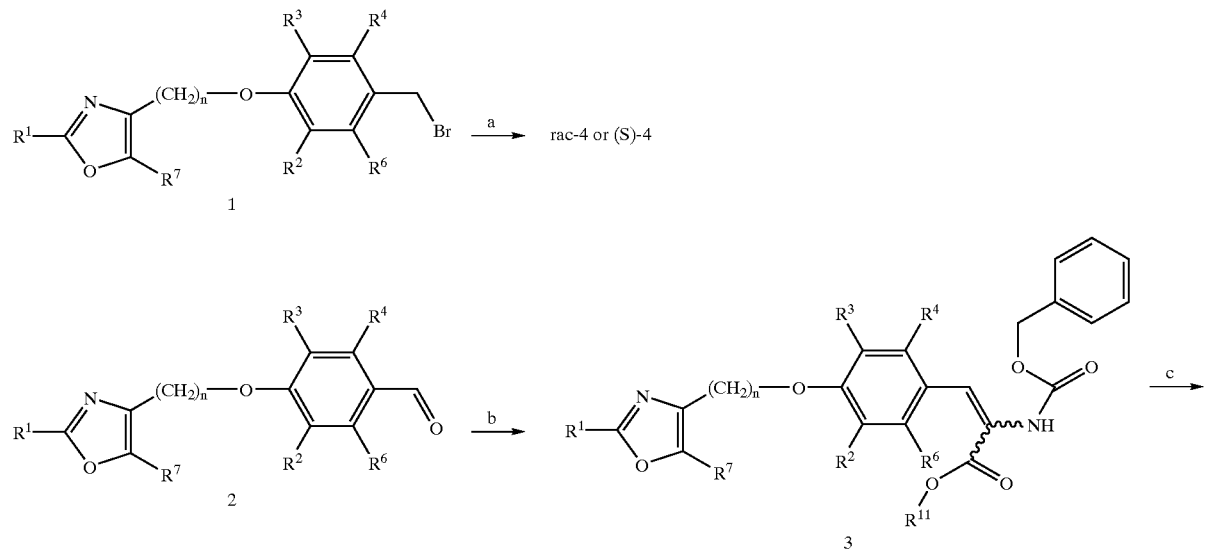

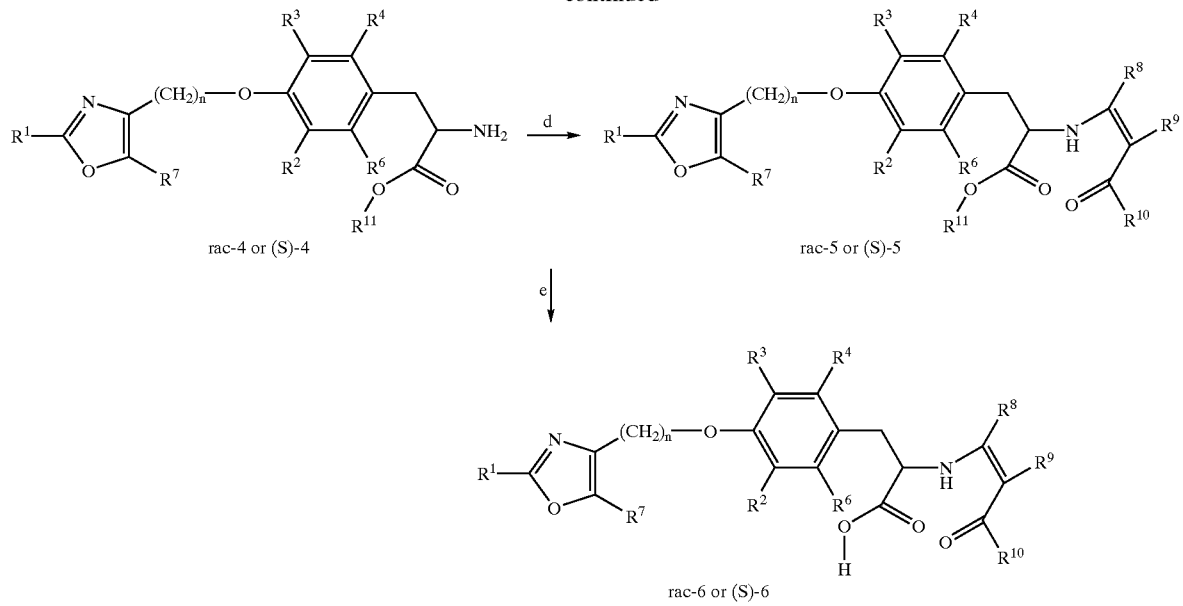

rac-4 or (S)-4   rac-5 or (S)-5 rac-6 or (S)-6

Alpha amino esters 4 may be prepared by i) transformation of a protected glycine ester, preferably N-(diphenylmethylene) glycine ethyl ester, into a corresponding enolate, preferably the lithium-enolate, preferably at −78° C., by treatment with a strong, non-nucleophilic base like lithium diisopropylamide in an inert solvent like tetrahydrofuran; ii) reaction of the thus formed enolate with benzylbromides 1 (compounds 4 in scheme 1), preferably between −78° C. and room temperature, preferably in the presence of a cosolvent which increases the reactivity of the nucleophile like hexamethylphosphoramide (HMPA) or 1,3-dimethyl-3,4,5,6-tetrahydro-2(1H)-pyrimidinone (DMPU); iii) hydrolysis of the imine intermediate with an acid, e.g. diluted hydrogen chloride solution (step a). Alternatively, alpha amino esters 4 can be prepared from aldehydes 2 (compounds 5 in scheme 1), by i) condensation with a suitable phosphonoglycine ester e.g. N-(benzyloxycarbonyl)-alpha-phosphonoglycine trimethyl ester in solvents like dichloromethane or tetrahydrofuran in the presence of a base like Huenig's base between room temperature and the reflux temperature of the solvent leading to enamine carbamates 3; ii) catalytic hydrogenation and deprotection of enamine carbamates 3 using e.g. hydrogen in the presence of palladium on charcoal in solvents like ethyl acetate, tetrahydrofuran or methanol (steps b, c). Optically pure alpha amino esters 4 (preferably the (S)-isomers) can be obtained i) by chromatographic separation into antipodes using a preparative chiral HPLC column or ii) by catalytic hydrogenation of enamine carbamates 3 in the presence of rhodium catalysts carrying chiral ligands like 1,2-bis[(2S, 5S)-2,5-diethylphospholano]-benzene [compare J. Am. Chem. Soc. (2000), 122(16), 3830–3838] in solvents like methanol followed by removal of the Z-protective group using standard reaction conditions like hydrogenolysis with the help of a palladium catalyst. Alpha amino esters 4 are then converted into enamines 5 by reaction with suitable ketones in inert solvents like toluene, optionally in the presence of a catalyst like p-toluene sulfonic acid, and at reflux temperature. In case 2-benzoyl-cyclohexanone is used as ketone component in an inert solvent like anisole in the presence of Pd on charcoal at temperatures around 180° C., enamine-formation is followed by aromatization (step d). Enamine-esters rac-5 or (S)-5 can optionally be saponified to acids rac-6 or (S)-6 using standard conditions of alkaline hydrolysis (step e).

Scheme 4

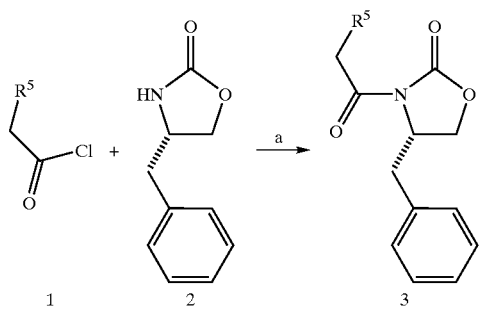

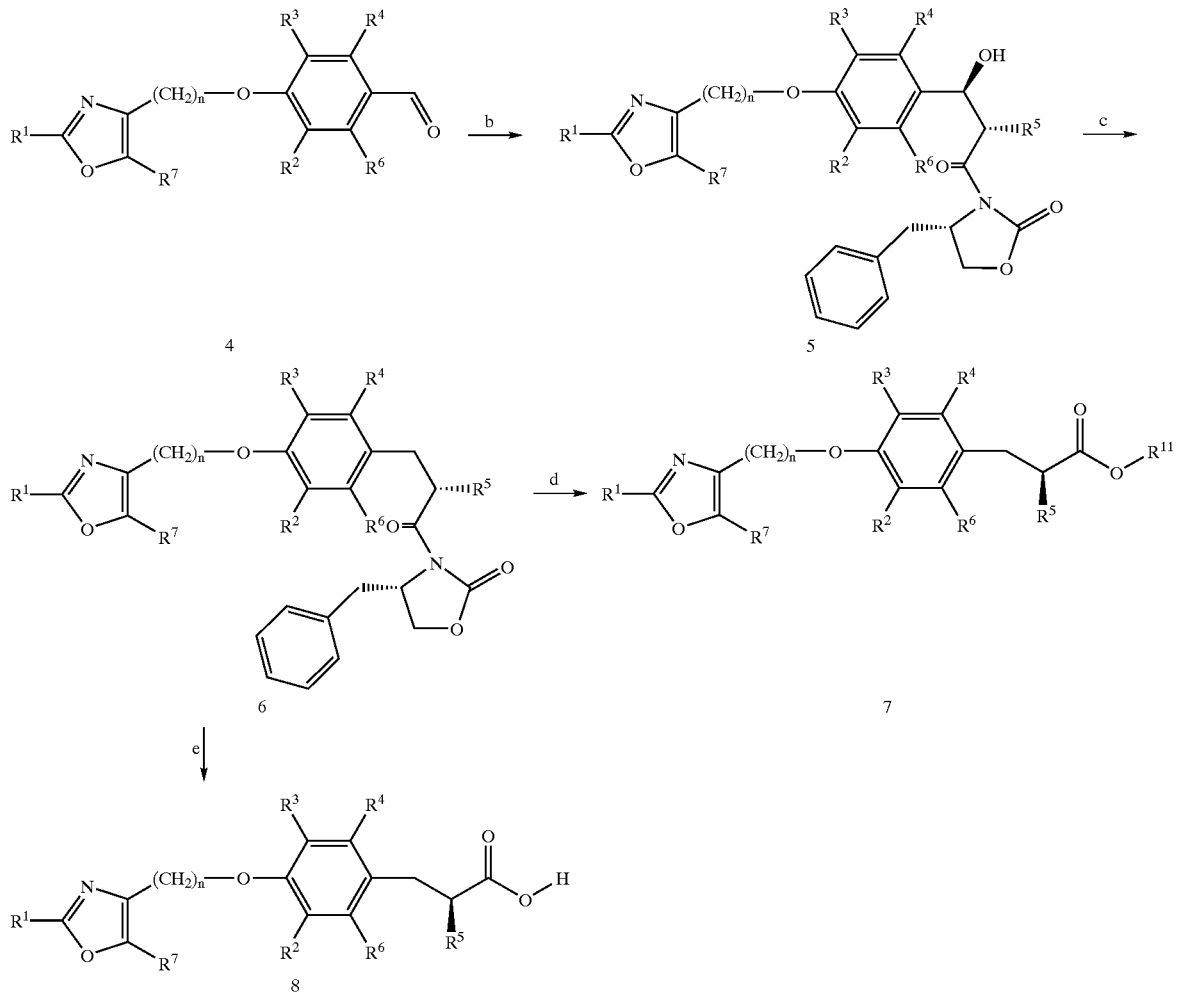

Homochiral alpha alkoxy phenyl-propionic acid compounds of formula 8 can be prepared according to the method depicted in scheme 4 or by analogous methods known in the art.

The well known chiral auxiliary 2 [(S)-4-benzyl-oxazolidin-2-one] is condensed with an alkoxy-acetyl chloride 1 in the presence of a strong base like n-butyl lithium in an inert solvent like tetrahydrofuran at temperatures around −78° C. to produce building block 3 (step a). The latter is then treated according to literature precedence [Tetrahedron Asymmetry (1999), 10, 1353–1367] with dibutylboron-triflate and a tertiary amine like triethylamine in dichloromethane to generate the corresponding boron enolate, which is subsequently reacted at low temperatures with benzaldehydes 4 (compounds 5 in scheme 1) resulting in compounds 5 (step b). In compounds 5, one of all four possible stereoisomers is strongly predominating (stereochemistry as indicated without rigorous proof). The benzylic hydroxy group is then reductively removed as described for the conversion of compounds 8 to compounds 9 in scheme 1 to yield the penultimate intermediate 6 (step c). Esters 7 or acid compounds 8 can finally be obtained without racemization by careful alcoholysis with a sodium alcoholate in the corresponding alcohol as solvent or in solvents like tetrahydrofuran or dioxane at temperatures around 0° C. (step d) or by careful hydrolysis with diluted NaOH in tetrahydrofuran/water at 0° C. (step e). The optical purity of compounds 7 and 8 can be determined by chiral HPLC or by 1H-NMR-spectroscopy in the presence of a chiral solvent like 1-(9-anthryl)-2,2,2-trifluoro-ethanol and has been found high in all cases exemplified.

Phenols 1 and/or aldehydes 6 (scheme 1), phenols 1 and/or protected phenols 2 and/or protected aldehydes 3 (scheme 2) and oxazoles 2 (scheme 1) are known or can be synthesized by methods known in the art. Examples for possible syntheses of these key intermediates are given in schemes 5–12.

Scheme 5

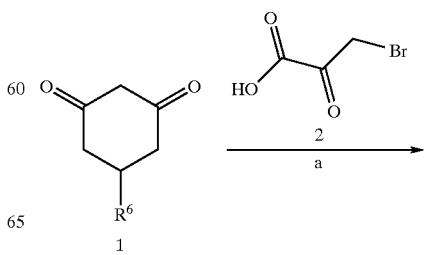

Scheme 6

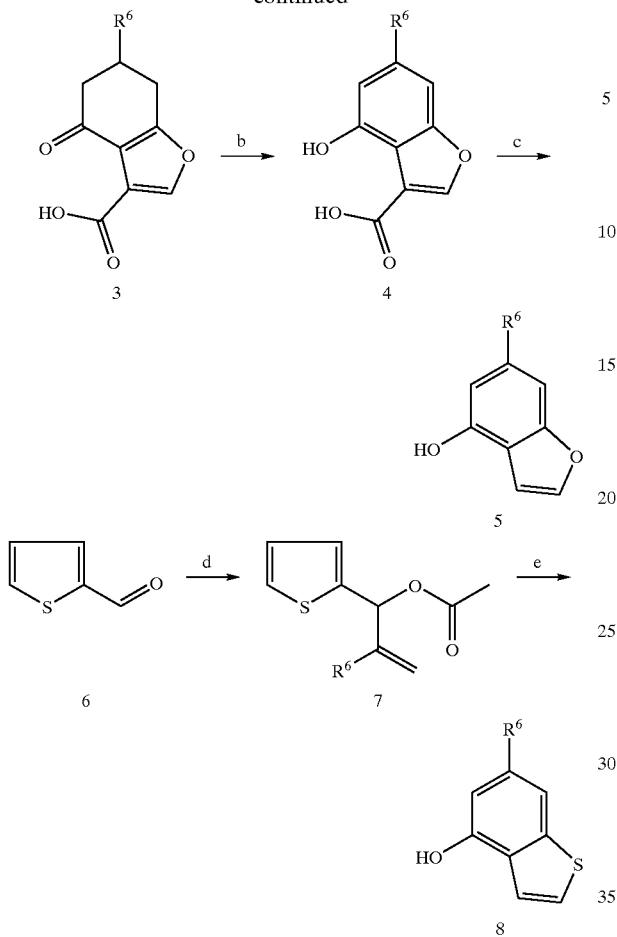
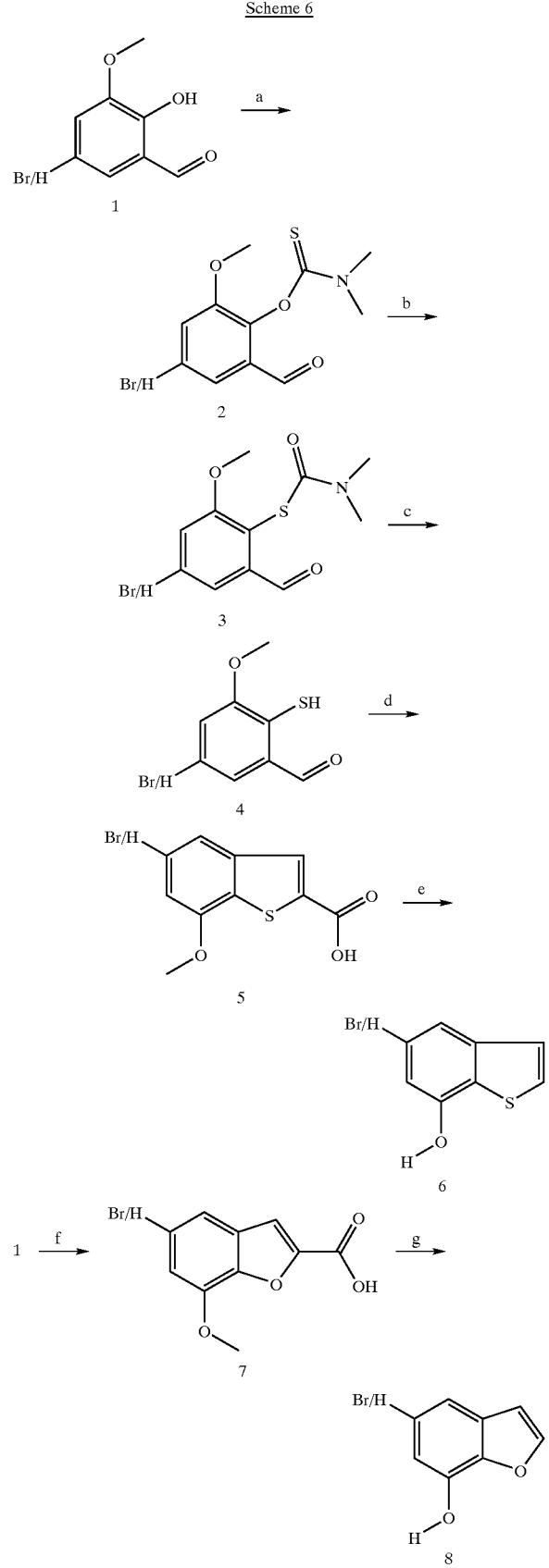

4-Hydroxy-benzofurans 5 [Synthetic Communications (1986), 16(13), 1635–1640; Helvetica Chimica Acta (1933), 16, 121–129] and 4-hydroxy-benzothiophenes 8 [Jpn. Kokai Tokkyo Koho (2001), 2001048876A2] are known. Thus, cyclohexane-1,3-diones 1 carrying variable substituents $R^6$ at the 5-position can be reacted with bromo-pyruvic acid in methanol in the presence of a base like potassium hydroxide at temperatures between 0° C. and the reflux temperature of methanol followed by treatment with hydrochloric acid at around 100° C. to give furan-carboxylic acids 3 (step a). Treatment of these furan-carboxylic acids 3 in an inert solvent like decahydro-naphthalene in the presence of a hydrogen acceptor like dodecene and palladium on carbon, preferably at reflux, provides carboxy-benzofurans 4 (step b), which are decarboxylated to benzofurans 5, e.g. by using copper powder in quinoline at temperatures between 200° C. and 240° C. (step c). Treatment of 2-thiophenecarbaldehyde 6 with suitable vinyl-lithium- or vinyl-magnesium-derivatives in solvents like tetrahydrofuran or 1,2-dimethoxy-ethane, preferably in a temperature range between −78° C. and room temperature, followed by in situ treatment with acetic anhydride yields thiophenes 7 with variable substitution $R^6$ (step d). Treatment of thiophenes 7 with carbon monoxide, preferably at a pressure of 20 to 60 bar, a palladium catalyst like palladium acetate, a phosphine like triphenylphosphine, in solvent mixtures which may typically contain acetic anhydride, triethylamine, toluene or tetrahydrofuran, preferably in a temperature range between 100° C. to 160° C., affords after saponification of the acetate function, benzothiophenes 8 (step e).

2-Hydroxy-3-methoxy-benzaldehyde 1, optionally substituted with bromine in position 5, can be transformed into benzo[b]thiophen-7-ol 6 or 5-bromo-benzo[b]thiophen-7-ol 6. This sequence can be carried out in analogy to the method described in J. Chem. Soc., Perkin Trans. 1 1983(12), 2973–7. For the transformation of 2-hydroxy-3-methoxy-benzaldehyde into benzo[b]thiophen-7-ol: treatment with N,N-dimethylthiocarbamoyl chloride in a solvent like tetrahydrofuran in the presence of an aqueous base like potassium hydroxide in water or in the presence of an organic base like diisopropyl-ethyl-amine, preferably at temperatures between 0° C. and room temperature, generates thionocarbamates 2 (step a); thermal rearrangement of 2 without solvent or preferably in an inert solvent like diphenyl ether at temperatures between 200° C. and 280° C. leads to S-arylthiocarbamates 3 (step b); saponification in a solvent like an alcohol with a base like sodium or potassium hydroxide, preferably between room temperature and the reflux temperature of the solvents, leads then to thiophenols 4 (step c); reaction of thiophenols 4 with sodium chloroacetate in water or a water alcohol mixture in the presence of a base like sodium or potassium hydroxide in a temperature range between room temperature and the reflux temperature of the solvents produces then benzothiophene-carboxylic acids 5 (step d); decarboxylation, e.g. in quinoline in the presence of copper bronze at temperatures between 200° C. and 240° C., followed by cleavage of the methyl ether function, e.g. by treatment with aqueous hydrobromic acid in acetic acid at reflux, then finally yields benzo[b]thiophen-7-ols 6 (step e). 7-Hydroxy-benzofuran is known and commercially available [J. Med. Chem. (1987), 30(1), 62–7]. In a sequence similar to that described above, the 5-bromo-analogue can be prepared from 2-hydroxy-3-methoxy-benzaldehyde 1 by reaction with ethyl chloro-actetate in a solvent like N,N-dimethylformamide in the presence of a base like potassium carbonate at temperatures between 60° C. and 120° C. yielding benzofuran carboxylic acid 7 (step f). Decarboxylation as described above and ensuing ether cleavage, preferably with pyridine hydrochloride at temperatures around 200° C., then leads to 5-bromo-7-hydroxy-benzofuran 8 (step g).

Scheme 7

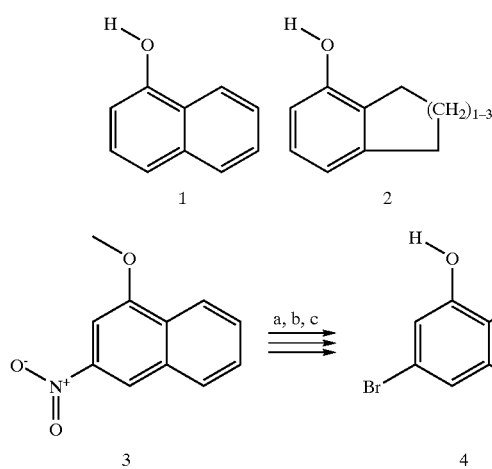

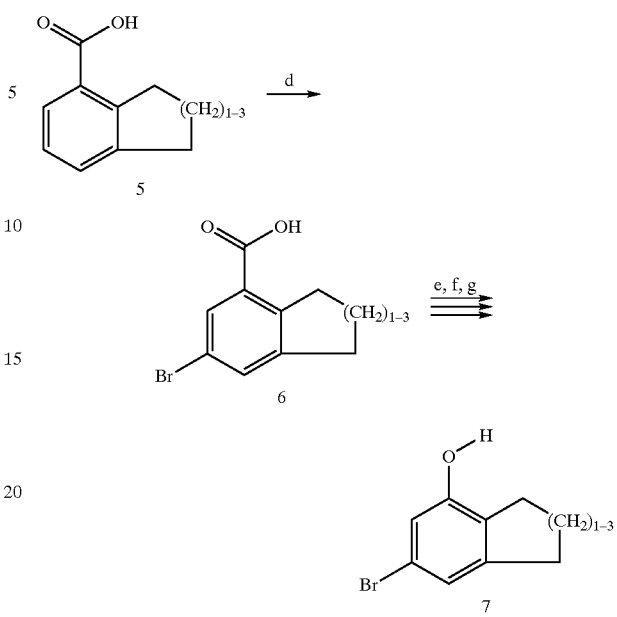

1-Hydroxy-naphthalene 1 and 2,3-annelated phenols 2 with a ring size of 5, 6 and 7 are commercially available or known [see J. Am. Chem. Soc. (1988), 110(19), 6471–6480; U.S. Pat. No. 6,121,397; (2000) PCT Int. Appl. (1999) WO99/10339]. 3-Bromo-1-hydroxy-naphthalene 4, an intermediate carrying a functionality, which allows synthetic modifications at a later stage, can be prepared from 3-nitro-1-methoxy-naphthalene 3 [Monatsh. Chem. (1992), 123 (6–7), 637–645] by well established procedures, i.e. reduction of the nitro function, e.g. by hydrogenation in the presence of a palladium catalyst, followed by diazotisation, Sandmeyer reaction and cleavage of the methyl ether function giving 3-bromo-1-hydroxy-naphthalene 4 (steps a, b, c). 2,3-Annelated carboxylic acids 5 are known, their 3-bromo analogues 6 are known or can be prepared by established methods of bromination of aromatic nuclei [J. Org. Chem. (1978), 43(11), 2167–70; Ger. Offen. (1977), DE 2633905] (step d). Such 3-bromo-benzoic acids can then be converted into the corresponding phenols 7 by known methods such as e.g. exhaustive reduction with borane to the corresponding alcohol, oxidation, e.g. by using Swern conditions (oxalyl chloride/dimethylsulfoxide/triethylamine in dichloromethane, −78° C. to room temperature) to the corresponding alehyde, followed by Baeyer-Villiger oxidation with peracetic acid (40%) in acetic acid (steps e, f, g).

Scheme 8

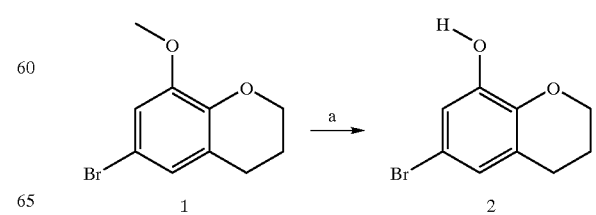

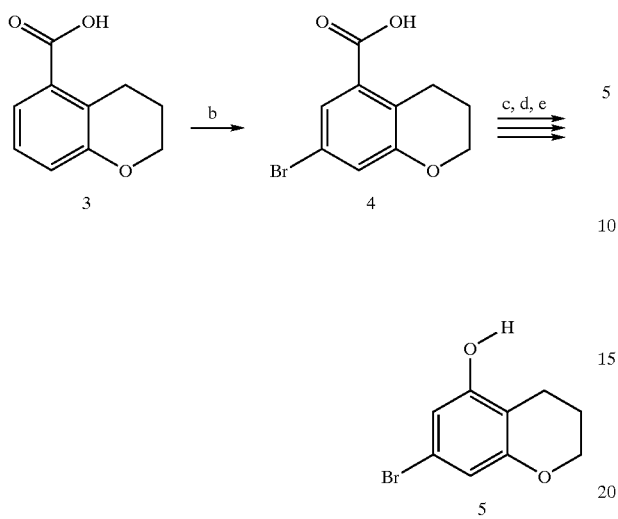

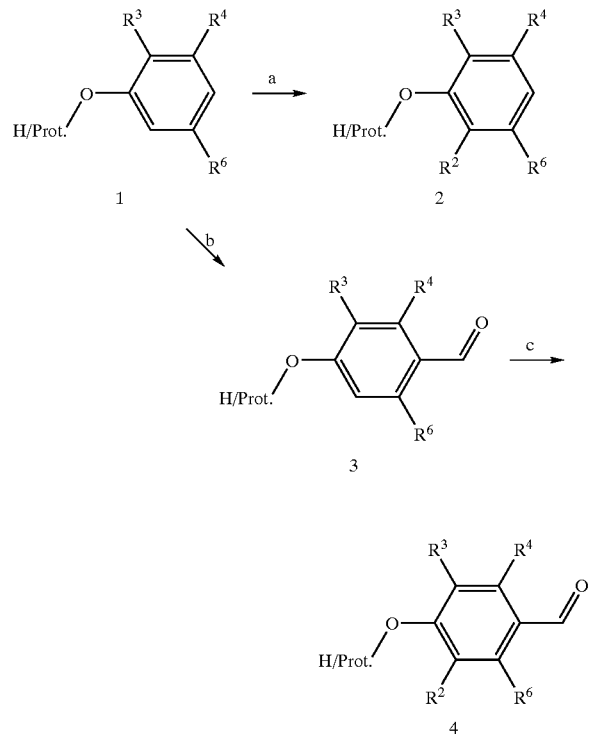

Scheme 10

Bromo-methoxy compound 1 characterized by an annelated hexahydropyran ring is known [Can. J. Chem. (1982), 60(16), 2093–8]. Cleavage of the methoxy ether function with pyridine hydrochloride at temperatures around 200° C. leads to 3-bromo-phenol 2 (step a). The isomeric building block can be obtained as follows: Carboxylic acid 3 [U.S. (1999), U.S. Pat. No. 5,856,529 A] can be brominated to give the 3-bromo derivative 4 (step b) which can be transformed into phenol 5 by a sequence analogous to that described for the transformaton of the compounds 6 into compounds 7 in scheme 7 (steps c, d, e).

Scheme 9

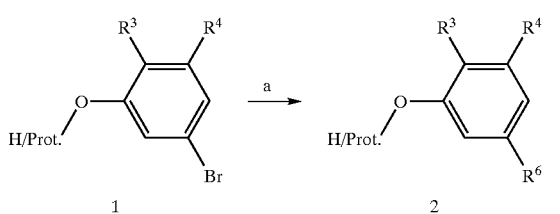

3-Bromo-phenols 1, optionally carrying a protective function, can be converted in analogous phenols 2 carrying variable substiutents $R^6$ by first transforming the bromo-compound into the corresponding aryl-lithium derivative (e.g. by using an alkyl lithium reagent in a solvent like tetrahydrofuran, preferably at a temperature around −78° C.) and then quenching the latter with a variety of electrophiles using methods well known in the art (step a). For the synthesis of phenols ($R^6$=OH), the aryl lithium compounds are reacted with trimethyl-borate at temperatures between −78° C. and the reflux temperature of tetrahydrofuran, followed by oxidation with e.g. N-methyl morpholine N-oxide, preferably at the reflux temperature of tetrahydrofuran [compare Synlett 1995(09), 931–932]. These phenols 2 with $R^6$ equal OH can then be transformed into the corresponding ether compounds by well known methods.

Phenols 1, optionally carrying a protective function, can be further functionalized into phenols 2 carrying additional substutents $R^2$ by known methods of electrophilic aromatic subsitution. In many cases, mixture of ortho/para-substitution-, and ortho/para-disubstitution-products will be formed in ratios depending on the precise reaction conditions. In such cases, the reaction conditions can be optimized in order to achieve the highest possible yield of mono-ortho product; optionally, product mixtures can also be separated into pure isomers by known methods such as silica gel chromatography (step a). 4-Formyl compounds 3 can be obtained from phenols 1, optionally carrying a protective function, by known formylation reactions such as the Vilsmeier formylation or by formylation with dichloromethyl methyl ether in the presence of titanium tetrachloride, preferably in dichloromethane at temperatures between −78° C. and the reflux temperature of the solvent (step b). 4-Formyl compounds 3 can then again be used as starting materials for known methods of electrophilic aromatic subsitution leading to compounds 4 carrying an additional $R^2$ substituent (step c).

Scheme 11

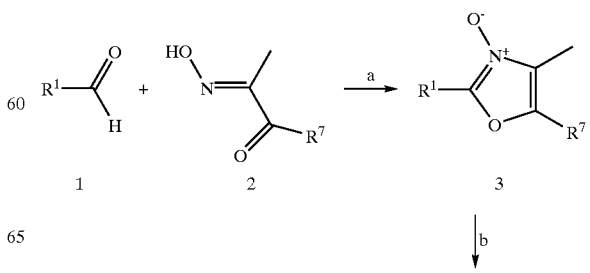

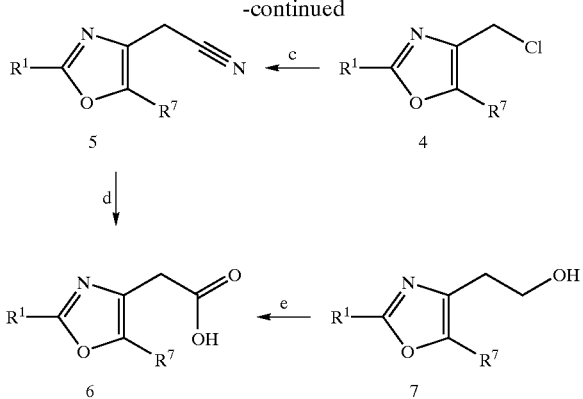

Aldehydes 1 are commercially available or known. They are condensed with diketo-monoximes 2 according to literature precedence (Diels, O.; Riley, K.; Chem Ber (1915), 48, 897) in the presence of a strong acid, typically HCl, in a polar solvent like ACOH to yield the oxazole-N-oxides 3 (step a). Subsequent treatment with $POCl_3$ in dichloromethane under reflux provides the corresponding primary chlorides 4 (Goto, Y.; Yamazaki, M.; Hamana, M.; Chem Pharm Bull (1971), 19, 2050, step b). These intermediates are either used as such, transformed according to well established methods into the corresponding alcohols or activated alcohols like mesylates or tosylates or into the bromides or iodides, or finally further elaborated via $S_N2$-reaction with NaCN to give, via nitrils 5 (step c), exhaustive hydrolysis (step d) and reduction (step e), e.g. with borane in tetrahydrofuran, the building blocks 7.

4-Chloromethyl-2-aryl or 2-heteroaryl-oxazoles 4 with $R^7$ equal hydrogen are preferably prepared from the corresponding aryl or heteroaryl carboxamides and 1,3-dichloroacetone as described e.g. in Bioorg. Med. Chem. Lett. (2000), 10(17), 2041–2044.

Scheme 12

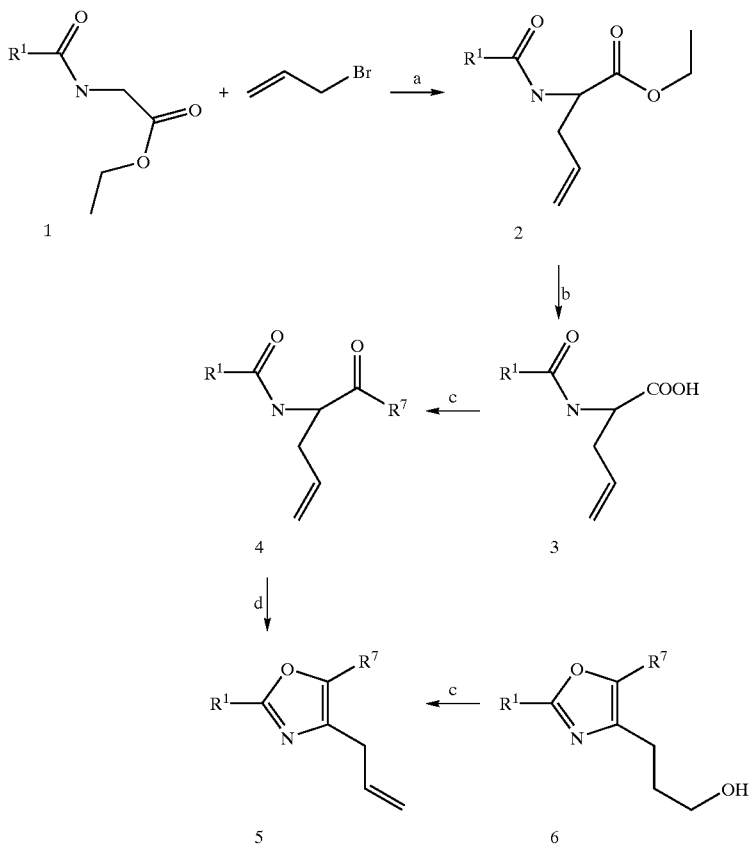

N-Acyl-glycine esters 1 are either commercially available, known, or can be prepared by standard operations of N-acylation. Mono-allylated esters 2 can easily be obtained by double deprotonation of 1 with a strong, non-nucleophilic base like LiHMDS in an aprotic solvent like THF, typically at –78° C., followed by treatment with allyl bromide to produce selectively the C-alkylated products 2 (step a). Standard hydrolysis generates intermediate acids 3 (step b), which are then transformed, following well established literature precedence (J. Med. Chem. (1996), 39, 3897), into compounds 4 (step c). Ring-closure to the oxazole using trifluoro-acetic acid and trifluoro-acetic anhydride as reagents generates key intermediates 5 (step d), which, finally, are elaborated via hydroboration to the target alcohols 6, e.g. with 9-BBN in THF and ensuing oxidative work-up with $H_2O_2$ and NaOH (step e).

The following tests were carried out in order to determine the activity of the compounds of formula I.

Background information on the performed assays can be found in: Nichols JS et al. "Development of a scintillation proximity assay for peroxisome proliferator-activated receptor gamma ligand binding domain", (1998) Anal. Biochem. 257:112–119.

Full-length cDNA clones for human PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARγ (aa 174 to 476) and PPARα (aa 167 to 469). To accomplish this, the portions of the cloned sequences encoding the LBDs were amplified from the full-length clones by PCR and then subcloned into the plasmid vectors pGEX4T-2(Pharmacia) and pFA-CMV(Stratagene). Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARα receptor binding was assayed in TKE10 (10 mM Tris-HCl, pH 8, 50 mM KCl, 2 mM EDTA, 0.1 mg/ml fatty acid free BSA and 10 mM DTT). For each 96 well 2.4 ug equivalent of GST-PPARα-LBD fusion protein and radioligand, e.g. 40000 dpm 2(S)-(2-benzoyl-phenylamino)-3-{4-[1,1-ditritio-2-(5-methyl-2-phenyl-oxazol-4-yl)-ethoxy]-phenyl}-propionic acid, were incubated in 100 ul volume at RT for 2 hrs. Bound ligand was removed from unbound ligand by solid phase separation using MultiScreen plates (Millipore) filled with 80 ul of SG25 according to the manufacturer's recommendations.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 ug SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the recptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6 well plates at a density of $10^5$ Cells/well and then batch-transfected with either the pFA-PPARγ-LBD or pFA-PPARα-LBD expression plasmids plus the pFR-luc reporter plasmid (Stratagene) and an expression plasmid encoding the secretable form of alkaline phosphatase (SEAP) as a normalization control. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final. 0.1% DMSO). Following incubation of the cells for 24 hours with substances, 50 ul of the supernatant was recovered and analyzed for SEAP activity (Roche Molecular Biochemicals). The remainder of the supernatant was discarded, 50 ul PBS was added per well followed by one volume of Luciferase Constant-Light Reagent (Roche Molecular Biochemicals) to lyse the cells and initiate the luciferase reaction. Luminescence for both SEAP and luciferase was measured in a Packard TopCount. Luciferase activity was normalized to the SEAP control and transcriptional activation in the presence of a test substance was expressed as fold-activation over cells incubated in the absence of the substance. EC50 values were calculated using the XLfit program (ID Business Solutions Ltd. UK).

The compounds of the present invention exhibit $IC_{50}$ values of 0.1 nM to 50 μM, preferably 1 nM to 10 μM, paricularly 1–3500 nM, more preferred 1–500 nM, for PPARα and PPARγ. The compounds further exhibit $EC_{50}$ values of 0.1 nM to 50 μM, preferably 1 nM to 10 μM, more preferably 1–3500 nM, particularly 1–500 nM, for PPARα and PPARγ.

|  | PPARα $IC_{50}$ | PPARγ $IC_{50}$ | PPARα $EC_{50}$ | PPARγ $EC_{50}$ |
|---|---|---|---|---|
| Example 1 | 117 nmol/l | 46 nmol/l | 27 nmol/l | 94 nmol/l |
| Example 2 | 21.7 nmol/l | 6.6 nmol/l | 13 nmol/l | 21 nmol/l |
| Example 7 | 114 nmol/l | 113 nmol/l | 17 nmol/l | 68 nmol/l |
| Example 11 | 38.2 nmol/l | 18.8 nmol/l | 50 nmol/l | 21 nmol/l |
| Example 48 | n.d | 3170 nmol/l | 8 nmol/l | 464 nmol/l |
| Example 83 | 109 nmol/l | 25 nmol/l | 746 nmol/l | 188 nmol/l |
| Example 106 | 259 nmol/l | 112 nmol/l | 138 nmol/l | 501 nmol/l |
| Rosiglitazone | inactive | 465 nmol/l | inactive | 25 nmol/l |

The compounds of formula I and their pharmaceutically acceptable salts and esters can be used as medicaments, e.g.

in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.5–500 mg, preferably 0.5–100 mg, of a compound of formula I.

The following Examples serve to illustrate the present invention in more detail. They are, however, not intended to limit its scope in any manner.

EXAMPLES

Abbreviations nBu$_2$BOTf=dibutylboron triflate, br.=broad, DBAD=di-tert-butyl azodicarboxylate, DBU=1,8-diazabicyclo[5.4.0]undec-7-ene, DEAD=diethyl azodicarboxylate, DIAD=diisopropyl azodicarboxylate, DMPU=1,3-dimethyl-3,4,5,6-tetrahydro-2(1H)-pyrimidinone, eq.=equivalents, HPLC=high performance liquid chromatography, LDA=lithium diisopropylamide, POCl$_3$ =phosphorous oxychloride, quint.=quintett, RT=room temperature, sept.=septett, sext.=sextett, THF=tetrahydrofuran.

Example 1 a] 2-Methoxy-3-{4-[2-(5-methyl-2-phenyl-oxazol-4-yl)-ethoxy]-benzo[b]thiophen-7-yl}-propionic acid ethyl ester LDA was prepared by adding via syringe 1.0 ml nBuLi (1.5 M, hexane) to a solution of 0.162 g (1.6 mmol) of diisopropylamine in 3 ml of abs. THF at −5°. After cooling to −78°, 0.177 g of methoxyacetic acid ethyl ester (1.50 mmol), dissolved in 1 ml of abs. THF, was added and the mixture kept for 15 Min. at that temperature to ensure complete deprotonation. 0.343 g of 4-[2-(7-Bromomethyl-benzo[b]thiophen-4-yloxy)-ethyl]-5-methyl-2-phenyl-oxazole (0.80 mmol), dissolved in 5 ml of abs. THF, was then added, followed by 3 ml of DMPU. After stirring for 15 Min. at dry ice temperature and 30 Min. at 0°, the reaction mixture was poured onto crashed ice, extracted twice with AcOEt, washed with water, dried over sodium sulfate, and evaporated to dryness. Flash chromatography (SiO$_2$, hexane/AcOEt=75/25) yielded, after crystallization from hexane at 0°, 0.206 g of the title compound as white solid, mp.59–61°.

MS: 465.1 (M)$^+$, 348.0, 186.0. NMR: (CDCl$_3$, 1H, δ, TMS) 1.21 (t, J=7, 3H), 2.43 (s, 3H), 3.09 (t, J=6.5, 2H), 3.15–3.3 (m, 2H), 3.33 (s, 3H), 4.15 (m, 1H), 4.17 (q, J=7, 2H), 4.40 (t, J=6.5, 1H), 6.74 (d, J=8, 1H), 7.12 (d, J=8.5, 1H), 7.32 (d, J=5.5, 1H), 7.42–7.50 (m, 4H), 8.01 (br d, J=8, 2H).

b] 2-Methoxy-3-{4-[2-(5-methyl-2-phenyl-oxazol-4-yl)-ethoxy]-benzo[b]thiophen-7-yl}-propionic acid 0.184 g of 2-Methoxy-3-{4-[2-(5-methyl-2-phenyl-oxazol-4-yl)-ethoxy]-benzo[b]thiophen-7-yl}-propionic acid ethyl ester (0.40 mmol) was dissolved in 1 ml of THF/MeOH=1/1 and treated with 0.670 ml of 3N NaOH. The reaction mixture was kept over night at RT and then quenched by pouring onto crashed ice/HCl. Twofold extraction with AcOEt, washing with water, drying over sodium sulfate, and evaporation of the solvents left a crude product, which was purified by crystallisation from AcOEt/hexane to yield 0.158 g of the title compound as white solid, mp.121–122°.

ISP MS: (MNa)$^+$460.3, (MH)$^+$438.3. IR (cm$^{-1}$): 3078, 2922, 2853, 1737, 1653, 1554, 1462, 1378, 1341, 1272, 1185, 1125, 1064, 1025, 719, 688. NMR: (DMSO-d$_6$, 1H, δ, TMS) 2.40 (s, 3H), 3.02 (t, J=6.5, 2H), 3.00–3.10 (m, 1H), 3.13 (dxd, J=5, J=14.5, 1H), 3.20 (s, 3H), 4.06 (m, 1H), 4.34 (t, J=6.5, 2H), 6.89 (d, J=8, 1H), 7.15 (d, J=8, 1H), 7.39 (d, J=5.5, 1H), 7.42–7.52 (m, 3H), 7.63 (d, J=5.5, 1H), 7.92 (br d, J=8, 2H), 12.8 (br s, 1H).

Example 2

2-Ethoxy-3-{4-[2-(5-methyl-2-phenyl-oxazol-4-yl)-ethoxy]-benzo[b]thiophen-7-yl}-propionic acid The title compound was prepared in analogy to example 1, but using in step a] ethoxyacetic acid ethyl ester instead of the methoxy-derivative, and was obtained as white crystals of mp.147–148°.

ISP MS: (M+Na)$^+$474.2, (M+H)$^+$452.4. NMR: (DMSO-d$_6$, 1H, δ, TMS) 0.99 (t, J=7, 3H), 2.39 (s, 3H), 3.02 (t, J=6.5, 2H), 3.00–3.10 (m, 1H), 3.12 (dxd, J=5, J=14.5, 1H), 3.22–3.32 (m, 1H), 3.48–3.58 (m, 1H), 4.12 (m, 1H), 4.35 (t, J=6.5, 2H), 6.90 (d, J=8, 1H), 7.15 (d, J=8, 1H), 7.39 (d, J=5, 1H), 7.45–7.53 (m, 3H), 7.63 (d, J=5.5, 1H), 7.91 (br d, J=8, 2H), 12.7 (br s, 1H).

Example 3

3-{4-[2-(5-Methyl-2-phenyl-oxazol-4-yl)-ethoxy]-benzo[b]thiophen-7-yl}-2-propoxy-propionic acid The title compound was prepared in analogy to example 1, but using in step a] propoxyacetic acid ethyl ester instead of the methoxy-derivative, and was obtained as an off-white solid of mp.106–109°.

ISP MS: $(M+K)^+$504.2, $(M+Na)^+$488.2, $(M+H)^+$466.3.

Example 4

2-Butoxy-3-{4-[2-(5-methyl-2-phenyl-oxazol-4-yl)-ethoxy]-benzo[b]thiophen-7-yl}-propionic acid The title compound was prepared in analogy to example 1, but using in step a] butoxyacetic acid ethyl ester instead of the methoxy-derivative, and was obtained as an off-white solid of mp. 123° (dec.).

MS: $(M-H)^-$478.3.

Example 5

2-Isobutoxy-3-{4-[2-(5-methyl-2-phenyl-oxazol-4-yl)-ethoxy]-benzo[b]thiophen-7-yl}-propionic acid The title compound was prepared in analogy to example 1, but using in step a] isobutoxyacetic acid ethyl ester instead of the methoxy-derivative, and was obtained as a white solid of mp.102° (dec.).

MS: $(M-H)^-$478.3. IR ($cm^{-1}$): 2924, 2853, 1737, 1653, 1555, 1461, 1384, 1342, 1271, 1174, 1121, 1066, 1030, 718, 689. NMR ($CDCl_3$, 1H, δ, TMS) 0.78, 0.79 (2×d, J=7, 2×3H), 1.75 (septett, J=7, 1H), 2.40 (s, 3H), 3.06 (t, J=6.5, 2H), 3.00–3.10 (m, 1H), 3.19 (d×d, J=8, J=14.5, 1H), 3.27 (m, 1H), 3.36 (d×d, J=4.5, J=14.5, 1H), 4.24 (m, 1H), 4.37 (t, J=6.5, 2H), 6.74 (d, J=8, 1H), 7.15 (d, J=8, 1H), 7.32 (d, J=5.5, 1H), 7.38–7.48 (m, 3H), 7.48 (d, J=5.5, 1H), 7.98 (br d, J=8, 2H), 9.5 (very br s, 1H).

Example 6

2-Hexyloxy-3-{4-[2-(5-methyl-2-phenyl-oxazol-4-yl)-ethoxy]-benzo[b]thiophen-7-yl}-propionic acid The title compound was prepared in analogy to example 1, but using in step a] hexyloxyacetic acid ethyl ester instead of the methoxy-derivative, and was obtained as a light yellow solid of mp. 79–82°.

ISP MS: $(M+K)^+$546.1, $(M+Na)^+$530.2, $(M+H)^+$508.4.

Example 7 a] 4-[2-(4-Bromomethyl-naphthalen-1-yloxy)-ethyl]-5-methyl-2-phenyl-oxazole 0.494 g of 5-Methyl-4-[2-(naphthalen-1-yloxy)-ethyl]-2-phenyl-oxazole (1.50 mmol) was dissolved under argon atmosphere in 6 ml of $CH_2Cl_2$ and cooled down to 0°. 0.455 ml of 62% aq. HBr was added, followed by 58 mg of trioxane (0.644 mmol, 1.29 eq.). After 2 h, additional 0.455 ml of 62% aq. HBr was added and stirring continued for totally 5 h under strict temperature control. The reaction mixture was then diluted with $CH_2Cl_2$, washed with sat. $NaHCO_3$-sol., the aqueous layer extracted once more with $CH_2Cl_2$, the combined organic phases dried over sodium sulfate and evaporated to dryness. This left 0.70 g of the crude title compound which was used as such for the next step. The product is quite unstable and can not be purified by column chromatography on $SiO_2$; it also decomposes readily on TLC-plates.

b] 2-Methoxy-3-{4-[2-(5-methyl-2-phenyl-oxazol-4-yl)-ethoxy]-naphthalen-1-yl}-propionic acid ethyl ester LDA was prepared by adding via syringe 1.0 ml nBuLi (1.5 M, hexane) to a solution of 0.162 g (1.6 mmol) of diisopropylamine in 3 ml of abs. THF at −5°. After cooling to −78°, 0.177 g of methoxyacetic acid ethyl ester (1.50 mmol), dissolved in 1 ml of abs. THF, was added and the mixture kept for 15 Min. at that temperature to ensure complete deprotonation. 0.38 g of crude 4-[2-(4-bromomethyl-naphthalen-1-yloxy)-ethyl]-5-methyl-2-phenyl-oxazole (<0.90 mmol, prepared as described above on a 1 mmol scale), dissolved in 6 ml of abs. THF, was then added, followed by 3 ml of DMPU. After stirring for 15 Min. at dry ice temperature and 30 Min. at 0°, the reaction mixture was poured onto crashed ice, extracted twice with AcOEt, washed with water, dried over sodium sulfate, and evaporated to dryness. Twofold flash chromatography ($SiO_2$, hexane/AcOEt=74/26, then 76/24) yielded 0.145 g of the title compound as colorless oil.

MS: 459.2 $(M)^+$, 386.1, 342.1.

c] 2-Methoxy-3-{4-[2-(5-methyl-2-phenyl-oxazol-4-yl)-ethoxy]-naphthalen-1-yl}-propionic acid 0.137 g of 2-Methoxy-3-{4-[2-(5-methyl-2-phenyl-oxazol-4-yl)-ethoxy]-naphthalen-1-yl}-propionic acid ethyl ester (0.298 mmol) was dissolved in 2 ml of THF/EtOH=1/1 and treated with 0.745 ml of 2N NaOH. The reaction mixture was kept for 24 h at ambient temperature and then quenched by pouring onto crashed ice/HCl. Twofold extraction with AcOEt, washing with water, drying over sodium sulfate, and evaporation of the solvents left a crude product, which was purified by twofold crystallisation from AcOEt/hexane to yield 0.076 g of the title compound as a white solid, mp.128–130°.

MS: $(M-H)^-$430.5. IR ($cm^{-1}$): 2924, 2854, 1733, 1650, 1585, 1553, 1460, 1381, 1343, 1270, 1249, 1165, 1112, 1094, 1026, 766, 714, 692. NMR (DMSO-$d_6$, 1H, δ, TMS) 2.42 (s, 3H), 3.08 (t, J=6, 2H), 3.17 (s, 3H), 3.19 (d×d, 1H), 3.36 (d×d, J=5, J=14.5, 1H), 3.96 (m, 1H), 4.38 (t, J=6.5, 2H), 6.94 (d, J=8, 1H), 7.26 (d, J=8, 1H), 7.45–7.55 (m, 4H), 7.57 (t, J=7, 1H), 7.92 (br d, J=8, 2H), 8.01 (d, J=8.5, 1H), 8.18 (d, J=8, 1H), 12.8 (br s, 1H).

Example 8

2-Ethoxy-3-{4-[2-(5-methyl-2-phenyl-oxazol-4-yl)-ethoxy]-naphthalen-1-yl}-propionic acid The title compound was prepared in analogy to example 7, but using in step b] ethoxyacetic acid ethyl ester instead of the methoxy-derivative, and was obtained as off-white crystals of mp.105–108°.

MS: $(M)^+$445.3.

Example 9

3-{4-[2-(5-Methyl-2-phenyl-oxazol-4-yl)-ethoxy]-naphthalen-1-yl}-2-propoxy-propionic acid The title compound was prepared in analogy to example 7, but using in step b] propoxyacetic acid ethyl ester instead of the methoxy-derivative, and was obtained as white crystals of mp.103–105°.

MS: 459.2(M)+, 415.2, 372.2, 342.1.

Example 10

2-Butoxy-3-{4-[2-(5-methyl-2-phenyl-oxazol-4-yl)-ethoxy]-naphthalen-1-yl}-propionic acid The title compound was prepared in analogy to example 7, but using in step b] butoxyacetic acid ethyl ester instead of the methoxy-derivative, and was obtained as white crystals of mp.88–90° (dec.).

MS: (M–H)⁻ 472.2.

Example 11 a] (S)-4-Benzyl-3-((2S,3R)-3-hydroxy-2-methoxy-3-{4-[2-(5-methyl-2-phenyl-oxazol-4-yl)-ethoxy]-benzo[b]thiophen-7-yl}-propionyl)-oxazolidin-2-one 0.249 g of (S)-4-Benzyl-3-methoxyacetyl-oxazolidin-2-one (1.00 mmol) was dissolved under an argon atmosphere in 2.5 ml of abs. $CH_2Cl_2$ and treated with 0.167 ml of triethylamine (1.2 eq.). After cooling to –78°, $nBu_2BOTf$ was added slowly (1.1 ml of 1M solution in $CH_2Cl_2$) and enolborinate formation allowed to proceed for 50 Min. at –78° and for 50 Min. at 0°. After recooling, a solution of 0.363 g of 4-[2-(5-methyl-2-phenyl-oxazol-4-yl)-ethoxy]-benzo[b]thiophene-7-carbaldehyde (1.0 mmol) in 3.5 ml of abs. $CH_2Cl_2$ was added via dropping funnel and the mixture kept for 30 Min. at –78° and for 60 Min. at 0°. Pouring onto crashed ice, twofold extraction with AcOEt, washing with brine and water, drying over magnesium sulfate, and evaporation of the solvents, followed by flash chromatography (silica gel, hexane/AcOEt=7/3) left finally 0.259 g of the title compound as light yellow foam. According to NMR, one of the four isomers is strongly predominating. The configuration was tentatively assigned as 2S, 3R according to *Tetrahedron Asymmetry* 1999, 1353.

b] (S)-4-Benzyl-3-((2S)-2-methoxy-3-{4-[2-(5-methyl-2-phenyl-oxazol-4-yl)-ethoxy]-benzo[b]thiophen-7-yl}-propionyl)-oxazolidin-2-one The above prepared (S)-4-benzyl-3-((2S,3R)-3-hydroxy-2-methoxy-3-{4-[2-(5-methyl-2-phenyl-oxazol-4-yl)-ethoxy]-benzo[b]thiophen-7-yl}-propionyl)-oxazolidin-2-one (0.255 g, 0.42 mmol) was dissolved in 2.2 ml of trifluoroacetic acid, treated at 0° with 0.663 ml of triethylsilane (10 eq.) and then kept for 3 h at ambient temperature, when TLC indicated the disappearance of starting material. The reaction mixture was poured onto crashed ice/AcOEt/$NaHCO_3$, the organic layer washed with water and brine (pH of aq. phase~8), dried over magnesium sulfate, and evaporated to dryness. Flash chromatography ($SiO_2$, hexane/AcOEt=7/3) delivered 0.196 g of the title compound as colorless foam.

MS: 596.4 (M)+, 564.3, 348.2. NMR: ($CDCl_3$, 1H, δ, TMS) 2.39 (s, 3H), 2.78 (dxd, J=9.5, J=13.5, 1H), 3.05 (t, J=6.5, 2H), 3.25–3.31 (m, 3H), 3.41 (s, 3H), 3.91 (t, J=8, 1H), 4.07 (m, 1H), 4.37 (t, J=6.5, 2H), 4.42 (m, 1H), 5.42 ((t, J=6.5, 1H), 6.75 (d, J=8, 1H), 7.17–7.4 (m, 7H), 7.40–7.46 (m, 4H), 7.98 (br d, J=8, 2H).

c] (S)-2-Methoxy-3-{4-[2-(5-methyl-2-phenyl-oxazol-4-yl)-ethoxy]-benzo[b]thiophen-7-yl}-propionic acid 0.195 g of the above prepared (S)-4-benzyl-3-((2S)-2-methoxy-3-{4-[2-(5-methyl-2-phenyl-oxazol-4-yl)-ethoxy]-benzo[b]thiophen-7-yl}-propionyl)-oxazolidin-2-one (0.32 mmol) was dissolved in 2.25 ml of THF and treated with 0.81 ml of 1N NaOH (2.5 eq.). The reaction mixture was kept at 0° and progress of the hydrolysis followed by TLC. After 1 h the reaction mixture was quenched by pouring onto crashed ice/HCl. Twofold extraction with AcOEt, washing with water and brine, drying over magnesium sulfate, and evaporation of the solvents left a crude product, which was purified by twofold crystallisation from AcOEt/hexane to remove the chiral auxiliary. Thereby, 0.102 g of the title compound was obtained as white solid, mp.118–120°. The enantiomeric excess was judged according to 1H-NMR in the presence of a large excess of optically pure trifluoromethyl-anthryl-ethanol to be >95%. According to chiral HPLC (Chiralpak-AD) it amounts to 99.3%.

MS: 436.3 (M–H)⁻, 404.3. NMR: ($CDCl_3$, 1H, δTMS) 2.40 (s, 3H), 3.06 (t, J=6.5, 2H), 3.20 (dxd, J=7.5, J=14.5, 1H), 3.32 (s, 3H), 3.36 (dxd, 1H), 4.20 (m, 1H), 4.36 (t, J=6.5, 2H), 6.74 (d, J=8, 1H), 7.15 (d, J=8, 1H), 7.32 (d, J=5.5, 1H), 7.40–7.45 (m, 3H), 7.48 (d, J=5.5, 1H), 7.97 (br d, J=8, 2H), COOH very br.

Example 12

(S)-2-Ethoxy-3-{4-[2-(5-methyl-2-phenyl-oxazol-4-yl)-ethoxy]-benzo[b]thiophen-7-yl}-propionic acid The title compound was prepared in analogy to example 11, but using in step a] (S)-4-benzyl-3-ethoxyacetyl-oxazolidin-2-one instead of the methoxy-derivative, and was obtained as white crystals of mp.133–134°(dec.). According to chiral HPLC of the corresponding methyl ester (Chiracel-ODH) the enantiomeric excess amounts to >99%. The compound is chemically contaminated with small amounts of the chiral auxiliary.

MS: (M–H)⁻ 450.3. NMR: ($CDCl_3$, 1H, δ, TMS) 1.09 (t, J=7, 3H), 2.40 (s, 3H), 3.07 (t, J=6.5, 2H), 3.18 (dxd, J=4.5, J=14.5, 1H), 3.33–3.39 (m, 2H), 3.52 (m, 1H), 4.27 (m, 1H), 4.37 (t, J=6.5, 2H), 6.74 (d, J=8, 1H), 7.15 (d, J=7.5, 1H), 7.32 (d, J=5.5, 1H), 7.41–7.48 (m, 3H), 7.48 (d, J=5.5, 1H), 7.98 (br d, J=8, 2H), COOH very br.

Example 13

(S)-2-Methoxy-3-{4-[2-(5-methyl-2-phenyl-oxazol-4-yl)-ethoxy]-naphthalen-1-yl}-propionic acid The title compound was prepared in analogy to example 11, but using in step a] 4-[2-(5-methyl-2-phenyl-oxazol-4-yl)-ethoxy]-naphthalene-1-carbaldehyde instead of 4-[2-(5-methyl-2-phenyl-oxazol-4-yl) -ethoxy]-benzo[b]thiophene-7-carbaldehyde, and was obtained as white crystals of mp.132–133°. The enantiomeric excess was judged according to 1H-NMR in the presence of a large excess of optically pure trifluoromethyl-anthryl-ethanol to be >95%. According to chiral HPLC (Chiralpak-AD) it amounts to 99.4%. The compound is chemically contaminated with small amounts of the chiral auxiliary.

MS: (M–H)⁻ 430.4. IR ($cm^{-1}$): 2926, 2854, 1773, 1650, 1585, 1552, 1461, 1381, 1343, 1270, 1249, 1164, 1110, 1095, 1026, 766, 714, 693. NMR: ($CDCl_3$, 1H, δ, TMS) 2.42 (s, 3H), 3.12 (t, J=6, 2H), 3.24 (s, 3H), 3.26 (dxd, 1H), 3.62 (dxd, J=4, J=14.5, 1H), 4.11 (m, 1H), 4.41 (t, J=6.5, 2H), 6.78 (d, J=7.5, 1H), 7.28 (d, J=8, 1H), 7.40–7.50 (m, 4H), 7.55 (t, J=7, 1H), 7.92 (br d, J=7, 2H), 8.00 (d, J=8.5, 1H), 8.30 (d, J=8, 1H).

Example 14

(S)-2-Ethoxy-3-{4-[2-(5-methyl-2-phenyl-oxazol-4-yl)-ethoxy]-naphthalen-1-yl}-propionic acid The title compound was prepared in analogy to example 13, but using in step a] (S)-4-benzyl-3-ethoxyacetyloxazolidin-2-one instead of the methoxy-derivative, and was obtained as white crystals of mp.133–134° (dec.). According to chiral HPLC (Chiralpak-AD) the enantiomeric excess amounts to >99%. The compound is chemically contaminated with small amounts of the chiral auxiliary.

MS: 445.4 (M)$^+$, 401.3, 372.2, 342.3.

Example 15 a] 2-(Benzhydrylidene-amino)-3-{4-[2-(5-methyl-2-phenyl-oxazol-4-yl)-ethoxy]-naphthalen-1-yl}-propionic acid ethyl ester LDA was prepared by adding via syringe 2.0 ml nBuLi (1.5 M, hexane) to a solution of 0.324 g (3.2 mmol) of diisopropylamine in 6 ml of abs. THF at −10°. After cooling to −78°, 0.802 g of N-(diphenylmethylene)glycine ethyl ester (3.0 mmol), dissolved in 2 ml of abs. THF, was added dropwise and the mixture kept for 15 Min. at that temperature to ensure complete deprotonation. 0.81 g of crude 4-[2-(4-bromomethyl-naphthalen-1-yloxy)-ethyl]-5-methyl-2-phenyl-oxazole (<0.20 mmol, prepared as described above [example 7a] on a 2.06 mmol scale), dissolved in 12 ml of abs. THF, was then added, followed by 5 ml of DMPU. After stirring for 30 Min. at dry ice temperature and 90 Min. at 0°, the homogeneous reaction mixture was poured onto crashed ice/NH$_4$Cl, extracted twice with AcOEt, washed with NH$_4$Cl to pH 7, dried over sodium sulfate, and evaporated to dryness. Flash chromatography (SiO$_2$, hexane/AcOEt=8/2) yielded 0.829 g of the title compound as colorless, sticky oil.

MS: (M)$^+$608.3.

b] 2-Amino-3-{4-[2-(5-methyl-2-phenyl-oxazol-4-yl)-ethoxy]-naphthalen-1-yl}-propionic acid ethyl ester The above prepared 2-(benzhydrylidene-amino)-3-{4-[2-(5-methyl-2-phenyl-oxazol-4-yl)-ethoxy]-naphthalen-1-yl}-propionic acid ethyl ester was dissolved in 20 ml of THF and treated at 0° with 5 ml of 2N HCl. The cleavage of the protecting group was monitored by TLC. After 5 h the reaction mixture was poured onto crushed ice/NaHCO$_3$ and extracted twice with AcOEt, washed with water, dried over sodium sulfate, and the solvents were removed i.V. Flash chromatography (SiO$_2$, AcOEt) produced 0.505 g of the title compound as colorless oil.

ISP MS: (M+Na)$^+$467.3, (M+H)$^+$445.4. NMR: (CDCl$_3$, 1H, δ, TMS) 1.22 (t, J=7, 3H), 1.49 (br s, 2H), 2.43 (s, 3H), 3.05 (dxd, J=8.5, J=14, 1H), 3.13 (t, J=6.5, 2H), 3.58 (dxd, J=5, J=14, 1H), 3.83 (dxd, J=5, J=8.5, 1H), 4.14 (q, J=7, 2H), 4.42 (t, J=6.5, 2H), 6.79 (d, J=7.5, 1H), 7.23 (d, J=7.5, 1H), 7.40–7.50 (m, 4H), 7.54 (br t, J=7, 1H), 7.96–8.02 (m, 3H), 8.30 (d, J=8.5, 1H).

c] 2-(2-Benzoyl-phenylamino)-3-{4-[2-(5-methyl-2-phenyl-oxazol-4-yl)-ethoxy]-naphthalen-1-yl}-propionic acid ethyl ester 0.345 g of 2-Amino-3-{4-[2-(5-methyl-2-phenyl-oxazol-4-yl)-ethoxy]-naphthalen-1-yl}-propionic acid ethyl ester was dissolved in 6 ml of anisole and treated successively with 0.181 g (1.15 eq.) of 2-benzoyl-cyclohexanone and 60 mg of Pd/C (10%) and heated under Ar to 180–185° C. After 80 Min., additional 60 mg of fresh catalyst was added and heating continued for another 3.5 h. Cooling to RT, pouring onto crashed ice, twofold extraction with AcOEt, washing with water, drying over sodium sulfate, and purification by flash chromatography (SiO$_2$, hexane/AcOEt 7/3) produced 0.075 g of the title compound in the less polar fractions and 0.285 g of intermediate enamine, which was processed once again as just described. Final purification left a combined crop of 0.221 g of 2-(2-benzoyl-phenylamino)-3-{4-[2-(5-methyl-2-phenyl-oxazol-4-yl)-ethoxy]-naphthalen-1-yl}-propionic acid ethyl ester as yellow, sticky oil.

ISP MS: (M+Na)$^+$647.2, (M+H)$^+$625.1. NMR: (CDCl$_3$, 1H, δ, TMS) 1.13 (t, J=7, 3H), 2.41 (s, 3H), 3.10 (t, J=6.5, 2H), 3.44 (dxd, J=8.5, J=14, 1H), 3.71 (dxd, J=5.5, J=14, 1H), 4.13 (q, J=7, 2H), 4.38 (t, J=6.5, 2H), 4.52 (q, J=7, 1H), 6.52 (m, 2H), 6.76 (d, J=8, 1H), 7.23 (t, J=7.5, 1H), 7.35–7.6 (m, 12H), 7.97 (br d, J=7.5, 2H), 8.04 (d, J=8.5, 1H), 8.28 (d, J=8.5, 1H), 8.96 (d, J=7, 1H).

d] 2-(2-Benzoyl-phenylamino)-3-{4-[2-(5-methyl-2-phenyl-oxazol-4-yl)-ethoxy]-naphthalen-1-yl}-propionic acid 0.213 g (0.341 mmol) of 2-(2-Benzoyl-phenylamino)-3-{4-[2-(5-methyl-2-phenyl-oxazol-4-yl)-ethoxy]-naphthalen-1-yl}-propionic acid ethyl ester was dissolved in 1.6 ml of THF/EtOH=1/1 and treated with 0.568 ml of 3N NaOH(5 eq). The reaction flask was stirred for 20 h at ambient temperature. The mixture was then poured onto crashed ice/NH$_4$Cl, extracted twice with AcOEt, washed with brine, dried over sodium sulfate, and evaporated to dryness. Twofold crystallization from hexane/AcOEt yielded 0.199 g of the title product as yellow crystals of mp. 125° (dec.).

ISP MS: (M+K)$^+$635.1, (M+Na)$^+$619.1, (M+H)$^+$597.1. IR (cm$^{-1}$): 3318, 2925, 2854, 1734, 1622, 1585, 1514, 1460, 1379, 1336, 1249, 1157, 1090, 1047, 1025, 938, 701, 643. NMR: (DMSO-d$_6$, 1H, δ, TMS) 2.40 (s, 3H), 3.03 (t, J=6, 2H), 3.41 (dxd, 1H), 3.70 (dxd, 1H), 4.29 (m, 1H), 4.31 (t, J=6, 2H), 6.37 (t, J=7.5, 1H), 6.46 (d, J=8.5, 1H), 6.85 (d, J=8, 1H), 7.13 (t, J=7.5, 1H), 7.20 (d, J=7.5, 1H), 7.31 (d, J=8, 1H), 7.40–7.60 (m, 10H), 7.91 (br d, J=8, 2H), 8.12 (t, J=7.5, 2H), 8.87 (d, J=7, 1H), 14 (very br s, 1H).

Example 16

2-(2-Benzoyl-phenylamino)-3-{4-[2-(5-methyl-2-phenyl-oxazol-4-yl)-ethoxy]-benzo[b]thiophen-7-yl}-propionic acid The title compound was prepared in analogy to example 15, but using in step a] 4-[2-(7-bromomethyl-benzo[b]thiophen-4-yloxy)-ethyl]-5-methyl-2-phenyl-oxazole instead of 4-[2-(4-bromomethyl-naphthalen-1-yloxy)-ethyl]-5-methyl-2-phenyl-oxazole, and was obtained as yellow solid of mp. 124–127°.

ISP MS: (M+K)$^+$641.1, (M+Na)$^+$625.1, (M+H)$^+$603.0. IR (cm$^{-1}$): 3303, 2925, 2854, 1732, 1624, 1574, 1516, 1460, 1379, 1346, 1258, 1179, 1095, 1047, 1027,937, 701, 643. NMR: (DMSO-d$_6$, 1H, δ, TMS) 2.35 (s, 3H), 2.98 (t, J=6.5, 2H), 3.24 (dxd, J=7.5, J=14.5, 1H), 3.37 (dxd, J=4.5, J=14.5, 1H), 4.30 (t, J=6.5, 2H), 4.63 (m, 1H), 6.54 (t, J=7.5, 1H), 6.76 (d, J=8.5, 1H), 6.84 (d, J=8, 1H), 7.20 (d, J=8, 1H), 7.29 (d, J=8, 1H), 7.30–7.40 (m, 2H), 7.45–7.60 (m, 9H), 7.90 (br d, J=6, 2H), 8.73 (d, J=7.5, 1H), 13.5 (very br s, 1H).

Example 17 a] 4-[2-(2,6-Dimethyl-phenoxy)-ethyl]-5-methyl-2-phenyl-oxazole 1.1 g of 2,6-Dimethylphenol, 2.01 g of 2-(5-methyl-2-phenyl-oxazole-4yl)-ethanol 2.6 g of triphenylphosphin were dissolved in 30 ml THF and treated at 0° with 1.6 ml DEAD (Diethyl azodicarboxylate). The reaction mixture was kept overnight at RT. Water was added. Twofold extraction with AcOEt, washing with brine, drying over sodium sulfate, and evaporation of the solvents provided a crude product, which was purified by chromatography (SiO$_2$; ether/cyclohexane) to yield 0.89 g of the title compound as a slightly yellow oil.

MS: (M)$^+$307.2. NMR (DMSO-d$_6$, 1H, δ, TMS): 2.14 (s, 6H), 2.39 (s, 3H), 2.93 (t, J=7, 2H), 3.99 (t, J=7, 2H), 6.87–7.02 (m, 3H), 7.45–7.55 (m, 3H), 7.90–7.97 (m, 2H).

b] 4-[2-(4-Bromomethyl-2,6-dimethyl-phenoxy)-ethyl]-5-methyl-2-phenyl-oxazole

A solution of 0.86 g of 4-[2-(2,6-dimethyl-phenoxy)-ethyl]-5-methyl-2-phenyl-oxazole and 0.19 g paraformaldehyde in HBr in acetic acid (33%) was allowed to stand 3 days at RT. The mixture was poured onto crashed ice and extracted with methylene chloride. The combined organic layers were extracted with a saturated sodium bicarbonate solution, washed with brine, dried over magnesium sulfate, and evaporated. The obtained crude product was purified by chromatography (SiO$_2$; ether/cyclohexane) and crystallisation from hexane to yield 0.50 g of the title compound as a white solid.

MS: (M)$^+$399.1. NMR (CDCl$_3$, 1H, δ, TMS): 2.20 (s, 6H), 2.39 (s, 3H), 2.98 (t, J=6.5, 2H), 4.04 (t, J=6.6, 2H), 4.41 (s, 2H), 7.02 (s, 2H), 7.41–7.44 (m, 3H), 7.97–8.01 (m, 2H).

c] 3-{3,5-Dimethyl-4-[2-(5-methyl-2-phenyl-oxazol-4-yl)-ethoxy]-phenyl}-2-ethoxy-propionic acid The title compound was prepared in analogy to example 2, but using 4-[2-(4-bromomethyl-2,6-dimethyl-phenoxy)-ethyl]-5-methyl-2-phenyl-oxazole instead of 4-[2-(7-bromomethyl-benzo[b]thiophen-4-yloxy)-ethyl]-5-methyl-2-phenyl-oxazole as starting material, and was obtained as slightly yellow oil.

ISP MS: (M+K)$^+$462.2, (M+Na)$^+$446.3, (M+H)$^+$424.4. NMR (CDCl$_3$, 1H, δ, TMS): 1.16 (t, J=6.9, 3H), 2.18 (s, 6H), 2.39 (s, 3H), 2.85 (dxd, J=14.1 7.8, 1H), 2.95–3.03 (m, 3H), 3.39–3.50 (m, 1H), 3.52–3.60 (m, 1H), 3.99–4.04 (m, 3H), 6.85 (s, 2H), 7.40–7.45 (m, 3H), 7.96–8.00 (m, 2H).

Example 18

2-Ethoxy-3-{3-methyl-4-[2-(5-methyl-2-phenyl-oxazol-4-yl)-ethoxy]-phenyl}-propionic acid The title compound was prepared in analogy to example 17, but using o-cresol instead of 2,6-dimethylphenol as starting material, and was obtained as a white solid.

ISN MS: (M–H)$^-$408.4. NMR (DMSO-d$_6$, 1H, δ, TMS): 1.03 (t, J=7.0, 3H), 2.06 (s, 3H), 2.35 (s, 3H), 2.74 (dxd, J=12 8, 1H), 2.83 (dxd, J=12 8, 1H), 2.92 (t, J=7, 2H), 3.22–3.39 (m, 1H), 3.41–3.56 (m, 1H), 3.87–3.95 (m, 1H), 4.17 (t, J=7, 2H), 6.84 (d, J=8, 1H), 6.97 (s, 1H), 6.98 (d, J=7, 1H), 7.45–7.55 (m, 3H), 7.87–7.96 (m, 2H).

Example 19

2-(2-Benzoyl-phenylamino)-3-{3,5-dimethyl-4-[2-(5-methyl-2-phenyl-oxazol-4-yl)-ethoxy]-phenyl}-propionic acid The title compound was prepared in analogy to example 15, but using 4-[2-(4-bromomethyl-2,6-dimethyl-phenoxy)-ethyl]-5-methyl-2-phenyl-oxazole (example 17 b) instead of 4-[2-(7-bromomethyl-benzo[b]thiophen-4-yloxy)-ethyl]-5-methyl-2-phenyl-oxazole as starting material, yielding slightly yellow crystals.

ISN MS: (M–H)$^-$573.2. NMR (DMSO-d$_6$, 1H, δ, TMS): 2.02 (s, 6H), 2.35 (s, 3H), 2.88 (t, J=6.3, 2H), 2.94 (dxd, J=13.8 6.6, 1H), 3.07 (dxd, J=13.8 5.1, 1H), 3.91 (t, J=6.3, 2H), 4.52 (dxd, J=7.2 7.2, 1H), 6.60 (t, J=7.2, 1H), 6.81 (s, 2H), 6.83 (d, J=9, 1H), 7.34–7.58 (m, 10H), 7.89–7.92 (m, 2H), 8.64 (d, J=7.8, 1H), 13 (very br s, 1H).

Example 20

2-(2-Benzoyl-phenylamino)-3-{3-methyl-4-[2-(5-methyl-2-phenyl-oxazol-4-yl)-ethoxy]-phenyl}propionic acid The title compound was prepared in analogy to example 15, but using 4-[2-(4-bromomethyl-2-methyl-phenoxy)-ethyl]-5-methyl-2-phenyl-oxazole (prepared in analogy to the synthesis of 4-[2-(4-bromomethyl-2,6-dimethyl-phenoxy)-ethyl]-5-methyl-2-phenyl-oxazole (example 17)) instead of 4-[2-(7-bromomethyl-benzo[b]thiophen-4-yloxy)-ethyl]-5-methyl-2-phenyl-oxazole as starting material, yielding slightly yellow crystals.

ISP MS: (M+K)$^+$599.1, (M+Na)$^+$583.1, (M+H)$^+$561.3. NMR (CDCl$_3$, 1H, δ, TMS): 2.11 (s, 3H), 2.34 (s, 3H), 2.96 (t, J=6.3, 2H), 3.11 (dxd, J=13.8 6.9, 1H), 3.22 (dxd, J=13.8 6.0, 1H), 4.13 (t, J=6.3, 2H), 4.36 (dxd, J=6 6, 1H), 6.61 (t, J=8, 1H), 6.71 (t, J=7.5, 2H), 7.06 (s, 1H), 7.07 (d, J=8.7, 1H), 7.34–7.60 (m, 10H), 7.93–7.96 (m, 2H), 8.82 (br d, J=6, 1H).

Example 21 a] 4,5-Dimethyl-2-(4-trifluoromethyl-phenyl)-oxazole 3-oxide 17.4 g of 4-trifluoromethyl-benzaldehyde (100 mmol) was dissolved in 50 ml of AcOH and treated with 1 eq. of diacetyl monooxime (10.1 g). The reaction flask was cooled down to 0° C. and a stream of dry HCl was bubbled for 30 min. through the solution (slightly exothermic). After additional ¼ h, 150 ml of EtOEt was added and the precipitate isolated by filtration. Thereby, one obtained 18. 6 g of the title molecule as white crystals of mp. 179–81°.

EI MS: (M)$^+$257.1, (M–OH)$^+$240.

b] 4-Chloromethyl-5-methyl-2-(4-trifluoromethyl-phenyl)-oxazole 18.5 g of the above prepared 4,5-dimethyl-2-(4-trifluoromethyl-phenyl)-oxazole 3-oxide (72 mmol) was dissolved in 250 ml of CH$_2$Cl$_2$ and treated with 7.909 ml of POCl$_3$ (86.4 mmol). The reaction mixture was refluxed over night and then quenched by carefully pouring onto crashed ice/3N NaOH. Separation of the layers, additional extraction of the aqueous phase with CH$_2$Cl$_2$ and drying of the combined organic layers over magnesium sulfate left, after evaporation of the solvents, 19.78 g of crude product as light brown crystals, which was used as such for the next step.

ISP MS: (M+H)$^+$276.2.

c] [5-Methyl-2-(4-trifluoromethyl-phenyl)-oxazol-4-yl]-acetonitrile

To 5.39 g of NaCN (110 mol), dissolved in 72 ml of DMSO, was added via dropping funnel a solution of 19.57 g of the above prepared 4-chloromethyl-5-methyl-2-(4-trifluoromethyl-phenyl)-oxazole in 144 ml of DMSO (slightly exothermic). The reaction mixture was then kept for 1 h at 35° C. and 40° C. for 1 night. The reaction mixture was then poured onto crashed ice/AcOEt, the organic layer washed with water and brine, dried over magnesium sulfate, and evaporated to dryness. Flash chromatography (SiO$_2$, hexane/AcOEt=8/2) delivered 8.81 g of the title compound as light yellow crystals of mp. 85–86°.

EI MS: (M)$^+$266.1.

d] [5-Methyl-2-(4-trifluoromethyl-phenyl)-oxazol-4-yl]-acetic acid 8.69 g of the above prepared [5-methyl-2-(4-trifluoromethyl-phenyl)-oxazol-4-yl]-acetonitrile (32.6 mmol) was dissolved in 100 ml EtOH/water=1/1 and treated with 10 eq. of NaOH-pellets (13 g). Hydrolysis was allowed to proceed over night at 85° C. Pouring onto crashed ice/HCl, twofold extraction with AcOEt, washing with water, drying over magnesium sulfate, evaporation of the solvents, followed by recrystallization from AcOEt/hexane, yielded 7.35 g of the title acid as off-white crystals.

EI MS: (M)$^+$285.1.

e] 2-[5-Methyl-2-(4-trifluoromethyl-phenyl)-oxazol-4-yl]-ethanol 7.33 g of the above prepared [5-methyl-2-(4-trifluoromethyl-phenyl)-oxazol-4-yl]-acetic acid (25.7 mmol) was dissolved in 120 ml of abs. THF and treated at 0° C. with 64 ml 1M BH$_3$THF (2.5 eq.). The reaction mixture was then kept over night et ambient temperature. Careful quenching with MeOH and ice, twofold extraction with AcOEt, washing with water and brine, drying over magnesium sulfate, and evaporation of the solvents left a crude product which was refluxed for 30 min. in MeOH to liberate quantitatively the free alcohol. Flash chromatography (SiO$_2$, hexane/AcOEt=7/3) delivered finally 6.38 g of the title compound as off-white crystals.

f] 4-{2-[5-Methyl-2-(4-trifluoromethyl-phenyl)-oxazol-4-yl]-ethoxy}-naphthalene-1-carbaldehyde 2.00 g of 2-[5-Methyl-2-(4-trifluoromethyl-phenyl)-oxazol-4-yl]-ethanol (7.37 mmol) was dissolved in 37 ml of toluene and treated successively at 0° C. with 1.27 g of 4-hydroxy-naphthalene-1-carbaldehyde (7.37 mmol), 1.93 g of triphenylphosphine (7.37 mmol), and 1.49 g (7.37 mmol) of DIAD. The cooling bath was then removed and stirring continued for 2 h. The reaction mixture was then evaporated to dryness in vacuo. Flash chromatography (SiO$_2$, hexane/AcOEt=75/25), followed by boiling up in ether, delivered 1.28 g of the title compound as off-white crystals.

g] (S)-4-Benzyl-3-[(2S,3R)-3-hydroxy-2-methoxy-3-(4-{2-[5-methyl-2-(4-trifluoromethyl-phenyl)-oxazol-4-yl]-ethoxy}-naphthalen-1-yl)-propionyl]-oxazolidin-2-one 0.374 g of (S)-4-benzyl-3-methoxyacetyl-oxazolidin-2-one (1.50 mmol) was dissolved under an argon atmosphere in 16 ml of abs. CH$_2$Cl$_2$ and treated with 0.251 ml of triethylamine (1.2 eq.). After cooling to −78°, nBu$_2$BOTf was added slowly (1.65 ml of 1M solution in CH$_2$Cl$_2$) and enolborinate formation allowed to proceed for 15 min. at −78° and for 50 min. at 0°. After recooling, a solution of 0.638 g of 4-{2-[5-methyl-2-(4-trifluoromethyl-phenyl)-oxazol-4-yl]-ethoxy}1-naphthalene-1-carbaldehyde (1.5 mmol) in 12 ml of abs. CH$_2$Cl$_2$ was added via dropping funnel and the mixture kept for 30 min. at −78° and for 60 min. at 0°. Pouring onto crashed ice, twofold extraction with AcOEt, washing with brine and water, drying over magnesium sulfate, and evaporation of the solvents, followed by flash chromatography (silica gel, hexane/AcOEt=1/1) left finally 0.840 g of the title compound as white foam.

ISP MS: (M+H)$^+$675.1, (M+Na)$^+$697.

h] (S)-4-Benzyl-3-[(S)-2-methoxy-3-(4-{2-[5-methyl-2-(4-trifluoromethyl-phenyl)-oxazol-4-yl]-ethoxy}-naphthalen-1-yl)-propionyl]-oxazolidin-2-one 0.837 g of the above prepared (S)-4-benzyl-3-[(2S,3R)-3-hydroxy-2-methoxy-3-(4-{2-[5-methyl-2-(4-trifluoromethyl-phenyl)-oxazol-4-yl]-ethoxy}-naphthalen-1-yl)-propionyl]-oxazolidin-2-one (1.23 mmol) was dissolved in 3.2 ml of trifluoroacetic acid, treated at 0° with 0.977 ml of triethylsilane (5 eq.) and then kept for 16 h at ambient temperature, when TLC indicated the disappearance of starting material. The reaction mixture was then poured onto crashed ice/AcOEt/NaHCO$_3$, the organic layer washed with water and brine (pH of aq. phase~8), dried over magnesium sulfate, and evaporated to dryness. Flash chromatography (SiO$_2$, hexane/AcOEt=7/3) delivered 0.702 g of the title compound as white foam.

ISP MS: (M+H)$^+$659.1, (M+Na)$^+$681.1.

i] (S)-2-Methoxy-3-(4-{2-[5-methyl-2-(4-trifluoromethyl-phenyl)-oxazol-4-yl]-ethoxy}-naphthalen-1-yl)-propionic acid 0.698 g of the above prepared (S)-4-benzyl-3-[(S)-2-methoxy-3-(4-{2-[5-methyl-2-(4-trifluoromethyl-phenyl)-oxazol-4-yl]-ethoxy}-naphthalen-1-yl)-propionyl]-oxazolidin-2-one (1.03 mmol) was dissolved in 7.5 ml of THF and treated with 2.57 ml of 1N NaOH (2.5 eq.). The reaction mixture was kept at 0° and progress of the hydrolysis followed by TLC. After 1 h the reaction mixture was poured onto crashed ice and extracted with ether to remove the chiral auxiliary. The aqueous layer was then acidified with HCl, extracted twice with AcOEt, washed with water, dried over magnesium sulfate, and evaporated to dryness. Crystallization from AcOEt yielded finally 0.356 g of the title product as white crystals of mp. 167–68°.

ISN-MS: 498.2 (M−H)$^+$. NMR: (CDCl$_3$, 1H, δ, TMS) 2.44 (s, 3H), 3.14 (t, J=6.5, 2H), 3.25 (s, 3H), 3.28 (dxd, J=9, J=14.5, 1H), 3.61 (dxd, J=14.5, J=4, 1H), 4.11 (m, 1H), 4.41 (t, J=6.5, 2H), 6.78 (d, J=8, 1H), 7.30 (d, J=8, 1H), 7.49 (m, 1H), 7.55 (m, 1H), 7.68 (d, J=8.5, 2H), 8.02 (d, J=8.5, 1H), 8.09 (d, J=8.5, 2H), 8.28 (d, J=7, 1H), COOH very br.

Example 22

(S)-2-Ethoxy-3-(4-{2-[5-methyl-2-(4-trifluoromethyl-phenyl)-oxazol-4-yl]-ethoxy}-naphthalen-1-yl)-propionic acid was prepared in analogy to example 21, but using in step g] (S)-4-benzyl-3-ethoxyacetyl-oxazolidin-2-one instead of the methoxy-derivative as white crystals of mp. 153–55°.

ISN-MS: 512.2 (M−H)$^+$. NMR: (CDCl$_3$, 1H, δ, TMS) 1.015 (t, J=7, 3H), 2.45 (s, 3H), 3.14 (t, J=6.5, 2H), 3.2–3.3 (m, 2H), 3.44 (m, 1H), 3.63 (dxd, J=14.5, J=4, 1H), 4.17 (m, 1H), 4.42 (t, J=6.5, 2H), 6.79 (d, J=8, 1H), 7.29 (d, J=8, 1H), 7.48 (m, 1H), 7.55 (m, 1H), 7.68 (d, J=8.5, 2H), 8.03 (d, J=8.5, 1H), 8.09 (d, J=8.5, 2H), 8.28 (d, J=8.5, 1H), COOH very br.

Example 23

(S)-2-Methoxy-3-(4-{2-[5-methyl-2-(4-trifluoromethyl-phenyl)-oxazol-4-yl]-ethoxy}-benzo[b]thiophen-7-yl)-propionic acid was prepared in analogy to example 21, but using in step f] 4-hydroxy-benzo[b]thiophene-7-carbaldehyde [Ger.

Offen. (1998) DE 19711617 A1] instead of 4-hydroxy-naphthalene-1-carbaldehyde as off-white crystals of mp. 173–75°.

ISN-MS: 504.2 (M−H)⁺. NMR: (CDCl₃, 1H, δ, TMS) 2.43 (s, 3H), 3.08 (t, J=6.5, 2H), 3.21 (dxd, J=8, J=14.5, 1H), 3.33 (s, 3H), 3.38 (dxd, J=14.5, J=4.5, 1H), 4.20 (m, 1H), 4.38 (t, J=6.5, 2H), 6.74 (d, J=8, 1H), 7.15 (d, J=8.5, 1H), 7.33 (d, J=5.5, 1H), 7.47 (d, J=5.5, 1H), 7.68 (d, J=8, 2H), 8.08 (d, J=8.5, 2H), COOH very br.

Example 24

(S)-2-Ethoxy-3-(4-{2-[5-methyl-2-(4-trifluoromethyl-phenyl)-oxazol-4-yl]-ethoxy}-benzo[b]thiophen-7-yl)-propionic acid was prepared in analogy to example 22, but using in step f] 4-hydroxy-benzo[b]thiophene-7-carbaldehyde [Ger. Offen. (1998) DE 19711617 A1] instead of 4-hydroxy-naphthalene-1-carbaldehyde as white crystals of mp. 126–28°.

ISN-MS: 518.1 (M−H)⁺. NMR: (CDCl₃, 1H, δ, TMS) 1.09 (t, J=7, 3H), 2.42 (s, 3H), 3.07 (t, J=6.5 2H), 3.20 (dxd, J=8, J=14.5, 1H), 3.3–3.4 (m, 2H), 3.51 (m, 1H), 4.27 (m, 1H), 4.38 (t, J=6.5 2H), 6.74 (d, J=8, 1H), 7.15 (d, J=8, 1H), 7.33 (d, J=5, 1H), 7.48 (d, J=5, 1H), 7.68 (d, J=8.5, 2H), 8.08 (d, J=8.5, 1H), COOH very br.

Example 25

(S)-3-{4-[2-(2-Biphenyl-4-yl-5-methyl-oxazol-4-yl)-ethoxy]-naphthalen-1-yl}-2-ethoxy-propionic acid was prepared in analogy to example 22, but starting the sequence with 4-phenyl-benzaldehyde instead of 4-trifluoromethyl-benzaldehyde as a white solid of mp. 140–45°.

ISN-MS: 520.3 (M−H)⁺.

Example 26

(S)-3-{4-[2-(2-Biphenyl-4-yl-5-methyl-oxazol-4-yl)-ethoxy]-naphthalen-1-yl}-2-propoxy-propionic acid was prepared in analogy to example 25, but using in the aldol-coupling step (S)-4-benzyl-3-propoxyacetyl-oxazolidin-2-one instead of the ethoxy-analogue as a white solid of mp. 151–54°.

ISN-MS: 534.2 (M−H)⁺.

Example 27

(S)-3-{4-[2-(2-Biphenyl-4-yl-5-methyl-oxazol-4-yl)-ethoxy]-benzo[b]thiophen-7-yl}-2-propoxy-propionic acid was prepared in analogy to example 26, but using in the Mitsunobu-reaction 4-hydroxy-benzo[b]thiophene-7-carbaldehyde [Ger. Offen. (1998) DE 19711617 A1] instead of 4-hydroxy-naphthalene-1-carbaldehyde as an off-white solid of mp. 147–51°.

ISN-MS: 540.2 (M−H)⁺.

Example 28

(S)-3-{4-[2-(2-Biphenyl-4-yl-5-methyl-oxazol-4-yl)-ethoxy]-naphthalen-1-yl}-2-methoxy-propionic acid was prepared in analogy to example 26, but using in the aldol-coupling step (S)-4-benzyl-3-methoxyacetyl-oxazolidin-2-one instead of the propoxy-derivative as a white solid of mp. 156–59°.

ISP-MS: 508.4 (M+H)⁺.

Example 29

(S)-3-{4-[2-(2-Biphenyl-4-yl-5-methyl-oxazol-4-yl)-ethoxy]-naphthalen-1-yl}-2-(2,2,2-trifluoro-ethoxy)-propionic acid was prepared in analogy to example 28, but using in the aldol-coupling step (S)-4-benzyl-3-[(2,2,2-trifluoro-ethoxy)-acetyl]-oxazolidin-2-one instead of the methoxy-derivative as a white solid of mp. 199–200°.

ISN-MS: 574.0 (M−H)⁺.

Example 30

(S)-3-{4-[2-(2-Biphenyl-4-yl-5-methyl-oxazol-4-yl)-ethoxy]-benzo[b]thiophen-7-yl}-2-ethoxy-propionic acid was prepared in analogy to example 27, but using in the aldol-coupling step (S)-4-benzyl-3-ethoxyacetyl-oxazolidin-2-one instead of the propoxy-derivative as a white solid of mp. 163–164°.

ISN-MS: 526.0 (M−H)⁺.

Example 31

(S)-3-(4-{2-[2-(4-Isopropyl-phenyl)-5-methyl-oxazol-4-yl]-ethoxy}-benzo[b]thiophen-7-yl-2-methoxy-propionic acid was prepared in analogy to example 23, but using 4-isopropyl-benzaldehyde as starting material instead of 4-trifluoromethyl-benzaldehyde as light yellow crystals of mp. 95–97°.

ISN-MS: 478.2 (M−H)⁺.

Example 32

(S)-3-(4-{2-[2-(4-Isopropyl-phenyl)-5-methyl-oxazol-4-yl]-ethoxy}-benzo[b]thiophen-7-yl)-2-(2,2,2-trifluoro-ethoxy)-propionic acid was prepared in analogy to example 31, but using in the aldol-coupling step (S)-4-benzyl-3-[(2,2,2-trifluoro-ethoxy)-acetyl]-oxazolidin-2-one instead of the methoxy-derivative as white crystals of mp. 181–182°.

ISP-MS: 548.2 (M+H)⁺.

Example 33

(S)-3-(4-{2-[2-(3,5-Dimethyl-phenyl)-5-methyl-oxazol-4-yl]-ethoxy}-benzo[b]thiophen-7-yl)-2-methoxy-propionic acid was prepared in analogy to example 23, but starting the whole reaction sequence with 3,5-dimethylbenzaldehyde as white crystals of mp. 184–185°.

ISN-MS: 464.2 (M−H)⁺.

Example 34

(S)-3-(4-{2-[2-(3,5-Dimethoxy-phenyl)-5-methyl-oxazol-4-yl]-ethoxy}-benzo[b]thiophen-7-yl)-2-methoxy-propionic acid was prepared in analogy to example 23, but starting the whole reaction sequence with 3,5-dimethoxybenzaldehyde instead of 4-trifluoromethyl-benzaldehyde as white crystals of mp. 194–195°.

ISN-MS: 496.0 (M–H)⁺.

Example 35

(S)-3-(4-{2-[2-(3,5-Dimethyl-phenyl)-5-methyl-oxazol-4-yl]-ethoxy}-naphthalen-1-yl)-2-methoxy-propionic acid was prepared in analogy to example 28, but starting the whole reaction sequence with 3,5-dimethylbenzaldehyde instead of 4-phenylbenzaldehyde as white crystals of mp. 197–198°.

ISN-MS: 458.3 (M–H)⁺.

Example 36 a] 3-(4-{2-[2-(3,5-Dichloro-phenyl)-5-methyl-oxazol-4-yl]-ethoxy}-benzo[b]thiophen-7-yl)-3-hydroxy-2-methoxy-propionic acid ethyl ester LDA-solution in THF was prepared according to standard procedures from 0.171 g of diisopropylamine (1.69 mmol) and 1.02 ml of 1.5 M nBuLi (hexane) in 3 ml of abs. THF at −10°. After cooling to −78°, 0.181 g of ethyl methoxy-acetate (1.54 mmol), dissolved in 1 ml of THF, was added and stirring continued for 15 min. to complete enolate formation. 0.166 g of 4-{2-[2-(3,5-dichloro-phenyl)-5-methyl-oxazol-4-yl]-ethoxy}-benzo[b]thiophene-7-carbaldehyde (0.38 mmol), dissolved in 1.5 ml of THF, was added and the mixture kept for another 30 min. at this temperature. Pouring onto crashed ice/NH₄Cl, twofold extraction with AcOEt, washing with water and brine, drying over magnesium sulfate, and evaporation of the solvents, followed by flash chromatography (SiO₂, hexane/AcOEt=7/3) delivered 0.174 g of the title compound as syn/anti-isomers. The necessary aldehyde (4-{2-[2-(3,5-dichloro-phenyl)-5-methyl-oxazol-4-yl]-ethoxy}-benzo[b]thiophene-7-carbaldehyde) was prepared as described in example 21 a]-f], but starting the whole reaction sequence with 3,5-dichloro-benzaldehyde instead of 4-trifluoromethyl-benzaldehyde and using for the Mitsunobu reaction 4-hydroxy-benzo[b]thiophene-7-carbaldehyde [Ger. Offen. (1998) DE 19711617 A1] instead of 4-hydroxy-naphthalene-1-carbaldehyde.

ISP-MS: 550.1 (M+H)⁺.

b] [rac]-3-(4-{2-[2-(3,5-Dichloro-phenyl)-5-methyl-oxazol-4-yl]-ethoxy}-benzo[b]thiophen-7-yl)-2-methoxy-propionic acid ethyl ester 0.173 g of the above prepared 3-(4-{2-[2-(3,5-dichloro-phenyl)-5-methyl-oxazol-4-yl]-ethoxy}-benzo[b]thiophen-7-yl)-3-hydroxy-2-methoxy-propionic acid ethyl ester (0.31 mmol) was dissolved in 1.0 ml of trifluoroacetic acid, treated at 0° with 0.250 ml of triethylsilane (5 eq.) and then kept for 4 h at this temperature, when TLC indicated the disappearance of starting material. The reaction mixture was then poured onto crashed ice/AcOEt/NaHCO₃ (pH of aq. layer ~7.5), the organic layer washed with water and brine (pH of aq. phase~8), dried over magnesium sulfate, and evaporated to dryness. Flash chromatography (SiO₂, hexane/AcOEt=85/15) afforded 0.143 g of the title compound as white crystals of mp. 100–102°.

ISP-MS: 535.3 (M+H)⁺.

c] [rac]-3-(4-{2-[2-(3,5-Dichloro-phenyl)-5-methyl-oxazol-4-yl]-ethoxy}-benzo[b]thiophen-7-yl)-2-methoxy-propionic acid 0.142 g of the above prepared [rac]-3-(4-{2-[2-(3,5-dichloro-phenyl)-5-methyl-oxazol-4-yl]-ethoxy}-benzo[b]thiophen-7-yl)-2-methoxy-propionic acid ethyl ester (0.27 mmol) was dissolved in 4 ml of THF/EtOH=1/1 and treated with 0.68 ml of 1N NaOH (2.5 eq.). The reaction mixture was stirred at ambient temperature and progress of the hydrolysis followed by TLC. After 2 h, the reaction mixture was poured onto crashed ice/HCl dil. and extracted twice with AcOEt. The organic layer was washed with water and brine, dried over magnesium sulfate, and evaporated to dryness. Crystallization from AcOEt/hexane yielded finally 0.107 g of the title product as white crystals of mp. 160–61°.

ISN-MS: 504.1 (M–H)⁺. NMR: (CDCl₃, 1H, δ, TMS) 2.41 (s, 3H), 3.06 (t, J=6.5, 2H), 3.21 (d×d, J=8, J=14.5, 1H), 3.34 (s, 3H), 3.36 (m, 1H), 4.20 (m, 1H), 4.37 (t, J=6.5, 2H), 6.74 (d, J=8, 1H), 7.15 (d, J=8, 1H), 7.33 (d, J=5.5, 1H), 7.37 (s, 1H), 7.46 (d, J=5.5, 1H), 7.86 (d, J=1.5, 2H), COOH very br.

Example 37

[rac]-3-(4-{2-[2-(3,5-Difluoro-phenyl)-5-methyl-oxazol-4-yl]-ethoxy}-benzo[b]thiophen-7-yl)-2-methoxy-propionic acid was prepared in analogy to example 36, but starting the whole reaction sequence with 3,5-difluoro-benzaldehyde instead of 3,5-dichloro-benzaldehyde as white crystals of mp. 141–142°.

ISP-MS: 474.3 (M+H)⁺.

Example 38

[rac]-2-Butoxy-3-(4-{2-[2-(3,5-difluoro-phenyl)-5-methyl-oxazol-4-yl]-ethoxy}-benzo[b]thiophen-7-yl)-propionic acid was prepared in analogy to example 37, but using for the aldol-reaction as coupling partner butyl butoxy-acetate instead of ethyl methoxy-acetate as white crystals of mp. 95–96°.

ISN-MS: 514.2 (M–H)⁺.

Example 39

[rac]-2-Butoxy-3-(4-{2-[2-(3,5-dimethoxy-phenyl)-5-methyl-oxazol-4-yl]-ethoxy}-benzo[b]thiophen-7-yl)-propionic acid was prepared in analogy to example 38, but starting the whole reaction sequence with 3,5-dimethoxy-benzaldehyde instead of 3,5-difluoro-benzaldehyde as white crystals of mp. 161–162°.

ISN-MS: 538.2 (M–H)⁺.

Example 40

[rac]-2-Butoxy-3-(4-{2-[2-(3,5-dimethyl-phenyl)-5-methyl-oxazol-4-yl]-ethoxy}-benzo[b]thiophen-7-yl)-propionic acid was prepared in analogy to example 38, but starting the whole reaction sequence with 3,5-dimethyl-benzaldehyde instead of 3,5-difluoro-benzaldehyde as white crystals of mp. 174–175°.

ISN-MS: 506.2 (M–H)⁺.

Example 41

[rac]-3-(4-{2-[2-(3,5-Difluoro-phenyl)-5-methyl-oxazol-4-yl]-ethoxy}-benzo[b]thiophen-7-yl)-2-ethoxy-propionic acid was prepared in analogy to example 38, but using for the aldol-reaction as coupling partner ethyl ethoxy-acetate instead of ethyl methoxy-acetate as white crystals of mp. 148–150°.

ISN-MS: 486.2 (M−H)+.

Example 42 a] 2-(4-Methoxy-benzoylamino)-pent-4-enoic acid ethyl ester

A solution of 11.7 g of (4-methoxy-benzoylamino)-acetic acid ethyl ester (49.6 mmol) in 250 ml of abs. THF was cooled down to −78° and treated with 2.1 eq. of lithium hexamethyldisilazide (104 ml 1M[hexane]). After stirring for 30 min., 1.1 eq. of allyl bromide (4.62 ml) was added neat via syringe and the reaction mixture kept for 15 min. at −78° and for 30 min. at 0°. Pouring onto crashed ice, twofold extraction with AcOEt, twice washing with water, drying over natrium sulfate and evaporation of the solvents, followed by flash chromatography ($SiO_2$, hexane/AcOEt=85/15) afforded 10.56 g of the title compound as off-white solid of mp. 76–78°, besides of 2.74 g of dialkylated product as yellowish oil.

ISP-MS: 278.2 (M+H)+.

b] 2-(4-Methoxy-benzoylamino)-pent-4-enoic acid 10.56 g of the above prepared 2-(4-methoxy-benzoylamino)-pent-4-enoic acid ethyl ester (38.1 mmol) was dissolved in 120 ml of THF/EtOH=1/1 and treated at 0° with 38 ml of 2N NaOH. The reaction mixture was kept at this temperature for 3 h. It was then poured onto crashed ice/HCl, extracted twice with AcOEt, washed with brine, and dried over natrium sulfate. Evaporation of the solvents, followed by crystallisation from AcOEt at −20°, yielded 8.41 g of the title acid as white crystals of m.p. 121–124°.

ISN-MS: 248.1 (M−H)+.

c] N-(1-Acetyl-but-3-enyl)-4-methoxy-benzamide

To a solution of 8.41 g of the above prepared 2-(4-methoxy-benzoylamino)-pent-4-enoic acid (33.7 mmol) was added successively 21.2 ml of pyridine and 15.95 ml of $Ac_2O$ (5 eq.). The reaction mixture was then kept for 45 min. at 90°. After cooling, 15.8 ml of water was added and the mixture again kept for 30 min. at 85° to ensure complete hydrolysis. Afterwards, it was poured onto crashed ice/HCl, extracted twice with AcOEt, washed with 2N HCl and water, and dried over natrium sulfate. Evaporation of the solvents, followed by flash chromatography ($SiO_2$, hexane/AcOEt=7/3) afforded 6.45 g of the title compound as yellow solid of mp. 58–59°.

ISP-MS: 248.3 (M+H)+.

d] 4-Allyl-2-(4-methoxy-phenyl)-5-methyl-oxazole

The above prepared N-(1-acetyl-but-3-enyl)-4-methoxy-benzamide (6.45 g, 26.1 mmol) was stirred in a mixture of 43.9 ml of trifluoro-acetic acid (22 eq.) and 21.75 ml of trifluoro-acetic anhydride (6 eq.) for 7 h at 40° and for 16 h at ambient temperature. Pouring onto crashed ice, twofold extraction with EtOEt, three times washing with $Na_2CO_3$-solution, drying over natrium sulfate and evaporation of the solvents, followed by flash chromatography ($SiO_2$, hexane/AcOEt=9/1) produced finally 4.51 g of the title compound as colorless oil.

EI-MS: 229.2 (M)+.

e] 3-[2-(4-Methoxy-phenyl)-5-methyl-oxazol-4-yl]-propan-1-ol

The above prepared 4-allyl-2-(4-methoxy-phenyl)-5-methyl-oxazole (4.51 g, 19.7 mmol) was dissolved in 60 ml of abs. THF and and treated at 0° with 100 ml of 9-BBN-solution (0.5 M hexane). Hydroboration was allowed to proceed for 2 h at RT. Afterwards, 56 ml of 3N NaOH and 114.5 ml of 30% $H_2O_2$ was added simultaneously, whereby the internal temperature rose to 45°. After 1 h, the heterogeneous mixture was diluted with ice and water, extracted twice with AcOEt, washed water, and dried over natrium sulfate. Evaporation of the solvents, followed by flash chromatography ($SiO_2$, hexane/AcOEt=1/3) yielded 4.54 g of the title compound as colorless oil.

EI-MS: 247.1 (M)+. NMR: ($CDCl_3$, 1H, δ, TMS) 1.89 (quint., J=5.5, 2H), 2.31 (s, 3H), 2.62 (t, J=6.5, 2H), 3.55 (br s, OH), 3.75 (t, J=5.5, 2H), 3.85 (s, 3H), 6.94 (d, J=7, 2H), 7.89 (d, J=7, 2H).

f] 4-{3-[2-(4-Methoxy-phenyl)-5-methyl-oxazol-4-yl]-propoxy}-naphthalene-1-carbaldehyde g of the above prepared 3-[2-(4-methoxy-phenyl)-5-methyl-oxazol-4-yl]-propan-1ol (4.04 mmol) was dissolved in 21 ml of toluene and treated successively at 0° C. with 0.696 g of 4-hydroxy-naphthalene-1-carbaldehyde (4.04 mmol), 1.061 g of triphenylphosphine (4.04 mmol), and 0.818 g (4.04 mmol) of DIAD. The cooling bath was then removed and stirring continued for 3 h. Pouring onto crashed ice, twofold extraction with AcOEt, washing with 3N NaOH and water, drying over magnesium sulfate, and evaporation of the solvents, followed by flash chromatography (silica gel, hexane/AcOEt=7/3) left finally 1.084 g of the title compound as light yellow gum.

ISP-MS: 402.5 (M+H)+.

g] 3-Hydroxy-2-methoxy-3-(4-{3-[2-(4-methoxy-phenyl)-5-methyl-oxazol-4-yl]-propoxy}-naphthalen-1-yl)-propionic acid ethyl ester LDA-solution in THF was prepared according to standard procedures from 0.166 g of diisopropylamine (1.64 mmol) and 0.964 ml of 1.5 M nBuLi (hexane) in 4 ml of abs. THF at −10°. After cooling to −78°, 0.177 g of ethyl methoxy-acetate (1.49 mmol), dissolved in 1.3 ml of THF, was added and stirring continued for 15 min. to complete enolate formation. 0.200 g of the above prepared 4-{3-[2-(4-methoxy-phenyl)-5-methyl-oxazol-4-yl]-propoxy}-naphthalene-1-carbaldehyde (0.50 mmol), dissolved in 2 ml of THF, was added and the mixture kept for another 30 min. at this temperature. Pouring onto crashed ice/$NH_4Cl$, twofold extraction with AcOEt, washing with water, drying over sodium sulfate, and evaporation of the solvents, followed by flash chromatography ($SiO_2$, hexane/AcOEt=1/1) delivered 0.228 g of the title compound as syn/anti-isomers (colorless gum).

ISP-MS: 520.3 (M+H)+.

h] [rac]-2-Methoxy-3-(4-{3-[2-(4-methoxy-phenyl)-5-methyl-oxazol-4-yl]-propoxy}-naphthalen-1-yl)-propionic acid ethyl ester 0.228 g of the above prepared 3-hydroxy-2-methoxy-3-(4-{3-[2-(4-methoxy-phenyl)-5-methyl-oxazol-4-yl]-propoxy}-naphthalen-1-yl)-propionic acid ethyl ester (0.44 mmol) was dissolved in 2.3 ml of trifluoroacetic acid, treated at 0° with 0.697 ml of triethylsilane (10 eq.) and then kept for 4 h at 0°. The reaction mixture was then poured onto crashed ice/AcOEt/NaHCO₃, the organic layer washed twice with water, dried over sodium sulfate, and evaporated to dryness. Flash chromatography (SiO₂, hexane/AcOEt=7/3) yielded 0.143 g of the title compound as colorless oil.

ISP-MS: (M+H)⁺504.4.

i] [rac]-2-Methoxy-3-(4-{3-[2-(4-methoxy-phenyl)-5-methyl-oxazol-4-yl]-propoxy}-naphthalen-1-yl)-propionic acid 0.143 g of the above prepared [rac]-2-methoxy-3-(4-{3-[2-(4-methoxy-phenyl)-5-methyl-oxazol-4-yl]-propoxy}-naphthalen-1-yl)-propionic acid ethyl ester (0.28 mmol) was dissolved in 1.5 ml of THF/EtOH=1/1 and treated with 0.47 ml of 3N NaOH (5 eq.). The reaction mixture was stirred at ambient temperature for 2 h and was then poured onto crashed ice/HCl dil. and extracted twice with AcOEt. The organic layer was washed with water, dried over sodium sulfate, and evaporated to dryness. Crystallization from AcOEt/hexane afforded finally 0.120 g of the title product as white crystals of mp. 67–70°.

ISN-MS: (M+H)⁺474.1. NMR: (CDCl₃, 1H, δ, TMS) 2.22 (s, 3H), 2.29 (quint., J=6.5, 2H), 2.79 (t, J=6.5, 2H), 3.26 (s, 3H), 3.28 (d×d, J=8.5, J=14.5, 1H), 3.63 (d×d, J=14.5, J=4, 1H), 3.86 (s, 3(s, 3H), 4.1–4.2 (m, 3H), 6.72 (d, J=8, 1H), 6.94 (d, J=9, 2H), 7.28 (d, J=8, 1H), 7.48 (m, 1H), 7.55 (m, 1H), 7.92 (d, J=8.5, 2H), 8.03 (d, J=8.5, 1H), 8.35 (d, J=8.5, 1H), COOH very br.

Example 43

[rac]-3-(4-{3-[2-(4-Chloro-phenyl)-5-methyl-oxazol-4-yl]-propoxy}-naphthalen-1-yl)-2-methoxy-propionic acid was prepared in analogy to example 42, but starting the sequence with 4-chloro-benzaldehyde instead of 4-methoxy-benzaldehyde as a white foam.

ISN-MS: 478.2 (M−H)⁺.

Example 44

[rac]-2-Methoxy-3-(4-{3-[5-methyl-2-(4-trifluoromethyl-phenyl)-oxazol-4-yl]-propoxy}-benzo[b]thiophen-7-yl)-propionic acid was prepared in analogy to example 42, but starting the sequence with 4-trifluoromethyl-benzaldehyde instead of 4-methoxy-benzaldehyde and using for the Mitsunobu-reaction (step f]) 4-hydroxy-benzo[b]thiophene-7-carbaldehyde [Ger. Offen. (1998) DE 19711617 A1] instead of 4-hydroxy-naphthalene-1-carbaldehyde as white crystals of mp. 115–116°.

ISN-MS: 518.0 (M−H)⁺.

Example 45

[rac]-2-Ethoxy-3-(4-{3-[5-methyl-2-(4-trifluoromethyl-phenyl)-oxazol-4-yl]-propoxy}-benzo[b]thiophen-7-yl)-propionic acid was prepared in analogy to example 44, but using for the aldol-reaction (step g]) ethyl ethoxyacetate instead of ethyl methoxyacetate as coupling partner as white crystals of mp. 112–114°.

ISN-MS: 532.1 (M−H)⁺.

Example 46

[rac]-3-(4-{3-[2-(4-Chloro-phenyl)-5-methyl-oxazol-4-yl]-propoxy}-naphthalen-1-yl)-2-isopropoxy-propionic acid was prepared in analogy to example 43, but using for the aldol-reaction (step g]) ethyl isopropoxyacetate instead of ethyl methoxyacetate as off-white crystals of mp. 157–158°.

ISN-MS: 506.2 (M−H)⁺.

Example 47

(S)-2-Methoxy-3-(4-{3-[5-methyl-2-(4-trifluoromethyl-phenyl)-oxazol-4-yl]-propoxy}-naphthalen-1-yl)-propionic acid was prepared in analogy to example 21, but using for the Mitsunobu-reaction (step f]) 3-[5-methyl-2-(4-trifluoromethyl-phenyl)-oxazol-4-yl]-propan-1-ol (prepared in analogy to example 42 a]- e]) instead of 2-[5-methyl-2-(4-trifluoromethyl-phenyl)-oxazol-4-yl]-ethanol as colorless foam.

ISN-MS: 512.3 (M−H)⁺.

Example 48

[rac]-3-(4-{3-[2-(4-Chloro-phenyl)-5-methyl-oxazol-4-yl]-propoxy}-benzo[b]thiophen-7-yl)-2-methoxy-propionic acid was prepared in analogy to example 43, but using for the Mitsunobu-reaction (step f]) 4-hydroxy-benzo[b]thiophene-7-carbaldehyde [Ger. Offen. (1998) DE 19711617 A1] instead of 4-hydroxy-naphthalene-1-carbaldehyde as white crystals of mp. 105–107°.

ISN-MS: 484.1 (M−H)⁺.

Example 49

[rac]-2-Ethoxy-3-(4-{3-[2-(4-methoxy-phenyl)-5-methyl-oxazol-4-yl]-propoxy}-naphthalen-1-yl)-propionic acid was prepared in analogy to example 42, but using for the aldol-reaction as coupling partner ethyl ethoxy-acetate instead of ethyl methoxy-acetate as off-white crystals of mp. 141–142°.

ISN-MS: 488.2 (M−H)⁺.

Example 50

[rac]-2-Ethoxy-3-(4-{3-[2-(4-isopropyl-phenyl)-5-methyl-oxazol-4-yl]-propoxy}-naphthalen-1-yl)-propionic acid was prepared in analogy to example 49, but starting the sequence with 4-isopropyl-benzaldehyde instead of 4-methoxy-benzaldehyde as a white foam.

ISN-MS: 500.3 (M−H)⁺.

Example 51

[rac]-3-(4-{3-[2-(4-Chloro-phenyl)-5-methyl-oxazol-4-yl]-propoxy}-naphthalen-1-yl)-2-ethoxy-propionic acid was prepared in analogy to example 49, but starting the sequence with 4-chloro-benzaldehyde instead of 4-methoxy-benzaldehyde as an off-white solid of mp. 147–149°.

ISN-MS: 492.1 (M−H)⁺.

Example 52

[rac]-3-(4-{3-[2-(4-Isopropyl-phenyl)-5-methyl-oxazol-4-yl]-propoxy}-naphthalen-1-yl)-2-methoxy-propionic acid was prepared in analogy to example 50, but using for the aldol-reaction as coupling partner ethyl methoxy-acetate instead of ethyl ethoxy-acetate as a white foam.

ISN-MS: 486.3 (M−H)⁺.

Example 53

[rac]-3-(4-{2-[2-(3,5-Dimethyl-phenyl)-5-methyl-oxazol-4-yl]-ethoxy}-benzo[b]thiophen-7-yl)-2-ethoxy-propionic acid was prepared in analogy to example 40, but using for the aldol-reaction as coupling partner ethyl ethoxy-acetate instead of butyl butoxy-acetate as white crystals of mp. 149–150°.

ISN-MS: 478.2 (M−H)+.

Example 54

[rac]-3-(4-{2-[2-(3,5-Dimethoxy-phenyl)-5-methyl-oxazol-4-yl]-ethoxy}-benzo[b]thiophen-7-yl)-2-ethoxy-propionic acid was prepared in analogy to example 39, but using for the aldol-reaction as coupling partner ethyl ethoxy-acetate instead of butyl butoxy-acetate as white crystals of mp. 158–159°.

ISN-MS: 510.2 (M−H)+.

Example 55

[rac]-2-Ethoxy-3-(4-{3-[2-(4-methoxy-phenyl)-5-methyl-oxazol-4-yl]-propoxy}-benzo[b]thiophen-7-yl)-propionic acid was prepared in analogy to example 49, but using for the Mitsunobu-reaction (step f]) 4-hydroxy-benzo[b]thiophene-7-carbaldehyde [Ger. Offen. (1998) DE 19711617 A1] instead of 4-hydroxy-naphthalene-1-carbaldehyde as off-white crystals of mp. 121–123°.

ISN-MS: 494.1 (M−H)+.

Example 56

[rac]-2-Methoxy-3-(4-{3-[2-(4-methoxy-phenyl)-5-methyl-oxazol-4-yl]-propoxy}-benzo[b]thiophen-7-yl)-propionic acid was prepared in analogy to example 55, but using for the aldol-reaction as coupling partner ethyl methoxy-acetate instead of ethyl ethoxy-acetate as white crystals of mp. 127–129°.

ISN-MS: 480.2 (M−H)+.

Example 57

[rac]-2-Ethoxy-3-(4-{3-[2-(4-isopropyl-phenyl)-5-methyl-oxazol-4-yl]-propoxy}-benzo[b]thiophen-7-yl)-propionic acid was prepared in analogy to example 55, but starting the sequence with 4-isopropyl-benzaldehyde instead of 4-methoxy-benzaldehyde as a white solid of mp. 90–93°.

ISN-MS: 506.2 (M−H)+.

Example 58

[rac]-3-(4-{3-[2-(4-Isopropyl-phenyl)-5-methyl-oxazol-4-yl]-propoxy}-benzo[b]thiophen-7-yl)-2-methoxy-propionic acid was prepared in analogy to example 57, but using for the aldol-reaction as coupling partner ethyl methoxy-acetate instead of ethyl ethoxy-acetate as white crystals of mp. 103–105°.

ISN-MS: 492.2 (M−H)+.

Example 59

[rac]-3-(4-{3-[2-(4-Chloro-phenyl)-5-methyl-oxazol-4-yl]-propoxy}-benzo[b]thiophen-7-yl)-2-ethoxy-propionic acid was prepared in analogy to example 57, but starting the sequence with 4-chloro-benzaldehyde instead of 4-isopropyl-benzaldehyde as a white solid of mp. 89–95°.

ISN-MS: 498.0 (M−H)+.

Example 60

[rac]-3-(4-{3-[2-(4-Chloro-phenyl)-5-methyl-oxazol-4-yl]-propoxy}-benzo[b]thiophen-7-yl)-2-methoxy-propionic acid was prepared in analogy to example 59, but using for the aldol-reaction as coupling partner ethyl methoxy-acetate instead of ethyl ethoxy-acetate as white crystals of mp. 105–107°.

ISN-MS: 484.1 (M−H)+.

Example 61

[rac]-2-Ethoxy-3-(4-{3-[2-(4-methoxy-phenyl)-5-methyl-oxazol-4-yl]-propoxy}-naphthalen-1-yl)-propionic acid was prepared in analogy to example 42, but using for the aldol-reaction as coupling partner ethyl ethoxy-acetate instead of ethyl methoxy-acetate as off-white crystals of mp. 141–142°.

ISN-MS: 488.2 (M−H)+.

Example 62

[rac]-2-Ethoxy-3-(4-{3-[2-(4-isopropyl-phenyl)-5-methyl-oxazol-4-yl]-propoxy}-naphthalen-1-yl)-propionic acid was prepared in analogy to example 61, but starting the sequence with 4-isopropyl-benzaldehyde instead of 4-methoxy-benzaldehyde as a white foam.

ISN-MS: 500.3 (M−H)+.

Example 63

[rac]-3-(4-{3-[2-(4-Chloro-phenyl)-5-methyl-oxazol-4-yl]-propoxy}-naphthalen-1-yl)-2-ethoxy-propionic acid was prepared in analogy to example 61, but starting sequence with 4-chloro-benzaldehyde instead of 4-methoxy-benzaldehyde as an off-white solid of mp. 147–149°.

ISN-MS: 492.1 (M−H)+.

Example 64

[rac]-2-Ethoxy-3-(4-{2-[2-(4-isopropyl-phenyl)-5-methyl-oxazol-4-yl]-ethoxy}-benzo[b]thiophen-7-yl)-propionic acid was prepared in analogy to example 53, but starting the whole reaction sequence with 4-isopropyl-benzaldehyde instead of 3,5-dimethyl-benzaldehyde as white crystals of mp. 128–129°.

ISN-MS: 492.1 (M−H)+.

Example 65

(S)-2-But-3-enyloxy-3-(4-{2-[2-(4-isopropyl-phenyl)-5-methyl-oxazol-4-yl]-ethoxy}-benzo[b]thiophen-7-yl)-propionic acid was prepared in analogy to example 31, but using in the aldol-coupling step (S)-4-benzyl-3-but-3-enyloxyacetyl-oxazolidin-2-one instead of (S)-4-benzyl-3-methoxyacetyl-oxazolidin-2-one as white crystals of mp. 124–126°.

ISN-MS: 518.1 (M–H)+.

The necessary building block (S)-4-benzyl-3-but-3-enyloxyacetyl-oxazolidin-2-one was prepared as follows:

a] But-3-enyloxy-acetic acid

To 480 mg of NaH (50% in mineral oil, ~20 mmol) in 10 ml of abs. THF was added at 0° 721 mg of 3-buten-1-ol (10 mmol) and the mixture stirred for 5 min. ($H_2$-evolution). 1.39 g of bromo-acetic acid (10 mmol), dissolved in 10 ml of THF, was then added and the mixture kept for additional 5 min. at 0° and for 2 h at ambient temperature. Pouring onto crashed ice/HCl dil., twofold extraction with AcOEt, washing with brine, drying over natrium sulfate and evaporation of the solvents afforded 1.65 g of the title compound, contaminated with mineral oil, but sufficiently pure for the next step.

b] (S)-4-Benzyl-3-but-3-enyloxyacetyl-oxazolidin-2-one 1.6 g of the above prepared but-3-enyloxy-acetic acid (9.9 mmol) was treated with 3.35 ml=5.03 g of oxalic acid chloride (4 eq.) and one drop of abs. DMF. Immediate gas-evolution set in and the reaction mixture was kept for 3 h. Careful evaporation of the excess of reagent and drying yielded 1.35 g of acid chloride which was used for the next step without further purification.

1.77 g of (S)-4-Benzyl-2-oxazolidinone (10 mmol) was dissolved in 30 ml of abs. THF and cooled down to –78°. 6.67 ml of 1.5M nBuLi (hexane) was added via syringe (strongly exothermic) to deprotonate the NH. 10 min. later, the crude, above prepared acid chloride, dissolved in 10 ml of THF, was added and stirring continued for 30 min. at –78° and for 30 min. at 0°. Pouring onto crashed ice/$NH_4Cl$, twofold extraction with AcOEt, washing with water, drying over sodium sulfate, and evaporation of the solvents, followed by flash chromatography ($SiO_2$, hexane/AcOEt=7/3) afforded 0.691 g of the title compound as colorless, viscous oil.

ISP-MS: 290.3 (M+H)+, 307.4 (M+$NH_4$)+. NMR: ($CDCl_3$, 1H, δ, TMS) 2.46 (m, 2H), 2.81 (d×d, J=9.5, J=13.5, 1H), 3.34 (d×d, J=3, J=13.5, 1H), 3.66 (t, J=7, 2H), 4.20–4.34 (m, 2H), 4.62–4.76 (m, 3H), 5.09 (d, J=10.5, 1H), 5.15 (d, J=17, 1H), 5.86 (m, 1H), 7.20–7.39 (m, 5H).

Example 66

[rac]-3-(4-{2-[2-(4-Isopropyl-phenyl)-5-methyl-oxazol-4-yl]-ethoxy}-naphthalen-1-yl)-2-propoxy-propionic acid was prepared in analogy to example 64, but using for the Mitsunobu-reaction 4-hydroxy-naphthalene-1-carbaldehyde instead of 4-hydroxy-benzo[b]thiophene-7-carbaldehyde and in the aldol-coupling step ethyl propoxy-acetate instead of ethyl ethoxy-acetate as white foam.

ISN-MS: 500.2 (M–H)+.

Example 67

[rac]-2-Ethoxy-3-(4-{2-[2-(4-isopropyl-phenyl)-5-methyl-oxazol-4-yl]-ethoxy}-naphthalen-1-yl)-propionic acid was prepared in analogy to example 66, but using in the aldol-coupling step ethyl ethoxy-acetate instead of step ethyl propoxy-acetate as white foam.

ISN-MS: 486.3 (M–H)+.

Example 68

[rac]-3-(4-{2-[2-(3,5-Dimethoxy-phenyl)-5-methyl-oxazol-4-yl]-ethoxy}-benzo[b]thiophen-7-yl)-2-isopropoxy-propionic acid was prepared in analogy to example 39, but using in the aldol-coupling step ethyl isopropoxy-acetate instead of butyl butoxy-acetate as white crystals of mp. 148–150°. The former reagent was synthesized as described above for but-3-enyloxy-acetic acid (see example 65) from iPrOH, NaH, and bromo-acetic acid, followed by acid catalyzed esterification with EtOH.

ISN-MS: 524.1 (M–H)+.

Example 69

(S)-3-(4-{2-[2-(3,5-Dimethoxy-phenyl)-5-methyl-oxazol-4-yl]-ethoxy}-benzo[b]thiophen-7-yl)-2-isopropoxy-propionic acid was prepared in analogy to example 33, but starting the whole reaction sequence with 3,5-dimethoxy-benzaldehyde instead of 3,5-dimethyl-benzaldehyde and using in the aldol-coupling step (S)-4-benzyl-3-isopropoxyacetyl-oxazolidin-2-one instead of (S)-4-benzyl-3-methoxyacetyl-oxazolidin-2-one as white solid; the mp. has not been determined, since the product was contaminated with tiny amounts of chiral auxliary.

ISN-MS: 524.1 (M–H)+.

Example 70

[rac]-3-(4-{3-[2-(4-Isopropyl-phenyl)-5-methyl-oxazol-4-yl]-propoxy}-benzo[b]thiophen-7-yl)-2-propoxy-propionic acid was prepared in analogy to example 58, but using in the aldol-coupling step ethyl propoxy-acetate instead of ethyl methoxy-acetate as white crystals of mp. 72–73°.

ISN-MS: 520.2 (M–H)+.

Example 71

[rac]-3-(4-{2-[2-(3,5-Dimethoxy-phenyl)-5-methyl-oxazol-4-yl]-ethoxy}-naphthalen-1-yl)-2-ethoxy-propionic acid was prepared in analogy to example 54, but using for the Mitsunobu-reaction 4-hydroxy-naphthalene-1-carbaldehyde instead of 4-hydroxy-benzo[b]thiophene-7-carbaldehyde as white crystals of mp. 164–165°.

ISN-MS: 504.2 (M–H)+.

Example 72

[rac]-3-(4-{2-[2-(3,5-Dimethoxy-phenyl)-5-methyl-oxazol-4-yl]-ethoxy}-naphthalen-2-propoxy-propionic acid was prepared in analogy to example 71, but using in the aldol-coupling step ethyl propoxy-acetate instead of ethyl ethoxy-acetate as white crystals of mp. 140–141°.

ISN-MS: 518.1 (M–H)+.

Example 73

[rac]-3-(4-{2-[2-(3,5-Dimethoxy-phenyl)-5-methyl-oxazol-4-yl]-ethoxy}-naphthalen-1-yl)-2-isopropoxy-propionic acid was prepared in analogy to example 68, but using for the Mitsunobu-reaction 4-hydroxy-naphthalene-1-carbaldehyde instead of 4-hydroxy-benzo[b]thiophene-7-carbaldehyde as white crystals of mp. 166–167°.

ISN-MS: 518.1 (M−H)+.

Example 74

[rac]-2-Isopropoxy-3-(4-{2-[2-(4-isopropyl-phenyl)-5-methyl-oxazol-4-yl]-ethoxy}-naphthalen-1-yl)-propionic acid was prepared in analogy to example 73, but starting the whole reaction sequence with 4-isopropyl-benzaldehyde instead of 3,5-dimethoxy-benzaldehyde as white foam.

ISN-MS: 500.2 (M−H)+.

Example 75 a] 5-Methyl-2-phenyl-4-(2-m-tolyloxy-ethyl)-oxazole

A solution of 3.50 g of m-cresol, 9.87 g of 2-(5-methyl-2-phenyl-oxazole-4yl)-ethanol and 12.73 g of triphenylphosphine in 190 ml of THF was treated at 0° C. with a solution of 8.45 g of diethyl azodicarboxylate (DEAD) in 75 ml of THF over 20 min and the brown solution was stirred at 22° C. for 24 h. The solution was evaporated and the residue partitioned between $CH_2Cl_2$ (300 ml) and 0.1 N aqueous NaOH (100 ml). The organic layer was washed twice with water (2×100 ml), dried, the organic solvent was evaporated and the residue was chromatographed on silica (n-hexane/AcOEt, 20:1) to give 7.43 g (78%) of the title compound as white crystals.

MS: (M+H)+294.3. NMR (CDCl$_3$, 1H, δ, TMS): 7.97 (m, 2H), 7.45–7.35 (m, 3H), 7.14 (t, J=7.6, 1H), 6.77–6.67 (m, 3H), 4.23 (t, J=6.8, 2H), 2.97 (t, J=6.8, 2H), 2.38 (s, 3H), 2.31 (s, 3H).

b] 2-Methyl-4-[2-(5-methyl-2-phenyl-oxazol-4-yl)-ethoxy]-benzaldehyde

A solution of 6.00 g of 5-methyl-2-phenyl-4-(2-m-tolyloxy-ethyl)-oxazole and 4.70 g of dichloromethylmethylether in 30 ml of $CH_2Cl_2$ was treated at 0° C. with 11.2 ml $TiCl_4$ over 15 min and stirring was continued at 0° C. for 2.5 h. The red solution was treated at 0° with 600 ml of 1 N aqueous HCl, the organic layer was washed with 0.1 N aqueous NaOH and twice with brine. The organic layer was dried, the solvent evaporated and the residue was chromatographed on silica (n-hexane/AcOEt, 7:1) to give 3.42 g (52%) of the title compound as a pale yellow solid.

MS: (M)+321.2. IR (nujol): 1691 s and 1679 s (C=O). NMR (CDCl$_3$, 1H, δ, TMS): 10.10 (s, 1H), 7.96 (m, 2H), 7.73 (d, J=8.6, 1H), 7.45–7.36, m, 3H), 6.84 (d×d, J=8.6, 2.8, 1H), 6.73 (d, J=2.8, 1H), 4.32 (t, J=6.8, 2H), 3.00 (t, J=3.8, 2H), 2.62 (s, 3H), 2.38 (s, 3H).

c] 2Z-Ethoxy-3-{2-methyl-4-[2-(5-methyl-2-phenyl-oxazol-4-yl)-ethoxy]-phenyl}-acrylic acid ethyl ester A suspension of 1.50 g of 2-methyl-4-[2-(5-methyl-2-phenyl-oxazol-4-yl)-ethoxy]-benzaldehyde, 3.00 g of the Wittig salt [(ethoxy-ethoxycarbonylmethyl)-triphenylphosphonium chloride, Tetrahedron 50(25), 7543–56(1994)] and 0.97 g of potassium carbonate in 30 ml of i-PrOH was stirred at 22° C. for 6 d. A further portion of 1.50 g of the Wittig salt and 0.48 g of potassium carbonate was added and stirring was continued overnight at 60° and again a further portion of 1.50 g of the Wittig salt and 0.48 g of potassium carbonate was added and stirring was continued overnight at 60° C. after which time the conversion was complete. The mixture was evaporated and the residue partitioned between 40 ml of $CH_2Cl_2$ and 40 ml of sat. aqueous NH$_4$Cl. The organic layer was washed with 40 ml of water, dried and evaporated. The residue was chromatographed on silica (n-hexane/AcOEt, 8:1) to give 1.53 g (75%) of the title compound as a pale yellow solid.

MS: (M)+435.2. IR (nujol): 1715 s (C=O). NMR (CDCl$_3$, 1H, δ, TMS): 8.05 (d, J=8.8, 1H), 7.97 (m, 2H), 7.45–7.35 (m, 3H), 7.16 (s, 1H), 6.75 (d×d, J=8.8, 2.4, 1H), 6.72 (d, J=2.4, 1H), 4.29 (q, J=6.8, 2H), 4.27 (t, J=6.8, 2H), 3.89 (q, J=6.8, 2H), 2.98 (t, J=6.8, 2H), 2.38 (s, 3H), 2.35 (s, 3H), 1.35 (t, J=6.8, 3H), 1.28 (t, J=6.8, 3H).

d] 2Z-Ethoxy-3-{2-methyl-4-[2-(5-methyl-2-phenyl-oxazol-4-yl)-ethoxy]-phenyl}-acrylic acid To a solution of 0.40 g of 2Z-ethoxy-3-{2-methyl-4-[2-(5-methyl-2-phenyl-oxazol-4-yl)-ethoxy]-phenyl}-acrylic acid ethyl ester in 10 ml of THF, 5 ml of MeOH and 5 ml of water was added at 22° C. 0.116 g of LiOHxH$_2$O and stirring was continued for 2 d. The yellow solution was evaporated, the residue dissolved in 20 ml of water and the pH was adjusted to 5 using ca. 2.6 ml of 1 N aqueous HCl. The suspension was filtered, the residue washed with water and dried to give 0.34 g (91%) of the title compound as a white solid.

MS: (M+H)+408.3. IR (nujol): 3100–2500 m, br. (COOH), 1705 s (C=O). NMR (CDCl$_3$, 1H, δ, TMS): 10.5 (s, very br., 1H), 8.03 (d, J=8.8, 1H), 7.98 (m, 2H), 7.47–7.37 (m, 3H), 7.31 (s, 1H), 6.77 (d×d, J=8.8, 2.8, 1H), 6.73 (d, J=2.8, 1H), 4.27 (t, J=6.8, 2H), 3.91 (q, J=7.2, 2H), 2.99 (t, J=6.8, 2H), 2.38 (s, 3H), 2.35 (s, 3H), 1.30 t, J=7.2, 3H).

Example 76

[rac]-2-Ethoxy-3-{2-methyl-4-[2-(5-methyl-2-phenyl-oxazol-4-yl)-ethoxy]-phenyl}-propionic acid A suspension of 100 mg of 2Z-ethoxy-3-{2-methyl-4-[2-(5-methyl-2-phenyl-oxazol-4-yl)-ethoxy]-phenyl}-acrylic acid and 26 mg of Pd/C (10%) in 2 ml of MeOH was hydrogenated at 22° C./1 bar for 2 d. The suspension was filtered, the filtrate evaporated and dried to give 89 mg (89%) of the title compound as a pale yellow solid.

MS: (M+H)+410.4. IR (MIR): 3100–2400 m, br. (COOH) 1725 m (C=O). NMR (CDCl$_3$, 1H, δ, TMS): 10.5 (s, very br., 1H), 7.96 (m, 2H), 7.45–7.35 (m 3H), 7.09 (d, J=8.4 1H), 6.68 (s, br., 1H), 6.66 (d, br. J=8.4, 1H), 4.19 (t, J=6.8, 2H), 3.96 (m, 1H), 3.50 (m, 1H), 3.27 (m, 1H), 3.07 (m, 1H), 2.95 (t, J=6.8,2H), 2.87 (m, 1H), 2.36 (s, 3H), 2.30 (s, 3H), 1.08 (t, J=7.2, 3H).

Example 77, 78 a] [rac]-2-Ethoxy-3-{2-methyl-4-[2-(5-methyl-2-phenyl-oxazol-4-yl)-ethoxy]-phenyl}-propionic acid ethyl ester A suspension of 400 mg of 2Z-ethoxy-3-{2-methyl-4-[2-(5-methyl-2-phenyl-oxazol-4-yl)-ethoxy]-phenyl}-acrylic acid ethyl ester and 98 mg of Pd/C (10%) in 8 ml of MeOH, 2 ml of THF and 0.5 ml of AcOH was hydrogenated at 22° C./1 bar overnight. The suspension was filtered, the filtrate evaporated and dried to give 380 mg (95%) of the title compound as colourless oil.

b] 2(S)- and 2(R)-Ethoxy-3-{2-methyl-4-[2-(5-methyl-2-phenyl-oxazol-4-yl)-ethoxy]-phenyl}-propionic acid ethyl ester The two title compounds were prepared by resolution of [rac]-2-ethoxy-3-{2-methyl-4-[2-(5-methyl-2-phenyloxazol-4-yl)-ethoxy]-phenyl]propionic acid ethyl ester on a prep. column (Chiralpak AD, n-heptane/EtOH, 98:2) the 2(S)-enantiomer eluting first.

2(S)- and 2(R)-Ethoxy-3-{2-methyl-4-[2-(5-methyl-2-phenyl-oxazol-4-yl)-ethoxy]-phenyl}-propionic acid The hydrolysis of the esters were carried out as described in example 75 d] to give the two title compounds with an e.e. >99% (Chiralpak AD, n-heptane/EtOH, 97:3).

Spectroscopic data were identical with those of the racemic compound described in example 76. The absolute configuration was established by an X-ray analysis of the 2(S)-acid. Crystals were grown from $CHCl_3$/n-hexane at 22° C.

Example 79 a] 4-[2-(2,3-Dimethyl-phenoxy)-ethyl]-5-methyl-2-phenyl-oxazole

The title compound was prepared in analogy to example 75 a], but using 2,3-dimethylphenol instead of m-cresol, to give a pale yellow solid (6.72 g, 67%).

MS: (M)$^+$307.3. NMR (CDCl$_3$, 1H, δ, TMS): 7.97 (m, 2H), 7.45–7.35 (m, 3H), 7.02 (t, J=7.6, 1H, 6.77–6.70 (m, 2H), 4.23 (t, J=6.8, 2H), 2.99 (t, J=6.8, 2H), 2.38 (s, 3H), 2.25 (s, 3H), 2.11 (s, 3H).

b] 2,3-Dimethyl-4-[2-(5-methyl-2-phenyl-oxazol-4-yl)-ethoxy]-benzaldehyde

The title compound was prepared in analogy to example 75 b], but using 4-[2-(2,3-dimethyl-phenoxy)-ethyl]-5-methyl-2-phenyl-oxazole as the starting material, to give a pale yellow solid (4.12 g, 71%).

MS: (M)$^+$335.1. IR (nujol): 1689 s (C=O). NMR (CDCl$_3$, 1H, δ, TMS): 10.13 (s, 1H), 7.98 (m, 2H), 7.64 (d, J=8.4, 1H), 7.46–7.36 (m, 3H), 6.85 (d, J=8.4, 1H), 4.33 (t, J=6.4, 2H), 3.03 (t, J=6.4, 2H), 2.58 (s, 3H), 2.39 (s, 3H), 2.16 (s, 3H).

c] 3-{2,3-Dimethyl-4-[2-(5-methyl-2-phenyl-oxazol-4-yl)-ethoxy]-phenyl}-2Z-ethoxy-acrylic acid ethyl ester The title compound was prepared in analogy to example 75 c], but using 2,3-dimethyl-4-[2-(5-methyl-2-phenyl-oxazol-4-yl)-ethoxy]-benzaldehyde as the starting material, to give a white solid (50 mg, 54%).

MS: (M+H)$^+$450.4. IR (nujol): 1709 s (C=O). NMR (CDCl$_3$, 1H, δ, TMS): 7.97 (m, 2H), 7.81 (d, J=8.8, 1H), 7.45–7.35 (m, 3H), 7.24 (s, 1H), 6.76 (d, J=8.8, 1H), 4.29 (q, J=7.2, 2H), 4.27 (t, J=6.4, 2H), 3.84 (q, J=6.8, 2H), 3.00 (t, J=6.4, 2H), 2.38 (s, 3H), 2.26 (s, 3H), 2.15 (s, 3H), 1.36 (t, J=7.2, 3H), 1.24 (t, J=6.8, 2H).

d] 3-{2,3-Dimethyl-4-[2-(5-methyl-2-phenyl-oxazol-4-yl)-ethoxy]-phenyl}-2Z-ethoxy-acrylic acid The title compound was prepared in analogy to example 75 d], but using 3-{2,3-dimethyl-4-[2-(5-methyl-2-phenyl-oxazol-4-yl)-ethoxy]-phenyl}-2Z-ethoxy-acrylic acid ethyl ester as the starting material, to give a white solid (0.32 g, 86%).

MS: (M+H)$^+$422.3. IR (nujol): 3100–2500 m, br. (COOH), 1698 s (C=O). NMR (CDCl$_3$, 1H, δ, TMS): 11–10 (s, very br., 1H), 7.98 (m, 2H), 7.80 (d, J=8.8, 1H), 7.46–7.36 (m, 4H), 6.77 (d, J=8.8, 1H), 4.28 (t, J=6.4, 2H), 3.85 (q, J=7.2, 2H), 3.02 (t, J=6.4, 2H), 2.39 (s, 3H), 2.27 (s, 3H), 2,15 (s, 3H), 1.26 (t, J=7.2, 3H).

Example 80

[rac]-3-{2,3-Dimethyl-4-[2-(5-methyl-2-phenyl-oxazol-4-yl)-ethoxy]-phenyl}-2-ethoxy-propionic acid The title compound was prepared in analogy to example 76, but using 3-{2,3-dimethyl-4-[2-(5-methyl-2-phenyl-oxazol-4-yl)-ethoxy]-phenyl}-2Z-ethoxy-acrylic acid as the starting material, to give a white solid (92 mg, 91%).

MS: (M+H)$^+$424.4. IR (nujol): 3100–2500 m, br. (COOH), 1724 s (C=O). NMR (CDCl$_3$, 1H, δ, TMS): 11–10 (s, very br., 1H), 7.97 (m, 2H), 7.46–7.36 (m, 3H), 6.98 (d, J=8.4, 1H), 6.66 (d, J=8.4, 1H), 4.19 (t, J=6.4, 2H), 3.97 (m, 1H), 3.49 (m, 1H), 3.29 (m, 1H), 3.15 (d×d, J=14.4, 4, 1H), 2.98 (t, J=6.4, 2H), 2.91 (d×d, J=14.4, 8.8, 1H), 2.37 (s, 3H), 2.23 (s, 3H), 2.13 (s, 3H), 1.09 (t, J=6.8, 3H).

Example 81 a] 4-[2-(3,5-Dimethyl-phenoxy)-ethyl]-5-methyl-2-phenyl-oxazole

The title compound was prepared in analogy to example 75 a], but using 3,5-dimethylphenol instead of m-cresol, to give a pale yellow oil (5.94 g, 59%).

MS: (M+H)$^+$308.2. NMR (CDCl$_3$, 1H, δ, TMS): 7.97 (m, 2H), 7.43–7.33 (m, 3H), 6.59 (s, br., 1H), 6.53 (s, br., 2H), 4.20 (t, J=6.4, 2H), 2.96 (t, J=6.4, 2H), 2.38 (s, 3H), 2.26 (s, 6H).

b] 2,6-Dimethyl-4-[2-(5-methyl-2-phenyl-oxazol-4-yl)-ethoxy]-benzaldehyde

The title compound was prepared in analogy to example 75 b], but using 4-[2-(3,5-dimethyl-phenoxy)-ethyl]-5-methyl-2-phenyl-oxazole as the starting material, to give a 1:1 mixture of position isomers as a pale yellow solid (83 mg, 78%). The mixture was separated on prep. HPLC (RP-18, $CH_3CN/H_2O$, gradient) to give the title compound as a white solid (41 mg, 38%).

MS: (M)$^+$335.2. IR (nujol): 1672 NMR (CDCl$_3$, 1H, δ, TMS): 10.46 (s, 1H), 7.97 (m, 2H), 7.46–7.36 (m, 3H), 6.59 (s, 2H), 4.30 (t, J=6.4, 2H), 2.99 (t, J=6.4, 2H), 2.58 (s, 6H), 2.38 (s, 3H).

c] 3-2,6-Dimethyl-4-[2-(5-methyl-2-phenyl-oxazol-4-yl)-ethoxy]-phenyl}-2Z-ethoxy-acrylic acid ethyl ester A suspension of 2.88 g of the Wittig salt [(ethoxy-ethoxycarbonylmethyl)-triphenylphosphonium chloride, Tetrahedron 50(25), 7543–56(1994)] and 15 ml of THF was cooled to −78° C., treated with 6.7 ml of LiN(TMS)$_2$ (1 M in THF), the yellow solution was warmed to 22° C. over 1 h and cooled to −78° C. The solution was treated with a solution of 1.40 g of 2,6-dimethyl-4-[2-(5-methyl-2-phenyl-oxazol-4-yl)-ethoxy]-benzaldehyde in 15 ml of THF and stirring was continued at 70° C. for 7 d. The mixture was treated again with 1.44 g of the Wittig salt and with 3.35 ml of LiN(TMS)$_2$ (1 M in THF) and stirring was continued at 70° C. for 6 d. The reaction mixture was evaporated and the residue partitioned between $CH_2Cl_2$ and sat. aqueous $NH_4Cl$. The organic layer was washed with water, dried and evaporated. The residue was chromatographed on silica (n-hexane/AcOEt, 8:1) to give 0.55 g (29%) of the title compound as a pale yellow oil.

MS: (M)+449.2. IR (neat): 1721 s (C=O). NMR (CDCl$_3$, 1H, δ, TMS): 7.97 (m, 2H), 7.46–7.36 (m, 3H), 7.03 (s, 1H), 6.60 (s, 2H), 4.30 (q, J=7.2, 2H), 4.23 (t, J=6.4, 2H), 3.56 (q, J=7.2, 2H), 2.97 (t, J=6.4, 2H), 2.37 (s, 3H), 2.22 (s, 6H), 1.35 (t, 7.2, 3H), 1.05 (t, J=7.2, 3H).

d] 3-{2,6-Dimethyl-4-[2-(5-methyl-2-phenyl-oxazol-4-yl)-ethoxy]-phenyl}-2Z-ethoxy-acrylic acid The title compound was prepared in analogy to example 75 d], but using 3-{2,6-dimethyl-4-[2-(5-methyl-2-phenyl-oxazol-4-yl)-ethoxy]-phenyl}-2Z-ethoxy-acrylic acid ethyl ester as the starting material, to give a white solid (155 mg, 41%).

MS: (M+H)+422.3. IR (nujol): 3100–2500 m, br. (COOH), 1716 s (C=O). NMR (CDCl$_3$, 1H, δ, TMS): 9.50 (s, br., 1H), 7.98 (m, 2H), 7.46–7.36 (m, 3H), 7.15 (s, 1H), 6.61 (s, 2H), 4.23 (t, J=6.4, 2H), 3.54 (q, J=7.2, 2H), 2.98 (t, J=6.4, 2H), 2.38 (s, 3H), 2.21 (s, 6H), 1.10 (t, J=7.2, 3H).

Example 82 a] [rac]-3-{2,6-Dimethyl-4-[2-(5-methyl-2-phenyl-oxazol-4-yl)-ethoxy]-phenyl}-2-ethoxy-propionic acid methyl ester To a solution of 30 mg of 3-{2,6-dimethyl-4-[2-(5-methyl-2-phenyl-oxazol-4-yl)-ethoxy]-phenyl}-2Z-ethoxy-acrylic acid ethyl ester in 1.5 ml of methanol was subsequently added 1 mg of iodine and 17 mg of magnesium and stirring was continued for 3 h. A further portion of 67 mg of magnesium was added and stirring was continued for 1.5 h. The suspension was filtered, the filtrate evaporated and the residue separated on prep. HPLC (RP-18, CH$_3$CN/H$_2$O, gradient) to give 2 mg (7%) of the title compound as a white solid.

NMR (CDCl$_3$, 1H, δ, TMS): 7.98 (m, 2H), 7.45–7.35 (m, 3H), 6.57 (s, 2H), 4.20 (t, J=6.4, 2H), 3.92 (d×d, J=8.8, 4.8, 1H), 3.72 (s, 3H), 3.52 (m, 1H), 3.21 (m, 1H), 3.05–2.93 (m, 4H), 2.38 (s, 3H), 2.31 (s, 6H), 1.09 (t, J=7.2, 3H).

b] [rac]-3-{2,6-Dimethyl-4-[2-(5-methyl-2-phenyl-oxazol-4-yl)-ethoxy]-phenyl}-2-ethoxy-propionic acid The title compound was prepared in analogy to example 75 d], but using [rac]-3-{2,6-dimethyl-4-[2-(5-methyl-2-phenyl-oxazol-4-yl)-ethoxy]-phenyl}-2-ethoxy-propionic acid methyl ester as the starting material, to give a white solid (1.4 mg, 72%).

MS: (M+H)+424.3. NMR (CDCl$_3$, 1H, δ, TMS): 7.97 (m, 2H), 7.46–7.36 (m, 3H), 6.59 (s, 2H), 4.21 (t, J=6.4, 2H), 3.95 (m, 1H), 3.45 (m, 1H), 3.18 (m, 1H), 3.10 (m, 1H), 3.05–2.94 (m, 4H), 2.38 (s, 3H), 2.33 (s, 6H), 1.05 (t, J=7.2, 3H).

Example 83, 84 a] 4-[2-(Benzofuran-4-yloxy)-ethyl]-5-methyl-2-phenyl-oxazole

The title compound was prepared in analogy to example 75 a], but using 4-hydroxy-benzofuran [Synthetic Communications (1986), 16(13) 1635–1640; Helvetica Chimica Acta (1933), 16, 121–129] instead of m-cresol, to give a white solid (2.41 g, 76%).

MS: (M)+319.1. NMR (CDCl$_3$, 1H, δ, TMS): 7.97 (m, 2H), 7.52 (d, J=2.4, 1H), 7.46–7.36 (m, 3H), 7.19 (t, J=8.0, 1H), 7.12 (d, J=8.0, 1H), 6.83 (d, J=2.4, 1H), 6.68 (d, J=8.0, 1H), 4.39 (t, J=6.4, 2H), 3.06 (t, J=6.4, 2H), 2.40 (s, 3H).

b] 4-[2-(5-Methyl-2-phenyl-oxazol-4-yl)-ethoxy]-benzofuran-7-carbaldehyde

The title compound was prepared in analogy to example 75 b], but using 4-[2-(benzofuran-4-yloxy)-ethyl]-5-methyl-2-phenyl-oxazole as the starting material, to give a white solid (0.82 g, 33%).

MS: (M+H)+348.4. IR (MIR): 1680 s (C=O). NMR (CDCl$_3$, 1H, δ, TMS): 10.21 (s, 1H), 7.98 (m, 2H), 7.74 (d, J=8.4, 1H), 7.67 (d, J=2.0, 1H), 7.46–7.38 (m, 3H), 6.89 (d, J=2.0, 1H), 6.81 (d, J=8.4, 1H), 4.49 (t, J=6.4, 2H), 3.09 (t, J=6.4, 2H), 2.41 (s, 3H).

c] 2Z- and 2E-Ethoxy-3-{4-[2-(5-methyl-2-phenyl-oxazol-4-yl)-ethoxy]-benzofuran-7-yl}-acrylic acid ethyl ester The title compounds were prepared in analogy to example 75 c], but using 4-[2-(5-methyl-2-phenyl-oxazol-4-yl)-ethoxy]-benzofuran-7-carbaldehyde as the starting material, to give the 2Z-isomer as a white solid (0.64 g, 65%). In a second fraction the 2E-isomer was obtained (79 mg, 8%) as a colourless oil.

Data of the 2Z-isomer

MS: (M+H)+462.3. IR (nujol): 1713 s and 1704 s (C=O). NMR (CDCl$_3$, 1H, δ, TMS): 8.14 (d, J=8.4, 1H), 7.98 (m, 2H), 7.56 (d, J=2, 1H), 7.52 (s, 1H), 7.46–7.36 (m, 3H), 6.84 (d, J=2, 1H), 6.72 (d, J=8.4, 1H), 4.43 (t, J=6.4, 2H), 4.31 (q, J=7.2, 2H), 4.03 (q, J=7.2, 2H), 3.06 (t, J=6.4, 2H), 2.40 (s, 3H), 1.39 (t, J=7.2, 3H), 1.38 (t, J=7.2, 3H).

Data of the 2E-isomer

MS: (M+H)+462.3. IR (neat): 1732 s, br. (C=O). NMR (CDCl$_3$, 1H, δ, TMS): 7.99 (m, 2H), 7.49 (d, J=2, 1H), 7.46–7.36 (m, 3H), 7.07 (d, J=8, 1H), 6.82 (d, J=2, 1H), 6.63 (d, J=8, 1H), 6.22 (s, 1H), 4.37 (t, J=6.4, 2H), 4.05 (q, J=7.2, 2H), 4.00 (q, J=7.2, 2H), 3.05 (t, J=6.4, 2H), 2.40 (s, 3H), 1.43 (t, J=7.2, 3H), 0.96 (t, J=7.2, 3H).

d] 2Z- and 2E-Ethoxy-3-{4-[2-(5-methyl-2-phenyl-oxazol-4-yl)-ethoxy]-benzofuran-7-yl}-acrylic acid The title compounds were prepared in analogy to example 75 d], but using 2Z- and 2E-ethoxy-3-{4-[2-(5-methyl-2-phenyl-oxazol-4-yl)-ethoxy]-benzofuran-7-yl}-acrylic acid ethyl ester as the starting materials, to give the 2Z-isomer as a white solid (0.53 g, 94%) and the 2E-isomer (40 mg, 67%) as a white solid.

Data of the 2Z-isomer

MS: (M–H)−432.4. IR (nujol): 3100–2500 w, br. (COOH), 1709 s (C=O). NMR (CDCl$_3$, 1H, δ, TMS): 10.5, (s, very br., 1H), 8.15 (d, J=8.8, 1H), 7.99 (m, 2H), 7.68 (s, 1H), 7.55 (d, J=2, 1H), 7.46–7.36 (m 3H), 6.83 (d, J=2, 1H), 6.74 (d, J=8.8, 1H), 4.45 (t, J=6.4, 2H), 4.05 (q, J=7.2, 2H), 3.09 (t, J=6.4, 2H), 2.41 (s, 3H), 1.38 (t, J=7.2, 3H).

Data of the 2E-isomer

MS: (M–H)−432.4. IR (MIR): 3100–2500 w, br. (COOH), 1712 m, br. (C=O). NMR (CDCl$_3$, 1H, δ, TMS): 10 (s, very br., 1H), 7.95 (m, 2H), 7.48 (d, J=2, 1H), 7.45–7.35 (m, 3H), 7.32 (d, J=8.4, 1H), 6.78 (d, J=2, 1H), 6.58 (d, J=8.4, 1H), 6.38 (s, 1H), 4.28 (t, J=6.4, 2H), 4.04 (q, J=7.2, 2H), 3.02 (t, J=6.4, 2H), 2.39 (s, 3H), 1.45 (t, J=7.2, 3H).

Example 85

[rac]-2-Ethoxy-3-{4-[2-(5-methyl-2-phenyl-oxazol-4-yl)-ethoxy]-benzofuran-7-yl}-propionic acid A suspension of 50 mg of 2Z-ethoxy-3-{4-[2-(5-methyl-2-phenyl-oxazol-4-yl-ethoxy]-benzofuran-7-yl}-acrylic acid and 12 mg of Pd/C (10%) in 1 ml of MeOH and 1 ml of $CH_2Cl_2$ was hydrogenated at 22° C./1bar for 1 h. The suspension was filtered, the filtrate evaporated and the residue purified by prep. HPLC (RP-18, $CH_3CN/H_2O$, gradient) to give the title compound (29 mg, 57%) as a white solid.

MS: $(M-H)^-$434.4. IR (MIR): 3100–2500 w, br. (COOH), 1724 s, br. (C=O). NMR ($CDCl_3$, 1H, δ, TMS): 9.5 (s, very br., 1H), 7.98 (m, 2H), 7.53 (d, J=2.4, 1H), 7.46–7.36 (m, 3H), 7.06 (d, J=8, 1H), 6.82 (d, J=2.4, 1H), 6.61 (d, J=8, 1H), 4.35 (t, J=6.4, 2H), 4.26 (m, 1H), 3.57–3.41 (m, 3H), 3.19 (m, 1H), 3.06 (t, J=6.4, 2H), 2.40 (s, 3H), 1.08 (t, J=7.4, 3H).

Example 86

[rac]-2-Ethoxy-3-{4-[2-(5-methyl-2-phenyl-oxazol-4-yl)-ethoxy]-2,3-dihydro-benzofuran-7-yl}-propionic acid A suspension of 100 mg of 2Z-ethoxy-3-{4-[2-(5-methyl-2-phenyl-oxazol-4-yl)-ethoxy]-benzofuran-7-yl}-acrylic acid and 25 mg of Pd/C (10%) in 2 ml of MeOH and 2 ml of $CH_2Cl_2$ was hydrogenated at 22° C./1bar overnight. The suspension was filtered and the filtrate was again hydrogenated with 25 mg of fresh catalyst overnight. The suspension was filtered, the filtrate evaporated and the residue purified by prep. HPLC (RP-18, $CH_3CN/H_2O$, gradient) to give the title compound (56 mg, 56%) as a pale yellow solid.

MS: $(M-H)^-$436.4. IR (nujol): 3100–2400 w, br. (COOH), 1715 s, br. (C=O). NMR ($CDCl_3$, 1H, δ, TMS): 9.5 (s, very br., 1H), 7.97 (m, 2H), 7.46–7.35 (m, 3H), 6.90 (d, J=8.4, 1H), 6.34 (d, J=8.4, 1H), 4.56 (t, J=8.8, 2H), 4.23 (t, J=6.4, 2H), 4.15 (m, 1H), 3.53 (m, 2H), 3.15–3.05 (m, 3H), 2.96 (t, 6.4, 2H), 2.88 (m, 1H), 2.37 (s, 3H), 1.14 (t, J=7.2, 3H).

Example 87, 88 a] 4-[2-(Benzofuran-7-yloxy)-ethyl]-5-methyl-2-phenyl-oxazole

The title compound was prepared in analogy to example 75 a], but using 7-hydroxy-benzofuran [J. Med. Chem. (1987), 30(1), 62–7] instead of m-cresol, to give a white solid (2.54 g, 80%).

MS: $(M)^+$319.1. NMR ($CDCl_3$, 1H, δ, TMS): 7.97 (m, 2H), 7.61 (d, J=2.0, 1H), 7.45–7.35 (m, 3H), 7.18 (d, J=7.8, 1H), 7.14 (t, J=7.8, 1H), 6.83 (d, J=7.8, 1H), 6.75 (d, J=2.0, 1H), 4.47 (t, (J=6.4, 2H), 3.09 (t, J=6.4, 2H), 2.40 (s, 3H).

b] 7-[2-(5-Methyl-2-phenyl-oxazol-4-yl)-ethoxy]-benzofuran-4-carbaldehyde

The title compound was prepared in analogy to example 75 b], but using 4-[2-(benzofuran-7-yloxy)-ethyl]-5-methyl-2-phenyl-oxazole as the starting material. Purification was accomplished by crystallisation from $CH_2Cl_2$/n-hexane instead of chromatography, to give a white solid (1.57 g, 71%).

MS: $(M)^+$347.1. IR (nujol): 1690 s (C=O). NMR ($CDCl_3$, 1H, δ, TMS): 10.03 (s, 1H), 7.97 (m, 2H), 7.77 (d, J=2.0, 1H), 7.65 (d, J=8, 1H), 7.52 (d, J=2, 1H), 7.47–7.37 (m, 3H), 6.93 (d, J=8, 1H), 4.57 (t, J=6.4, 2H), 3.13 (t, J=6.4, 2H), 2.42 (s, 3H).

c] 2Z- and 2E-Ethoxy-3-{7-[2-(5-methyl-2-phenyl-oxazol-4-yl)-ethoxy]-benzofuran-4-yl)-ethoxy]-benzofuran-4-yl}-acrylic acid ethyl ester The title compounds were prepared in analogy to example 75 c], but using 7-[2-(5-methyl-2-phenyl-oxazol-4-yl)-ethoxy}-benzofuran-4-carbaldehyde as the starting material, to give the 2Z-isomer as a white solid (0.93 g, 80%). In a second fraction the 2E-isomer was obtained (85 mg, 7%) as a colourless oil.

Data of the 2Z-isomer

MS: $(M+H)^+$462.3. IR (nujol): 1715 s and 1703 s (C=O). NMR ($CDCl_3$, 1H, δ, TMS): 7.99 (m, 3H), 7.65 (d, J=2.0, 1H), 7.45–7.35 (m, 3H), 7.26 (s, 1H), 6.98 (d, J=2.0, 1H), 6.86 (d, J=7.2, 1H), 4.51 (t, J=6.4, 2H), 4.32 (q, J=7.2, 2H), 3.96 (q, J=7.2, 2H), 3.10 (t, J=6.4, 2H), 2.40 (s, 3H), 1.38 (t, J=7.2, 3H), 1.33 (t, J=7.2, 3H).

Data of the 2E-isomer

MS: $(M)^+$461.2. IR (neat): 1730 s (C=O). NMR ($CDCl_3$, 1H, δ, TMS): 7.97 (m, 2H), 7.60 (d, J=2.0, 1H), 7.46–7.35 (m, 3H), 6.97 (d, J=8, 1H), 6.76 (d, J=8, 1H), 6.70 (d, J=2.0, 1H), 6.23 (s, 1H), 4.45 (t, J=6.4, 2H), 4.02 (q, J=7.2, 2H), 3.98 (q, J=7.2, 2H), 3.09 (t, J=6.4, 2H), 2.40 (s, 3H), 1.44 (t, J=7.2, 3H), 0.95 (t, J=7.2, 3H).

d] 2Z- and 2E-Ethoxy-3-{7-[2-(5-methyl-2-phenyl-oxazol-4-yl)-ethoxy]-benzofuran-4-yl}-acrylic acid The title compounds were prepared in analogy to example 75 d], but using 2Z- and 2E-ethoxy-3-{7-[2-(5-methyl-2-phenyl-oxazol-4-yl)-ethoxy]-benzofuran-4-yl}-acrylic acid ethyl ester as the starting materials, to give the 2Z-isomer as a white solid (0.61 g, 97%) and the 2E-isomer (48 mg, 72%) as a white solid.

Data of the 2Z-isomer

MS: $(M-H)^-$432.3. IR (nujol): 3100–2500 w, br. (COOH), 1708 s (C=O). NMR ($CDCl_3$, 1H, δ, TMS): 11 (s, very br., 1H), 7.99 (m, 3H), 7.66 (d, J=2.0, 1H), 7.47–7.37 (m, 4H), 6.97 (d, J=2.0, 1H), 6.88 (d, J=8.8, 1H), 4.52 (t, J=6.4, 2H), 3.99 (q, J=7.2, 2H), 3.12 (t, J=6.4, 2H), 2.42 (s, 3H), 1.24 (t, J=7.2, 3H).

Data of the 2E-isomer

MS: $(M-H)^-$432.3. IR (nujol): 3100–2500 w, br. (COOH), 1710 s (C=O). NMR (DMSO-$d_6$, 1H, δ, TMS): 13.0 (s, 1H), 7.95 (d, J=2.0, 1H), 7.91 (m, 2H), 7.55–7.45 (m 3H), 7.01 (d, J=8, 1H), 6.96 (d, J=2.0, 1H), 6.88 (d, J=8, 1H), 6.17 (s, 1H), 4.39 (t, J=6.4, 2H), 3.95 (q, J=7.2, 2H), 3.00 (t, J=6.4, 2H), 2.38 (s, 3H), 1.32 (t, J=7.2, 3H).

Example 89, 90

[rac]-2-Ethoxy-3-{7-[2-(5-methyl-2-phenyl-oxazol-4-yl)-ethoxy]-benzofuran-4-yl}-propionic acid and
[rac]-2-ethoxy-3-{7-[2-(5-methyl-2-phenyl-oxazol-4-yl)-ethoxy]-2,3-dihydro-benzofuran-4-yl}-propionic acid A suspension of 100 mg of 2Z-ethoxy-3-{7-[2-(5-methyl-2-phenyl-oxazol-4-ethoxy]-benzofuran-4-yl}-acrylic acid and 25 mg of Pd/C (10%) in 2 ml of MeOH and 2 ml of CH₂Cl₂ was hydrogenated at 22° C./1bar overnight. The suspension was filtered, the filtrate evaporated and the mixture separated by prep. HPLC (RP-18, CH₃CN/H₂O, gradient) to give [rac]-2-ethoxy-3-{7-[2-(5-methyl-2-phenyl-oxazol-4-yl)-ethoxy]-2,3-dihydro-benzofuran-4-yl}-propionic acid (12.5 mg, 12%). The second fraction contained [rac]-2-ethoxy-3-{7-[2-(5-methyl-2-phenyl-oxazol-4-yl)-ethoxy]-benzofuran-4-yl}-propionic acid (50 mg, 50%) as a white solid.

Data of [rac]-2-ethoxy-3-{7-[2-(5-methyl-2-phenyl-oxazol-4-yl)-ethoxy]-2,3-dihydro-benzofuran-4-yl}-propionic acid MS: (M+H)⁺438.4. IR (nujol): 3100–2500 w, br. (COOH), 1736 s and 1716 s (C=O). NMR (CDCl₃, 1H, δ, TMS): 10 (s, very br. 1H), 7.97 (m, 2H), 7.46–7.36 (m, 3H), 6.72 (d, J=8.4, 1H), 6.66 (d, J=8.4, 1H), 4.61 (t, J=8.8, 2H), 4.29 (t, J=6.4, 2H), 4.04 (m, 1H), 3.57 (m, 1H), 3.42 (m, 1H), 3.21 (m, 2H), 3.06–2.97 (m, 3H), 2.88 (m 1H), 2.36 (s, 3H), 1.16 (t, J=7.2, 3H).

Data of [rac]-2-ethoxy-3-{7-[2-(5-methyl-2-phenyl-oxazol-4-yl)-ethoxy]-benzofuran-4-yl}-propionic acid:

MS: (M+H)⁺436.4. IR (nujol): 3100–2500 w, br. (COOH), 1733 s, br. (C=O). NMR (CDCl₃, 1H, δ, TMS): 10 (s, very br., 1H), 7.97 (m, 2H), 7.61 (d, J=2.0, 1H), 7.46–7.36 (m, 3H), 7.00 (d, J=8, 1H), 6.85 (d, J=2.0, 1H), 6.76 (d, J=8, 1H), 4.43 (t, J=6.4, 2H), 4.11 (m, 1H), 3.52 (m, 1H), 3.40–3.27 (m, 2H), 3.13 (m, 1H), 3.08 (t, J=6.4, 2H), 2.40 (s, 3H), 1.10 (t, J=7.2, 3H).

Example 91 a] 4-[2-(Indan-4-yloxy)-ethyl]-5-methyl-2-phenyl-oxazole 4.00 g of methanesulfonic acid 2-(5-methyl-2-phenyl-oxazol-4-yl)-ethyl ester [PCT Int. Appl. (2000) WO0008002] (14.22 mmol), 2.00 g of 4-indanol (14.93 mmol) and 487.6 mg of tetrabutylammonium hydrogen sulfate were dissolved in 65 ml of toluene and heated to 80° C. KOH was then slowly added (10.66 ml of a 2M solution in H₂O, 21.33 mmol), keeping the temperature at 75–80° C. The resulting mixture was stirred for 4 hours at 80° C. 35 ml of water were added, the mixture stirred for another 5 minutes at 80° C. and the water phase was then removed. 20 ml of water were added to the toluene phase, the mixture stirred for 5 minutes at 80° C., and the water phase removed. The water phase was extracted 3 times with dichloromethane. The combined organic phases were dried over MgSO₄ and evaporated to afford 4.90 g (100%) of 4-[2-(indan-4-yloxy)-ethyl]-5-methyl-2-phenyl-oxazole as brown solid.

MS: 319.2 (M)⁺, 186.2 (M-Indanol)⁺. NMR: (CDCl₃, 1H, δ, TMS, 300 MHz) 2.05 (quint., J=7.5, 2H), 2.36 (s, 3H), 2.83 (t, J=7.5, 2H), 2.90 (t, J=7.5, 2H), 2.98 (t, J=6.5, 2H), 4.25 (t, J=6.5, 2H), 6.66 (d, J=7.5, 1H), 6.82 (d, J=7.5, 1H) 7.08 (t, J=8, 1H), 7.25–7.45 (m, 3H), 7.97 (br d, J=8, 2H).

b] 7-[2-(5-Methyl-2-phenyl-oxazol-4-yl)-ethoxy]-indan-4-carbaldehyde 4.00 g of 4-[2-(indan-4-yloxy)-ethyl]-5-methyl-2-phenyl-oxazole (12.52 mmol) and 2.29 ml of dichloromethyl methyl ether (25.05 mmol) were dissolved in 300 ml of dichloromethane. This solution was cooled down to 0° C., and 5 ml of titanium tetrachloride (44.69 mmol) in 75 ml of dichloromethane were added slowly. The resulting dark solution was stirred at 0° C. for 30 minutes, and then 200 ml of 1N HCl were added slowly at 0° C. The mixture was stirred for 30 minutes at 0° C., the 2 phases were separated and the aqueous phase was extracted 3 times with dichloromethane. The combined organic phases were dried over MgSO₄ and evaporated to afford 4.5 g of a beige solid. Flash chromatography (silica gel, cyclohexane/ethylacetate=9/1, then cyclohexane/ethylacetate=4/1) left finally 2.96 g (68%) of 7-[2-(5-methyl-2-phenyl-oxazol-4-yl)-ethoxy]-indan-4-carbaldehyde as beige crystals.

MS: 347.3 (M)⁺, 187.2. NMR: (CDCl₃, 1H, δ, TMS, 300 MHz) 2.12 (quint., J=7.5, 2H), 2.39 (s, 3H), 2.82 (t, J=7.5, 2H), 3.02 (t, J=6.5, 2H), 3.28 (t, J=7.5, 2H), 4.35 (t, J=6.5, 2H), 6.81 (d, J=8.4, 1H), 7.43 (m, 3H), 7.62 (d, J=8.5, 1H), 7.96–7.99 (m, 2H), 9.98 (s, 1H).

c] 2Z-Ethoxy-3-{7-[2-(5-methyl-2-phenyl-oxazol-4-yl)-ethoxy]-indan-4-yl}-acrylic acid ethyl ester 1.39 g of 7-[2-(5-methyl-2-phenyl-oxazol-4-yl)-ethoxy]-indan-4-carbaldehyde (4.00 mmol) and 1.89 g of (ethoxy-ethoxycarbonyl-methyl)-triphenyl-phosphonium chloride [Tetrahedron 50(25), 7543–56(1994)] (4.40 mmol) were dissolved in 9 ml of dichloromethane/2-propanol (1/1, v/v) under argon. This solution was cooled down to –10° C. and 855 mg of potassium carbonate (6.00 mmol) was added. The resulting suspension was stirred overnight and allowed to reach room temperature. Additional 1.89 g of (ethoxy-ethoxycarbonyl-methyl)-triphenyl-phosphonium chloride (4.40 mmol) were added, the solution was cooled down to –10° C. and 855 mg of potassium carbonate (6.00 mmol) were added. The resulting suspension was stirred for 60 hours and allowed to reach room temperature. Again, 1.89 g of (ethoxy-ethoxycarbonyl-methyl)-triphenyl-phosphonium chloride (4.40 mmol) were added, the solution was cooled down to –10° C. and 855 mg of potassium carbonate (6.00 mmol) were added. The resulting suspension was stirred overnight and allowed to reach room temperature. The mixture was filtered, washed with dichloromethane and the filtrate evaporated. The residue was dissolved in dichloromethane and washed with brine. Drying over magnesium sulfate, and evaporation of the solvents, followed by flash chromatography (silica gel, cyclohexane, then cyclohexane/ethylacetate=95/5, then cyclohexane/ethylacetate=4/1) left finally 1.215 g (65.8%) of 2Z-ethoxy-3-{7-[2-(5-methyl-2-phenyl-oxazol-4-yl)-ethoxy]-indan-4-yl}-acrylic acid ethyl ester as beige crystals.

MS: 461.2 (M)⁺, 186.1. NMR: (CDCl₃, 1H, δ, TMS, 300 MHz) 1.33 (t, J=6.6, 3H), 1.36 (t, J=6.6, 3H), 2.07 (quint., J=7.5, 2H), 2.38 (s, 3H), 2.86 (t, J=7.5, 2H), 2.99 (t, J=6.9, 4H), 3.93 (q, J=7.1 2H), 4.28 (q, J=7.2, 2H), 4.29 (t, J~7 Hz, 2H), 6.73 (d, J=8.7, 1H), 7.05 (s, 1H), 7.39–7.46 (m, 3H), 7.96–7.99 (m, 2H), 8.05 (d, J=8.7, 1H).

d] [rac]-2-Ethoxy-3-{7-[2-(5-methyl-2-phenyl-oxazol-4-yl)-ethoxy]-indan-4-yl}-propionic acid ethyl ester 250 mg of Pd/C were added under argon to 850 mg of 2Z-ethoxy-3-{7-[2-(5-methyl-2-phenyl-oxazol-4-yl)-ethoxy]-indan-4-yl}-acrylic acid ethyl ester (1.84 mmol) dissolved in 10 ml of tetrahydrofuran. The atmosphere was then replaced with H₂, and the suspension was rapidly stirred at room temperature under the atmosphere of H₂ for four hours. Filtration over dicalite and evaporation of the solvents left 850 mg (99.6%) of [rac]-2-ethoxy-3-{7-[2-(5- methyl-2-phenyl-oxazol-4-yl)-ethoxy]-indan-4-yl}-propionic acid ethyl ester as brown oil.

MS: 464.4 (M+H)⁺. NMR: (CDCl₃, 1H, δ, TMS, 300 MHz) 1.14 (t, J=6.9, 3H), 1.21 (t, J=7.1, 3H), 2.04 (quint., J=7.5, 2H), 2.38 (s, 3H), 2.84 (t, J=7.5, 2H), 2.95 (m, 6H), 3.32 (m, 1H), 3.56 (m, 1H), 3.95 (t, J=6.8, 1H), 4.15 (q, J=7.1, 2H), 4.22 (t, J=6.4, 2H), 6.61(d, J=8.3, 1H), 6.95 (d, J=8.2, 1H), 7.40–7.46 (m, 3H), 7.96–7.99 (m, 2H).

e] [rac]-2-Ethoxy-3-{7-[2-(5-methyl-2-phenyl-oxazol-4-yl)-ethoxy]-indan-4-yl}-propionic acid

[rac]-2-Ethoxy-3-{7-[2-(5-methyl-2-phenyl-oxazol-4-yl)-ethoxy]-indan-4-yl}-propionic acid ethyl ester (850 mg, 1.83 mmol) was dissolved in 10 ml of dioxane; 5 ml of water and LiOH (4.58 ml of a 1N solution in water, 4.58 mmol) were then added slowly at room temperature. The resulting mixture was stirred overnight at room temperature and then poured onto ice, neutralized to pH 4 with HCl (1N) and extracted 3 times with AcOEt. The combined organic phases were washed with water, dried over magnesium sulfate and evaporated to give a colorless solid that was triturated in CH₃CN for 15 minutes, filtered and dried to yield 470 mg (58.9%) of [rac]-2-ethoxy-3-{7-[2-(5-methyl-2-phenyl-oxazol-4-yl)-ethoxy]-indan-4-yl}-propionic acid as colorless crystals.

MS: 434.4 (M–H)⁻. NMR: (CDCl₃, 1H, δ, TMS, 300 MHz) 1.14 (t, J=7, 3H), 2.04 (quint., J=7.4, 2H), 2.38 (s, 3H), 2.84 (t, J=7.5, 2H), 2.88–2.90 (m, 3H), 2.93 (t, J=6.3, 2H), 3.01 (dxd, J=4.8 and 9, 1H), 3.37 (m, 1H), 3.55 (m, 1H), 4.01 (dxd, J=4.8 and 8.1, 1H), 4.21 (t, J=6.3 Hz, 2H), 6.62 (d, J=8.1, 1H), 6.98 (d, J=8.1, 1H), 7.39–7.46 (m, 3H), 7.95–7.98 (m, 2H), COOH very br.

Example 92 a] 4-[2-(5-Methyl-2-phenyl-oxazol-4-yl)-ethoxy]-5,6,7,8-tetrahydro-naphthalene-1-carbaldehyde In analogy to the procedures described in examples 91 a] and b] 5,6,7,8-tetrahydro-naphthalen-1-ol was reacted with methanesulfonic acid 2-(5-methyl-2-phenyl-oxazol-4-yl)-ethyl ester [PCT Int. Appl. (2000) WO0008002] to give 5-methyl-2-phenyl-4-[2-(5,6,7,8-tetrahydro-naphthalen-1-yloxy)-ethyl]-oxazole. Treatment of 5-methyl-2-phenyl-4-[2-(5,6,7,8-tetrahydro-naphthalen-1-yloxy)-ethyl]-oxazole with dichloromethyl methyl ether and titanium tetrachloride then gave 4-[2-(5-methyl-2-phenyl-oxazol-4-yl)-ethoxy]-5,6,7,8-tetrahydro-naphthalene-1-carbaldehyde as yellow solid.

MS: 361.2 (M)⁺, 186.2. NMR: (CDCl₃, 1H, δ, TMS, 300 MHz) 1.76 (br, 4H), 2.38 (s, 3H), 2.63(br, 2H), 3.02 (t, J=6.5, 2H), 3.17 (br, 2H), 4.32(t, J=6.5, 2H), 6.80 (d, J=8.5, 1H), 7.40–7.47 (m, 3H), 7.62 (d, J=8.5, 1H), 7.95–7.99 (m, 2H), 10.08 (s, 1H).

b] 2Z-Ethoxy-3-{4-[2-(5-methyl-2-phenyl-oxazol-4-yl)-ethoxy]-5,6,7,8-tetrahydro-naphthalen-1-yl}-acrylic acid ethyl ester In analogy to the procedure described in example 91 c], 4-[2-(5-methyl-2-phenyl-oxazol-4-yl)-ethoxy]-5,6,7,8-tetrahydro-naphthalene-1-carbaldehyde was reacted with (ethoxy-ethoxycarbonyl-methyl)-triphenyl-phosphonium chloride to yield 2Z-ethoxy-3-{4-[2-(5-methyl-2-phenyl-oxazol-4-yl)-ethoxy]-5,6,7,8-tetrahydro-naphthalen-1-yl}-acrylic acid ethyl ester as beige solid.

MS: 476.2 (M+H)⁺. NMR: (CDCl₃, 1H, δ, TMS, 300 MHz) 1.27 (t, J=7.1, 3H), 1.35 (t, J=7.1, 3H), 1.76 (br, 4H), 2.38 (s, 3H), 2.62 (t, J=5.8, 2H), 2.75 (t, J=5.8, 2H), 2.99 (t, J=6.4, 2H), 3.86 (q, J=7.0, 2H), 4.28 (m, 4H), 6.71 (d, J=8.7, 1H), 7.18 (s, 1H), 7.39–7.46 (m, 3H), 7.90 (d, J=8.7, 1H), 7.96–7.99 (m, 2H).

c] [rac]-2-Ethoxy-3-{4-[2-(5-methyl-2-phenyl-oxazol-4-yl)-ethoxy]-5,6,7,8-tetrahydro-naphthalen-1-yl}-propionic acid In analogy to the procedures describes in examples 91 d] and e], 2Z-ethoxy-3-{4-[2-(5-methyl-2-phenyl-oxazol-4-yl)-ethoxy]-5,6,7,8-tetrahydro-naphthalen-1-yl}-acrylic acid ethyl ester was hydrogenated to give [rac]-2-ethoxy-3-{4-[2-(5-methyl-2-phenyl-oxazol-4-yl)-ethoxy]-5,6,7,8-tetrahydro-naphthalen-1-yl}-propionic acid ethyl ester. [rac]-2-Ethoxy-3-{4-[2-(5-methyl-2-phenyl-oxazol-4-yl)-ethoxy]-5,6,7,8-tetrahydro-naphthalen-1-yl}-propionic acid ethyl ester was then saponified to yield [rac]-2-ethoxy-3-{4-[2-(5-methyl-2-phenyl-oxazol-4-yl)-ethoxy]-5,6,7,8-tetrahydro-naphthalen-1-yl}-propionic acid as colorless crystals.

MS: 450.4 (M+H)⁺. NMR: (CDCl₃, 1H, δ, TMS, 300 MHz) 1.12 (t, J=6.9, 3H), 1.74 (br, 4H), 2.37 (s, 3H), 2.62 (br, 2H), 2.72 (br, 2H), 2.89 (dxd, J=14.4, 8.7, 1H), 2.98 (t, J=6., 2H), 3.05 (dxd, J=14.4, 4.2, 1H), 3.31 (quasi-quint., J~7, 1H), 3.52 (quasi-quint., J~7, 1H), 3.98 (dxd, J=8.7, 4.2, 1H), 4.19 (t, J=6.3, 2H), 6.63 (d, J=8.1, 1H), 6.98 (d, J=8.4, 1H), 7.39–7.46 (m, 3H), 7.96–7.99 (m, 2H), COOH very br.

Example 93 a] (3-(4-Benzyloxy-benzo[b]thiophen-7-yl)-2(Z,E)-ethoxy-acrylic acid ethyl ester 0.537 g (2.00 mmol) 4-Benzyloxy-benzo[b]thiophene-7-carbaldehyde [Ger. Offen. (1998) DE 19711617 A1] were dissolved under an argon atmosphere in 15 ml of 2-propanol. After cooling to –20° C., 0.944 g (2.20 mmol) (ethoxy-ethoxycarbonyl-methyl)-triphenyl-phosphonium chloride [Tetrahedron 50(25), 7543–56(1994)], and 0.415 g (3.00 mmol) of dry potassium carbonate were added. The resulting suspension was stirred in an ice bath and allowed to reach room temperature and stirred overnight at ambient temperature. A second addition of the same amounts of Wittig-reagent and potassium carbonate at –20° C. was performed as described above. After filtration and evaporation of the solvent, the residue was purified by flash chromatography (silica gel, hexane/EtOAc from 98:2 to 9:1) left finally 0.586 g (77%) 3-(4-benzyloxy-benzo[b]thiophen-7-yl)-2(Z,E)-ethoxy-acrylic acid ethyl ester as a light yellow oil.

MS: 382.2 (M)⁺, 291.2, 189.1. NMR: (CDCl₃, 1H, δ, TMS, 300 MHz) 1.36 (t, J=7, 3H), 1.40 (t, J=7, 3H), 4.01 (q, J=7, 2H), 4.34 (q, J=7, 2H), 5.26 (s,2H), 6.88 (d, J=8, 1H), 7.23 (s, 1H), 7.35–7.45 (m, 4H), 7.50 (m, 2H), 7.59 (d, J=5, 1H), 8.19 (d, J=8, 1H).

b] [rac]-3-(4-Benzyloxy-benzo[b]thiophen-7-yl)-2-ethoxy-propionic acid methyl ester 0.383 g (1.00 mmol) 3-(4-Benzyloxy-benzo[b]thiophen-7-yl)-2(Z,E)-ethoxy-acrylic acid ethyl ester were dissolved under an argon atmosphere in 20 ml THF/MeOH (1:1). 0.248 g (10.2 mmol) of magnesium were added and the reaction mixture then warmed up to 50° C. After 30 minutes, it was cooled down to room temperature and stirred overnight at ambient temperature. After addition of 5 ml HCl (25% in water) at 25° C., the reaction mixture was stirred vigorously for one hour, then extracted with EtOAc (three times); the organic phases were washed with brine, dried over MgSO₄, filtered and evaporated. Purification of the yellow oil by flash chromatography (silica gel, hexane/EtOAc from 9:1 to 4:1) afforded 0.366 g (99%) [rac]-3-(4-benzyloxy-benzo[b]thiophen-7-yl)-2-ethoxy-propionic acid methyl ester as a yellowish oil.

MS: 370.1 (M)$^+$, 311.2, 253.1. NMR: (CDCl$_3$, 1H, δ, TMS, 300 MHz) 1.13 (t, J=8, 3H), 3.23 (m, 2H), 3.35 (m, 1H), 3.60 (m, 1H), 3.70 (s, 3H), 4.24 (m, 1H), 5.21 (s, 2H), 6.78 (d, J=9, 1H), 7.13 (d, J=9, 1H), 7.38–7.48 (m, 6H), 7.59 (d, J=6, 1H).

c] [rac]-2-Ethoxy-3-(4-hydroxy-benzo[b]thiophen-7-yl)-propionic acid methyl ester 4.68 g (12.6 mmol) [rac]-3-(4-benzyloxy-benzo[b]thiophen-7-yl)-2-ethoxy-propion acid methyl ester were dissolved under an argon atmosphere in 150 ml CH$_2$Cl$_2$ at room temperature. 23.9 ml Dimethyl sulfide and 16.03 ml boron trifluoride diethyl etherate were added drop by drop. After 5 hours stirring at room temperature, the reaction mixture was quenched by pouring it into crashed ice water, then extracted three times with CH$_2$Cl$_2$. The organic phases were washed with brine, dried over MgSO$_4$, filtered and evaporated to afford 4.92 g of a yellow oil. Purification by flash chromatography (silica gel, hexane, CH$_2$Cl$_2$ and MeOH) gave 3.51 g (99%) [rac]-2-ethoxy-3-(4-hydroxy-benzo[b]thiophen-7-yl)-propionic acid methyl ester as light yellow solid.

MS: 279.1 (M–H)$^-$. NMR: (CDCl$_3$, 1H, δ, TMS, 300 MHz) 1.13 (t, J=7, 3H), 3.22 (m, 2H), 3.35 (m, 1H) 3.61 (m, 1H), 3.71 (s, 3H), 4.24 (m, 1H), 5.32 (s, 1H), 6.66 (d, J=8, 1H), 7.07 (d, J=8, 1H), 7.35 (d, J=5, 1H), 7.48 (d, J=5, 1H).

d] [rac]-3-(4-{2-[2-(4-Chloro-phenyl)-5-methyl-oxazol-4-yl]-ethoxy}-benzo[b]thiophen-7-yl)-2-ethoxy-propionic acid In analogy to the procedure described in example 17 a], [rac]-2-ethoxy-3-(4-hydroxy-benzo[b]thiophen-7-yl)-propionic acid methyl ester was reacted with 2-[2-(4-chloro-phenyl)-5-methyl-oxazol-4-yl]-ethanol (prepared by conversion of the 4-chloro-benzaldehyde into 2-[2-(4-chloro-phenyl)-5-methyl-oxazol-4-yl]-ethanol in analogy to the sequence described in examples 21 a] to 21 e]) in the presence of triphenylphosphine and DEAD (diethyl azodicarboxylate) to yield [rac]-3-(4-{2-[2-(4-chloro-phenyl)-5-methyl-oxazol-4-yl]-ethoxy}-benzo[b]thiophen-7-yl)-2-ethoxy-propionic acid methyl ester, which was further saponified in analogy to the procedure described in example 91 e] to yield [rac]-3-(4-{2-[2-(4-chloro-phenyl)-5-methyl-oxazol-4-yl]-ethoxy}-benzo[b]thiophen-7-yl)-2-ethoxy-propionic acid as light yellow solid.

MS: 484.3 (M–H)$^-$, 438.3. NMR: (CDCl$_3$, 1H, δ, TMS, 300 MHz) 1.09 (t, J=7, 3H), 2.39 (s, 3H), 3.06 (t, J=6, 2H), 3.18 (m, 1H), 3.28–3.43 (m, 2H), 3.50–3.63 (m, 1H), 4.20–4.29 (q, J=5, 1H), 4.35 (t, J=6, 2H), 6.74 (d, J=8, 1H), 7.11–7.24 (m, 3H), 7.32 (d, J=6, 1H), 7.47 (d, J=6, 1), 7.88 (d, J=9, 2H), COOH very br.

Example 94

[rac]-2-Ethoxy-3-(4-{2-[2-(4-fluoro-phenyl)-5-methyl-oxazol-4-yl]-ethoxy}-benzo[b]thiophen-7-yl)-propionic acid In analogy to the procedure described in example 17 a], [rac]-2-ethoxy-3-(4-hydroxy-benzo[b]thiophen-7-yl)-propionic acid methyl ester was reacted with 2-[2-(4-fluoro-phenyl)-5-methyl-oxazol-4-yl]-ethanol [J. Med. Chem. (1998), 41(25), 5037–5054] in the presence of triphenylphosphine and DEAD (diethyl azodicarboxylate) to yield [rac]-2-ethoxy-3-(4-{2-[2-(4-fluoro-phenyl)-5-methyl-oxazol-4-yl]-ethoxy}-benzo[b]thiophen-7-yl)-propionic acid methyl ester, which was further saponified in analogy to the procedure described in example 91 e] to yield [rac]-2-ethoxy-3-(4-{2-[2-(4-fluoro-phenyl)-5-methyl-oxazol-4-yl]-ethoxy}-benzo[b]thiophen-7-yl)-propionic acid as light yellow solid.

MS: 468.2 (M–H)$^-$, 422.2. NMR: (CDCl$_3$, 1H, δ, TMS, 300 MHz) 1.10 (t, J=7, 3H), 2.39 (s, 3H), 3.05 (t, J=6, 2H), 3.16–3.24 (m, 1H), 3.31–3.43 (m, 2H), 3.51–3.63 (m, 1H), 4.23–4.29 (m, 1H), 4.35 (t, J=6, 2H), 6.72 (d, J=8, 1H), 7.05–7.16 (m, 3H), 7.32 (d, J=5, 1H), 7.48 (d, J=5, 1H), 7.93–7.99 (m, 2H), COOH very br.

Example 95

[rac]-2-Ethoxy-3-(4-{2-[2-(2-ethoxy-4-fluoro-phenyl)-5-methyl-oxazol-4-yl]-ethoxy}-benzo[b]thiophen-7-yl)-propionic acid In analogy to the procedure described in example 17 a], [rac]-2-ethoxy-3-(4-hydroxy-benzo[b]thiophen-7-yl)-propionic acid methyl ester was reacted with 2-[2-(2-ethoxy-4-fluoro-phenyl)-5-methyl-oxazol-4-yl]-ethanol (prepared from 4-fluoro-2-hydroxy-benzaldehyde [J. Chem. Soc., Perkin Trans. 1 (1994), (13), 1823–31] by i) treatment with ethyl iodide, potassium carbonate in N,N-dimethylformamide to give 2-ethoxy-4-fluoro-benzaldehyde; ii) conversion of the 2-ethoxy-4-fluoro-benzaldehyde into 2-[2-(2-ethoxy-4-fluoro-phenyl)-5-methyl-oxazol-4-yl]-ethanol in analogy to the sequence described in examples 21 a] to 21 e]) in the presence of triphenylphosphine and DEAD (diethyl azodicarboxylate) to yield [rac]-2-ethoxy-3-(4-{2-[2-(2-ethoxy-4-fluoro-phenyl)-5-methyl-oxazol-4-yl]-ethoxy}-benzo[b]thiophen-7-yl)-propionic acid methyl ester, which was further saponified in analogy to the procedure described in example 91 e] to yield [rac]-2-ethoxy-3-(4-{2-[2-(2-ethoxy-4-fluoro-phenyl)-5-methyl-oxazol-4-yl]-ethoxy-}-benzo[b]thiophen-7-yl)-propionic acid as light yellow solid.

MS: 512.2 (M–H)$^-$, 494.1, 466.2. NMR: (CDCl$_3$, 1H, δ, TMS, 300 MHz): 1.09 (t, J=7, 3H), 1.44 (t, J=7, 3H), 2.38 (s, 3H), 3.09 (t, J=6, 2H), 3.12–3.39 (m, 3H), 3.51–3.61 (m, 1H), 4.08 (q, J=6, 2H), 4.25 (m, 1H), 4.36 (t, J=6, 2H), 6.64–6.75 (m, 3H), 7.11–7.24 (m, 1H), 7.29 (d, J=6 Hz, 1H), 7.48 (d, J=6, 1H), 7.80 (dxd, 1H), COOH very broad.

Example 96

[rac]-2-Ethoxy-3-(4-[2-[2-(4-methoxy-phenyl)-5-methyl-oxazol-4-yl]-ethoxy}-benzo[b]thiophen-7-yl)-propionic acid In analogy to the procedure described in example 17 a], [rac]-2-ethoxy-3-(4-hydroxy-benzo[b]thiophen-7-yl)-propionic acid methyl ester was reacted with 2-[2-(4-methoxy-phenyl)-5-methyl-oxazol-4-yl]-ethanol [J. Med. Chem. (1998), 41(25), 5037–5054] in the presence of triphenylphosphine and DEAD (diethyl azodicarboxylate) to yield [rac]-2-ethoxy-3-(4-{2-[2-(4-methoxy-phenyl)-5-methyl-oxazol-4-yl]-ethoxy}-benzo[b]thiophen-7-yl)-propionic acid methyl ester, which was further saponified in analogy to the procedure described in example 91 e] to yield [rac]-2-ethoxy-3-(4-{2-[2-(4-methoxy-phenyl)-5-methyl-oxazol-4-yl]-ethoxy]-benzo[b]thiophen-7-yl)-propionic acid as colorless amorphous solid.

MS: 480.3 (M–H)⁻, 434.3. NMR: (CDCl₃, 1H, δ, TMS, 300 MHz): 1.09 (t, J=7, 3H), 2.38 (s, 3H), 3.05 (t, J=6, 2H), 3.13–3.60 (m, 4H), 3.85 (s, 3H), 4.25 (m, 1H), 4.33 (t, J=6, 2H), 6.71 (d, J=8, 1H), 6.93 (d, J=9, 2H), 7.13 (d, J=8, 1H), 7.31 (d, J=5, 1H), 7.64–7.73 (m, 1H), 7.91 (d, J=9, 2H), COOH very broad.

Example 97

[rac]-2-Ethoxy-3-(4-{2-[2-(4-isopropoxy-phenyl)-5-methyl-oxazol-4-yl]-ethoxy}-benzo[b]thiophen-7-yl)-propionic acid In analogy to the procedure described in example 17 a], [rac]-2-ethoxy-3-(4-hydroxy-benzo[b]thiophen-7-yl)-propionic acid methyl ester was reacted with 2-[2-(4-isopropoxy-phenyl)-5-methyl-oxazol-4-yl]-ethanol [PCT Int. Appl. (2000), WO0008002A1] in the presence of triphenylphosphine and DEAD (diethyl azodicarboxylate) to yield [rac]-2-ethoxy-3-(4-{2-[2-(4-isopropoxy-phenyl)-5-methyl-oxazol-4-yl]-ethoxy}-benzo[b]thiophen-7-yl)-propionic acid methyl ester, which was further saponified in analogy to the procedure described in example 91 e] to yield [rac]-2-ethoxy-3-(4-{2-[2-(4-isopropoxy-phenyl-5-methyl-oxazol-4-yl]-ethoxy}-benzo[b]thiophen-7-yl)-propionic acid as light yellow amorphous solid.

MS: 508.3 (M–H)⁻, 462.3. NMR: (CDCl₃, 1H, δ, TMS, 300 MHz) 1.09 (t, J=6, 3H), 1.35 (d, J=6, 6H), 2.37 (s, 3H), 3.04 t, J=6, 2H), 3.12–3.40 (m, 3H), 3.52–3.61 (m, 1H), 4.22–4.29 (m, 1H), 4.35 (t, J=6, 2H), 4.55–4.67 (m, 1H), 6.72 (d, J=7, 1H), 6.89 (d, J=8, 2H), 7.15 (d, J=8, 1H), 7.31 (d, J=5, 1H), 7.63–7.73 (m, 1H), 7.88 (d, J=8, 2H), COOH very broad.

Example 98 a] 7-[2-(5-Methyl-2-phenyl-oxazol-4-yl)-ethoxy]-benzo[b]thiophene-4-carbaldehyde In analogy to the procedures described in example 91 a] and b], benzo[b]thiophen-7-ol [J. Chem. Soc., Perkin Trans. 1 (1983), (12), 2973–7] was reacted with methanesulfonic acid 2-(5-methyl-2-phenyl-oxazol-4-yl)-ethyl ester [PCT Int. Appl. (2000) WO0008002]) to yield 4-[2-(benzo[b]thiophen-7-yloxy)-ethyl]-5-methyl-2-phenyl-oxazole. Treatment of 4-[2-(benzo[b]thiophen-7-yloxy)-ethyl]-5-methyl-2-phenyl-oxazole with dichloromethyl methyl ether and titanium tetrachloride then gave 7-[2-(5-methyl-2-phenyl-oxazol-4-yl)-ethoxy]-benzo[b]thiophene-4-carbaldehyde as a yellow solid. NMR: (CDCl₃, 1H, δ, TMS, 300 MHz) 2.45 (s, 3H), 3.12 (t, J=6, 2H), 4.55 (t, J=6, 2H), 6.92 (d, J=8, 1H), 7.39–7.46 (m, 3H), 7.66 (d, J=5, 1H), 7.80 (d, J=8, 1H), 7.95–7.99 (m, 2H), 8.35 (d, J=5, 1H), 10.1 (s, 1H).

b] (S)-2-Methoxy-3-{7-[2-(5-methyl-2-phenyl-oxazol-4-yl)-ethoxy]-benzo[b]thiophen-4-yl}-propionic acid In analogy to the procedures described in examples 11 a] to 11 c], 7-[2-(5-methyl-phenyl-oxazol-4-yl)-ethoxy]-benzo[b]thiophene-4-carbaldehyde was reacted with (S)-4-benzyl-3-methoxyacetyl-oxazolidin-2-one and nBu₂BOTf to yield (S)-4-benzyl-3-[(2S,3R)-3-hydroxy-2-methoxy-3-{7-[2-(5-methyl-2-phenyl-oxazol-4-yl)-ethoxy]-benzo[b]thiophen-4-yl}-propionyl]-oxazolidin-2-one (according to NMR, one of the four isomers is strongly predominating; the configuration was tentatively assigned as 2S, 3R according to *Tetrahedron Asymmetry* 1999, 1353). Reduction of (S)-4-benzyl-3-[(2S,3R)-3-hydroxy-2-methoxy-3-{7-[2-(5-methyl-2-phenyl-oxazol-4-yl)-ethoxy]-benzo[b]thiophen-4-yl}-propionyl]-oxazolidin-2-one with triethylsilane in trifluoroacetic acid then gave (S)-4-benzyl-3-(2(S)-methoxy-3-{7-[2-(5-methyl-2-phenyl-oxazol-4-yl)-ethoxy]-benzo[b]thiophen-4-yl}-propionyl)-oxazolidin-2-one. The (S)-4-benzyl-3-(2(S)-methoxy-3-{7-[2-(5-methyl-2-phenyl-oxazol-4-yl)-ethoxy]-benzo[b]thiophen-4-yl}-propionyl)-oxazolidin-2-one was subsequently saponified with 1N NaOH in THF to yield (S)-2-methoxy-3-{7-[2-(5-methyl-2-phenyl-oxazol-4-yl)-ethoxy]-benzo[b]thiophen-4-yl}-propionic acid as colorless solid.

MS: 436.4 (M–H)⁻. NMR: (CDCl₃, 1H, δ, TMS, 300 MHz) 2.44 (s, 3H), 3.06 (t, J=6, 2H), 3.21–3.31 (m, 4H), 3.40–3.46 (d×d, J₁=4, J₂=14, 1H), 4.04–4.08 (m, 1H), 4.38 (t, J=6, 2H), 6.73 (d, J=8, 1H), 7.17 (d, J=8, 1H), 7.40–7.47 (m, 5H), 7.95–7.98 (m, 2H), COOH very broad.

Example 99

2Z-Ethoxy-3-{7-[2-(5-methyl-2-phenyl-oxazol-4-yl)-ethoxy]-indan-4-yl}-acrylic acid 2Z-Ethoxy-3-{7-[2-(5-methyl-2-phenyl-oxazol-4-yl)-ethoxy]-indan-4-yl}-acrylic acid ethyl ester (example 91 c]) (150 mg, 0.325 mmol) was dissolved in 1.7 ml of dioxane, 0.9 ml of water were added and LiOH (0.812 ml of a 1N solution in water, 0.813 mmol) was then added slowly at room temperature. The resulting mixture was stirred overnight at room temperature. It was then poured onto ice, neutralized to pH 4 with HCl (1N) and extracted 3 times with AcOEt. The combined organic phases were washed with water, dried over magnesium sulfate and evaporated to give 140 mg (99.4%) of 2Z-ethoxy-3-{7-[2-(5-methyl-2-phenyl-oxazol-4-yl)-ethoxy]-indan-4-yl}-acrylic acid as colorless crystals.

MS: 432.5 (M–H)⁻. NMR: (CDCl₃, 1H, δ, TMS, 300 MHz) 1.32 (t, J=7.1, 3H), 2.08 (quint., J=7.5, 2H), 2.39 (s, 3H), 2.86 (t, J=7.5, 2H), 3.00 (m, 4H), 3.95 (q, J=7.1, 2H), 4.30 (t, J=6.5, 2H), 6.74 (d, J=8.7, 1H), 7.20 (s, 1H), 7.39–7.46 (m, 3H), 7.96–7.99 (m, 2H), 8.02 (d, J=8.7, 1H), COOH very br.

Example 100

(S)-2-Methoxy-3-{7-[2-(5-methyl-2-phenyl-oxazol-4-yl)-ethoxy]-indan-4-yl}-propionic acid In analogy to the procedures described in examples 11 a] to 11 c], 7-[2-(5-methyl-2-phenyl-oxazol-4-yl)-ethoxy]-indan-4-carbaldehyde (example 91 b]) was reacted with (S)-4-benzyl-3-methoxyacetyl-oxazolidin-2-one and nBu₂BOTf to yield (S)-4-benzyl-3-[(2S,3R)-3-hydroxy-2-methoxy-3-{7-[2-(5-methyl-2-phenyl-oxazol-4-yl)-ethoxy[-indan-4-yl}-propionyl]-oxazolidin-2-one (according to NMR, one of the four isomers is strongly predominating; the configuration was tentatively assigned as 2S, 3R according to *Tetrahedron Asymmetry* 1999, 1353). Reduction of (S)-4-benzyl-3-[(2S,3R)-3-hydroxy-2-methoxy-3-{7-[2-(5-methyl-2-phenyl-oxazol-4-yl)-ethoxy]-indan-4-yl}-propionyl]oxazolidin-2-one with triethylsilane in trifluoroacetic acid then gave (S)-4-benzyl-3-(2(S)-methoxy-3-{7-[2-(5-methyl-2-phenyl-oxazol-4-yl)-ethoxy]-indan-4-yl}-propionyl)-oxazolidin-2-one. The (S)-4-benzyl-3-(2(S)-methoxy-3-{7-[2-(5-methyl-2-phenyl-oxazol-4-yl)-ethoxy]-indan-4-yl}-propionyl)-oxazolidin-2-one was subsequently saponified with 1N NaOH in THF to yield (S)-2-methoxy-3-{7-[2-(5-methyl-2-phenyl-oxazol-4-yl)- ethoxy]-in dan-4-yl}-propionic acid as colorless solid after crystallization from AcOEt/hexane. The enantiomeric excess was judged according to chiral HPLC (Chiralpak-AD) to be 97.7%.

MS: 420.4 (M–H)⁻. NMR: (CDCl₃, 1H, δ, TMS) 2.05 (quint., J=7.5, 2H), 2.38 (s, 3H), 2.84 (t, J=7.5, 2H), 2.87–3.00 (m, 5H), 3.05 (d×d, J=14.4, 4.8, 1H), 3.35 (s, 3H), 3.95 (d×d, J=7.8, 4.8, 1H), 4.21 (t, J=6.3, 2H), 6.63 (d, J=8.4, 1H), 6.98 (d, J=8.4, 1H), 7.40–7.46 (m, 3H), 7.95–7.99 (m, 2H), COOH very br.

Example 101 a] [rac]-3-(4-Hydroxy-naphthalen-1-yl)-2-methoxy-propionic acid methyl ester

In analogy to the procedure described in example 93 a], 4-benzyloxy-naphthalene-1-carbaldehyde (prepared from 4-hydroxy-naphthalene-1-carbaldehyde, benzylchloride, potassium carbonate in N,N-dimethylformamide at room temperature) was reacted with (methoxy-methoxycarbonyl-methyl)-triphenyl-phosphonium bromide [Tetrahedron 53(50), 17097–17114(1997)] to yield 3-(4-benzyloxy-naphthalen-1-yl)-2(Z,E)-methoxy-acrylic acid methyl ester. Hydrogenation of 3-(4-benzyloxy-naphthalen-1-yl)-2(Z,E)-methoxy-acrylic acid methyl ester as described in example 91 d] yielded [rac]-3-(4-hydroxy-naphthalen-1-yl)-2-methoxy-propionic acid methyl ester light rose oil.

MS: 259.1 (M–H)⁻, 229.2. NMR: (CDCl₃, 1H, δ, TMS, 300 MHz): 3.31–3.38 (m, 4H), 3.44–3.49 (q, J=5, 1H), 3.72 (s, 3H), 4.09–4.13 (d×d, J₁=5, J₂=8, 1H), 5.63 (s, 1H), 6.71 (d, J=7, 1H), 7.18 (d, J=8, 1H), 7.47–7.58 (m, 2H), 8.00–8.03 (m, 1H), 8.23–8.26 (m, 1H).

b] [rac]-3-(4-{2-[2-(2-Ethoxy-4-fluoro-phenyl)-5-methyl-oxazol-4-yl]-ethoxy}-naphthalen-1-yl)-2-methoxy-propionic acid In analogy to the procedure described in example 17 a], [rac]-3-(4-hydroxy-naphthalen-1-yl)-2-methoxy-propionic acid methyl ester was reacted with 2-[2-(2-ethoxy-4-fluoro-phenyl)-5-methyl-oxazol-4-yl]-ethanol (example 95) in the presence of triphenylphosphine and DEAD (diethyl azodicarboxylate) to yield [rac]-3-(4-{2-[2-(2-ethoxy-4-fluoro-phenyl)-5-methyl-oxazol-4-yl]-ethoxy}-naphthalen-1-yl)-2-methoxy-propionic acid methyl ester, which was further saponified in analogy to the procedure described in example 91 e] to yield [rac]-3-(4-{2-[2-(2-ethoxy-4-fluoro-phenyl)-5-methyl-oxazol-4-yl]-ethoxy}-naphthalen-1-yl)-2-methoxy-propionic acid as colorless solid.

MS: 492.2 (M–H)⁻. NMR: (CDCl₃, 1H, δ, TMS, 300 MHz): 1.42 (t, J=7, 3H), 2.41 (s, 3H), 3.12 (t, J=6, 2H), 3.23–3.31 (m, 4H), 3.52–3.58 (d×d, J₁=4, J₂=14, 1H), 4.04–4.11 (m, 3H), 4.37 (t, J=7, 2H), 6.65–6.77 (m, 3H), 7.25–7.27 (m, 1H), 7.44–7.56 (m, 2H), 7.79–7.84 (d×d, J₁=6, J₂=9, 1H), 8.01 (d, J=8, 1H), 8.28 (m, 1H), COOH very broad.

Example 102

[rac]-2-Methoxy-3-(4-{2-[2-(4-methoxy-phenyl)-5-methyl-oxazol-4-yl]-ethoxy}-naphthalen-1-yl)-propionic acid In analogy to the procedure described in example 17 a], [rac]-3-(4-hydroxy-naphthalen-1-yl)-2-methoxy-propionic acid methyl ester was reacted with 2-[2-(4-methoxy-phenyl)-5-methyl-oxazol-4-yl]-ethanol [J. Med. Chem. (1998), 41(25), 5037–5054] in the presence of triph-enylphosphine and DEAD (diethyl azodicarboxylate) to yield [rac]-2-methoxy-3-(4-{2-[2-(4-methoxy-phenyl)-5-methyl-oxazol-4-yl]-ethoxy}-naphthalen-1-yl)-propionic acid methyl ester, which was further saponified in analogy to the procedure described in example 91 e] to yield [rac]-2-methoxy-3-(4-{2-[2-(4-methoxy-phenyl-5-methyl-oxazol-4-yl]-ethoxy}-naphthalen-1-yl)-propionic acid as colorless solid.

MS: 460.3 (M–H)⁻, 428.3. NMR: (CDCl₃, 1H, δ, TMS, 300 MHz) 2.40 (s, 3H), 3.10 (t, J=6, 2H), 3.26–3.32 (m, 4H), 3.55–3.61 (d×d, J₁32 4, J₂=14, 1H), 3.84 (s, 3H), 4.09–4.13 (d×d, J₁=4, J₂9, 1H), 4.36 (t, J=7, 2H), 6.75 (d, J=8, 1H), 6.92–6.95 (m, 2H), 7.28 (m, 1H), 7.44–7.57 (m, 2H), 7.88–7.92 (m, 2H), 8.02 (d, J=8, 1H), 8.28 (m, 1H), COOH very broad.

Example 103

2Z-Ethoxy-3-{7-[2-(5-methyl-2-phenyl-oxazol-4-yl)-ethoxy]-benzo[b]thiophen-4-yl}-acrylic acid In analogy to the procedure described in example 91 c], 7-[2-(5-methyl-2-phenyl-oxazol-4-yl)-ethoxy]-benzo[b]thiophene-4-carbaldehyde (example 98 a]) was treated with (ethoxy-ethoxycarbonyl-methyl)-triphenyl-phosphonium chloride [Tetrahedron 50(25), 7543–56(1994)]in 2-propanol in the presence of potassium carbonate to yield the 2Z-ethoxy-3-{7-[2-(5-methyl-2-phenyl-oxazol-4-yl)-ethoxy]-benzo[b]thiophen-4-yl}-acrylic acid ethyl ester. The 2Z-ethoxy-3-{7-[2-(5-methyl-2-phenyl-oxazol-4-yl)-ethoxy]-benzo[b]thiophen-4-yl}-acrylic acid ethyl ester was further saponified in analogy to the procedure described in example 99 to yield the 2Z-ethoxy-3-{7-[2-(5-methyl-2-phenyl-oxazol-4-yl)-ethoxy]-benzo[b]thiophen-4-yl}-acrylic acid as colorless solid.

MS: 448.2 (M–H)⁻, 376.2. NMR: (CDCl₃, 1H, δ, TMS, 300 MHz) 1.33 (t, J=6, 3H), 2.45 (s, 3H), 3.11 (t, J=5, 2H), 3.99 (q, J=6, 2H), 4.50 (t, J=5, 2H), 6.87 (d, J=7, 1H), 7.39–7.46 (m, 3H), 7.49–7.57 (m, 2H), 7.64 (s, 1H), 7.97–8.00 (m, 2H), 8.24 (d, J=7, 1H), COOH very broad.

Example 104

[rac]-2-Ethoxy-3-{7-[2-(5-methyl-2-phenyl-oxazol-4-yl)-ethoxy]-benzo[b]thiophen-4-yl}-propionic acid 0.175 g (0.39 mmol) 2Z-Ethoxy-3-{7-[2-(5-methyl-2-phenyl-oxazol-4-yl)-ethoxy]-benzo[b]thiophen-4-yl}-acrylic acid (example 103) were hydrogenated with racemic Ru(OAc)₂[3,5-xyl-MeOBIPHEP] catalyst in ethanol at 60° C. and a pressure of 60 bar to give 0.167 g [rac]-2-ethoxy-3-{7-[2-(5-methyl-2-phenyl-oxazol-4-yl)-ethoxy]-benzo[b]thiophen-4-yl}-propionic acid as light grey solid.

MS: 450.2 (M–H)⁻, 404.0. NMR: (CDCl₃, 1H, δ, TMS, 300 MHz) 1.06 (t, J=6, 3H), 2.44 (s, 3H), 3.07 (t, J=5, 2H), 3.22–3.31 (m, 2H), 3.40–3.55 (m, 2H), 4.10–4.14 (m, 1H), 4.38 (t, J=5, 2H), 6.72 (d, J=7, 1H), 7.16 (d, J=7, 1H), 7.40–7.47 (m, 6H), 7.95–7.98 (m, 2H).

Example 105 a] [rac]-2-[1-Methyl-3-oxo-3-phenyl-(Z)-propenylamino]-3-{4-[2-(5-methyl-2-phenyl-oxazol-4-yl)-ethoxy]-benzo[b]thiophen-7-yl}-propionic acid ethyl ester 0.334 g (0.75 mmol) [rac]-2-Amino-3-{4-[2-(5-methyl-2-phenyl-oxazol-4-yl)-ethoxy]-benzo[b]thiophen-7-yl}-propionic acid ethyl ester (prepared from 4-[2-(7- bromomethyl-benzo[b]thiophen-4-yloxy)-ethyl]-5-methyl-2-phenyl-oxazole [PCT Int. Appl. (2001) WO01/79202] and N-(diphenylmethylene)glycine ethyl ester in analogy to the sequence described in examples 15 a] and 15 b]) and 0.161 g (0.97 mmol) benzoylacetone were dissolved in 25 ml of toluene. Then, 0.21 ml (1.5 mmol) triethylamine and 0.026 g (0.15 mmol) 4-toluene sulfonic acid were added and the reaction mixture was heated at reflux for 2 hours. After removing the solvent under reduced pressure, the residue was diluted in water/sodium hydrogen carbonate solution and the reaction mixture was extracted with dichloromethane. The combined organic phases were dried over $MgSO_4$ and evaporated. Purification of the residue by flash-chromatography (silica gel, eluent: gradient of hexane and ethyl acetate) gave 0.38 g (85%) [rac]-2-[1-methyl-3-oxo-3-phenyl-(Z)-propenylamino]-3-{4-[2-(5-methyl-2-phenyl-oxazol-4-yl)-ethoxy]-benzo[b]thiophen-7-yl}-propionic acid ethyl ester as light yellow oil.

MS: 595.1 (M+H)$^+$. NMR: (CDCl$_3$, 1H, δ, TMS, 300 MHz) 1.26 (t, J=6, 3H), 1.64 (s, 3H), 2.39 (s, 3H), 3.03–3.08 (t, J=6, 2H), 3.17–3.25 (d×d, J$_1$=8, J$_2$=13, 1H), 3.44–3.51 (d×d, J$_1$32 5, J$_2$=12, 1H), 4.19–4.26 (q, J=6, 2H), 4.34–4.39 (t, J=5, 2H), 4.58–4.66 (m, 1H), 6.70–6.73 (d, J=7, 1H), 7.12–7.14 (d, J=7, 1H), 7.26–7.52 (m, 9H), 7.84–7.99 (m, 4H), 11.73–11.76 (d, J=8, 1H).

b] [rac]-2-[1-Methyl-3-oxo-3-phenyl-(Z)-propenylamino]-3-{4-[2-(5-methyl-2-phenyl-oxazol-4-yl)-ethoxy]-benzo[b]thiophen-7-yl}-propionic acid 0.333 g (0.56 mmol) [rac]-2-[1-Methyl-3-oxo-3-phenyl-(Z)-propenylamino]-3-{4-[2-(5-methyl-2-phenyl-oxazol-4-yl)-ethoxy]-benzo[b]thiophen-7-yl}-propionic acid ethyl ester were dissolved in THF/EtOH 1:1 (10 ml) and treated with 1.4 ml (1.4 mmol) aqueous sodium hydroxide solution (1 molar) and the reaction mixture was stirred for 1 hour at room temperature. It was then acidified with 1N hydrochloric acid and extracted with dichloromethane. The combined organic phases were dried over MgSO$_4$ and evaporated. Purification by flash-chromatography (silica gel, eluent: gradient of dichloromethane and methanol) gave 0.218 g (69%) [rac]-2-[1-methyl-3-oxo-3-phenyl-(Z)-propenylamino]-3-{4-[2-(5-methyl-2-phenyl-oxazol-4-yl)-ethoxy]-benzo[b]thiophen-7-yl}-propionic acid as light yellow amorphous solid.

MS: 565.1 (M–H)$^-$, 521.2. NMR: (CDCl$_3$, 1H, δ, TMS, 300 MHz) 1.56 (s, 3H), 2.38 (s, 3H), 3.03–3.07 (t, J=6, 2H), 3.20–3.28 (m, 1H), 3.54–3.59 (m, 1H), 4.30–4.32 (t, J=6, 2H), 4.64 (m, 1H), 5.55 (s, 1H), 6.66–6.69 (d, J=7, 1H), 7.10–7.13 (d, J=7, 1H), 7.26–7.53 (m, 9H), 7.84–7.98 (m, 4H), 11.85–11.88 (d, J=8, 1H).

Example 106 a] 1-(4-Trifluoromethyl-phenyl)-butane-1,3-dione

To a stirred suspension of 1.70 g (39 mmol) sodium hydride in 20 ml THF kept under argon were added at room temperature 3.94 ml (40 mmol) ethyl acetate, followed by 0.1 ml of ethanol. Then, a solution of 3.76 g (20 mmol) 4-trifluoromethyl-acetophenone in 20 ml THF was added below 25° C., finally 0.12 g (0.32 mmol) dibenzo-18-crown-6 were added and the reaction mixture heated at reflux for 90 minutes. After cooling to approximately 0° C., the reaction mixture was acidified with 20 ml sulfuric acid (10% solution in water) and the reaction product was isolated by extraction with ether. The combined organic phases were dried over MgSO$_4$ and evaporated. The residue formed was finally purified by flash-chromatography (silica gel, eluent: gradient of hexane and ethyl acetate) to give 3.54 g (77%) of 1-(4-trifluoromethyl-phenyl)-butane-1,3-dione as yellow crystals.

MS: 230.1 (M), 215.0, 173.0. NMR: (CDCl$_3$, 1H, δ, TMS, 300 MHz) 2.24 (s, 3H), 6.20 (s, 1H), 7.69–7.72 (d, J=7, 2H), 7.96–7.99 (d, J=7, 2H), 15.99 (s, 1H).

b] [rac]-2-[1-Methyl-3-oxo-3-(4-trifluoromethyl-phenyl)-(Z)-propenylamino]-3-{4-[2-(5-methyl-2-phenyl-oxazol-4-yl)-ethoxy]-benzo[b]thiophen-7-yl}-propionic acid In analogy to the procedure described in example 105 a], [rac]-2-amino-3-{4-[2-(5-methyl-2-phenyl-oxazol-4-yl)-ethoxy]-benzo[b]thiophen-7-yl}-propionic acid ethyl ester was reacted with 1-(4-trifluoromethyl-phenyl)-butane-1,3-dione in toluene in the presence of a catalytic amount of p-toluene sulfonic acid at reflux to yield [rac]-2-[1-methyl-3-oxo-3-(4-trifluoromethyl-phenyl)-(Z)-propenylamino]-3-{4-[2-(5-methyl-2-phenyl-oxazol-4-yl)-ethoxy]-benzo[b]thiophen-7-yl}-propionic acid ethyl ester, which was further saponified in analogy to the procedure described in example 105 b] to yield [rac]-2-[1-methyl-3-oxo-3-(4-trifluoromethyl-phenyl)-(Z)-propenylamino]-3-{4-[2-(5-methyl-2-phenyl-oxazol-4-yl)-ethoxy]-benzo[b]thiophen-7-yl}-propionic acid as light yellow solid.

MS: 635.1 (M+H)$^+$, 591.1. NMR: (CDCl$_3$, 1H, δ, TMS, 300 MHz) 1.59 (s, 3H), 2.39 (s, 3H), 3.04–3.09 (t, J=6, 2H), 3.23–3.28 (m, 1H), 3.53–3.59 (m, 1H), 4.30–4.34 (t, J=6, 2H), 4.67 (m, 1H), 5.53 (s, 1H), 6.67–6.70 (d, J=7, 1H), 7.10–7.12 (d, J=7, 1H), 7.29–7.31 (d, J=5, 1H), 7.40–7.48 (m, 4H), 7.61–7.64 (d, J=7, 2H), 7.92–7.97 (m, 4H), 11.93–11.96 (d, J=8, 1H), COOH very broad.

Example 107 a] [rac]-3-{4-[2-(5-Methyl-2-phenyl-oxazol-4-yl)-ethoxy]-benzo[b]thiophen-7-yl}-2-[3-oxo-3-phenyl-1-trifluoromethyl-(Z)-propenylamino]-propionic acid ethyl ester 0.41 ml (2.3 mmol) N-Ethyl-diisopropylamine were added below 5° C. to a solution of 0.347 g (0.77 mmol) [rac]-2-amino-3-{4-[2-(5-methyl-2-phenyl-oxazol-4-yl)-ethoxy]-benzo[b]thiophen-7-yl}-propionic acid ethyl ester and 0.322 g (1.16 mmol) (E/Z)-3-bromo-4,4,4-trifluoro-1-phenyl-but-2-en-1-one [PCT Int. Appl. (2000), WO0008002A1] in 10 ml MeOH and the reaction mixture was stirred for 18 hours at ambient temperature. It was then diluted with water and extracted with ethyl acetate. The combined organic phases were dried over MgSO$_4$ and evaporated. The residue formed was purified by flash-chromatography (silica gel, eluent: gradient of hexane and ethyl acetate) to yield 0.49 g (98%) of [rac]-3-{4-[2-(5-methyl-2-phenyl-oxazol-4-yl)-ethoxy]-benzo[b]thiophen-7-yl}-2-[3-oxo-3-phenyl-1-trifluoromethyl-(Z)-propenylamino]-propionic acid ethyl ester as light yellow solid.

MS: 649.2 (M+H)$^+$. NMR: (CDCl$_3$, 1H, δ, TMS, 300 MHz) 1.15 (t, J=6, 3H), 2.38 (s, 3H), 3.03–3.07 (t, J=6, 2H), 3.27–3.34 (m, 1H), 3.40–3.47 (m, 1H), 4.10–4.17 (q, J=6, 2H), 4.37 (t, J=6, 2H), 4.70–4.73 (m, 1H), 6.22 (s, 1H), 6.71–6.74 (d, J=7, 1H), 7.11–7.14 (d, J=7, 1H), 7.30–7.32 (d, J=5, 1H), 7.40–7.49 (m, 7H), 7.87–7.99 (m, 4H), 10.96–10.99 (d, J=9, 1H).

b] [rac]-3-{4-[2-(5-Methyl-2-phenyl-oxazol-4-yl)-ethoxy]-benzo[b]thiophen-7-yl}-2-[3-oxo-3-phenyl-1-trifluoromethyl-(Z)-propenylamino]-propionic acid In analogy to the procedure described in example 105 b], [rac]-3-{4-[2-(5-methyl-2-phenyl-oxazol-4-yl)-ethoxy]- benzo[b]thiophen-7-yl}-2-[3-oxo-3-phenyl-1-trifluoromethyl-(Z)-propenylamino]-propionic acid ethyl ester was saponified to yield [rac]-3-{4-[2-(5-methyl-2-phenyl-oxazol-4-yl)-ethoxy]-benzo[b]thiophen-7-yl}-2-[3-oxo-3-phenyl-1-trifluoromethyl-(Z)-propenylamino]-propionic acid as rose solid.

MS: 619.0 (M−H)⁻, 575.0. NMR: (CDCl₃, 1H, δ, TMS, 300 MHz) 2.37 (s, 3H), 3.02–3.06 (t, J=6, 2H), 3.39–3.45 (m, 2H), 4.22–4.26 (t, J=6, 2H), 4.77–4.81 (m, 1H), 6.23 (s, 1H), 6.65–6.68 (d, J=7, 1H), 7.15–7.18 (d, J=7, 1H), 7.26–7.28 (d, J=5, 1H), 7.38–7.51 (m, 7H), 7.85–7.95 (m, 4H), 11.01–11.04 d, J=9, 1H), COOH very broad.

Example 108 a] 4-Benzyloxy-5,6,7,8-tetrahydro-naphthalene-1-carbaldehyde

In analogy to the procedure described in examples 91 b], 5-benzyloxy-1,2,3,4-tetrahydro-naphthalene [J. Org. Chem. (2001), 66(5), 1775–1780] was treated with dichloromethyl methyl ether and titanium tetrachloride to give 4-benzyloxy-5,6,7,8-tetrahydro-naphthalene-1-carbaldehyde as yellow solid.

MS: 266.2 (M), 91.2. NMR: (CDCl₃, 1H, δ, TMS, 300 MHz) 1.78–1.82 (m, 4H), 2.74–2.76 (m, 2H), 3.18–3.20 (m, 2H), 5.16 (s, 2H), 6.84–6.87 (d, J=7, 1H), 7.34–7.45 (m, 5H), 7.63–7.66 (d, J=7, 1H), 10.12 (s, 1H).

b] [rac]-2-Ethoxy-3-(4-hydroxy-5,6,7,8-tetrahydro-naphthalen-1-yl)-propionic acid ethyl ester In analogy to the procedure described in example 93 a], 4-benzyloxy-5,6,7,8-tetrahydro-naphthalene-1-carbaldehyde was reacted with (ethoxy-ethoxycarbonyl-methyl)-triphenyl-phosphonium chloride [Tetrahedron 50(25), 7543–56(1994)] to yield 3-(4-benzyloxy-5,6,7,8-tetrahydro-naphthalen-1-yl)-2(Z,E)-ethoxy-acrylic acid ethyl ester. Hydrogenation of 3-(4-benzyloxy-5,6,7,8-tetrahydro-naphthalen-1-yl)-2(Z,E)-ethoxy-acrylic acid ethyl ester as described in example 91 d] yielded [rac]-2-ethoxy-3-(4-hydroxy-5,6,7,8-tetrahydro-naphthalen-1-yl)-propionic acid ethyl ester as light yellow oil.

MS: 310.4 (M+NH₄)⁺, 293.4 (M+H)⁺, 247.3, 201.2. NMR: (CDCl₃, 1H, δ, TMS, 300 MHz) 1.14–1.17 (t, J=7, 3H), 1.21–1.25 (t, J=7, 3H), 1.79–1.80 (m, 4H), 2.64–2.79 (m, 4H), 2.92–2.94 (d, J=6, 2H), 3.29–3.36 (m, 1H), 3.53–3.61 (m, 1H), 3.94–3.97 (t, J=6, 1H), 4.14–4.20 (q, J=7, 2H), 4.58 (s, 1H), 6.55–6.57 (J=8, 1H), 6.90–6.92 (d, J=8, 1H).

c] [rac]-2-Ethoxy-3-{4-[2-(4-isopropyl-phenyl)-5-methyl-oxazol-4-ylmethoxy]-5,6,7,8-tetrahydro-naphthalen-1-yl}-propionic acid ethyl ester 0.037 g (1.54 mmol) Sodium hydride was added in small portions below 30° C. and under argon to a solution of 0.30 g (1.03 mmol) [rac]-2-ethoxy-3-(4-hydroxy-5,6,7,8-tetrahydro-naphthalen-1-yl)-propionic acid ethyl ester in 5.0 ml N,N-dimethylformamide. After 10 minutes, 0.384 g (1.54 mmol) 4-chloromethyl-2-(4-isopropyl-phenyl)-5-methyl-oxazole (prepared from 4-isopropyl-benzaldehyde and diacetyl monoxyme followed by treatment with POCl₃ in analogy to the procedures described in examples 21 a] and b]) were added and the reaction mixture then stirred for 16 hours at ambient temperature. It was then diluted with water and extracted with ether. The combined organic phases were dried over MgSO₄ and evaporated. The residue formed was purified by flash-chromatography (silica gel; eluent: gradient of hexane and ethyl acetate) to give 0.35 g (67%) of [rac]-2-ethoxy-3-{4-[2-(4-isopropyl-phenyl)-5-methyl-oxazol-4-ylmethoxy]-5,6,7,8-tetrahydro-naphthalen-1-yl}-propionic acid ethyl ester as colorless oil.

MS: 506.5 (M+H)⁺, 528.4 (M+Na)⁺. NMR: (CDCl₃, 1H, δ, TMS, 300 MHz) 1.14–1.17 (t, J=7, 3H), 1.20–1.24 (t, J=7, 3H), 1.27–1.28 (d, J=7, 6H), 1.76 (m, 4H), 2.42 (s, 3H), 2.70–2.75 (m, 4H), 2.94–2.96 (m, 3H), 3.31–3.35 (m, 1H), 3.55–3.59 (m, 1H), 3.96–3.99 (t, J=7, 1H), 4.14–4.19 (q, J=7, 2H), 4.97 (s, 2H), 6.74–6.76 (d, J=8, 1H), 6.98–7.00 (d, J=8, 1H), 7.29–7.31 (d, J=8, 2H), 7.92–7.94 (d, J=8, 2H).

d] [rac]-2-Ethoxy-3-{4-[2-(4-isopropyl-phenyl)-5-methyl-oxazol-4-ylmethoxy]-5,6,7,8-tetrahydro-naphthalen-1-yl}-propionic acid In analogy to the procedure described in example 91 e], [rac]-2-ethoxy-3-{4-[2-(4-isopropyl-phenyl)-5-methyl-oxazol-4-ylmethoxy]-5,6,7,8-tetrahydro-naphthalen-1-yl}-propionic acid ethyl ester was saponified to yield [rac]-2-ethoxy-3-{4-[2-(4-isopropyl-phenyl)-5-methyl-oxazol-4-ylmethoxy]-5,6,7,8-tetrahydro-naphthalen-1-yl}-propionic acid as colorless solid.

MS: 476.2 (M−H)⁻. NMR: (CDCl₃, 1H, δ, TMS, 300 MHz) 1.11–1.15 (t, J=9, 3H), 1.26–1.29 (d, J=8, 6H), 1.74–1.76 (m, 4H), 2.43 (s, 3H), 2.65–2.97 (m, 6H), 3.07–3.12 (d×d, $J_1$=4, $J_2$=13, 1H), 3.29–3.36 (m, 1H), 3.50–3.56 (m, 1H), 3.98–4.03 (d×d, $j_1$=4, $J_2$=8, 1H), 4.97 (s, 2H), 6.75–6.78 (d, J=7, 1H), 7.01–7.04 (d, J=7, 1H), 7.28–7.31 (d, J=7, 2H), 7.91–7.94 (d, J=7, 2H), COOH very broad.

Example 109

[rac]-2-Ethoxy-3-[4-(5-methyl-2-phenyl-oxazol-4-ylmethoxy)-5,6,7,8-tetrahydro-naphthalen-1-yl]-propionic acid In analogy to the procedure described in example 108 c], [rac]-2-ethoxy-3-(4-hydroxy-5,6,7,8-tetrahydro-naphthalen-1-yl)-propionic acid ethyl ester was treated with 4-chloromethyl-5-methyl-2-phenyloxazole and sodium hydride in N,N-dimethylformamide to yield [rac]-2-ethoxy-3-[4-(5-methyl-2-phenyl-oxazol-4-ylmethoxy)-5,6,7,8-tetrahydro-naphthalen-1-yl]-propionic acid ethyl ester, which was further saponified in analogy to the procedure described in example 91 e] to yield [rac]-2-ethoxy-3-[4-(5-methyl-2-phenyl-oxazol-4-ylmethoxy)-5,6,7,8-tetrahydro-naphthalen-1-yl]-propionic acid as colorless solid.

MS: 434.3 (M−H)⁻. NMR: (CDCl₃, 1H, δ, TMS, 300 MHz) 1.11–1.15 (t, J=7, 3H), 1.69–1.82 (m, 4H), 2.44 (s, 3H), 2.66–2.94 (m, 5H), 3.07–3.12 (m, 1H), 3.29–3.37 (m, 1H), 3.50–3.57 (m, 1H), 4.00–4.03 (m, 1H), 4.99 (s, 2H), 6.76–6.78 (d, J=8, 1H), 7.02–7.04 (d, J=8, 1H), 7.43–7.47 (m, 3H), 8.00–8.02 (m, 2H), COOH very broad.

Example 110

[rac]-2-Ethoxy-3-(4-{2-[2-(2-ethoxy-4-fluoro-phenyl)-5-methyl-oxazol-4-yl]-ethoxy}-5,6,7,8-tetrahydro-naphthalen-1-yl)-propionic acid In analogy to the procedure described in example 17 a], [rac]-2-ethoxy-3-(4-hydroxy-5,6,7,8-tetrahydro-naphthalen-1-yl)-propionic acid ethyl ester (example 108 b]) was reacted with 2-[2-(2-ethoxy-4-fluoro-phenyl)-5-methyl-oxazol-4-yl]-ethanol (example 95) in the presence of triphenylphosphine and DEAD (diethyl azodicarboxylate) to yield [rac]-2-ethoxy-3-(4-{2-[2-(2-ethoxy-4-fluoro-phenyl)-5-methyl-oxazol-4-yl]-ethoxy}-5,6,7,8-tetrahydro-naphthalen-1-yl)-propionic acid ethyl ester, which was further saponified in analogy to the procedure described in example 91 e] to yield [rac]-2-ethoxy-3-(4-{2-[2-(2-ethoxy-4-fluoro-phenyl)-5-methyl-oxazol-4-yl]-ethoxy}-5,6,7,8-tetrahydro-naphthalen-1-yl)-propionic acid as colorless solid.

MS: 510.3 (M–H)⁻. NMR: (CDCl₃, 1H, δ, TMS, 300 MHz) 1.10–1.14 (t, J=7, 3H), 1.44–1.47 (t, J=7, 3H), 1.67–1.82 (m, 4H), 2.36 (s, 3H), 2.63–2.75 (m, 4H), 2.86–2.92 (m, 1H), 2.97–3.00 (t, J=6, 2H), 3.06–3.10 (m, 1H), 3.30–3.36 (m, 1H), 3.47–3.55 (m, 1H), 3.97–4.00 (m, 1H), 4.07–4.13 (q, J=7, 2H), 4.18–4.21 (t, J=7, 2H), 6.62–6.64 (d, J=8, 1H), 6.67–6.72 (m, 2H), 6.97–6.99 (d, J=8, 1H), 7.80–7.84 (m, 1H), COOH very broad.

Example 111

[rac]-2-Ethoxy-3-(4-{2-[2-(4-fluoro-phenyl)-5-methyl-oxazol-4-yl]-ethoxy}-5,6,7,8-tetrahydro-naphthalen-1-yl)-propionic acid In analogy to the procedure described in example 17 a], [rac]-2-ethoxy-3-(4-hydroxy-5,6,7,8-tetrahydro-naphthalen-1-yl)-propionic acid ethyl ester (example 108 b]) was reacted with 2-[2-(4-fluoro-phenyl)-5-methyl-oxazol-4-yl]-ethanol [J. Med. Chem. (1998), 41(25), 5037–5054] in the presence of triphenylphosphine and DEAD (diethyl azodicarboxylate) to yield [rac]-2-ethoxy-3-(4-{2-[2-(4-fluoro-phenyl)-5-methyl-oxazol-4-yl]-ethoxy}-5,6,7,8-tetrahydro-naphthalen-1-yl)-propionic acid ethyl ester, which was further saponified in analogy to the procedure described in example 91 e] to yield [rac]-2-ethoxy-3-(4-{2-[2-(4-fluoro-phenyl)-5-methyl-oxazol-4-yl]-ethoxy}-5,6,7,8-tetrahydro-naphthalen-1-yl)-propionic acid as colorless solid.

MS: 466.2 (M–H)⁻, 422.3. NMR: (CDCl₃, 1H, δ, TMS, 400 MHz) 1.12 (t, J=7.2, 3H), 1.74 (m, 4H), 2.37 (s, 3H), 2.62–2.92 (m, 5H), 2.97 (t, J=6.4, 2H), 3.09 (dxd, J₁=4, J₂=14.4, 1H), 3.31–3.35 (m, 1H), 3.49–3.53 (m, 1H), 3.98–4.01 (m, 1H), 4.18–4.23 (m, 2H), 6.63 (d, J=8, 1H), 6.98 (d, J=8, 1H), 7.09–7.13 (m, 2H), 7.94–7.98 (m, 2H), COOH very br.

Example 112

[rac]-2-Ethoxy-3-(4-{3-[2-(4-methoxy-phenyl)-5-methyl-oxazol-4-yl]-propoxy}-5,6,7,8-tetrahydro-naphthalen-1-yl)-propionic acid In analogy to the procedure described in example 17 a], [rac]-2-ethoxy-3-(4-hydroxy-5,6,7,8-tetrahydro-naphthalen-1-yl)-propionic acid ethyl ester (example 108 b]) was reacted with 3-[2-(4-methoxy-phenyl)-5-methyl-oxazol-4-yl]-propanol (example 42 e]) in the presence of triphenylphosphine and DEAD (diethyl azodicarboxylate) to yield [rac]-2-ethoxy-3-(4-{3-[2-(4-methoxy-phenyl)-5-methyl-oxazol-4-yl]-propoxy}-5,6,7,8-tetrahydro-naphthalen-1-yl)-propionic acid ethyl ester, which was further saponified in analogy to the procedure described in example 91 e] to yield [rac]-2-ethoxy-3-(4-{3-[2-(4-methoxy-phenyl)-5-methyl-oxazol-4-yl]-propoxy}-5,6,7,8-tetrahydro-naphthalen-1-yl)-propionic acid as colorless solid.

MS: 492.2 (M–H)⁻, 448.3. NMR: (CDCl₃, 1H, δ, TMS, 400 MHz) 1.11 (t, 3H), 1.74 (m, 4H), 2.13 (t, J=6.4, 2H), 2.24 (s, 3H), 2.66–2.93 (m, 7H), 3.08 (d, J=12.4, 1H), 3.32 (m, 1H), 3.55 (m, 1H), 3.84–3.98 (m, 6H), 6.57 (d, J=8.4, 1H), 6.93 (d, J=8.8, 2H), 6.99 (d, J=8.4, 1H), 7.90 (d, J=8.8, 2H), COOH very broad.

Example 113

[rac]-2-Ethoxy-3-(4-{2-[5-methyl-2-(4-trifluoromethyl-phenyl)-oxazol-4-yl]-ethoxy}-5,6,7,8-tetrahydro-naphthalen-1-yl)-propionic acid In analogy to the procedure described in example 17 a], [rac]-2-ethoxy-3-(4-hydroxy-5,6,7,8-tetrahydro-naphthalen-1-yl)-propionic acid ethyl ester (example 108 b]) was reacted with 2-[5-methyl-2-(4-trifluoromethyl-phenyl)-oxazol-4-yl]-ethanol (prepared by conversion of the 4-trifluoromethyl-benzaldehyde into 2-[5-methyl-2-(4-trifluoromethyl-phenyl)-oxazol-4-yl]-ethanol in analogy to the sequence described in examples 21 a] to 21 e]) in the presence of triphenylphosphine and DEAD (diethyl azodicarboxylate) to yield [rac]-2-ethoxy-3-(4-{2-[5-methyl-2-(4-trifluoromethyl-phenyl)-oxazol-4-yl]-ethoxy}-5,6,7,8-tetrahydro-naphthalen-1-yl)-propionic acid ethyl ester, which was further saponified in analogy to the procedure described in example 91 e] to yield [rac]-2-ethoxy-3-(4-{2-[5-methyl-2-(4-trifluoromethyl-phenyl)-oxazol-4-yl]-ethoxy}-5,6,7,8-tetrahydro-naphthalen-1-yl)-propionic acid as colorless solid.

MS: 516.2 (M–H)⁻, 472.1. NMR: (CDCl₃, 1H, δ, TMS, 300 MHz) 1.13 (t, J=7.0, 3H), 1.69–1.80 (m, 4H), 2.40 (s, 3H), 2.60–2.74 (m, 4H), 2.86–3.05 (m, 4H), 3.30–3.35 (m, 1H), 3.51–3.57 (m, 1H), 3.97–4.01 (m, 1H), 4.20 (t, J=6.4, 2H), 6.63 (d, J=8.4, 1H), 6.99 (d, J=8.4, 1H), 7.66 (d, J=8.2, 2H), 8.08 (d, J=8.1, 2H), COOH very broad.

Example 114 a] (Benzyloxycarbonyl-methoxy-methyl)-triphenyl-phosphonium chloride

Methyl dimethoxyacetate (1.094 g, 8.15 mmol) and LiOH (420 mg, 10 mmol) were dissolved in 5 ml dioxane and 5 ml water at 0° C. and the reaction mixture stirred 30 minutes at 0° C. and 0.75 hours at r.t. It was then diluted with tBuOMe and washed with NaOH 1M/ice. The aqueous layer was acidified to pH 2 and extracted three times with AcOEt, the combined organic phases dried over Na₂SO₄ and evaporated to give the dimethoxy-acetic acid as a yellow oil (600 mg). Dimethoxy-acetic acid (8.86 g, 73.8 mmol), obtained from an analogous preparation, was dissolved in 100 ml acetonitrile at 0° C., benzylalcohol (7.3 ml, 70 mmol), EDCI (15 g, 80 mmol) and DMAP (855 mg, 7 mmol) were added and the reaction mixture kept at r.t. during 18 hours. It was then diluted with AcOEt, washed with water, HCl 1M, brine, Na₂CO₃ (10%) and brine again and the combined organic phases were dried over Na₂SO₄ and evaporated to give dimethoxy-acetic acid benzyl ester (10.4 g). To crude dimethoxy-acetic acid benzyl ester (4.86 g), were added acetylchloride (2 ml) and iodine (100 mg) as catalyst and the mixture was heated during 4 hours at 65° C., evaporated after addition of 100 ml of ether, diluted with 10 ml CH₂Cl₂ and added to a solution of triphenylphosphine (25 mmol, 6.63 g) in 50 ml CH₂Cl₂ and stirred 24 hours at r.t. A chromatography (silicagel; 0.6 kg; elution AcOEt and 1/1 AcOEt/ethanol) provided (benzyloxycarbonyl-methoxy-methyl)-triphenyl-phosphonium chloride as a white foam (6.87 g, 62%).

MS: (M+H⁺)⁺442.3. NMR (CDCl₃, 1H, δ, TMS): 3.91 (s, 3H), 4.92–5.17 (d, 2H), 6.98 (dxd, 2H), 7.19–7.31 (m, 3H), 7.55–7.90 (m, 15H), 8.64 (br.d, 1H).

b] 3-Methyl-4-[2-(5-methyl-2-phenyl-oxazol-4-yl)-ethoxy]-benzaldehyde

4-Hydroxy-3-methylbenzaldehyde (9 g, 66.10 mmol), methanesulfonic acid 2-(5-methyl-2-phenyl-oxazol-4-yl)-ethyl ester [PCT Int. Appl. (2000) WO0008002] (22.5 g, 80 mmol), KOH (80 mmol, 4.48 g) and tetrabutylammonium-hydrogensulfate (2 g) in 400 ml toluene/100 ml water were heated at 80° C. during 17 hours. The reaction mixture was then cooled to 0° C., washed with water/ice and brine, the aqueous layer extracted with tBuOMe, the combined organic layers dried over $Na_2SO_4$ and evaporated. The crude product was purified by chromatography ($SiO_2$; AcOEt/heptane) and the product was crystallized from $CH_2Cl_2$/heptane to yield 15 g (72%) of the title compound as a white solid.

MS: $(M+H^+)^+$322.3, $(2M+H^+)^+$643.2. NMR ($CDCl_3$, 1H, δ, TMS): 2.23 (s, 3H), 2.38 (s, 3H), 3.03 (t, 2H), 4.35 (t, 2H), 6.94 (d×d, 1H), 7.40–7.45 (m, 3H), 7.66–7.68 (m, 2H), 7.96–7.99 (m, 2H), 9.83 (s, 1H).

c] 2(Z,E)-Methoxy-3-{3-methyl-4-[2-(5-methyl-2-phenyl-oxazol-4-yl)-ethoxy]-phenyl}-acrylic acid benzyl ester 3-Methyl-4-[2-(5-methyl-2-phenyl-oxazol-4-yl)-ethoxy]-benzaldehyde (540 mg, 1.68 mmol) were dissolved in 2 ml $CH_2Cl_2$ and cooled at 0° C., (benzyloxycarbonyl-methoxy-methyl)-triphenyl-phosphonium chloride (1.04 g, 2.18 mmol) was added, followed by 1,1,3,3-tetramethylguanidine and the reaction mixture was stirred at r.t. during 3 days with two more additions of the phosphonium salt and the base (one equivalent of each). The reaction mixture was diluted with AcOEt, washed with HCl 1M/ice and brine, the aqueous layers extracted with AcOEt, the combined organic phases dried over $Na_2SO_4$ and evaporated. The crude product was purified by chromatography ($SiO_2$; AcOEt/heptane) to leave 605 mg (74%) of the title compound as a yellow oil.

MS: $(M+H^+)^+$484.4. NMR (DMSO-$d_6$, 1H, δ, TMS): 2.10 (s, 3H), 2.36 (s, 3H), 2.96 (t, 2H), 3.67 (s, 3H), 4.25 (t, 2H), 5.25 (s, 2H), 6.81 (s, 1H), 7.00 (d×d, 1H), 7.30–7.63 (m, 10H), 7.90–7.92 (m, 2H).

d] [rac]-2-Methoxy-3-{3-methyl-4-[2-(5-methyl-2-phenyl-oxazol-4-yl)-ethoxy]-phenyl}-propionic acid 2(Z,E)-Methoxy-3-{3-methyl-4-[2-(5-methyl-2-phenyl-oxazol-4-yl)-ethoxy]-phenyl}-acrylic acid benzyl ester (600 mg, 1.24 mmol) dissolved in 5 ml ethanol were treated with Pd-C 10% and the reaction mixture was vigorously stirred at r.t under a $H_2$ atmosphere for 7 hours. It was then filtered through celite, evaporated, chromatographed ($SiO_2$; AcOEt) and crystallized (AcOEt/heptane) to yield 145 mg (30%) of the title compound as a white solid.

MS: $(M-H)^-$394.2. NMR (DMSO-$d_6$, 1H, δ, TMS): 2.05 (s, 3H), 2.36 (s, 3H), 2.71–2.76 (2×d×d, 2×1H), 2.92 (t, 2H), 3.20 (s, 3H), 3.81–3.85 (m, 1H), 4.16 (t, 2H), 6.84 (d×d, 1H), 6.95–6.97 (m, 2H), 7.48–7.50 (m, 3H), 7.90–7.92 (m, 2H), 12.8 (br.s, 1H).

Example 115

[rac]-2-Methoxy-3-}3-methoxy-{4-[2-(5-methyl-2-phenyl-oxazol-4-yl)-ethoxy]-phenyl}-propionic acid In analogy to the procedures described in examples 114 b], c] and d], vanilline was reacted with methanesulfonic acid 2-(5-methyl-2-phenyl-oxazol-4-yl)-ethyl ester [PCT Int. Appl. (2000) WO0008002] to give 3-methoxy-4-[2-(5-methyl-2-phenyl-oxazol-4-yl)-ethoxy]-benzaldehyde. Treatment of 3-methoxy-4-[2-(5-methyl-2-phenyl-oxazol-4-yl)-ethoxy]-benzaldehyde with (benzyloxycarbonyl-methoxy-methyl)-triphenyl-phosphonium chloride then gave 2(Z,E)-methoxy-3-{3-methoxy-4-[2-(5-methyl-2-phenyl-oxazol-4-yl)-ethoxy]-phenyl}-acrylic acid benzyl ester, which was hydrogenated to yield [rac]-2-methoxy-3-{3-methoxy-4-[2-(5-methyl-2-phenyl-oxazol-4-yl)-ethoxy]-phenyl}-propionic acid as colorless solid.

MS: $(M-H)^-$410.4. NMR (DMSO-$d_6$, 1H, δ, TMS): 2.36 (s, 3H), 2.76 (d×d, 1H), 2.86 (d×d, 1H), 2.91 (t, 2H), 3.21 (s, 3H), 3.71 (s, 3H), 3.84–3.88 (m, 1H), 4.14 (t, 2H), 6.70 (d×d, 1H), 6.85 (d, 1H), 7.46–7.52 (m, 3H), 7.89–7.92 (m, 2H), 12.90 (br.s, 1H).

Example 116 a] [rac]-2-Ethoxy-3-(4-hydroxy-3-methoxy-phenyl)-propionic acid ethyl ester

In analogy to the procedure described in example 93 a], 4-benzyloxy-3-methoxy-benzaldehyde was reacted with (ethoxy-ethoxycarbonyl-methyl)-triphenyl-phosphonium chloride [Tetrahedron 50(25), 7543–56(1994)] to yield 3-(4-benzyloxy-3-methoxy-phenyl)-2(Z,E)-ethoxy-acrylic acid ethyl ester. Hydrogenation of 3-(4-benzyloxy-3-methoxy-phenyl)-2(Z,E)-ethoxy-acrylic acid ethyl ester as described in example 91 d] yielded [rac]-2-ethoxy-3-(4-hydroxy-3-methoxy-phenyl)-propionic acid ethyl ester as colorless solid.

MS: $(M)^+$268.1. NMR (DMSO-$d_6$, 1H, δ, TMS): 1.03 (t, 3H), 1.12 (t, 3H), 2.80 (d×d, 2H), 3.30–3.40 (m, 1H), 3.42–3.52 (m, 1H), 3.73 (s, 3H), 4.01–4.09 (m, 3H), 6.57 (d×d, 1H), 6.65 (d, 1H), 6.77 (d, 1H), 8.74 (br.s, 1H).

b] [rac]-2-Ethoxy-3-{3-methoxy-4-[2-(5-methyl-2-phenyl-oxazol-4-yl)-ethoxy]-phenyl}-propionic acid ethyl ester In analogy to the procedure described in example 17 a], [rac]-2-ethoxy-3-(4-hydroxy-3-methoxy-phenyl)-propionic acid ethyl ester was reacted with 2-(2-phenyl-5-methyl-oxazol-4yl)-ethanol in the presence of triphenylphosphine and DBAD (di-tert-butyl azodicarboxylate) to yield [rac]-2-ethoxy-3-{3-methoxy-4-[2-(5-methyl-2-phenyl-oxazol-4-yl)-ethoxy]-phenyl}-propionic acid ethyl ester as colorless oil.

MS: $(M+H^+)^+$454.3, $(M+2H^+)^+$455.2.

c] [rac]-Lithium 2-ethoxy-3-{3-methoxy-4-[2-(5-methyl-2-phenyl-oxazol-4yl)-ethoxy]-phenyl}-propionate

[rac]-2-Ethoxy-3-{3-methoxy-4-[2-(5-methyl-2-phenyl-oxazol-4yl)-ethoxy]-phenyl}-propionic acid ethyl ester (306 mg, 0.67 mmol) were dissolved in 3 ml dioxane and 2 ml water, 50 mg lithium hydroxide were added and the mixture stirred at r.t. during 24 hours. The reaction mixture was then chromatographed (MCI-gel; $CH_3CN/H_2O$) as lithium salt to yield 125 mg (43%) of the title compound as a white gum.

MS: $(M-H)^-$424.4. NMR (DMSO-$d_6$, 1H, δ, TMS): 0.98 (t, 3H), 2.36 (s, 3H), 2.55 (d×d, 1H), 2.80 (d×d, 1H), 2.85 (t, 2H), 3.05–3.15 (m, 1H), 3.48 (d×d, 1H), 3.52–3.62 (m, 1H), 3.70 (s, 3H), 4.13 (t, 2H), 6.67 (d×d, 1H), 6.80–6.83 (m, 2H), 7.47–7.51 (m, 3H), 7.92 (d×d, 2H).

Example 117

[rac]-3-{3,5-Dimethyl-4-[2-(5-methyl-2-phenyl-oxazol-4-yl)-ethoxy]-phenyl}-2-methoxy-propionic acid In analogy to the procedures described in examples 114 b], c] and d], 3,5-dimethyl-4-hydroxy-benzaldehyde was reacted with methanesulfonic acid 2-(5-methyl-2-phenyl-oxazol-4-yl)-ethyl ester [PCT Int. Appl. (2000) WO0008002] to give 3,5-dimethyl-4-[2-(5-methyl-2-phenyl-oxazol-4-yl)-ethoxy]-benzaldehyde. Treatment of 3,5-dimethyl-4-[2-(5-methyl-2-phenyl-oxazol-4-yl)-ethoxy]-benzaldehyde with (benzyloxycarbonyl-methoxy-methyl)-triphenyl-phosphonium chloride then gave 3-{3,5-dimethyl-4-[2-(5-methyl-2-phenyl-oxazol-4-yl)-ethoxy]-phenyl}-2(Z,E)-methoxy-acrylic acid benzyl ester, which was hydrogenated to yield [rac]-3-{3,5-dimethyl-4-[2-(5-methyl-2-phenyl-oxazol-4-yl)-ethoxy]-phenyl}-2-methoxy-propionic acid as light yellow oil.

MS: (M−H)⁻408.2. NMR (DMSO-$d_6$, 1H, δ, TMS): 2.09 (s, 6H), 2.38 (s, 3H), 2.67–2.80 (2×d×d, 2×1H), 2.91 (t, 2H), 3.20 (s, 3H), 3.84–3.90 (m, 1H), 3.95 (t, 2H), 6.82 (s, 2H), 7.45–7.55 (m, 3H), 7.92 (d×d, 2H), 12.8 (br.s, 1H).

Example 118 a] 2-Hydroxy-4-[2-(5-methyl-2-phenyl-oxazol-4-yl)-ethoxy]-benzaldehyde

A solution of 2,4-dihydroxy-benzaldehyde (2 g, 14.5 mmol) in 20 ml THF was cooled to 0° C. To this solution were added triphenylphosphine (9.7 g, 37 mmol), 2-(2-phenyl-5-methyl-oxazol-4-yl)-ethanol (2.84 g, 14 mmol) and finally during 0.75 hours a solution of di-tert-butyl azodicarboxylate (8.52 g, 37 mmol) in 20 ml THF. The reaction mixture was stirred overnight at room temperature, evaporated to dryness, purified by chromatography (SiO$_2$; AcOEt/heptane) and the product was crystallized from AcOEt/ether/heptane to yield 2.2 g (46%) as a colorless solid.

NMR (CDCl$_3$, 1H, δ, TMS): 2.37 (s, 3H), 2.97 (t, 2H), 4.31 (t, 2H), 6.44 (d, 1H), 6.53 (d×d, 1H), 7.39–7.43 (m, 4H), 7.95–7.99 (m, 2H), 9.70 (s, 1H), 11.42 (s, 1H).

b] 2-(4-Methoxy-benzyloxy)-4-[2-(5-methyl-2-phenyl-oxazol-4-yl)-ethoxy]-benzaldehyde A mixture of 2-hydroxy-4-[2-(5-methyl-2-phenyl-oxazol-4-yl)-ethoxy]-benzaldehyde (54 mg, 0.167 mmol), 4-methoxy-benzylchloride (58 mg, 0.368 mmol), KOH (56 mg, 1 mmol) and tetrabutylammonium-hydrogensulfate (50 mg) in 6 ml toluene and 5 ml water was heated at 80° C. during 6 hours. The reaction mixture was then cooled to 0° C., washed with water/ice and brine, the aqueous layer extracted with AcOEt, the combined organic layers dried over Na$_2$SO$_4$ and evaporated. The crude product was purified by chromatography (SiO$_2$; AcOEt/heptane) and the product was crystallized from heptane to yield 25 mg (34%) as a white solid.

MS: (M+H⁺)⁺444.4, (M+Na⁺)⁺466.3. NMR (CDCl$_3$, 1H, δ, TMS): 2.37 (s, 3H), 2.99 (t, 2H), 3.82 (s, 3H), 4.31 (t, 2H), 5.06 (s, 2H), 6.52 (d, 1H), 6.55 (d×d, 1H), 6.91 (d, 2H), 7.33 (d, 2H), 7.40–7.43 (m, 3H), 7.80 (d, 1H), 7.98 (d×d, 2H), 10.32 (s, 1H).

c] 2(Z,E)-Methoxy-3-{2-(4-methoxy-benzyloxy)-4-[2-(5-methyl-2-phenyl-oxazol-4yl)-ethoxy]-phenyl}-acrylic acid benzyl ester 2-(4-Methoxy-benzyloxy)-4-[2-(5-methyl-2-phenyl-oxazol-4-yl)-ethoxy]-benzaldehyde (400 mg, 0.90 mmol) were dissolved in 2 ml CH$_2$Cl$_2$ and cooled to 0° C., (benzyloxycarbonyl-methoxy-methyl)-triphenyl-phosphonium chloride (example 114 a]) (1.04 g, 2.18 mmol) were added, followed by 1,1,3,3-tetramethylguanidine (1 ml, 8 mmol) and the reaction mixture stirred at r.t. during 3 days. It was then diluted with AcOEt, washed with HCl (1M)/ice and brine and the aqueous layers extracted with AcOEt. The combined organic phases were dried over Na$_2$SO$_4$ and evaporated. The crude product was purified by chromatography (SiO$_2$; AcOEt/heptane) to leave 424 mg (purity 50%) as an oil.

MS: (M+H⁺)⁺606.0, (M+Na⁺)⁺628.1.

d] [rac]-3-{2-Hydroxy-4-[2-(5-methyl-2-phenyl-oxazol-4-yl)-ethoxy]-phenyl}-2-methoxy-propionic acid 2(Z,E)-Methoxy-3-{2-(4-methoxy-benzyloxy)-4-[2-(5-methyl-2-phenyl-oxazol-4-yl)-ethoxy]-phenyl}-acrylic acid benzyl ester (360 mg, 0.6 mmol) were dissolved in 5 ml AcOEt and the reaction mixture was vigorously stirred in the presence of Pd-C 10% at r.t. under a H$_2$ atmosphere for 18 hours. It was then filtered through celite, evaporated, chromatographed (MCI-gel, CH$_3$CN, H$_2$O) and crystallised (AcOEt/heptane) to yield 30 mg (13%) of the title compound as a white solid.

MS: (M+H⁺)⁺398.3. NMR (DMSO-$d_6$, 1H, δ, TMS): 2.36 (s, 3H), 2.55 (d×d, 1H), 2.87–2.92 (m, 3H), 3.25 (s, 3H), 3.46 (m, 1H), 4.10 (t, 2H), 6.24–6.26 (m, 2H), 6.90 (d, 1H), 7.48–7.50 (m, 3H), 7.90–7.92 (m, 2H), 12.8 (br.s, 2H).

Example 119 a] 2(Z,E)-Benzyloxycarbonylamino-3-{3-methyl-4-[2-(5-methyl-2-phenyl-oxazol-4-yl)-ethoxy]-phenyl}-acrylic acid methyl ester To a solution of 3-methyl-4-[2-(5-methyl-2-phenyl-oxazol-4-yl)-ethoxy]-benzaldehyde (500 mg, 1.56 mmol) (example 114 b]) in 2 ml CH$_2$Cl$_2$ and 1 ml THF cooled to 0° C., N-(benzyloxycarbonyl)-alpha-phosphonoglycine trimethyl ester (773 mg, 2.33 mmol) was added, followed by Hunig's base (0.5 ml) and the reaction mixture was stirred at r.t. for 6 hours. It was then diluted with AcOEt, washed with HCl 1M/ice and brine, the aqueous layers extracted with AcOEt, the combined organic phases dried over Na$_2$SO$_4$ and evaporated. The crude product was purified by chromatography (SiO$_2$; AcOEt/heptane) and crystallised (AcOEt/heptane) to leave 548 mg (67%) of the title compound as white solid.

MS: (M+H⁺)⁺527.2. NMR (DMSO-$d_6$, 1H, δ, TMS): 2.06 (s, 3H), 2.36 (s, 3H), 2.96 (t, 2H), 3.69 (s, 3H), 4.26 (t, 2H), 5.10 (s, 2H), 6.99 (d, 1H), 7.23–7.40 (m, 6H), 7.45–7.55 (m, 5H), 7.90–7.92 (m, 2H), 9.01 (br.s, 1H).

b] [rac]-2-Amino-3-{3-methyl-4-[2-(5-methyl-2-phenyl-oxazol-4-yl)-ethoxy]-phenyl}-propionic acid methyl ester, hydrochloride 2(Z,E)-Benzyloxycarbonylamino-3-{3-methyl-4-[2-(5-methyl-2-phenyl-oxazol-4-yl)-ethoxy]-phenyl}-acrylic acid methyl ester (552 mg, 1.05 mmol) dissolved in 20 ml AcOEt were vigorously stirred in the presence of Pd-C 10% at r.t. under a H$_2$ atmosphere for 16 hours. The reaction mixture was then filtered through celite, evaporated, chromatographed (SiO$_2$; AcOEt) and the product crystallized (HCl in ether) to yield 174 mg (40%) of the title compound as a white solid.

MS: (M+H⁺)⁺395.4. NMR (DMSO-$d_6$, 1H, δ, TMS): 2.07 (s, 3H), 2.37 (s, 3H), 2.93 (t, 2H), 2.95–3.06 (m, 2H), 3.67 (s, 3H), 4.18 (t, 2H), 6.89–6.99 (m, 3H), 7.47–7.52 (m, 3H), 7.90–7.92 (m, 2H), 8.45 (br.s, 3H).

c] [rac]-3-{3-Methyl-4-[2-(5-methyl-2-phenyl-oxazol-4-yl)-ethoxy]-phenyl}-2-(1-methyl-3-oxo-3-phenyl-(Z)-propenylamino)-propionic acid methyl ester A mixture of [rac]-2-amino-3-{3-methyl-4-[2-(5-methyl-2-phenyl-oxazol-4-yl)-ethoxy]-phenyl}-propionic acid methyl ester [1.83 g, 4.64 mmol, obtained via extraction of the HCl salt (dichloromethane, aqueous sodium carbonate)] and benzoylacetone (7.52 g, 46 mmol) in anisole (20 ml) was refluxed at 190° C. during 3 days, evaporated, chromatographed (SiO$_2$; AcOEt/heptane) and crystallized to deliver 840 mg (33%) of a white powder.

MS: (M+H$^+$)$^+$539.3. NMR (DMSO-d$_6$, 1H, δ, TMS): 1.88 (s, 3H), 2.03 (s, 3H), 2.33 (s, 3H), 2.93 (t, 2H), 2.95 (dxd, 1H), 3.02 (dxd, 1H), 3.67 (s, 3H), 4.17 (t, 2H), 4.63–4.69 (m, 1H), 5.76 (s, 1H), 6.87 (d, 1H), 6.97–6.99 (m, 2H), 7.40–7.49 (m, 6H), 7.82 (dxd, 2H), 7.91 (dxd, 2H), 11.4 , (s, 1H).

d] [rac]-3-{3-Methyl-4-[2-(5-methyl-2-phenyl-oxazol-4-yl)-ethoxy-phenyl}-2-(1-methyl-3-oxo-3-phenyl-(Z)-propenylamino)-propionic acid, calcium salt (1:0.5)

In analogy to the procedure described in example 105 b], [rac]-3-{3-methyl-4-[2-(5-methyl-2-phenyl-oxazol-4-yl)-ethoxy]-phenyl}-2-(1-methyl-3-oxo-3-phenyl-(Z)-propenylamino)-propionic acid methyl ester was saponified to yield crude [rac]-3-{3-methyl-4-[2-(5-methyl-2-phenyl-oxazol-4-yl)-ethoxy]-phenyl}-2-(1-methyl-3-oxo-3-phenyl-(Z)-propenylamino)-propionic acid (0.798 g, 1.52 mmol), which was dissolved in 10 ml of ethanol in the presence of triethylamine (2.28 mmol). This reaction mixture was heated to 60° C. during 70 minutes, cooled to room temperature and added over 15 minutes to a solution of Ca(CH$_3$COO)$_2$ (132 mg, 0.84 mmol) in 5 ml of water. The suspension was diluted with 50 ml of water, cooled and stirred for one hour. The calcium-salt was isolated by filtration, washed with 50 ml water and dried to obtain an off-white solid (620 mg, 75%).

MS: (M−H)$^-$523.1. NMR (DMSO-d$_6$, 1H, δ, TMS): 1.65 (s, 3H), 2.01 (s, 3H), 2.33 (s, 3H), 2.68 (dxd, 1H), 2.89 (t, 2H), 3.12 (dxd, 1H), 3.95–4.02 (m, 1H), 4.14 (t, 2H), 5.15 (s, 1H), 6.81 (d, 1H), 6.97–6.99 (m, 2H), 7.37–7.49 (2m, 2x3H), 7.76 (dxd, 2H), 7.90 (dxd, 2H), 11.4 (d, 1H), Example 120 a] 4-Benzyloxy-benzofuran

To a suspension of potassium carbonate (2.68 g, 19.4 mmol) in N,N-dimethylformamide (8 ml) was added a solution of 4-hydroxy-benzofuran (2.6 g, 19.4 mmol) in N,N-dimethylformamide (8 ml) at 2° C. under an argon atmosphere (for the preparation of 4-hydroxy-benzofuran see: G. Kneen, P. J. Maddocks, Syn. Commun. 1986, 16, 1635–1640.). After stirring for 50 min at 2° C., benzyl bromide (3.3 ml, 19.4 mmol) was added over a period of 15 min at 2° C. The suspension was stirred for additional 30 min at 2° C. and for 1.5 h at ambient temperature. After adding ice water (20 ml), the solution was extracted two times with diethyl ether. The combined extracts were washed three times with brine and dried over sodium sulfate. Evaporation of the solvent gave a yellow oil which was purified by column chromatography (silica gel, hexane) to give 4.3 g (19.2 mmol, 99%) of the title compound as colorless oil.

MS: 224.1 (M)$^+$, 91.2. NMR: (CDCl$_3$, 1H, 400 MHz, δ, TMS) 5.21 (s, 2H), 6.72 (d, J=8, 1H), 6.91 (d, J=2, 1H), 7.14–7.26 (m, 2H), 7.31–7.42 (m, 3H), 7.48 (d, J=8, 2H), 7.54 (d, J=2, 1H).

b] 4-Benzyloxy-benzofuran-7-carbaldehyde

Dry N,N-dimethylformamide (12.1 g, 166 mmol) was added dropwise with stirring and cooling under an argon atmosphere to phosphorous oxychloride (11.4 g, 75 mmol) at such a rate that the temperature did not exceed 10° C. After 30 min at 10° C., a solution of 4-benzyloxy-benzofuran (9.3 g, 41 mmol) in N,N-dimethylformamide (9 ml) was added dropwise within 30 min. The reaction mixture was stirred 30 min at ambient temperature and then continuously heated to 100° C. After 10 min at 100° C. the mixture was heated at 85° C. for 3 h, cooled to 10° C., neutralized with 25% aqueous sodium acetate, with cooling, and extracted with diethyl ether. The extract was washed with saturated aqueous sodium bicarbonate and water and dried over sodium sulfate. Removal of the solvent under reduced pressure gave a brown oil which was purified by column chromatography (silica gel, hexane/AcOEt=19/1) to give 1.8 g (7 mmol, 17%) of the title compound as yellow oil.

MS: 252.1 (M)$^+$, 91.1. NMR: (CDCl$_3$, 1H, 400 MHz, δ, TMS) 5.30 (s, 2H), 6.85 (d, J=8, 1H), 6.97 (d, J=2, 1H), 7.36–7.48 (m, 5H), 7.69 (d, J=2, 1H), 7.75 (d, J=8, 1H), 10.24 (s, 1H).

c] 3-(4-Benzyloxy-benzofuran-7-yl)-2Z-ethoxy-acrylic acid ethyl ester

A suspension of (ethoxy-ethoxycarbonyl-methyl)-triphenyl-phosphonium chloride (2.04 g, 4.8 mmol) and DBU (0.8 g, 5.2 mmol) in THF (40 ml) was stirred for 10 min at ambient temperature under an argon atmosphere [for the preparation of (ethoxy-ethoxycarbonyl-methyl)-triphenyl-phosphonium chloride see: K. K. Bach, H. R. El-Seedi, H. M. Jensen, H. B. Nielsen, I. Thomson, K. B. G. Torssell, Tetrahedron 1994, 50, 7543–7556]. 4-Benzyloxy-benzofuran-7-carbaldehyde (0.8 g, 3.2 mmol) was added and the mixture was heated under reflux for 12 h. The solvent was concentrated at reduced pressure, the residue taken up with ethyl acetate, washed with saturated aqueous NH$_4$Cl solution and two times with brine. The organic layer was dried over sodium sulfate, the solvent removed under reduced pressure and the residue purified by column chromatography (silica gel, hexane/AcOEt=9/1) to give 0.8 g (2.2 mmol, 69%) of the title compound as colorless oil.

MS: 366.1 (M)$^+$, 275.1, 173.0, 91.1. NMR: (CDCl$_3$, 1H, 400 MHz, δ, TMS) 1.37–1.45 (m, 6H), 4.04 (q, J=8, 2H), 4.32 (q, J=8, 2H), 5.24 (s, 2H), 6.77 (d, J=9, 1H), 6.92 (d, J=2, 1H), 7.33–7.49 (m, 5H), 7.53 (s, 1H), 7.58 (d, J=2, 1H), 8.15 (d, J=8, 1H).

d] [rac]-3-(4-Benzyloxy-benzofuran-7-yl)-2-ethoxy-propionic acid methyl ester

Magnesium turnings (0.5 g, 20.6 mmol) were added to a stirred solution of 3-(4-benzyloxy-benzofuran-7-yl)-2Z-ethoxy-acrylic acid ethyl ester (0.8 g, 2.18 mmol) in methanol (26 ml) and THF (13 ml) at ambient temperature. The suspension was warmed to 40° C. until evolution of hydrogen commenced. Then, the heating bath was replaced by a water bath, additional magnesium turnings (1 g, 41.2 mmol) were added and stirring of the reaction mixture was continued for 12 h. The suspension was cooled to 0° C., then 25% aqueous hydrochloric acid was added till all the solid had dissolved. The mixture was extracted twice with ethyl acetate and the combined ethyl acetate solutions were washed three times with water and dried over sodium sulfate. The solvent was evaporated to afford the title compound (0.77 g, 2.16 mmol, 99%) which was used in the next stage without further purification.

MS: 354.2 (M)⁺, 237.2, 91.2. NMR: (CDCl₃, 1H, 400 MHz, δ, TMS) 1.12 (t, J=7.2, 3H), 3.19–3.38 (m, 3H), 3.55–3.61 (m, 1H), 3.68 (s, 3H), 4.23 (d×d, J=8.8, J=6.4, 1H), 5.18 (s, 2H), 6.65 (d, J=8.8, 1H), 6.90 (d, J=2.4, 1H), 7.05 (d, J=8.8, 1H), 7.34–7.42 (m, 3H), 7.47 (d, J=8, 2H), 7.55 (d, J=2.4, 1H).

e] [rac]-2-Ethoxy-3-(4-hydroxy-benzofuran-7-yl)-propionic acid methyl ester

Dimethyl sulfide (4.4 ml, 60 mmol) and boron trifluoride diethyl etherate (46% purity, 3.3 ml, 12 mmol) were added to a ice cold solution of [rac]-3-(4-benzyloxy-benzofuran-7-yl)-2-ethoxy-propionic acid methyl ester (0.85 g, 2.4 mmol) in dichloromethane (25 ml) under an argon atmosphere. The mixture was stirred for 6 h at ambient temperature, poured into ice water and extracted three times with dichloromethane. The combined extract was washed with brine and dried over sodium sulfate. Removal of the solvent under reduced pressure gave a brown oil which was purified by column chromatography (silica gel, hexane/AcOEt=4/1) to give 0.45 g (1.7 mmol, 71%) of the title compound as light yellow oil.

MS: 263.0 (M−H)⁻. NMR: (CDCl₃, 1H, 400 MHz, δ, TMS) 1.13 (t, J=7.2, 3H), 3.19–3.41 (m, 3H), 3.56–3.65 (m, 1H), 3.67 (s, 3H), 4.22 (d×d, J=8, J=7.2, 1H), 5.04 (s, 1H), 6.54 (d, J=8.8, 1H), 6.83 (d, J=2.4, 1H), 6.99 (d, J=8.8, 1H), 7.56 (d, J=2.4, 1H).

f] [rac]-2-Ethoxy-3-[4-(5-methyl-2-phenyl-oxazol-4-ylmethoxy)-benzofuran-7-yl]-propionic acid Potassium carbonate (37 mg, 300 μmol, 1.4 eq.) and potassium iodide (4 mg, 30 μmol, 0.1 eq.) were added to a solution of [rac]-2-ethoxy-3-(4-hydroxy-benzofuran-7-yl)-propionic acid methyl ester (50 mg, 189 μmol) and 4-chloromethyl-5-methyl-2-phenyl-oxazole (39 mg, 189 μmol, 1 eq.) in N,N-dimethylformamide (0.5 ml). The mixture was shaken at 80° C. for 12 h, filtered off and the filtrate evaporated in vacuo to give [rac]-2-ethoxy-3-[4-(5-methyl-2-phenyl-oxazol-4-ylmethoxy)-benzofuran-7-yl]-propionic acid methyl ester. Crude [rac]-2-ethoxy-3-[4-(5-methyl-2-phenyl-oxazol-4-ylmethoxy)-benzofuran-7-yl]-propionic acid methyl ester was dissolved in a 2:1:1 mixture of THF/ethanol/water. Lithium hydroxide (40 mg, 945 μmol, 5 eq.) was added and the solution was shaken at ambient temperature for 12 h. Acidification with 25% aqueous hydrochloric acid and evaporation of the solvent in vacuo were followed by purification through a preparative HPLC column to give the title compound (28 mg, 66 μmol, 35%) as white solid.

MS: 420.2 (M−H)⁻, 374.2, 249.1. NMR: (DMSO-d₆, 1H, 400 MHz, δ, TMS) 1.00 (t, J=7.2, 3H), 2.46 (s, 3H), 3.09 (d×d, J=15.2, J=8, 1H), 3.19 (d×d, J=15.2, J=6.4, 1H), 3.28–3.30 (m, 1H), 3.47–3.53 (m, 1H), 4.13 (d×d, J=8.8, J=5.6, 1H), 5.13 (s, 2H), 6.90 (d, J=8.0, 1H), 6.91 (d, J=2.4, 1H), 7.12 (d, J=8.0, 1H), 7.52–7.54 (m, 3H), 7.90 (d, J=2.4, 1H), 7.94–7.97 (m, 2H), 12.69 (s, 1H).

Example 121

[rac]-2-Ethoxy-3-[4-(5-methyl-2-thiophen-2-yl-oxazol-4-ylmethoxy)-benzofuran-7-yl]-propionic acid In analogy to the procedure described in example 120 f], 2-ethoxy-3-(4-hydroxy-benzofuran-7-yl)-propionic acid methyl ester (example 120 e]) was reacted with 4-chloromethyl-5-methyl-2-thiophen-2-yl-oxazole (prepared from thiophen-2-carbaldehyde and diacetyl monoxyme followed by treatment with POCl₃ in analogy to the procedures described in examples 21 a] and b]) in the presence of potassium carbonate and potassium iodide to yield [rac]-2-ethoxy-3-[4-(5-methyl-2-thiophen-2-yl-oxazol-4-ylmethoxy)-benzofuran-7-yl]-propionic acid methyl ester, which was further saponified in analogy to the procedure described in example 120 f] to yield [rac]-2-ethoxy-3-[4-(5-methyl-2-thiophen-2-yl-oxazol-4-ylmethoxy)-benzofuran-7-yl]-propionic acid as white solid.

MS: 426.2 (M−H)⁻, 380.2,249.0. NMR: (DMSO-d₆, 1H, 400 MHz, δ, TMS) 1.00 (t, J=7.2, 3H), 2.43 (s, 3H), 3.07 (d×d, J=15.2, J=8, 1H), 3.19 (d×d, J=15.2, J=6.4, 1H), 3.28–3.32 (m, 1H), 3.49–3.53 (m, 1H), 4.12 (d×d, J=8, J=6.4, 1H), 5.10 (s, 2H), 6.87 (d, J=8, 1H), 6.90 (d, J=2.4, 1H), 7.12 (d, J=8, 1H), 7.21 (t, J=4, 1H), 7.66 (d, J=4, 1H), 7.76 (d, J=4, 1H), 7.90 (d, J=2.4, 1H), 12.70 (br.s, 1H).

Example 122 a] 4-Chloromethyl-2-(4-ethyl-phenyl)-5-methyl-oxazole

In analogy to the procedure described in example 21 a], 4-ethyl-benzaldehyde was reacted with diacetyl monoxyme in the presence of glacial acetic acid and a stream of dry hydrogen chloride to yield 2-(4-ethyl-phenyl)-4,5-dimethyl-oxazole 3-oxide, which was further treated with phosphorous oxychloride in dichloromethane in analogy to the procedure described in example 21 b] to yield 4-chloromethyl-2-(4-ethyl-phenyl)-5-methyl-oxazole as colorless crystals.

MS: 236.2 (M+H)⁺, 200.3, 129.0. NMR: (CDCl₃, 1H, 400 MHz, δ, TMS) 1.26 (t, J=7.2, 3H), 2.42 (s, 3H), 2.69 (q, J=7.2, 2H), 4.55 (s, 2H), 7.27 (d, J=8, 2H), 7.91 (d, J=8, 2H).

b] [rac]-2-Ethoxy-3-{4-[2-(4-ethyl-phenyl)-5-methyl-oxazol-4-ylmethoxy]-benzofuran-7-yl}-propionic acid In analogy to the procedure described in example 120 f], 2-ethoxy-3-(4-hydroxy-benzofuran-7 7-yl)-propionic acid methyl ester (example 120 e]) was reacted with 4-chloromethyl-2-(4-ethyl-phenyl)-5-methyl-oxazole in the presence of potassium carbonate and potassium iodide to yield [rac]-2-ethoxy-3-{4-[2-(4-ethyl-phenyl)-5-methyl-oxazol-4-ylmethoxy]-benzofuran-7-yl}-propionic acid methyl ester, which was further saponified in analogy to the procedure described in example 120 f] to yield [rac]-2-ethoxy-3-{4-[2-(4-ethyl-phenyl)-5-methyl-oxazol-4-ylmethoxy]-benzofuran-7-yl}-propionic acid as white solid.

MS: 448.2 (M−H)⁻, 375.1, 281.2. NMR: (DMSO-d₆, 1H, 400 MHz, δ, TMS) 1.00 (t, J=7.2, 3H), 1.21 (t, J=8, 3H), 2.45 (s, 3H), 2.67 (q, J=8, 2H), 3.06 (d×d, J=15.2, J=8, 1H), 3.19 (d×d, J=15.2, J=6.4, 1H), 3.28–3.32 (m, 1H), 3.49–3.53 (m, 1H), 4.12 (d×d, J=8, J=6.4, 1H), 5.12 (s, 2H), 6.90 (d, J=8, 1H), 6.91 (d, J=2.4, 1H), 7.12 (d, J=8, 1H), 7.36 (d, J=8, 2H), 7.86 (d, J=8, 2H), 7.90 (d, J=2.4, 1H), 12.70 (br. s, 1H).

Example 123 a] 2-(4-tert-Butyl-phenyl)-4-chloromethyl-5-methyl-oxazole

In analogy to the procedure described in example 21 a], 4-tert-butyl-benzaldehyde was reacted with diacetyl monoxyme in the presence of glacial acetic acid and a stream of dry hydrogen chloride to yield 2-(4-tert-butyl-phenyl)-4,5-dimethyl-oxazole 3-oxide, which was further treated with phosphorous oxychloride in dichloromethane in analogy to the procedure described in example 21 b] to yield 2-(4-tert-butyl-phenyl)-4-chloromethyl-5-methyl-oxazole as colorless solid.

MS: 264.3 (M+H)$^+$, 228.3, 187.2. NMR: (CDCl$_3$, 1H, 400 MHz, δ, TMS) 1.34 (s, 9H), 2.42 (s, 3H), 4.56 (s, 2H), 7.45 (d, J=8.8, 2H), 7.92 (d, J=8.8, 2H).

b] [rac]-3-{4-[2-(4-tert-Butyl-phenyl)-5-methyl-oxazol-4-ylmethoxy]-benzofuran-7-yl}-2-ethoxy-propionic acid In analogy to the procedure described in example 120 f], 2-ethoxy-3-(4-hydroxy-benzofuran-7-yl)-propionic acid methyl ester (example 120 e]) was reacted with 2-(4-tert-butyl-phenyl)-4-chloromethyl-5-methyl-oxazole in the presence of potassium carbonate and potassium iodide to yield [rac]-3-{4-[2-(4-tert-butyl-phenyl)-5-methyl-oxazol-4-ylmethoxy]-benzofuran-7-yl}-2-ethoxy-propionic acid methyl ester, which was further saponified in analogy to the procedure described in example 120 f] to yield [rac]-3-{4-[2-(4-tert-butyl-phenyl)-5-methyl-oxazol-4-ylmethoxy]-benzofuran-7-yl}-2-ethoxy-propionic acid as white solid.

MS: 476.2 (M−H)$^−$, 430.3, 381.1, 281.2. NMR: (DMSO-d$_6$, 1H, 400 MHz, δ, TMS) 1.00 (t, J=7.2, 3H), 1.31 (s, 9H), 2.45 (s, 3H), 3.07 (dxd, J=15.2, J=8, 1H), 3.19 (dxd, J=15.2, J=6.4, 1H), 3.26–3.32 (m, 1H), 3.48–3.55 (m, 1H), 4.12 (dxd, J=8, J=6.4, 1H), 5.12 (s, 2H), 6.89 (d, J=8, 1H), 6.90 (d, J=2.4, 1H), 7.11 (d, J=8, 1H), 7.54 (d, J=8, 2H), 7.88 (d, J=8, 2H), 7.90 (d, J=2.4, 1H), 12.70 (br, s, 1H).

Example 124 a] 4-Chloromethyl-2-(4-isopropoxy-phenyl)-5-methyl-oxazole

In analogy to the procedure described in example 21 a], 4-isopropoxy-benzaldehyde was reacted with diacetyl monoxyme in the presence of glacial acetic acid and a stream of dry hydrogen chloride to yield 2-(4-isopropoxy-phenyl)-4,5-dimethyl-oxazole 3-oxide, which was further treated with phosphorous oxychloride in dichloromethane in analogy to the procedure described in example 21 b] to yield 4-chloromethyl-2-(4-isopropoxy-phenyl)-5-methyl-oxazole as colorless liquid.

MS: 266.3 (M+H)$^+$, 224.2, 188.3. NMR: (CDCl$_3$, 1H, 400 MHz, δ, TMS) 1.36 (d, J=7.2, 6H), 2.40 (s, 3H), 4.54 (s, 2H), 4.61 sept., J=7.2, 1H), 6.92 (d, J=8, 2H), 7.91 (d, J=8, 2H).

b] [rac]-2-Ethoxy-3-{4-[2-(4-isopropoxy-phenyl)-5-methyl-oxazol-4-ylmethoxy]-benzofuran-7-yl}-propionic acid In analogy to the procedure described in example 120 f], 2-ethoxy-3-(4-hydroxy-benzofuran-7-yl)-propionic acid methyl ester (example 120 e]) was reacted with 4-chloromethyl-2-(4-isopropoxy-phenyl)-5-methyl-oxazole in the presence of potassium carbonate and potassium iodide to yield [rac]-2-ethoxy-3-{4-[2-(4-isopropoxy-phenyl)-5-methyl-oxazol-4-ylmethoxy]-benzofuran-7-yl}-propionic acid methyl ester, which was further saponified in analogy to the procedure described in example 120 f] to yield [rac]-2-ethoxy-3-{4-[2-(4-isopropoxy-phenyl)-5-methyl-oxazol-4-ylmethoxy]-benzofuran-7-yl}-propionic acid as white solid.

MS: 478.2 (M−H)$^−$, 432.6, 375.2, 281.2. NMR: (DMSO-d$_6$, 1H, 400 MHz, δ, TMS) 1.00 (t, J=7.2, 3H), 1.29 (d, J=6.4, 6H), 2.43 (s, 3H), 3.07 (dxd, J=15.2, J=8, 1H), 3.19 (dxd, J=15.2, J=6.4, 1H), 3.27–3.33 (m, 1H), 3.48–3.55 (m, 1H), 4.13 (dxd, J=8, J=6.4, 1H), 4.70 (sept., J=6.4, 1H), 5.10 (s, 2H), 6.89 (d, J=8, 1H), 6.91 (d, J=2.4, 1H), 7.03 (d, J=8.8, 2H), 7.11 (d, J=8, 1H), 7.85 (d, J=8.8, 2H), 7.90 (d, J=2.4, 1H), 12.70 (br. s, 1H).

Example 125 a] [rac]-2-Ethoxy-3-(4-hydroxy-2,3-dihydro-benzofuran-7-yl)-propionic acid ethyl ester A solution of 3-(4-benzyloxy-benzofuran-7-yl)-2Z-ethoxy-acrylic acid ethyl ester (420 mg, 1.15 mmol) (example 120 c]) in methanol (17 ml) was hydrogenated over 10% palladium on charcoal (100 mg) at ambient temperature for 20 h. The catalyst was filtered off, the solvent evaporated under reduced pressure and the residue chromatographed (silica gel, hexane/AcOEt=4/1) to give 240 mg (0.86 mmol, 75%) of the title compound as colorless liquid.

MS: 279.1 (M−H)$^−$, 265.2, 217.1, 141.0. NMR: (CDCl$_3$, 1H, 400 MHz, δ, TMS) 1.16 (t, J=7.2, 3H), 1.22 (t, J=7.2, 3H), 2.87–2.97 (m, 2H), 3.15 (t, J=7.2, 2H), 3.36–3.44 (m, 1H), 3.55–3.62 (m, 1H), 4.08 (t, J=7.2, 1H), 4.15 (q, J=7.2, 2H), 4.59 (t, J=8, 2H), 4.64 (br. s, 1H), 6.22 (d, J=8, 1H), 6.84 (d, J=8, 1H).

b] [rac]-2-Ethoxy-3-[4-(5-methyl-2-phenyl-oxazol-4-ylmethoxy)-2,3-dihydro-benzofuran-7-yl]-propionic acid In analogy to the procedure described in example 120 f], [rac]-2-ethoxy-3-(4-hydroxy-2,3-dihydro-benzofuran-7-yl)-propionic acid ethyl ester was reacted with 4-chloromethyl-5-methyl-2-phenyl-oxazole in the presence of potassium carbonate and potassium iodide to yield [rac]-2-ethoxy-3-[4-(5-methyl-2-phenyl-oxazol-4-ylmethoxy)-2,3-dihydro-benzofuran-7-yl]-propionic acid ethyl ester, which was further saponified in analogy to the procedure described in example 120 f] to yield [rac]-2-ethoxy-3-[4-(5-methyl-2-phenyl-oxazol-4-ylmethoxy)-2,3-dihydro-benzofuran-7-yl]-propionic acid as white solid.

MS: 422.2 (M−H)$^−$, 378.3, 251.1. NMR: (DMSO-d$_6$, 1H, 400 MHz, δ, TMS) 1.03 (t, J=7.2, 3H), 2.44 (s, 3H), 2.71 (dxd, J=15.2, J=8, 1H), 2.83 (dxd, J=15.2, J=6.4, 1H), 3.06 (t, J=8,2H), 3.25–3.32 (m, 1H), 3.45–3.52 (m, 1H), 3.96 (dxd, J=8, J=6.4, 1H), 4.52 (t, J=8, 2H), 5.00 (s, 2H), 6.58 (d, J=8, 1H), 6.93 (d, J=8, 1H), 7.48–7.55 (m, 3H), 7.93–7.96 (m, 2H), 12.55 (br. s, 1H).

Example 126

[rac]-2-Ethoxy-3-{4-[2-(4-ethyl-phenyl)-5-methyl-oxazol-4-ylmethoxy]-2,3-dihydro-benzofuran-7-yl}-propionic acid In analogy to the procedure described in example 120 f], [rac]-2-ethoxy-3-(4-hydroxy-2,3-dihydro-benzofuran-7-yl)-propionic acid ethyl ester (example 125 a]) was reacted with 4-chloromethyl-2-(4-ethyl-phenyl)-5-methyl-oxazole (example 122 a]) in the presence of potassium carbonate and potassium iodide to yield [rac]-2-ethoxy-3-{4-[2-(4-ethyl-phenyl)-5-methyl-oxazol-4-ylmethoxy]-2,3-dihydro-benzofuran-7-yl}-propionic acid ethyl ester, which was further saponified in analogy to the procedure described in example 120 f] to yield [rac]-2-ethoxy-3-{4-[2-(4-ethyl-phenyl)-5-methyl-oxazol-4-ylmethoxy]-2,3-dihydro-benzofuran-7-yl}-propionic acid as white solid.

MS: 450.3 (M−H)⁻, 406.2, 251.1. NMR: (DMSO-$d_6$, 1H, 400 MHz, δ, TMS) 1.03 (t, J=7.2, 3H), 1.21 (t, J=8, 3H), 2.43 (s, 3H), 2.64–2.74 (m, 3H), 2.83 (dxd, J=15.2, J=6.4, 1H), 3.06 (t, J=8, 2H), 3.25–3.32 (m, 1H), 3.45–3.52 (m, 1H), 3.96 (dxd, J=8, J=6.4, 1H), 4.51 (t, J=8, 2H), 4.98 (s, 2H), 6.58 (d, J=8, 1H), 6.92 (d, J=8, 1H), 7.36 (d, J=8, 2H), 7.85 (d, J=8, 2H), 12.60 (br. s, 1H).

Example 127

[rac]-3-{4-[2-(4-tert-Butyl-phenyl)-5-methyl-oxazol-4-ylmethoxy]-2,3-dihydro-benzofuran-7-yl}-2-ethoxy-propionic acid In analogy to the procedure described in example 120 f], [rac]-2-ethoxy-3-(4-hydroxy-2,3-dihydro-benzofuran-7-yl)-propionic acid ethyl ester (example 125 a]) was reacted with 2-(4-tert-butyl-phenyl)-4-chloromethyl-5-methyl-oxazole (example 123 a]) in the presence of potassium carbonate and potassium iodide to yield [rac]-3-{4-[2-(4-tert-butyl-phenyl)-5-methyl-oxazol-4-ylmethoxy]-2,3-dihydro-benzofuran-7-yl}-2-ethoxy-propionic acid ethyl ester, which was further saponified in analogy to the procedure described in example 120 f] to yield [rac]-3-{4-[2-(4-tert-butyl-phenyl)-5-methyl-oxazol-4-ylmethoxy]-2,3-dihydro-benzofuran-7-yl}-2-ethoxy-propionic acid as white solid.

MS: 478.2 (M−H)⁻, 434.4, 375.1, 299.1, 281.2, 251.1. NMR: (DMSO-$d_6$, 1H, 400 MHz, δ, TMS) 1.03 (t, J=7.2, 3H), 1.31 (s, 9H), 2.43 (s, 3H), 2.71 (dxd, J=15.2, J=8, 1H), 2.83 (dxd, J=15.2, J=6.4, 1H), 3.06 (t, J=8, 2H), 3.25–3.32 (m, 1H), 3.45–3.52 (m, 1H), 3.95 (dxd, J=8, J=6.4, 1H), 4.51 (t, J=8, 2H), 4.99 (s, 2H), 6.58 (d, J=8, 1H), 6.92 (d, J=8, 1H), 7.54 (d, J=8, 2H), 7.87 (d, J=8, 2H), 12.60 (br. s, 1H).

Example 128

[rac]-2-Ethoxy-3-{4-[2-(4-isopropoxy-phenyl)-5-methyl-oxazol-4-ylmethoxy]-2,3-dihydro-benzofuran-7-yl}-propionic acid In analogy to the procedure described in example 120 f], [rac]-2-ethoxy-3-(4-hydroxy-2,3-dihydro-benzofuran-7-yl)-propionic acid ethyl ester (example 125 a]) was reacted with 4-chloromethyl-2-(4-isopropoxy-phenyl)-5-methyl-oxazole (example 124 a]) in the presence of potassium carbonate and potassium iodide to yield [rac]-2-ethoxy-3-{4-[2-(4-isopropoxy-phenyl)-5-methyl-oxazol-4-ylmethoxy]-2,3-dihydro-benzofuran-7-yl}-propionic acid ethyl ester, which was further saponified in analogy to the procedure described in example 120 f] to yield [rac]-2-ethoxy-3-{4-[2-(4-isopropoxy-phenyl)-5-methyl-oxazol-4-ylmethoxy]-2,3-dihydro-benzofuran-7-yl}-propionic acid as white solid.

MS: 480.3 (M−H)⁻, 436.7, 281.2, 251.1. NMR: (DMSO-$d_6$, 1H, 400 MHz, δ, TMS) 1.03 (t, J=7.2, 3H), 1.29 (d, J=7.2, 6H), 2.41 (s, 3H), 2.71 (dxd, J=15.2, J=8, 1H), 2.83 (dxd, J=15.2, J=6.4, 1H), 3.06 (t, J=8, 2H), 3.25–3.32 (m, 1H), 3.45–3.52 (m, 1H), 3.96 (dxd, J=8, J=6.4, 1H), 4.51 (t, J=8, 2H), 4.70 (sept., J=7.2, 1H), 4.97 (s, 2H), 6.57 (d, J=8, 1H), 6.92 (d, J=8, 1H), 7.03 (d, J=8, 2H), 7.84 (d, J=8, 2H), 12.60 (br. s, 1H).

Example 129 a] 4-Benzyloxy-2-methyl-benzaldehyde

Dry N,N-dimethylformamide (34.2 ml, 444 mmol) was added dropwise with stirring and cooling under an argon atmosphere to phosphorous oxychloride (18.3 ml, 200 mmol) at such a rate that the temperature did not exceed 10° C. After 30 min stirring at 0° C., a solution of 1-benzyloxy-3-methyl-benzene (22 g, 111 mmol) in N,N-dimethylformamide (22 ml) was added dropwise within 30 min (for the preparation of 1-benzyloxy-3-methyl-benzene see: D. Bogdal, J. Pielichowski, A. Boron, *Syn. Commun.* 1998, 28, 3029–3039). The reaction mixture was stirred 30 min at ambient temperature and then continuously heated to 110° C. After 10 min at 110° C., the mixture was kept at 90° C. for 3.5 h, cooled to 10° C., neutralized with 25% aqueous sodium acetate, with cooling, and extracted with ethyl acetate. The combined organic layers were washed with saturated aqueous sodium bicarbonate and brine and dried over sodium sulfate. Removal of the solvent under reduced pressure gave a brown oil which was purified by column chromatography (silica gel, hexane/AcOEt=19/1) to give 4.3 g (19 mmol, 17%) of the title compound as yellow solid.

MS: 226.1 (M)⁺, 91.2. NMR: (CDCl₃, 1H, 400 MHz, δ, TMS) 2.65 (s, 3H), 5.13 (s, 2H), 6.83 (d, J=1.6, 1H), 6.91 (dxd, J=8.8, J=1.6, 1H), 7.32–7.44 (m, 5H), 7.75 (d, J=8.8, 1H), 10.12 (s, 1H).

b] 3-(4-Benzyloxy-2-methyl-phenyl)-2Z-ethoxy-acrylic acid ethyl ester (Ethoxy-ethoxycarbonyl-methyl)-triphenyl-phosphonium chloride (3.79 g, 8.8 mmol) and potassium carbonate (1.46 g, 10.6 mmol) were added to a solution of 4-benzyloxy-2-methyl-benzaldehyde (0.8 g, 3.5 mmol) in isopropanol (10 ml) at 10° C. under an argon atmosphere [for the preparation of (ethoxy-ethoxycarbonyl-methyl)-triphenyl-phosphonium chloride see: K. K. Bach, H. R. El-Seedi, H. M. Jensen, H. B. Nielsen, I. Thomson, K. B. G. Torssell, *Tetrahedron* 1994, 50, 7543–7556]. The suspension was heated to 60° C. After 12 h and after 20 h (ethoxy-ethoxycarbonyl-methyl)-triphenyl-phosphonium chloride (each time 3.79 g, 8.8 mmol) and potassium carbonate (each time 1.46 g, 10.6 mmol) were added again. After 36 h the suspension was filtered off and the filtrate was evaporated under reduced pressure. The residue was dissolved in dichloromethane, washed with saturated aqueous ammonium chloride and ice water and dried over sodium sulfate. The solvent was removed under reduced pressure and the residue purified by column chromatography (silica gel, dichloromethane) to give 0.7 g (2.1 mmol, 58%) of the title compound as yellow liquid.

MS: 340.2 (M)⁺, 249.2, 147.1, 91.1. NMR: (CDCl₃, 1H, 400 MHz, δ, TMS) 1.31 (t, J=7.2, 3H), 1.37 (t, J=7.2, 3H), 2.37 (s, 3H), 3.91 (q, J=7.2, 2H), 4.30 (q, J=7.2, 2H), 5.07 (s, 2H), 6.82–6.85 (m, 2H), 7.18 (s, 1H), 7.33–7.44 (m, 5H), 8.08 (d, J=8.8, 1H).

c] [rac]-2-Ethoxy-3-(4-hydroxy-2-methyl-phenyl)-propionic acid ethyl ester

A solution of 3-(4-benzyloxy-2-methyl-phenyl)-2Z-ethoxy-acrylic acid ethyl ester (1 g, 2.9 mmol) in ethanol (50 ml) was hydrogenated over 10% palladium on charcoal (250 mg) at ambient temperature for 2 h. The catalyst was filtered off and the solvent evaporated under reduced pressure to give 600 mg (2.4 mmol, 81%) of the title compound as yellow liquid which was used in the next stage without further purification.

MS: 270.4 (M+NH₄)⁺, 253 (M)⁺, 207.2, 165.3. NMR: (CDCl₃, 1H, 400 MHz, δ, TMS) 1.15 (t, J=7.2, 3H), 1.22 (t, J=7.2, 3H), 2.30 (s, 3H), 2.95 (d, J=7.2, 2H), 3.28–3.36 (m, 1H), 3.54–3.62 (m, 1H), 3.95 (t, J=7.2, 1H), 4.16 (q, J=7.2, 2H), 4.54 (s, 1H), 6.59 (dxd, J=8, J=1.6, 1H), 6.63 (d, J=1.6, 1H), 7.04 (d, J=8, 1H).

d] [rac]-2-Ethoxy-3-[2-methyl-4-(5-methyl-2-phenyl-oxazol-4-ylmethoxy)-phenyl]-propionic acid In analogy to the procedure described in example 120 f], [rac]-2-ethoxy-3-(4-hydroxy-2-methyl-phenyl)-propionic acid ethyl ester was reacted with 4-chloromethyl-5-methyl-2-phenyl-oxazole in the presence of potassium carbonate and potassium iodide to yield [rac]-2-ethoxy-3-[2-methyl-4-(5-methyl-2-phenyl-oxazol-4-ylmethoxy)-phenyl]-propionic acid ethyl ester, which was further saponified in analogy to the procedure described in example 120 f] to yield [rac]-2-ethoxy-3-[2-methyl-4-(5-methyl-2-phenyl-oxazol-4-ylmethoxy)-phenyl]-propionic acid as light yellow solid.

MS: 394.2 (M−H)$^-$, 348.5. NMR: (CDCl$_3$, 1H, 300 MHz, δ, TMS) 1.13 (t, J=7.2, 3H), 2.34 (s, 3H), 2.44 (s, 3H), 2.93 (dxd, J=15.2, J=8, 1H), 3.11 (dxd, J=15.2, J=4, 1H), 3.30–3.36 (m, 1H), 3.50–3.57 (m, 1H), 4.01 (dxd, J=8, J=4, 1H), 4.97 (s, 2H), 6.79 (dxd, J=8, J=1.6, 1H), 6.83 (d, J=1.6, 1H), 7.13 (d, J=8, 1H), 7.43–7.46 (m, 3H), 8.00–8.03 (m, 2H).

Example 130

[rac]-2-Ethoxy-3-[2-methyl-4-(5-methyl-2-thiophen-2-yl-oxazol-4-ylmethoxy)-phenyl]-propionic acid In analogy to the procedure described in example 120 f], [rac]-2-ethoxy-3-(4-hydroxy-2-methyl-phenyl)-propionic acid ethyl ester (example 129 c]) was reacted with 4-chloromethyl-5-methyl-2-thiophen-2-yl-oxazole in the presence of potassium carbonate and potassium iodide to yield [rac]-2-ethoxy-3-[2-methyl-4-(5-methyl-2-thiophen-2-yl-oxazol-4-ylmethoxy)-phenyl]-propionic acid ethyl ester, which was further saponified in analogy to the procedure described in example 120 f] to yield [rac]-2-ethoxy-3-[2-methyl-4-(5-methyl-2-thiophen-2-yl-oxazol-4-ylmethoxy)-phenyl]-propionic acid as light yellow solid. MS: 400.3 (M−H)$^-$, 354.1, 281.2. NMR: (CDCl$_3$, 1H, 300 MHz, δ, TMS) 1.13 (t, J=7.2, 3H), 2.34 (s, 3H), 2.41 (s, 3H), 2.93 (dxd, J=15.2, J=8.8, 1H), 3.12 (dxd, J=15.2, J=4, 1H), 3.30–3.38 (m, 1H), 3.49–3.57 (m, 1H), 4.01 (dxd, J=8, J=4.8, 1H), 4.94 (s, 2H), 6.78 (dxd, J=8, J=1.6, 1H), 6.82 (d, J=1.6, 1H), 7.08–7.14 (m, 2H), 7.40 (dxd, J=4.8, J=0.8, 1H), 7.64 (dxd, J=4.0, J=0.8, 1H).

Example 131

[rac]-2-Ethoxy-3-}4-[2-(4-ethyl-phenyl)-5-methyl-oxazol-4-ylmethoxy]-2-methyl-phenyl}-propionic acid In analogy to the procedure described in example 120 f], [rac]-2-ethoxy-3-(4-hydroxy-2-methyl-phenyl)-propionic acid ethyl ester (example 129 c]) was reacted with 4-chloromethyl-2-(4-ethyl-phenyl)-5-methyl-oxazole (example 122 a]) in the presence of potassium carbonate and potassium iodide to yield [rac]-2-ethoxy-3-{4-[2-(4-ethyl-phenyl)-5-methyl-oxazol-4-ylmethoxy]-2-methyl-phenyl}-propionic acid ethyl ester, which was further saponified in analogy to the procedure described in example 120 f] to yield [rac]-2-ethoxy-3-{4-[2-(4-ethyl-phenyl)-5-methyl-oxazol-4-ylmethoxy]-2-methyl-phenyl}-propionic acid as light yellow solid.

MS: 422.2 (M−H)$^-$, 376.3. NMR: (CDCl$_3$, 1H, 300 MHz, δ, TMS) 1.12 (t, J=7.2, 3H), 1.26 (t, J=8, 3H), 2.33 (s, 3H), 2.42 (s, 3H), 2.69 (q, J=8, 2H), 2.93 (dxd, J=15.2, J=8.8, 1H), 3.11 (dxd, J=15.2, J=4, 1H), 3.30 –3.35 (m, 1H), 3.49–3.57 (m, 1H), 4.00 (dxd, J=8, J=4, 1H), 4.95 (s, 2H), 6.79 (dxd, J=8, J=1.6, 1H), 6.82 (d, J=1.6, 1H), 7.12 (d, J=8, 1H), 7.27 (d, J=8, 2H), 7.92 (d, J=8, 2H).

Example 132

[rac]-3-{4-[2-(4-tert-Butyl-phenyl-5-methyl-oxazol-4-ylmethoxy]-2-methyl-phenyl}-2-ethoxy-propionic acid In analogy to the procedure described in example 120 f], [rac]-2-ethoxy-3-(4-hydroxy-2-methyl-phenyl)-propionic acid ethyl ester (example 129 c]) was reacted with 2-(4-tert-butyl-phenyl)-4-chloromethyl-5-methyl-oxazole (example 123 a]) in the presence of potassium carbonate and potassium iodide to yield [rac]-3-{4-[2-(4-tert-butyl-phenyl)-5-methyl-oxazol-4-ylmethoxy]-2-methyl-phenyl}-2-ethoxy-propionic acid ethyl ester, which was further saponified in analogy to the procedure described in example 120 f] to yield [rac]-3-{4-[2-(4-tert-butyl-phenyl)-5-methyl-oxazol-4-ylmethoxy]-2-methyl-phenyl}-2-ethoxy-propionic acid as light yellow solid.

MS: 450.3 (M−H)$^-$, 422.2, 404.3. NMR: (CDCl$_3$, 1H, 300 MHz, δ, TMS) 1.12 (t, J=7.2, 3H), 1.35 (s, 9H), 2.34 (s, 3H), 2.43 (s, 3H), 2.93 (dxd, J=15.2, J=8.8, 1H), 3.13 (dxd, J=15.2, J=4.8, 1H), 3.26–3.38 (m, 1H), 3.48–3.58 (m, 1H), 4.00 (dxd, J=8, J=4, 1H), 4.96 (s, 2H), 6.79 (dxd, J=8, J=1.6, 1H), 6.82 (d, J=1.6, 1H), 7.12 (d, J=8, 1H), 7.45 (d, J=8, 2H), 7.93 (d, J=8, 2H).

Example 133

[rac]-2-Ethoxy-3-{4-[2-(4-isopropoxy-phenyl)-5-methyl-oxazol-4-ylmethoxy]-2-methyl-phenyl}-propionic acid In analogy to the procedure described in example 120 f], [rac]-2-ethoxy-3-(4-hydroxy-2-methyl-phenyl)-propionic acid ethyl ester (example 129 c]) was reacted with 4-chloromethyl-2-(4-isopropoxy-phenyl)-5-methyl-oxazole (example 124 a]) in the presence of potassium carbonate and potassium iodide to yield [rac]-2-ethoxy-3-{4-[2-(4-isopropoxy-phenyl)-5-methyl-oxazol-4-ylmethoxy]-2-methyl-phenyl}-propionic acid ethyl ester, which was further saponified in analogy to the procedure described in example 120 f] to yield [rac]-2-ethoxy-3-{4-[2-(4-isopropoxy-phenyl)-5-methyl-oxazol-4-ylmethoxy]-2-methyl-phenyl}-propionic acid as light yellow solid.

MS: 452.3 (M−H)$^-$, 406.3,281.2. NMR: (CDCl$_3$, 1H, 300 MHz, δ, TMS) 1.12 (t, J=7.2, 3H), 1.36 (d, J=7.2, 6H), 2.37 (s, 3H), 2.41 (s, 3H), 2.92 (dxd, J=15.2, J=8.8, 1H), 3.12 (dxd, J=15.2, J=4.8, 1H), 3.26–3.36 (m, 1H), 3.48–3.58 (m, 1H), 4.01 (dxd, J=8, J=4, 1H), 4.61 (sept., J=7.2, 1H), 4.94 (s, 2H), 6.79 (dxd, J=8, J=1.6, 1H), 6.83 (d, J=1.6, 1H), 6.92 (d, J=8, 1H), 7.12 (d, J=8, 2H), 7.93 (d, J=8, 2H).

Example 134

(S)-2-But-3-enyloxy-3-{3,5-dimethyl-4-[2-(5-methyl-2-phenyl-oxazol-4-yl)-ethoxy]-phenyl}-propionic acid In analogy to the procedures described in example 11 a] to 11 c], 3,5-dimethyl-4-[2–5-methyl-2-phenyl-oxazol-4-yl)-ethoxy]-benzaldehyde (example 117) was reacted with (S)-4-benzyl-3-(2-but-3-enyloxy-acetyl)-oxazolidin-2-one (for the preparation of (S)-4-benzyl-3-(2-but-3-enyloxy-acetyl)-oxazolidin-2-one see: M. T. Crimmins, A. L. Choy, J. Am. Chem. Soc. 1999, 121, 5653–5660) and nBu$_2$BOTf to yield (S)-4-benzyl-3-((2S,3R)-2-but-3-enyloxy-3-{3,5- dimethyl-4-[2-(5-methyl-2-phenyl-oxazol-4-yl)-ethoxy]-phenyl}-3-hydroxy-propionyl)-oxazolidin-2-one (according to NMR, one of the four isomers is strongly predominating; the configuration was tentatively assigned as 2S, 3R according to D. Haigh, H. C. Birrell, B. C. C. Cantello, D. S. Eggleston, R. C. Haltiwanger, R. M. Hindley, A. Ramaswamy, N. C. Stevens, *Tetrahedron Asymmetry* 1999, 10, 1353–1367). Reduction of (S)-4-benzyl-3-((2S,3R)-2-but-3-enyloxy-3-{3,5-dimethyl-4-[2-(5-methyl-2-phenyl-oxaxol-4-yl)-ethoxy]-phenyl}-3-hydroxy-propionyl)-oxazolidin-2-one with triethylsilane in trifluoroacetic acid gave (S)-4-benzyl-3-((2S)-but-3-enyloxy-3-{3,5-dimethyl-4-[2-(5-methyl-2-phenyl-oxazol-4-yl)-ethoxy]-phenyl}-propionyl)-oxazolidin-2-one. (S)-4-Benzyl-3-((2S)-but-3-enyloxy-3-{3,5-dimethyl-4-[2-(5-methyl-2-phenyl-oxazol-4-yl)-ethoxyl-phenyl}-propionyl)-oxazolidin-2-one was subsequently saponified with 1 M NaOH in THF to yield (S)-2-but-3-enyloxy-3-{3,5-dimethyl-4-[2-(5-methyl-2-phenyl-oxazol-4-yl)-ethoxy]-phenyl}-propionic acid as colorless solid.

MS: 438.3 (M−H)$^-$, 394.2, 293.2, 263.1, 219.4. NMR: (DMSO-$d_6$, 1H, 400 MHz, δ, TMS) 2.10 (s, 6H), 2.18 (q, J=7.2,2H), 2.38 (s, 3H), 2.67–2.77 (m, 1H), 2.81 (dxd, J=15.2, J=5.6, 1H), 2.91 (t, J=7.2, 2H), 3.23–3.32 (m, 2H), 3.51–3.57 (m, 1H), 3.90–3.98 (m, 3H), 4.94 (dxd, J=8.8, J=0.8, 1H), 5.00 (dxd, J=16.8, J=0.8, 1H), 5.63–5.74 (m, 1H), 6.85 (s, 2H), 7.45–7.52 (m, 3H), 7.92 (dxd, J=8, J=0.8, 2H), 12.65 (br. s, 1H).

Example 135

3-{3,5-Dimethyl-4-[2-(5-methyl-2-phenyl-oxazol-4-yl)-ethoxy]-phenyl}-2Z-ethoxy-acrylic acid In analogy to the procedure described in example 120 f], 3-{3,5-dimethyl-4-[2-(5-methyl-2-phenyl-oxazol-4-yl)-ethoxy]-phenyl}-2Z-ethoxy-acrylic acid ethyl ester {prepared from 3,5-dimethyl-4-[2-(5-methyl-2-phenyl-oxazol-4-yl)-ethoxy]-benzaldehyde (example 117) and (ethoxy-ethoxycarbonyl-methyl)-triphenyl-phosphonium chloride (K. K. Bach, H. R. El-Seedi, H. M. Jensen, H. B. Nielsen, I. Thomson, K. B. G. Torssell, *Tetrahedron* 1994, 50, 7543–7556) in analogy to the procedure described in example 114 c]} was saponified to yield 3-{3,5-dimethyl-4-[2-(5-methyl-2-phenyl-oxazol-4-yl)-ethoxy]-phenyl}-2Z-ethoxy-acrylic acid as colorless crystals.

MS: 420.3 (M−H)$^-$, 348.3, 281.2, 255.2, 235.2. NMR: (CDCl$_3$, 1H, 400 MHz, δ, TMS) 1.38 (t, J=7.2, 3H), 2.23 (s, 6H), 2.40 (s, 3H), 3.01 (t, J=7.2, 2H), 3.98 (q, J=7.2, 2H), 4.09 (t, J=7.2, 2H), 7.02 (s, 1H), 7.41–7.46 (m, 5H), 7.99 (dxd, J=8, J=0.8, 2H).

Example 136

[rac]-3-{4-[2-(4-Chloro-phenyl)-5-methyl-oxazol-4-ylmethoxy]-benzofuran-7-yl}-2-ethoxy-propionic acid In analogy to the procedure described in example 21 f], [rac]-2-ethoxy-3-(4-hydroxy-benzofuran-7-yl)-propionic acid methyl ester (example 120 e]) was reacted with [2-(4-chloro-phenyl)-5-methyl-oxazol-4-yl]-methanol (R. C. Self, W. E. Barber, J. P. Machin, J. M. Osbond, C. E. Smithen, B. P. Tong, J. C. Wickens, D. P. Bloxham, D. Bradshaw, C. H. Cashin, B. B. Dodge, E. J. Lewis, D. Westmacott, *J. Med. Chem.* 1991, 34, 772–777) in the presence of triphenylphosphine and diethyl azodicarboxylate to yield [rac]-3-{4-[2-(4-chloro-phenyl)-5-methyl-oxazol-4-ylmethoxy]-benzofuran-7-yl}-2-ethoxy-propionic acid methyl ester, which was further saponified in analogy to the procedure described in example 120 f] to yield [rac]-3-{4-[2-(4-chloro-phenyl)-5-methyl-oxazol-4-ylmethoxy]-benzofuran-7-yl}-2-ethoxy-propionic acid as colorless solid.

MS: 454.2 (M−H)$^-$, 408.1, 299.1, 249.1. NMR: (DMSO-$d_6$, 1H, 400 MHz, δ, TMS) 0.99 (t, J=7.2, 3H), 2.46 (s, 3H), 3.06 (dxd, J=15.2, J=8, 1H), 3.19 (dxd, J=15.2, J=6.4, 1H), 3.23–3.45 (m, 1H), 3.47–3.55 (m, 1H), 4.10(t, J=7.2, 1H), 5.13 (s, 2H), 6.89 (d, J=8, 1H), 6.90 (d, J=1.6, 1H), 7.12 (d, J=8, 1H), 7.60 (d, J=8.8, 2H), 7.90 (d, J=1.6, 1H), 7.96 (d, J=8.8, 2H), 12.90 (br. s, 1H).

Example 137

[rac]-3–4-[2-(4-Chloro-phenyl)-5-methyl-oxazol-4-ylmethoxy]-2-methyl-phenyl}-2-ethoxy-propionic acid In analogy to the procedure described in example 21 f], [rac]-2-ethoxy-3-(4-hydroxy-2-methyl-phenyl)-propionic acid ethyl ester (example 129 c]) was reacted with [2-(4-chloro-phenyl)-5-methyl-oxazol-4-yl]-methanol (R. C. Self, W. E. Barber, J. P. Machin, J. M. Osbond, C. E. Smithen, B. P. Tong, J. C. Wickens, D. P. Bloxham, D. Bradshaw, C. H. Cashin, B. B. Dodge, E. J. Lewis, D. Westmacott, *J. Med. Chem.* 1991, 34, 772–777) in the presence of triphenylphosphine and diethyl azodicarboxylate to yield [rac]-3-{4-[2-(4-chloro-phenyl)-5-methyl-oxazol-4-ylmethoxy]-2-methyl-phenyl}-2-ethoxy-propionic acid ethyl ester, which was further saponified in analogy to the procedure described in example 120 f] to yield [rac]-3-{4-[2-(4-chloro-phenyl)-5-methyl-oxazol-4-ylmethoxy]-2-methyl-phenyl}-2-ethoxy-propionic acid as colorless solid.

MS: 428.32 (M−H)$^-$, 384.1, 349.0, 255.4. NMR: (CDCl$_3$, 1H, 400 MHz, δ, TMS) 1.06 (t, J=7.2, 3H), 2.23 (s, 3H), 2.36 (s, 3H), 2.88 (dxd, J=15.2, J=8, 1H), 3.05 (dxd, J=15.2, J=4.8, 1H), 3.22–3.31 (m, 1H), 3.43–3.51 (m, 1H), 3.94 (dxd, J=8, J=4.8, 1H), 4.88 (s, 2H), 6.73 (dxd, J=8, J=1.6, 1H), 6.76 (d, J=1.6, 1H), 7.06 (d, J=8, 1H), 7.34 (d, J=8, 2H), 7.88 (d, J=8, 2H).

Example 138

[rac]-3-{4-[2-(3,5-Dimethoxy-phenyl)-5-methyl-oxazol-4-ylmethoxy]-benzofuran-7-yl}-2-ethoxy-propionic acid In analogy to the procedure described in example 120 f], [rac]-2-ethoxy-3-(4-hydroxy-benzofuran-7-yl)-propionic acid methyl ester (example 120 e]) was reacted with 4-chloromethyl-2-(3,5-dimethoxy-phenyl)-5-methyl-oxazole (prepared from 3,5-dimethoxy-benzaldehyde and diacetyl monoxyme followed by treatment with POCl$_3$ in analogy to the procedures described in examples 21 a] and b]) in the presence of potassium carbonate and potassium iodide to yield [rac]-3-{4-[2-(3,5-dimethoxy-phenyl)-5-methyl-oxazol-4-ylmethoxy]-benzofuran-7-yl}-2-ethoxy-propionic acid methyl ester, which was further saponified in analogy to the procedure described in example 120 f] to yield [rac]-3-{4-[2-(3,5-dimethoxy-phenyl)-5-methyl-oxazol-4-ylmethoxy]-benzofuran-7-yl}-2-ethoxy-propionic acid as colorless solid.

MS: 480.2 (M−H)$^-$, 434.3, 390.2, 249.1. NMR: (DMSO-$d_6$, 1H, 400 MHz, δ, TMS) 1.00 (t, J=7.2, 3H), 2.46 (s, 3H), 3.08 (dxd, J=15.2, J=8, 1H), 3.19 (dxd, J=15.2, J=6.4, 1H), 3.26–3.32 (m, 1H), 3.47–3.55 (m, 1H), 3.82 (s, 6H), 4.13 (dxd, J=8, J=6.4, 1H), 5.12 (s, 2H), 6.64 (t, J=0.8, 1H), 6.89 (d, J=8, 1H), 6.91 (d, J=1.6, 1H), 7.06 (d, J=0.8, 2H), 7.12 (d, J=8, 1H), 7.90 (d, J=1.6, 1H), 12.70 (br. s, 1H).

Example 139

2Z-Ethoxy-3-{4-[2-(4-isopropyl-phenyl)-5-methyl-oxazol-4-ylmethoxy]-2-methyl-phenyl}-acrylic acid

In analogy to the procedure described in example 120 f], 4-hydroxy-2-methyl-benzaldehyde (for the preparation of 4-hydroxy-2-methyl-benzaldehyde see: H. H. Hodgson, T. A. Jenkinson, *J. Chem. Soc.* 1929, 469, 1639–1641) was reacted with 4-chloromethyl-2-(4-isopropyl-phenyl)-5-methyl-oxazole (prepared from 4-isopropyl-benzaldehyde and diacetyl monoxyme followed by treatment with $POCl_3$ in analogy to the procedures described in examples 21 a] and b]) in the presence of potassium carbonate to yield 4-[2-(4-isopropyl-phenyl)-5-methyl-oxazol-4-ylmethoxy]-2-methyl-benzaldehyde. 4-[2-(4-Isopropyl-phenyl)-5-methyl-oxazol-4-ylmethoxy]-2-methyl-benzaldehyde was reacted with (ethoxy-ethoxy-carbonyl-methyl)-triphenyl-phosphonium chloride [for the preparation of (ethoxy-ethoxycarbonyl-methyl)-triphenyl-phosphonium chloride see: K. K. Bach, H. R. El-Seedi, H. M. Jensen, H. B. Nielsen, I. Thomson, K. B. G. Torssell, *Tetrahedron* 1994, 50, 7543–7556] in the presence of DBU in analogy to the procedure described in example 120 c] to give 2Z-ethoxy-3-{4-[2-(4-isopropyl-phenyl)-5-methyl-oxazol-4-ylmethoxy]-2-methyl-phenyl}-acrylic acid ethyl ester, which was further saponified in analogy to the procedure described in example 120 f] to yield 2Z-ethoxy-3-{4-[2-(4-isopropyl-phenyl)-5-methyl-oxazol-4-ylmethoxy]-2-methyl-phenyl}-acrylic acid as light green solid.

MS: 434.3 (M–H)$^-$, 362.2, 293.2. NMR: (DMSO-$d_6$, 1H, 400 MHz, δ, TMS) 1.21 (t, J=8, 3H), 1.23 (d, J=7.2, 6H), 2.32 (s, 3H), 2.45 (s, 3H), 2.95 (sept., J=7.2, 1H), 3.90 (q, J=7.2, 2H), 5.01 (s, 2H), 6.92 (d×d, J=8, J=0.8, 1H), 6.95 (d, J=0.8, 1H), 7.03 (s, 1H), 7.40 (d, J=8, 2H), 7.87 (d, J=8, 2H), 8.00 (d, J=8, 1H), 12.80 (br. s, 1H).

Example 140

[rac]-2-Ethoxy-3-[3-methyl-4-(2-phenyl-oxazol-4-ylmethoxy)-phenyl]-propionic acid

In analogy to the procedure described in example 108 c], [rac]-2-ethoxy-3-(4-hydroxy-3-methyl-phenyl)-propionic acid ethyl ester [PCT Int. Appl. (2001), WO01/40172A1] was treated with 4-chloromethyl-2-phenyl-oxazole [prepared from benzamide and 1,3-dichloroacetone as described in Bioorg. Med. Chem. Lett. (2000), 10(17), 2041–2044] and sodium hydride in N,N-dimethylformamide to yield [rac]-2-ethoxy-3-[3-methyl-4-(2-phenyl-oxazol-4-ylmethoxy)-phenyl]-propionic acid ethyl ester, which was further saponified in analogy to the procedure described in example 91 e] to yield [rac]-2-ethoxy-3-[3-methyl-4-(2-phenyl-oxazol-4-ylmethoxy)-phenyl]-propionic acid as colorless gum.

MS: 380.2 (M–H)$^-$ NMR: (CDCl$_3$, 1H, 400 MHz, δ, TMS) 1.18 (t, J=7.0, 3H), 2.25 (s, 3H), 2.92 (d×d, J=14.4, J=7.6, 1H), 3.06 (d×d, J=14.4, J=4, 1H), 3.48 (d×q, J=13.6, J=7.2, 1H), 3.56 (d×q, J=13.6, J=7.2, 1H), 4.05 (d×d, J=8, J=4.4, 1H), 5.07 (s, 2H), 6.86 (d, J=8.8, 1H), 7.04 (arom.H, 2H), 7.45–7.48 (arom.H, 3H), 7.71 (s, 1H), 8.05 (m, arom. H, 2H), 8–11 (very broad, 1H).

Example 141

(S)-3-{3,5-Dimethyl-4-[2-(5-methyl-2-phenyl-oxazol-4-yl)-ethoxy]-phenyl}-2-propoxy-propionic acid

In analogy to the procedures described in examples 11 a] to 11 c], 3,5-dimethyl-4-[2-(5-methyl-2-phenyl-oxazol-4-yl)-ethoxy]-benzaldehyde (example 117) was reacted with (S)-4-benzyl-3-propoxyacetyl-oxazolidin-2-one (example 26) and nBu$_2$BOTf to yield (S)-4-benzyl-3-((2S,3R)-3-{3,5-dimethyl-4-[2-(5-methyl-2-phenyl-oxazol-4-yl)-ethoxy]-phenyl}-3-hydroxy-2-propoxy-propionyl)-oxazolidin-2-one (according to NMR, one of the four isomers is strongly predominating; the configuration was tentatively assigned as 2S, 3R according to D. Haigh, H. C. Birrell, B. C. C. Cantello, D. S. Eggleston, R. C. Haltiwanger, R. M. Hindley, A. Ramaswamy, N. C. Stevens, *Tetrahedron Asymmetry* 1999, 10, 1353–1367). Reduction of (S)-4-benzyl-3-((2S, 3R)-3-{3,5-dimethyl-4-[2-(5methyl-2-phenyl-oxazol-4-yl)-ethoxy]-phenyl}-3-hydroxy-2-propoxy-propionyl)-oxazolidin-2-one with triethylsilane in trifluoroacetic acid gave (S)-4-benzyl-3-((2S) -3-{3,5-dimethyl-4-[2-(5-methyl-2-phenyl-oxazol-4-yl)-ethoxy]-phenyl}-2-propoxy-propionyl)-oxazolidin-2-one. (S)-4-Benzyl-3-((2S)-3-{3,5-dimethyl-4-[2-(5-methyl-2-phenyl-oxazol-4-ethoxy]-phenyl}-2-propoxy-propionyl)-oxazolidin-2-one was subsequently saponified with 1 M NaOH in THF to yield (S)-3-{3,5-dimethyl-4-[2-(5-methyl-2-phenyl-oxazol-4-yl)-ethoxy]-phenyl}-2-propoxy-propionic acid as colorless solid.

MS: 436.4 (M–H)$^-$, 376.3, 251.1, 217.1. NMR: (DMSO-$d_6$, 1H, 400 MHz, δ, TMS) 0.87 (t, J=7.2, 3H), 1.56 (sext., J=7.2, 2H), 2.18 (s, 6H), 2.39 (s, 3H), 2.86 (d×d, J=15.2, J=8, 1H), 2.98 (t, J=7.2, 2H), 3.02 (d×d, J=15.2, J=4.8, 1H), 3.31–3.37 (m, 1H), 3.44–3.50 (m, 1H), 4.01–4.04 (m, 3H), 6.85 (s, 2H), 7.40–7.45 (m, 3H), 7.98 (d×d, J=8, J=0.8, 2H).

Example 142 a] 2-But-3-enyloxy-3-{3,5-dimethyl-4-[2-(5-methyl-2-phenyl-oxazol-4-yl)-ethoxy]-phenyl}-3-hydroxy-propionic acid ethyl ester

To a stirred 2 M solution of LDA in THF (0.38 ml, 0.76 mmol) was added a cooled (−78° C.) solution of but-3-enyloxy-acetic acid ethyl ester (120 mg, 0.76 mmol) in THF (3 ml) at −78° C. (for the preparation of but-3-enyloxy-acetic acid ethyl ester see: A. F. Noels, A. Demonceau, N. Petiniot, A. J. Hubert, P. Teyssié, *Tetrahedron* 1982, 38, 2733–2739). The solution was stirred for 10 min and then a solution of 3,5-dimethyl-4-[2-(5-methyl-2-phenyl-oxazol-4-yl)-ethoxy]-benzaldehyde (254 mg, 0.76 mmol, example 117) in THF (3 ml) was added. The reaction mixture was stirred 30 min at −78° C. and then quenched by the addition of sat. NH$_4$Cl at −78° C. The solution was diluted with water and ethyl acetate, the layers were separated and the aqueous phase was extracted two times with ethyl acetate. The combined organic layers were washed with brine and dried over sodium sulfate. Evaporation of the solvent gave a yellow oil which was purified by column chromatography (silica gel, hexane/AcOEt=9/1) to give 160 mg (0.32 mmol, 43%) of the title compound as a mixture of diastereomers as colorless oil.

MS: 494.2 (M+H)$^+$, 476.3, 446.3, 402.4, 186.4. NMR: (CDCl$_3$, 1H, 300 MHz, δ, TMS) 1.16 (t, J=7.2, 3H), 2.20 (s, 6H), 2.25–2.35 (m, 2H), 2.39 (s, 3H), 2.87 (d, J=4.8, 0.7H), 2.98 (t, J=7.2, 2H), 3.30–3.44 (m, 1H), 3.63–3.75 (m, 1H), 3.88 (d, J=7.2, 0.3H), 3.98–4.03 (m, 2H), 4.16 (q, J=7.2, 2H), 4.76 (t, J=6.4, 0.3H), 4.84 (t, J=6.4, 0.7H), 4.99–5.13 (m, 2H), 5.63–5.82 (m, 1H), 6.98 (s, 2H), 7.40–7.45 (m, 3H), 7.97–8.00 (m, 2H).

b] 2Z-But-3-enyloxy-3-{3,5-dimethyl-4-[2-(5-methyl-2-phenyl-oxazol-4-yl)-ethoxy]-phenyl}-acrylic acid ethyl ester

To a solution of 2-but-3-enyloxy-3-{3,5-dimethyl-4-[2-(5-methyl-2-phenyl-oxazol-4-yl)-ethoxy]-phenyl}-3- hydroxy-propionic acid ethyl ester (150 mg, 0.3 mmol) in dichloromethane (2 ml) at 0° C. was added successively triethylamine (55 μl, 0.4 mmol) and methanesulfonic acid chloride (42 μl, 0.36 mmol). The reaction was allowed to warm to ambient temperature over night and then quenched by the addition of sat. NaHCO$_3$. The layers were separated and the aqueous phase was extracted two times with dichloromethane. The combined organic layers were dried over sodium sulfate and concentrated in vacuo to afford crude 2-but-3-enyloxy-3-{3,5-dimethyl-4-[2-(5-methyl-2-phenyl-oxazol-4-yl)-ethoxy]-phenyl}-3-methanesulfonyloxy-propionic acid ethyl ester which was dissolved in THF (2 ml). DBU (139 μl, 0.9 mmol) was added at ambient temperature and the mixture was stirred for 8 h at 50° C. The reaction was quenched by the addition of water, the layers were separated, and the aqueous phase was extracted two times with dichloromethane. The combined organic layers were dried over sodium sulfate, and the solvent was removed under reduced pressure to afford a brown oil which was purified by column chromatography (silica gel, hexane/AcOEt=9/1) to give 79 mg (0.166 mmol, 55%) of the title compound as bright yellow oil and 29 mg (61 μmol, 20%) 2E-but-3-enyloxy-3-{3,5-dimethyl-4-[2-(5-methyl-2-phenyl-oxazol-4-yl)-ethoxy]-phenyl}-acrylic acid ethyl ester as bright yellow oil.

Data of the Z-isomer

MS: 476.3 (M+H)$^+$, 328.4, 293.4, 186.3. NMR: (CDCl$_3$, 1H, 400 MHz, δ, TMS) 1.35 (t, J=8, 3H), 2.22 (s, 6H), 2.40 (s, 3H), 2.51 (q, J=7.2, 2H), 2.99 (t, J=7.2, 2H), 3.94 (t, J=7.2, 2H), 4.08 (t, J=7.2, 2H), 4.28 (q, J=8, 2H), 5.09 (dxd, J=8.8, J=0.8, 1H), 5.16 (dxd, J=16.8, J=0.8, 1H), 5.84–5.94 (m, 1H), 6.89 (s, 1H), 7.39–7.46 (m, 5H), 7.99 (dxd, J=8, J=1.6, 2H).

c] 2Z-But-3-enyloxy-3-{3,5-dimethyl-4-[2-(5-methyl-2-phenyl-oxazol-4-yl)-ethoxy]-phenyl}-acrylic acid In analogy to the procedure described in example 120 f], 2Z-but-3-enyloxy-3-{3,5-dimethyl-4-[2-(5-methyl-2-phenyl-oxazol-4-yl)-ethoxy]-phenyl}-acrylic acid ethyl ester was saponified to yield 2Z-but-3-enyloxy-3-{3,5-dimethyl-4-[2-(5-methyl-2-phenyl-oxazol-4-yl)-ethoxy]-phenyl}-acrylic acid as colorless solid.

MS: 446.0 (M–H)$^-$, 391.7, 327.1, 256.9, 212.9, 185.6. NMR: (CDCl$_3$, 1H, 400 MHz, δ, TMS) 2.23 (s, 6H), 2.40 (s, 3H), 2.51 (q, J=7.2, 2H), 3.01 (t, J=7.2, 2H), 3.96 (t, J=7.2, 2H), 4.09 (t, J=7.2, 2H), 5.12 (dxd, J=8.8, J=0.8, 1H), 5.18 (dxd, J=16.8, J=0.8, 1H), 5.84–5.94 (m, 1H), 7.03 (s, 1H), 7.41–7.46 (m, 5H), 7.99 (dxd, J=8, J=1.6, 2H).

Example 143

2E-But-3-enyloxy-3-{3,5-dimethyl-4-[2-(5-methyl-2-phenyl-oxazol-4-yl)-ethoxy]-phenyl}-acrylic acid In analogy to the procedure described in example 120 f], 2E-but-3-enyloxy-3-{3,5-dimethyl-4-[2-(5-methyl-2-phenyl-oxazol-4-yl)-ethoxy]-phenyl}-acrylic acid ethyl ester (example 142 b]) was saponified to yield 2Z-but-3-enyloxy-3-{3,5-dimethyl-4-[2-(5-methyl-2-phenyl-oxazol-4-yl)-ethoxy]-phenyl}-acrylic acid as colorless oil.

MS: 446.1 (M–H)$^-$, 392.0, 384.4, 253.2, 216.6, 161.5. NMR: (CDCl$_3$, 1H, 400 MHz, δ, TMS) 2.17 (s, 6H), 2.39 (s, 3H), 2.55 (q, J=7.2, 2H), 2.98 (t, J=7.2, 2H), 3.93 (t, J=7.2, 2H), 4.03 (t, J=7.2, 2H), 5.15 (dxd, J=8.8, J=0.8, 1H), 5.19 (dxd, J=16.8, J=0.8, 1H), 5.83–5.91 (m, 1H), 6.20 (s, 1H), 7.02 (s, 2H), 7.42–7.51 (m, 3H), 7.98 (dxd, J=8, J=1.6, 2H).

Example 144 a] [rac]-3-{4-[2-(2-Chloro-phenyl)-5-methyl-oxazol-4-ylmethoxy]-2-methyl-phenyl}-ethoxy-propionic acid ethyl ester Cesium carbonate (97 mg, 300 μmol, 1.5 eq.) and a trace of potassium iodide were added to a solution of [rac]-2-ethoxy-3-(4-hydroxy-2-methyl-phenyl)-propionic acid ethyl ester (50 mg, 200 μmol, 1 eq., example 129 c]) and 4-chloromethyl-2-(2-chloro-phenyl)-5-methyl-oxazole (72 mg, 300 μmol, 1.5 eq., prepared from 2-chloro-benzaldehyde and diacetyl monoxyme followed by treatment with POCl$_3$ in analogy to the procedures described in examples 21 a] and b]) in acetone (4 ml). The mixture was heated under reflux for 12 h, filtered off and the filtrate evaporated in vacuo. The residue was taken up in ethyl acetate and ice cold 1 M hydrochloric acid. The organic layer was washed two times with brine and dried over sodium sulfate. Removal of the solvent under reduced pressure gave a yellow oil which was purified by column chromatography (silica gel, hexane/AcOEt=9/1) to give 72 mg (160 μmol, 79%) of the title compound as colorless oil.

MS: 458.3 (M+H)$^+$, 414.1, 384.1, 247.1, 206.1, 179.1. NMR: (CDCl$_3$, 1H, 300 MHz, δ, TMS) 1.15 (t, J=7.2, 3H), 1.22 (t, J=8, 3H), 2.33 (s, 3H), 2.46 (s, 3H), 2.97 (d, J=7.2, 2H), 3.25–3.37 (m, 1H), 3.52–3.62 (m, 1H), 3.96 (t, J=7.2, 1H), 4.16 (q, J=8, 2H), 5.00 (s, 2H), 6.79 (dxd, J=8, J=1.6, 1H), 6.83 (d, J=1.6, 1H), 7.10 (d, J=8, 1H), 7.33–7.37 (m, 2H), 7.47–7.50 (m, 1H), 7.95–7.98 (m, 1H).

b] [rac]-3-{4-[2-(2-Chloro-phenyl)-5-methyl-oxazol-4-ylmethoxy]-2-methyl-phenyl}-2-ethoxy-propionic acid In analogy to the procedure described in example 120 f], [rac]-3-{4-[2-(2-chloro-phenyl)-5-methyl-oxazol-4-ylmethoxy]-2-methyl-phenyl}-2-ethoxy-propionic acid ethyl ester was saponified to yield [rac]-3-{4-[2-(2-chloro-phenyl)-5-methyl-oxazol-4-ylmethoxy]-2-methyl-phenyl}-2-ethoxy-propionic acid as colorless oil.

MS: 428.2 (M–H)$^-$, 382.0, 222.7, 176.8. NMR: (CDCl$_3$, 1H, 300 MHz, δ, TMS) 1.13 (t, J=7.2, 3H), 2.34 (s, 3H), 2.46 (s, 3H), 2.93 (dxd, J=15.2, J=8.8, 1H), 3.13 (dxd, J=15.2, J=4, 1H), 3.31–3.37 (m, 1H), 3.48–3.56 (m, 1H), 4.01 (dxd, J=8.8, J=4.8, 1H), 5.30 (s, 2H), 6.81 (dxd, J=8, J=1.6, 1H), 6.85 (d, J=1.6 1H), 7.13 (d, J=8, 1H), 7.33–7.37 (m, 2H), 7.47–7.51 (m, 1H), 7.95–7.98 (m, 1H).

Example 145

[rac]-3-{4-[2-(3-Chloro-phenyl)-5-methyl-oxazol-4-ylmethoxy]-2-methyl-phenyl}-2-ethoxy-propionic acid In analogy to the procedure described in example 144 a], [rac]-2-ethoxy-3-(4-hydroxy-2-methyl-phenyl)-propionic acid ethyl ester (example 129 c]) was reacted with 4-chloromethyl-2-(3-chloro-phenyl)-5-methyl-oxazole (prepared from 3-chloro-benzaldehyde and diacetyl monoxyme followed by treatment with POCl$_3$ in analogy to the procedures described in examples 21 a] and b]) in the presence of cesium carbonate and potassium iodide to yield [rac]-3-{4-[2-(3-chloro-phenyl)-5-methyl-oxazol-4-ylmethoxy]-2-methyl-phenyl}-2-ethoxy-propionic acid ethyl ester, which was further saponified in analogy to the procedure described in example 120 f] to yield [rac]-3-{4-[2-(3-chloro-phenyl)-5-methyl-oxazol-4-ylmethoxy]-2-methyl-phenyl}-2-ethoxy-propionic acid as white solid.

MS: 428.2 (M−H)⁻, 382.1, 337.7, 223.0, 176.2. NMR: (CDCl$_3$, 1H, 300 MHz, δ, TMS) 1.13 (t, J=8, 3H), 2.34 (s, 3H), 2.44 (s, 3H), 2.93 (dxd, J=15.2, J=8.8, 1H), 3.14 (dxd, J=15.2, J=4, 1H), 3.31–3.39 (m, 1H), 3.49–3.57 (m, 1H), 4.02 (dxd, J=8.8, J=4, 1H), 4.96 (s, 2H), 6.80 (dxd, J=8, J=0.8, 1H), 6.83 (d, J=0.8, 1H), 7.13 (d, J=8, 1H), 7.34–7.42 (m, 2H), 7.90 (dxt, J=7.2, J=0.8, 1H), 8.01–8.02 (m, 1H).

Example 146

[rac]-2-Ethoxy-3-{2-methyl-4-[3-(5-methyl-2-phenyl-oxazol-4-yl)-propoxy]-phenyl}-propionic acid In analogy to the procedure described in example 21 f], [rac]-2-ethoxy-3-(4-hydroxy-2-methyl-phenyl)-propionic acid ethyl ester (example 129 c]) was reacted with 3-(5-methyl-2-phenyl-oxazol-4-yl)-propan-1-ol (J. L. Collins, M. Dezube, J. A. Oplinger, A. Jeffrey, T. M. Willson, International Patent Appl., Publication No. WO0008002(A1), 2000) in the presence of triphenylphosphine and diethyl azodicarboxylate to yield [rac]-2-ethoxy-3-{2-methyl-4-[3-(5-methyl-2-phenyl-oxazol-4-yl) -propoxy]-phenyl}-propionic acid ethyl ester, which was further saponified in analogy to the procedure described in example 120 f] to yield [rac]-2-ethoxy-3-{2-methyl-4-[3-(5-methyl-2-phenyl-oxazol-4-yl)-propoxy]-phenyl}-propionic acid as colorless oil.

MS: 422.2 (M−H)⁻, 375.9, 308.7, 222.8, 179.4. NMR: (CDCl$_3$, 1H, 300 MHz, δ, TMS) 1.13 (t, J=7.2, 3H), 2.14 (quint., J=7.2, 2H), 2.28 (s, 3H), 2.32 (s, 3H), 2.69 (t, J=7.2, 2H), 2.92 (dxd, J=15.2, J=8.8, 1H), 3.13 (dxd, J=15.2, J=4, 1H), 3.29–3.40 (m, 1H), 3.47–3.58 (m, 1H), 3.95 (t, J=7.2, 2H), 4.03 (dxd, J=8.8,J=4, 1H), 6.68 (dxd, J=8, J=1.6, 1H), 6.71 (d, J=1.6, 1H), 7.10 (d, J=8, 1H), 7.40–7.46 (m, 3H), 7.98 (dxd, J=8, J=0.8, 2H).

Example 147

[rac]-2-Ethoxy-3-{4-[2-(4-fluoro-3-methyl-phenyl)-5-methyl-oxazol-4-ylmethoxy]-2-methyl-phenyl}-propionic acid In analogy to the procedure described in example 144 a], [rac]-2-ethoxy-3-(4-hydroxy-2-methyl-phenyl)-propionic acid ethyl ester (example 129 c]) was reacted with 4-chloromethyl-2-(4-fluoro-3-methyl-phenyl)-5-methyl-oxazole (prepared from 4-fluoro-3-methyl-benzaldehyde and diacetyl monoxyme followed by treatment with POCl$_3$ in analogy to the procedures described in examples 21 a] and b]) in the presence of cesium carbonate and potassium iodide to yield [rac]-2-ethoxy-3-{4-[2-(4-fluoro-3-methyl-phenyl)-5-methyl-oxazol-4-ylmethoxy]-2-methyl-phenyl}-propionic acid ethyl ester, which was further saponified in analogy to the procedure described in example 120 f] to yield [rac]-2-ethoxy-3-{4-[2-(4-fluoro-3-methyl-phenyl)-5-methyl-oxazol-4-ylmethoxy]-2-methyl-phenyl}-propionic acid as colorless solid.

MS: 426.2 (M−H)⁻, 380.1, 336.5, 283.3, 255.4. NMR: (DMSO-d$_6$, 1H, 300 MHz, δ, TMS) 1.02 (t, J=7.2, 3H), 2.27 (s, 3H), 2.31 (s, 3H), 2.43 (s, 3H), 2.79 (dxd, J=15.2,J=8, 1H), 2.89 (dxd, J=15.2, J=6.4, 1H), 3.20–3.32 (m, 1H), 3.45–3.52 (m, 1H), 3.91 (dxd, J=8, J=6.4, 1H), 4.94 (s, 2H), 6.78 (dxd, J=8, J=0.8, 1H), 6.83 (d, J=0.8, 1H), 7.07 (d, J=8, 1H), 7.29 (t, J=8, 1H), 7.77–7.82 (m, 1H), 7.89 (dxd, J=8, J=0.8, 1H), 12.65 (br. s, 1H).

Example 148

[rac]-2-Ethoxy-3-{4-[2-(2-methoxy-phenyl)-5-methyl-oxazol-4-ylmethoxy]-2-methyl-phenyl}-propionic acid In analogy to the procedure described in example 144 a], [rac]-2-ethoxy-3-(4-hydroxy-2-methyl-phenyl)-propionic acid ethyl ester (example 129 c]) was reacted with 4-chloromethyl-2-(2-methoxy-phenyl)-5-methyl-oxazole (prepared from 2-methoxy-benzaldehyde and diacetyl monoxyme followed by treatment with POCl$_3$ in analogy to the procedures described in examples 21 a] and b]) in the presence of cesium carbonate and potassium iodide to yield [rac]-2-ethoxy-3-{4-[2-(2-methoxy-phenyl)-5-methyl-oxazol-4-ylmethoxy]-2-methyl-phenyl}-propionic acid ethyl ester, which was further saponified in analogy to the procedure described in example 120 f] to yield [rac]-2-ethoxy-3-{4-[2-(2-methoxy-phenyl)-5-methyl-oxazol-4-ylmethoxy]-2-methyl-phenyl}-propionic acid as white solid.

MS: 424.3 (M−H)⁻, 380.3, 334.8, 299.3, 255.3. NMR: (CDCl$_3$, 1H, 400 MHz, δ, TMS) 1.12 (t, J=7.2, 3H), 2.33 (s, 3H), 2.44 (s, 3H), 2.91 (dxd, J=15.2, J=8, 1H), 3.10 (dxd, J=15.2, J=4, 1H), 3.29–3.36 (m, 1H), 3.49–3.57 (m, 1H), 3.94 (s, 3H), 3.99 (dxd, J=8, J=4, 1H), 4.99 (s, 2H), 6.79 (dxd, J=8, J=1.6, 1H), 6.83 (d, J=1.6, 1H), 7.01–7.05 (m, 2H), 7.12 (d, J=8, 1H), 7.41 (dxt, J=8, J=0.8, 1H), 7.90 (dxd, J=8, J=0.8, 1H).

Example 149

[rac]-3-(4-{2-[2-(4-Chloro-phenyl)-5-methyl-oxazol-4-yl]-ethoxy}-5,6,7,8-tetrahydro-naphthalen-1-yl)-2-ethoxy-propionic acid In analogy to the procedure described in example 17 a], [rac]-2-ethoxy-3-(4-hydroxy-5,6,7,8-tetrahydro-naphthalen-1-yl)-propionic acid ethyl ester (example 108 b]) was reacted with 2-[2-(4-chloro-phenyl)-5-methyl-oxazol-4-yl]-ethanol (prepared by conversion of the 4-chloro-benzaldehyde into 2-[2-(4-chloro-phenyl)-5-methyl-oxazol-4-yl]-ethanol in analogy to the sequence described in examples 21 a] to 21 e]) in the presence of triphenylphosphine and DEAD (diethyl azodicarboxylate) to yield [rac]-3-(4-{2-[2-(4-chloro-phenyl)-5-methyl-oxazol-4-yl]-ethoxy}-5,6,7,8-tetrahydro-naphthalen-1-yl)-2-ethoxy-propionic acid ethyl ester, which was further saponified in analogy to the procedure described in example 91 e] to yield [rac]-3-(4-{2-[2-(4-chloro-phenyl)-5-methyl-oxazol-4-yl]-ethoxy}-5,6,7,8-tetrahydro-naphthalen-1-yl)-2-ethoxy-propionic acid as colorless oil.

MS: 484.3 (M+H)⁺, 506.2 (M+Na)⁺. NMR: (CDCl$_3$, 1H, δ, TMS, 300 MHz) 1.12 (t, J=7.2, 3H), 1.73–1.79 (m, 4H), 2.37 (s, 3H), 2.60–2.74 (m, 4H), 2.91–3.05 (m, 4H), 3.32–3.35 (m, 1H), 3.50–3.56 (m, 1H), 3.96–4.01 (m, 1H), 4.19 (t, J=6.3, 2H), 6.61 (d, J=8.4, 1H), 6.98 (d, J=8.4, 1H), 7.39 (d, J=6.9, 2H), 7,90 (d, 8.7, 2H), COOH very broad.

Example 150 a] [rac]-2-Ethoxy-3-(4-hydroxy-naphthalen-1-yl)-propionic acid ethyl ester

In analogy to the procedure described in example 93 a], 4-benzyloxy-naphthalene-1-carbaldehyde (prepared from 4-hydroxy-naphthalene-1-carbaldehyde, benzylchloride, potassium carbonate in N,N-dimethylformamide at room temperature) was reacted with (ethoxy-ethoxycarbonyl-methyl)-triphenyl-phosphonium chloride [Tetrahedron 50(25), 7543–56(1994)] to yield 3-(4-benzyloxy-naphthalen-1-yl)-2-ethoxy-(Z,E) -acrylic acid ethyl ester. Hydrogenation of 3-(4-benzyloxy-naphthalen-1-yl)-2-ethoxy-(Z,E)-acrylic acid ethyl ester as described in example 91 d] yielded [rac]-2-ethoxy-3-(4-hydroxy-naphthalen-1-yl)-propionic acid ethyl ester as light brown oil.

MS: 288.3 (M), 242.2, 215.3, 157.2. NMR: (CDCl$_3$, 1H, δ, TMS, 300 MHz) 1.11 (t, J=7.0, 3H), 1.17 (t, J=7.1, 3H), 3.26–3.60 (m, 4H), 4.10–4.19 (m, 3H), 5.67 (s, 1H), 6.82 (d, J=7.6, 1H), 7.20 (d, J=7.6, 1H), 7.46–7.58 (m, 2H), 8.03 (d, J=7.8, 1H), 8.24 (d, J=7.9, 1H).

b] [rac]-2-Ethoxy-3-[4-(5-methyl-2-phenyl-oxazol-4-ylmethoxy)-naphthalen-1-yl]-propionic acid In analogy to the procedure described in example 108 c], [rac]-2-ethoxy-3-(4-hydroxy-naphthalen-1-yl)-propionic acid ethyl ester was treated with 4-chloromethyl-5-methyl-2-phenyloxazole and sodium hydride in N,N-dimethylformamide to yield [rac]-2-ethoxy-3-[4-(5-methyl-2-phenyl-oxazol-4-ylmethoxy)-naphthalen-1-yl]-propionic acid ethyl ester, which was further saponified in analogy to the procedure described in example 91 e] to yield [rac]-2-ethoxy-3-[4-(5-methyl-2-phenyl-oxazol-4-ylmethoxy)-naphthalen-1-yl]-propionic acid as colorless solid.

MS: 430.3 (M–H)$^-$. NMR: (CDCl$_3$, 1H, δ, TMS, 300 MHz) 1.01 (t, J=7.0, 3H), 2.47 (s, 3H), 3.15–3.25 (m, 2H), 3.41–3.63 (m, 2H), 4.16 (dxd, J$_1$=3.9, J$_2$=6.9, 1H), 5.17 (s, 2H), 6.90 (d, J=7.9, 1H), 7.30 (d, J=7.9, 1H), 7.44–7.57 (m, 5H), 8.02–8.05 (m, 3H), 8.34 (d, J=8.2, 1H), COOH very broad.

Example 151 a] [rac]-2-Ethoxy-3-(7-hydroxy-benzo[b]thiophen-4-yl)-propionic acid methyl ester In analogy to the procedure described in example 91 b], 7-benzyloxy-benzo[b]thiophene (prepared from benzo[b]thiophen-7-ol [J. Chem. Soc., Perkin Trans. 1 (1983), (12), 2973–7], benzylchloride, potassium carbonate in N,N-dimethylformamide at room temperature) was reacted with dichloromethyl methyl ether in dichloromethane at 0° C. to give 7-benzyloxy-benzo[b]thiophene-4-carbaldehyde. Treatment of 7-benzyloxy-benzo[b]thiophene-4-carbaldehyde with (ethoxy-ethoxycarbonyl-methyl)-triphenyl-phosphonium chloride and potassium carbonate in 2-propanol in analogy to the procedure described in example 93 a] gave 3-(7-benzyloxy-benzo[b]thiophen-4-yl)-2(Z,E)-ethoxy-acrylic acid ethyl ester. Reduction of 3-(7-benzyloxy-benzo[b]thiophen-4-yl)-2(Z,E)-ethoxy-acrylic acid ethyl ester with magnesium in THF/MeOH (1:1) at 50° C. in analogy to the procedure described in example 93 b] yielded [rac]-3-(7-benzyloxy-benzo[b]thiophen-4-yl)-2-ethoxy-propionic acid methyl ester, subsequent removal of the benzyl protective function with dimethyl sulfide and boron trifluoride diethyl etherate in dichlormethane at room temperature in analogy the procedure described in example 93 c] gave [rac]-2-ethoxy-3-(7-hydroxy-benzo[b]thiophen-4-yl)-propionic acid methyl ester as light yellow oil.

MS: 279.0 (M–H)$^-$. NMR: (CDCl$_3$, 1H, δ, TMS, 300 MHz) 1.12 (t, J=7.0, 3H), 3.23–3.36 (m, 3H), 3.56–3.61 (m, 1H), 3.68 (s, 3H), 4.11–4.15 (dxd, J$_1$=5.5, J$_2$=7.7, 1H), 5.83 (s, 1H), 6.63 (d, J=7.8, 1H), 7.08 (d, J=7.8, 1H), 7.45 (s, 2H).

b] [rac]-2-Ethoxy-3-[7-(5-methyl-2-phenyl-oxazol-4-ylmethoxy)-benzo[b]thiophen-4-yl]-propionic acid In analogy to the procedure described in example 108 c], [rac]-2-ethoxy-3-(7-hydroxy-benzo[b]thiophen-4-yl)-propionic acid methyl ester was treated with 4-chloromethyl-5-methyl-2-phenyloxazole and sodium hydride in N,N-dimethylformamide to yield [rac]-2-ethoxy-3-[7-(5-methyl-2-phenyl-oxazol-4-ylmethoxy)-benzo[b]thiophen-4yl]-propionic acid methyl ester, which was further saponified in analogy to the procedure described in example 91 e] to yield [rac]-2-ethoxy-3-[7-(5-methyl-2-phenyl-oxazol-4-ylmethoxy)-benzo[b]thiophen-4-yl]-propionic acid as colorless solid.

MS: 436.2 (M–H)$^-$. NMR: (CDCl$_3$, 1H, δ, TMS, 300 MHz) 1.07 (t, J=7.0, 3H), 2.47 (s, 3H), 3.19–3.33 (m, 2H), 3.40–3.55 (m, 2H), 4.10–4.15 (dxd, J$_1$=4.1, J$_2$=8.3, 1H), 5.20 (s, 2H), 6.87 (d, J=8.0, 1H), 7.19 (d, J=8.0, 1H), 7.43–7.48 (m, 5H), 8.00–8.03 (m, 2H), COOH very broad.

Example 152

[rac]-2-Ethoxy-3-{7-[2-(4-isopropoxy-phenyl)-5-methyl-oxazol-4-ylmethoxy]-benzo[b]thiophen-4-yl}-propionic acid In analogy to the procedure described in example 108 c], [rac]-2-ethoxy-3-(7-hydroxy-benzo[b]thiophen-4-yl)-propionic acid methyl ester (example 151 a]) was treated with 4-chloromethyl-2-(4-isopropoxy-phenyl)-5-methyl-oxazole (prepared from 4-isopropoxy-benzaldehyde and diacetyl monoxyme followed by treatment with POCl$_3$ in analogy to the procedures described in examples 21 a] and b]) and sodium hydride in N,N-dimethylformamide to yield [rac]-2-ethoxy-3-{7-[2-(4-isopropoxy-phenyl)-5-methyl-oxazol-4-ylmethoxy]-benzo[b]thiophen-4-yl}-propionic acid methyl ester, which was further saponified in analogy to the procedure described in example 91 e] to yield [rac]-2-ethoxy-3-{7-[2-(4-isopropoxy-phenyl)-5-methyl-oxazol-4-ylmethoxy]-benzo[b]thiophen-4-yl}-propionic acid as colorless solid.

MS: 494.1 (M–H)$^-$. NMR: (CDCl$_3$, 1H, δ, TMS, 300 MHz) 1.07 (t, J=6.9, 3H), 1.36 (d, J=6.3, 6H), 2.44 (s, 3H), 3.18–3.30 (m, 2H), 3.38–3.44 (dxd, J$_1$=4.2, J$_2$=14.1, 1H), 3.49–3.55 (m, 1H), 4.09–4.13 (dxd, J$_1$=3.9, J$_2$=8.1, 1H), 4.58–4.66 (m, 1H), 5.17 (s, 2H), 6.86 (d, J=7.8, 1H), 6.93 (d, J=8.7, 2H), 7.18 (d, J=7.8, 1H), 7.42–7.47 (dxd, J$_1$=5.4, J$_2$=9.9, 2H), 7.91–7.94 (dxd, J$_1$=1.8, J$_2$=6.9, 2H), COOH very broad.

Example 153

[rac]-2-Ethoxy-3-(7-{2-[2-(2-ethoxy-4-fluoro-phenyl)-5-methyl-oxazol-4-yl]-ethoxy}-benzo[b]thiophen-4-yl)-propionic acid In analogy to the procedure described in example 17 a], [rac]-2-ethoxy-3-(7-hydroxy-benzo[b]thiophen-4-yl)-propionic acid methyl ester (example 151 a]) was reacted with 2-[2-(2-ethoxy-4-fluoro-phenyl)-5-methyl-oxazol-4-yl]-ethanol (example 95) in the presence of triphenylphosphine and DEAD (diethyl azodicarboxylate) to yield [rac]-2-ethoxy-3-(7-{2-[2-(2-ethoxy-4-fluoro-phenyl)-5-methyl-oxazol-4-yl]-ethoxy}-benzo[b]thiophen-4-yl)-propionic acid methyl ester, which was further saponified in analogy to the procedure described in example 91 e] to yield [rac]-2-ethoxy-3-(7-{2-[2-(2-ethoxy-4-fluoro-phenyl)-5-methyl-oxazol-4-yl]-ethoxy}-benzo[b]thiophen-4-yl)-propionic acid as colorless solid.

MS: 512.2 (M–H)$^-$. NMR: (DMSO-d$_6$, 1H, δ, TMS, 300 MHz) 0.99 (t, J=6.9, 3H), 1.33 (t, J=6.9, 3H), 2.36 (s, 3H), 2.98 (t, J=6.3, 2H), 3.17–3.33 (m, 3H), 3.46–3.57 (m, 1H), 3.99–4.04 (dxd, J$_1$=5.4, J$_2$=7.5, 1H), 4.09–4.16 (q, J=6.9, 2H), 4.37 (t, J=6.3, 2H), 6.83–6.91 (m, 2H), 7.04–7.08 (dxd, J$_1$=2.1, J$_2$=11.4, 1H), 7.15 (d, J=8.1, 1H), 7.49 (d, J=5.4, 1H), 7.71 (d, J=5.4, 1H), 7.76–7.81 (dxd, J$_1$=6.9, J$_2$=12, 1H), 12.67 (s, 1H).

Example 154

[rac]-3-(7-{2-[2-(4-Chloro-phenyl)-5-methyl-oxazol-4-yl]-ethoxy}-benzo[b]thiophen-4-yl)-2-ethoxy-propionic acid In analogy to the procedure described in example 17 a], [rac]-2-ethoxy-3-(7-hydroxy-benzo[b]thiophen-4-yl)- propionic acid methyl ester (example 151 a]) was reacted with 2-[2-(4-chloro-phenyl)-5-methyl-oxazol-4-yl]-ethanol (prepared by conversion of the 4-chloro-benzaldehyde into 2-[2-(4-chloro-phenyl)-5-methyl-oxazol-4-yl]-ethanol in analogy to the sequence described in examples 21 a] to 21 e]) in the presence of triphenylphosphine and DEAD (diethyl azodicarboxylate) to yield [rac]-3-(7-{2-[2-(4-chloro-phenyl)-5-methyl-oxazol-4-yl]-ethoxy}-benzo[b]thiophen-4-yl)-2-ethoxy-propionic acid methyl ester, which was further saponified in analogy to the procedure described in example 91 e] to yield [rac]-3-(7-{2-[2-(4-chloro-phenyl)-5-methyl-oxazol-4-yl]-ethoxy}-benzo[b]thiophen-4-yl)-2-ethoxy-propionic acid as colorless oil.

MS: 484.2 (M–H)⁻. NMR: (CDCl$_3$, 1H, δ, TMS, 300 MHz) 1.07 (t, J=7.0, 3H), 2.44 (s, 3H), 3.05 (t, J=6.2, 2H), 3.22–3.31 (m, 2H), 3.39–3.45 (d×d, J$_1$=4.4, J$_2$=14.2, 1H), 3.51–3.57 (m, 1H), 4.09–4.13 (d×d, J$_1$=4.4, J$_2$=8.1, 1H), 4.37 (t, J=6.2, 2H), 6.71 (d, J=8.0, 1H), 7.16 (d, J=8.0, 1H), 7.37–7.49 (m, 4H), 7.87–7.91 (m, 2H), COOH very broad.

Example 155

[rac]-3-{7-[2-(4-tert-Butyl-phenyl)-5-methyl-oxazol-4-ylmethoxy]-benzo[b]thiophen-4-yl}-2-ethoxy-propionic acid In analogy to the procedure described in example 108 c], [rac]-2-ethoxy-3-(7-hydroxy-benzo[b]thiophen-4-yl)-propionic acid methyl ester (example 151 a]) was treated with 4-chloromethyl-2-(4-tert-butyl-phenyl)-5-methyl-oxazole (prepared from 4-tert-butyl-benzaldehyde and diacetyl monoxyme followed by treatment with POCl$_3$ in analogy to the procedures described in examples 21 a] and b]) and sodium hydride in N,N-dimethylformamide to yield [rac]-3-{7-[2-(4-tert-butyl-phenyl)-5-methyl-oxazol-4-ylmethoxy]-benzo[b]thiophen-4-yl}-2-ethoxy-propionic acid methyl ester, which was further saponified in analogy to the procedure described in example 91 e] to yield [rac]-3-{7-[2-(4-tert-butyl-phenyl)-5-methyl-oxazol-4-ylmethoxy]-benzo[b]thiophen-4-yl}-2-ethoxy-propionic acid as colorless amorphous solid.

MS: 492.2 (M–H)⁻, 448.2. NMR: (CDCl$_3$, 1H, δ, TMS, 300 MHz) 1.07 (t, J=7.2, 3H), 1.35 (s, 9H), 2.46 (s, 3H), 3.26 (m, 2H), 3.51 (m, 2H), 4.13 (m, 1H), 5.20 (s, 2H), 6.87 (d, J=8.1, 1H), 7.19 (d, J=8.1, 1H), 7.45–7.48 (m, 4H), 7.94 (d, J=8.7, 2H), COOH very broad.

Example 156

(S)-2-Ethoxy-3-{3-methyl-4-[2-(5-methyl-2-phenyl-oxazol-4-yl)-ethoxy]-phenyl}-propionic acid In analogy to the procedures described in examples 11 a] to 11 c], 3-methyl-4-[2-(5-methyl-2-phenyl-oxazol-4-yl)-ethoxy]-benzaldehyde (example 114 b]) was reacted with (S)-4-benzyl-3-ethoxyacetyl-oxazolidin-2-one and nBu$_2$BOTf to yield (S)-4-benzyl-3-((2S,3R)-2-ethoxy-3-hydroxy-3-{3-methyl-4-[2-(5-methyl-2-phenyl-oxazol-4-yl)-ethoxy]-phenyl}-propionyl)-oxazolidin-2-one (according to NMR, one of the four isomers is strongly predominating; the configuration was tentatively assigned as 2S, 3R according to *Tetrahedron Asymmetry* 1999, 1353). Reduction of (S)-4-benzyl-3-((2S,3R)-2-ethoxy-3-hydroxy-3-{3-methyl-4-[2-(5-methyl-2-phenyl-oxazol-4-yl)-ethoxy]-phenyl}-propionyl)-oxazolidin-2-one with triethylsilane in trifluoroacetic acid then gave (S)-4-benzyl-3-((2S)-2-ethoxy-3-{3-methyl-4-[2-(5-methyl-2-phenyl-oxazol-4-yl)-ethoxy]-phenyl}-propionyl)-oxazolidin-2-one. The (S)-4-benzyl-3-((2S)-2-ethoxy-3-{3-methyl-4-[2-(5-methyl-2-phenyl-oxazol-4-yl)-ethoxy]-phenyl}-propionyl)-oxazolidin-2-one was subsequently saponified with 1N NaOH in THF to yield (S)-2-ethoxy-3-{3-methyl-4-[2-(5-methyl-2-phenyl-oxazol-4-yl)-ethoxy]-phenyl}-propionic acid as colorless solid. The enantiomeric excess was judged according to chiral HPLC (Chiralpak-AD) to be 99.3%.

MS: (M+H⁺)⁺⁻410.5. NMR (DMSO-d$_6$, 1H, δ, TMS): 1.03 (t, 3H), 2.06 (s, 3H), 2.35 (s, 3H), 2.75 (d×d, 1H), 2.82 (d×d, 1H), 2.91 (t, 2H), 3.23–3.32 (m, 1H), 3.45–3.52 (m, 1H), 3.90 (d×d, 1H), 4.18 (t, 2H), 6.69 (d×d, 1H), 6.95–6.99 (m, 2H), 7.47–7.52 (m, 3H), 7.92 (d×d, 2H), 12.6 (s, 1H).

Example 157

(2S)-3-{3,5-Dimethyl-4-[2-(5-methyl-2-phenyl-oxazol-4-yl)-ethoxy]-phenyl}-2-ethoxy-propionic acid In analogy to the procedures described in examples 11 a] to 11 c], 3,5-dimethyl-4-[2-(5-methyl-2-phenyl-oxazol-4-yl)-ethoxy]-benzaldehyde (example 117) was reacted with (S)-4-benzyl-3-ethoxyacetyl-oxazolidin-2-one and nBu$_2$BOTf to yield (S)-4-benzyl-3-((2S,3R)-3-{3,5-dimethyl-4-[2-(5-methyl-2-phenyl-oxazol-4-yl)-ethoxy]-phenyl}-2-ethoxy-3-hydroxy-propionyl)-oxazolidin-2-one (according to NMR, one of the four isomers is strongly predominating; the configuration was tentatively assigned as 2S, 3R according to *Tetrahedron Asymmetry* 1999, 1353). Reduction of (S)-4-benzyl-3-((2S,3R)-3-}3,5-dimethyl-4-[2-(5-methyl-2-phenyl-oxazol-4-yl)-ethoxy]-phenyl}-2-ethoxy-3-hydroxy-propionyl)-oxazolidin-2-one with triethylsilane in trifluoroacetic acid then gave (S)-4-benzyl-3-((2S)-3-{3,5-dimethyl-4-[2-(5-methyl-2-phenyl-oxazol-4-yl)-ethoxy]-phenyl}-2-ethoxy-propionyl)-oxazolidin-2-one. The (S)-4-benzyl-3-((2S)-3-{3,5-dimethyl-4-[2-(5-methyl-2-phenyl-oxazol-4-yl)-ethoxy]-phenyl}-2-ethoxy-propionyl)-oxazolidin-2-one was subsequently saponified with 1N NaOH in THF to yield (2S)-3-{3,5-dimethyl-4-[2-(5-methyl-2-phenyl-oxazol-4-yl)-ethoxy]-phenyl}-2-ethoxy-propionic acid as colorless solid. The enantiomeric excess was judged according to chiral HPLC (Chiralpak-AD) to be 98.8%.

MS: (M–H)⁻422.2. NMR (DMSO-d$_6$, 1H, δ, TMS): 1.03 (t, 3H), 2.09 (s, 6H), 2.38 (s, 3H), 2.72 (d×d, 1H), 2.80 (d×d, 1H), 2.91 (t, 2H), 3.23–3.32 (m, 1H), 3.45–3.52 (m, 1H), 3.90–4.02 (m, 3H), 6.84 (s, 2H), 7.47–7.52 (m, 3H), 7.92 (d×d, 2H), 12.8 (s, 1H).

Example 158

[rac]-2-Ethoxy-3-{3-fluoro-4-[2-(5-methyl-2-phenyl-oxazol-4-yl)-ethoxy]-phenyl}-propionic acid In analogy to the procedures described in examples 114 b], c] and d], 3-fluoro-4-hydroxy-benzaldehyde was reacted with methanesulfonic acid 2-(5-methyl-2-phenyl-oxazol-4-yl)-ethyl ester [PCT Int. Appl. (2000) WO0008002] to give 3-fluoro-4-[2-(5-methyl-2-phenyl-oxazol-4-yl)-ethoxy]-benzaldehyde. Treatment of 3-fluoro-4-[2-(5-methyl-2-phenyl-oxazol-4-yl)-ethoxy]-benzaldehyde with (benzyloxycarbonyl-ethoxy-methyl)-triphenyl-phosphonium chloride (prepared in analogy to the procedure described for the synthesis of (benzyloxycarbonyl-methoxy-methyl)-triphenyl-phosphonium chloride in example 114 a]) then gave 2(Z,E)-ethoxy-3-{3-fluoro-4-[2-(5-methyl-2-phenyl-oxazol-4-yl)-ethoxy]-phenyl}-acrylic acid benzyl ester, which was hydrogenated to yield [rac]-2-ethoxy-3-{3- fluoro-4-[2-(5-methyl-2-phenyl-oxazol-4-yl)-ethoxy]-phenyl}-propionic acid as colorless solid.

MS: (M–H)⁻ 412.2. NMR (DMSO-$d_6$, 1H, δ, TMS): 1.03 (t, 3H), 2.35 (s, 3H), 2.78 (dxd, 1H), 2.88 (dxd, 1H), 2.95 (t, 2H), 3.23–3.32 (m, 1H), 3.45–3.52 (m, 1H), 3.95–4.00 (m, 1H), 4.26 (t, 2H), 6.95 (d, 1H), 7.04–7.10 (m, 2H), 7.47–7.52 (m, 3H), 7.92 (dxd, 2H), 12.7 (s, 1H).

Example 159

[rac]-2-Ethoxy-3-{4-[2-(5-methyl-2-phenyl-oxazol-4-yl)-ethoxyl-3-propyl-phenyl}-propionic acid In analogy to the procedures described in examples 114 b], c] and d], 3-allyl-4-hydroxy-benzaldehyde was reacted with methanesulfonic acid 2-(5-methyl-2-phenyl-oxazol-4-yl)-ethyl ester [PCT Int. Appl. (2000) WO0008002] to give 3-allyl-4-[2-(5-methyl-2-phenyl-oxazol-4-yl)-ethoxy]-benzaldehyde. Treatment of 3-allyl-4-[2-(5-methyl-2-phenyl-oxazol-4-yl)-ethoxy]-benzaldehyde with (benzyloxycarbonyl-ethoxy-methyl)-triphenyl-phosphonium chloride (prepared in analogy to the procedure described for the synthesis of (benzyloxycarbonyl-methoxy-methyl)-triphenyl-phosphonium chloride in example 114 a]) then gave 3-{3-allyl-4-[2-(5-methyl-2-phenyl-oxazol-4-yl)-ethoxy]-phenyl}-2(Z,E)-ethoxy-acrylic acid benzyl ester, which was hydrogenated to yield [rac]-2-ethoxy-3-{4-[2-(5-methyl-2-phenyl-oxazol-4-yl)-ethoxy]-3-propyl-phenyl}-propionic acid as colorless solid.

MS: (M–H)⁻ 436.3. NMR (DMSO-$d_6$, 1H, δ, TMS): 0.77 (t, 3H), 1.03 (t, 3H), 1.32–1.42 (m, 2H), 2.35 (s, 3H), 2.35–2.45 (m, 2H), 2.76 (dxd, 1H), 2.85 (dxd, 1H), 2.92 (t, 2H), 3.23–3.32 (m, 1H), 3.45–3.52 (m, 1H), 3.90 (dxd, 1H), 4.19 (t, 2H), 6.82 (d, 1H), 6.92 (d, 1H), 6.97 (dxd, 1H), 7.47–7.52 (m, 3H), 7.92 (dxd, 2H), 12.7 (s, 1H).

Example 160

(2S)-2-Ethoxy-3-{3-methoxy-4-[2-(5-methyl-2-phenyl-oxazol-4-yl)-ethoxy]-phenyl }-propionic acid In analogy to the procedures described in examples 11 a] to 11 c], 3-methoxy-4-[2-(5-methyl2-phenyl-oxazol-4-yl)-ethoxy]-benzaldehyde (prepared from 4-hydroxy-3-methoxy-benzaldehyde and methanesulfonic acid 2-(5-methyl-2-phenyl-oxazol-4-yl)-ethyl ester in analogy to the procedure described in example 114 b]) was reacted with (S)-4-benzyl-3-ethoxyacetyl-oxazolidin-2-one and nBu₂BOTf to yield (S)-4-benzyl-3-((2S,3R) -2-ethoxy-3-hydroxy-3-{3-methoxy-4-[2-(5-methyl-2-phenyl-oxazol-4-yl)-ethoxy]-phenyl}-propionyl)-oxazolidin-2-one (according to NMR, one of the four isomers is strongly predominating; the configuration was tentatively assigned as 2S, 3R according to Tetrahedron Asymmetry 1999, 1353). Reduction of (S)-4-benzyl-3-((2S,3R)-2-ethoxy-3-hydroxy-3-{3-methoxy-4-[2-(5-methyl-2-phenyl-oxazol-4-yl)-ethoxy]-phenyl}-propionyl)-oxazolidin-2-one with triethylsilane in trifluoroacetic acid then gave (S)-4-benzyl-3-((2S)-2-ethoxy-3-{3-methoxy-4-[2-(5-methyl-2-phenyl-oxazol-4-yl)-ethoxy]-phenyl}-propionyl)-oxazolidin-2-one. The (S)-4-benzyl-3-((2S)-2-ethoxy-3-{3-methoxy-4-[2-(5-methyl-2-phenyl-oxazol-4-yl)-ethoxy]-phenyl}-propionyl)-oxazolidin-2-one was subsequently saponified with 1N NaOH in THF to yield (2S)-2-ethoxy-3-{3-methoxy-4-[2-(5-methyl-2-phenyl-oxazol-4-yl)-ethoxy]-phenyl}-propionic acid as colorless solid. The enantiomeric excess was judged according to chiral HPLC (Chiralcel-OJ) to be 98.7%.

MS: (M–H⁻) 424.3. NMR (DMSO-$d_6$, 1H, δ, TMS): 1.04 (t, 3H), 2.36 (s, 3H), 2.75–2.87 (2xdxd, 2x1H), 2.91 (t, 2H), 3.27–3.32 (m, 1H), 3.49–3.52 (m, 1H), 3.72 (s, 3H), 3.94–3.96 (m, 1H), 4.14 (t, 2H), 6.71 (dxd, 1H), 6.84–6.87 (m 2H), 7.48–7.50 (m, 3H), 7.90–7.92 (m, 2H), 12.7 (s, 1H).

Example 161

(2S)-2-Ethoxy-3-{2-methoxy-4-[2-(5-methyl-2-phenyl-oxazol-4-yl)-ethoxy]-phenyl}-propionic acid In analogy to the procedures described in examples 11 a] to 11 c], 2-methoxy-4-[2-(5-methyl-2-phenyl-oxazol-4-yl)-ethoxy]-benzaldehyde (prepared from 4-hydroxy-2-methoxy-benzaldehyde and methanesulfonic acid 2-(5-methyl-2-phenyl-oxazol-4-yl)-ethyl ester in analogy to the procedure described in example 114 b]) was reacted with (S)-4-benzyl-3-ethoxyacetyl-oxazolidin-2-one and nBu₂BOTf to yield (S)-4-benzyl-3-((2S,3R)-2-ethoxy-3-hydroxy-3-{2-methoxy-4-[2-(5-methyl-2-phenyl-oxazol-4yl)-ethoxy]-phenyl}-propionyl)-oxazolidin-2-one (according to NMR, one of the four isomers is strongly predominating; the configuration was tentatively assigned as 2S, 3R according to Tetrahedron Asymmetry 1999, 1353). Reduction of (S)-4-benzyl-3-((2S,3R)-2-ethoxy-3-hydroxy-3-{2-methoxy-4-[2-(5-methyl-2-phenyl-oxazol-4-yl)-ethoxy]-phenyl}-propionyl)-oxazolidin-2-one with triethylsilane in trifluoroacetic acid then gave (S)-4-benzyl-3-((2S)-2-ethoxy-3-{2-methoxy-4-[2-(5-methyl-2-phenyl-oxazol-4-yl)-ethoxy]-phenyl}-propionyl)-oxazolidin-2-one. The (S)-4-benzyl-3-((2S)-2-ethoxy-3-{2-methoxy-4-[2-(5-methyl-2-phenyl-oxazol-4-yl)-ethoxy]-phenyl}-propionyl)-oxazolidin-2-one was subsequently saponified with 1N NaOH in THF to yield (2S)-2-ethoxy-3-{2-methoxy-4-[2-(5-methyl-2-phenyl-oxazol-4-yl)-ethoxy]-phenyl}-propionic acid as colorless solid.

MS: (M–H⁻) 424.5. NMR (DMSO-$d_6$, 1H, δ, TMS): 1.01 (t, 3H), 2.36 (s, 3H), 2.72 (dxd, 1H), 2.84 (dxd, 1H), 2.92 (t, 2H), 3.22–3.29 (m, 1H), 3.41–3.49 (m, 1H), 3.75 (s, 3H), 3.89–3.92 (m, 1H), 4.19 (t, 2H), 6.44 (dxd, 1H), 6.50 (d, 1H), 6.99 (d, 1H), 7.48–7.50 (m, 3H), 7.90–7.92 (m, 2H), 12.6 (s, 1H).

Example 162

[rac]-2-Isopropoxy-3-{4-[2-(5-methyl-2-phenyl-oxazol-4-yl)-ethoxy]-benzo[b]thiophen-7-yl}-propionic acid was prepared in analogy to, example 68, but using in the aldol-step as electrophilic coupling partner the unsubstituted 4-[2-(5-methyl-2-phenyl-oxazol-4-yl)-ethoxy]-benzo[b]thiophene-7-carbaldehyde [prepared from 4-hydroxy-benzo[b]thiophene-7-carbaldehyde [Ger. Offen. (1998) DE 19711617 A1] and 2-(5-methyl-2-phenyl-oxazol-4-yl)-ethanol in tetrahydrofuran in the presence of triphenylphosphine and DEAD (diethyl azodicarboxylate)], as off-white solid of mp. 146–147°.

ISN-MS: 464.1 (M–H)⁺.

Example 163

(S)-2-Isopropoxy-3-{4-[2-(5-methyl-2-phenyl-oxazol-4-yl)-ethoxy]-benzo[b]thiophen-7-yl}-propionic acid was prepared in analogy to example 11, but using in step a] (S)-4-benzyl-3-isopropoxyacetyl-oxazolidin-2-one instead of (S)-4-benzyl-3-methoxyacetyl-oxazolidin-2-one as coupling partner, as off-white crystals of mp. 167–168°. The former reagent was prepared in analogy to the method described above in example 65 from isopropoxy-acetic acid and (S)-4-benzyl-2-oxazolidinone.

ISN-MS: 464.2 (M–H)⁺.

Example 164 a] [rac]-3-(3-Allyl-4-hydroxy-naphthalen-1-yl)-2-ethoxy-propionic acid ethyl ester 0.87 g (2.65 mmol) [rac]-3-(4-allyloxy-naphthalen-1-yl)-2-ethoxy-propionic acid ethyl ester [prepared from [rac]-2-ethoxy-3-(4-hydroxy-naphthalen-1-yl)-propionic acid ethyl ester (example 150 a] and allylbromide, potassium carbonate in acetone at 60° C.] was stirred for 2 hours at 160° C. without any solvent. The dark residue was purified by flash chromatography (silica gel, hexane/AcOEt=4:1) to yield 0.82 g (94%) of [rac]-3-(3-allyl-4-hydroxy-naphthalen-1-yl)-2-ethoxy-propionic acid ethyl ester as yellow oil.

MS: 327.2 (M–H)⁻. NMR: (CDCl$_3$, 1H, δ, TMS) 1.10 (t, J=7, 3H), 1.18 (t, J=7, 3H), 3.23–3.35 (m, 3H), 3.42–3.44 (d, J=5, 1H), 3.53–3.57 (m, 2H), 4.10–4.18 (m, 3H), 5.20–5.27 (m, 2H), (m, 2H), 5.47 (s, 1H), 6.02–6.11 (m, 1H), 7.13 (s, 1H), 7.47–7.54 (m, 2H), 8.00–8.03 (m, 1H), 8.20–8.23 (m, 1H).

b] [rac]-3-{3-Allyl-4-[2-(5-methyl-2-phenyl-oxazol-4-yl)-ethoxy]-naphthalen-1-yl}-2-ethoxy-propionic acid In analogy to the procedure described in example 17 a], [rac]-3-(3-allyl-4-hydroxy-naphthalen-1-yl)-2-ethoxy-propionic acid ethyl ester was reacted with 2-(5-methyl-2-phenyl-oxazole-4yl)-ethanol in tetrahydrofuran in the presence of triphenylphosphine and DBAD (di-tert-butyl azodicarboxylate) to yield [rac]-3-{3-allyl-4-[2-(5-methyl-2-phenyl-oxazol-4-yl)-ethoxy]-naphthalen-1-yl}-2-ethoxy-propionic acid ethyl ester, which was further saponified in analogy to the procedure described in example 91 e] to yield [rac]-3-{3-allyl-4-[2-(5-methyl-2-phenyl-oxazol-4-yl)-ethoxy]-naphthalen-1-yl}-2-ethoxy-propionic acid as colorless solid.

MS: 484.3 (M–H)⁻. NMR: (CDCl$_3$, 1H, δ, TMS) 0.97–1.02 (t, J=7, 3H), 2.43 (s, 3H), 3.08–3.22 (m, 4), 3.43–3.59 (m, 4H), 4.12–4.16 (dxd, J$_1$=3.5, J$_2$=9, 1H), 4.23–4.27 (t, J=6.5, 2H), 5.00–5.06 (m, 2H), 5.92–6.01 (m, 1H), 7.22 (s, 1H), 7.40–7.50 (m, 5H), 8.00–8.10 (m, 4H), COOH very br.

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

What is claimed is:
1. A compound of the formula

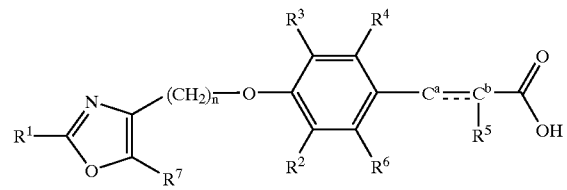

(I)

wherein
R$^1$ is aryl or heteroaryl;
R$^2$, R$^3$, R$^4$ and R$^6$ are independently selected from the group consisting of hydrogen, hydroxy, lower-alkenyl, halogen, lower-alkyl and lower-alkoxy, wherein at least one of R$^2$, R$^3$, R$^4$ and R$^6$ is not hydrogen, or
R$^2$ and R$^6$ are independently selected from the group consisting of hydrogen, hydroxy, lower-alkenyl, halogen, lower-alkyl and lower-alkoxy, and R$^3$ and R$^4$ are bonded to each other to form a ring together with the carbon atoms to which they are attached, and R$^3$ and R$^4$ together are —CH═CH—S—, —S—CH═CH—, —CH═CH—O—, —O—CH═CH—, —CH═CH—, —CH═CH—, —(CH$_2$)$_{3-5}$—, —O—(CH$_2$)$_{2-3}$— or —(CH$_2$)$_{2-3}$—O—;
R$^5$ is lower-alkoxy or lower-alkenyloxy;
R$^7$ is hydrogen or lower-alkyl;
n is 1, 2 or 3;
wherein the bond between the carbon atom C$^a$ and the carbon atom C$^b$ is a carbon carbon single or double bond;
and pharmaceutically acceptable salts and esters thereof.
2. The compound according claim 1, wherein R$^5$ is lower-alkoxy; and pharmaceutically acceptable salts thereof.
3. The compound according to claim 1, wherein R$^5$ is lower-alkenyloxy; and pharmaceutically acceptable salts thereof.
4. The compound according to claim 2, wherein
R$^2$, R$^3$ and R$^4$ independently from each other are hydrogen, halogen, lower-alkyl or lower-alkoxy, wherein at least one of R$^2$, R$^3$ and R$^4$ is not hydrogen, R$^6$ is hydrogen;

R[7] is methyl;

n is 2;

wherein the bond between the carbon atom C[a] and the carbon atom C[b] is a carbon carbon single bond;

and pharmaceutically acceptable salts thereof.

5. The compound according to claim 2, wherein

R[2] is hydrogen, halogen, lower-alkyl or lower-alkoxy,

R[3] and R[4] are bonded to each other to form a ring together with the carbon atoms to which they are attached, and R[3] and R[4] together are —CH=CH—S—, —S—CH=CH—, —CH=CH—O—, —O—CH=CH—, —CH=CH—CH=CH—, —(CH$_2$)$_{2-5}$—;

R[6] is hydrogen;

R[7] is methyl;

n is 2;

wherein the bond between the carbon atom C[a] and the carbon atom C[b] is a carbon carbon single bond;

and pharmaceutically acceptable salts thereof.

6. The compound according to claim 1, wherein R[1] is phenyl or phenyl substituted with 1 to 3 substituents independently selected from alkoxy and trifluoromethyl.

7. The compound according to claim 1, wherein R[2], R[3], R[4] and R[6] are independently selected from the group consisting of hydrogen, hydroxy, lower-alkyl and lower-alkoxy, wherein at least one of R[2], R[3], R[4] and R[6] is not hydrogen, or R[2] and R[6] are independently selected from the group consisting of hydrogen, hydroxy, lower-alkyl and lower-alkoxy, and R[3] and R[4] are bonded to each other to form a ring together with the carbon atoms to which they are attached, and R[3] and R[4] together are —CH=CH—S—, —S—CH=CH—, —CH=CH—O—, —O—CH=CH—, —CH=CH—CH=CH—.

8. The compound according to claim 1, wherein R[2] and R[6] are hydrogen and R[3] and R[4] are bonded to each other to form a ring together with the carbon atoms to which they are attached, and R[3] and R[4] together are —CH=CH—S— or —S—CH=CH—.

9. The compound according to claim 2, wherein R[5] is methoxy, ethoxy or propoxy.

10. The compound according to claim 1, wherein R[7] is methyl.

11. The compound according to claim 1, wherein n is 2.

12. The compound according to claim 1, of the formula

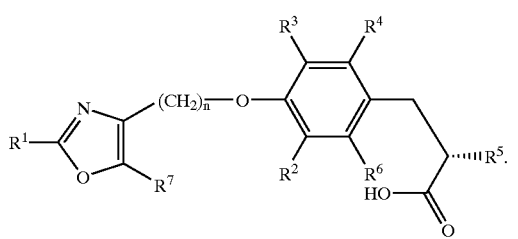

(Ia)

13. The compound according to claim 12, wherein R[5] is lower-alkoxy; and pharmaceutically acceptable salts thereof.

14. The compound according to claim 12, wherein R[5] is lower-alkenyloxy; and pharmaceutically acceptable salts thereof.

15. The compound according to claim 13, wherein

R[2], R[3] and R[4] independently from each other are hydrogen, halogen, lower-alkyl or lower-alkoxy, wherein at least one of R[2], R[3] and R[4] is not hydrogen, or R[6] is hydrogen;

R[7] is methyl;

n is 2;

wherein the bond between the carbon atom C[a] and the carbon atom C[b] is a carbon carbon single bond;

and pharmaceutically acceptable salts thereof.

16. The compound according to claim 13, wherein

R[2] is hydrogen, halogen, lower-alkyl or lower-alkoxy,

R[3] and R[4] are bonded to each other to form a ring together with the carbon atoms to which they are attached, and R[3] and R[4] together are —CH=CH—S—, —S—CH=CH—, —CH=CH—O—, —O—CH=CH—, —CH=CH—CH=CH—, —(CH$_2$)$_{3-5}$—;

R[6] is hydrogen;

R[7] is methyl;

n is 2;

wherein the bond between the carbon atom C[a] and the carbon atom C[b] is a carbon carbon single bond;

and pharmaceutically acceptable salts thereof.

17. The compound according to claim 12, wherein R[1] is phenyl or phenyl substituted with 1 to 3 substituents independently selected from alkoxy and trifluoromethyl.

18. The compound according to claim 12, wherein R[2], R[3], R[4] and R[6] are independently selected from the group consisting of hydrogen, hydroxy, lower-alkyl and lower-alkoxy, wherein at least one of R[2], R[3], R[4] and R[6] is not hydrogen, or R[2] and R[6] are independently selected from the group consisting of hydrogen, hydroxy, lower-alkyl, and lower-alkoxy, and R[3] and R[4] are bonded to each other to form a ring together with the carbon atoms to which they are attached, and R[3] and R[4] together are —CH=CH—S—, —S—CH=CH—, —CH=CH—O—, —O—CH=CH—, —CH=CH—CH=CH—.

19. The compound according to claim 12, wherein R[2] and R[6] are hydrogen and R[3] and R[4] are bonded to each other to form a ring together with the carbon atoms to which they are attached, and R[3] and R[4] together are —CH=CH—S— or —S—CH=CH—.

20. The compound according to claim 13, wherein R[5] is methoxy, ethoxy or propoxy.

21. The compound according to claim 14, wherein R[7] is methyl.

22. The compound according to claim 14, selected from the group consisting of

2-Methoxy-3-{4-[2-(5-methyl-2-phenyl-oxazol-4-yl)-ethoxy]-benzo[b]thiophen-7-yl}-propionic acid;

3-{4-[2-(5-Methyl-2-phenyl-oxazol-4-yl)-ethoxy]-benzo[b]thiophen-7-yl}-2-propoxy-propionic acid;

(S)-2-Methoxy-3-{4-[2-(5-methyl-2-phenyl-oxazol-4-yl)-ethoxy]-benzo[b]thiophen-7-yl}-propionic acid;

(S)-3-(4-{2-[2-(3,5-Dimethyl-phenyl)-5-methyl-oxazol-4-yl]-ethoxy}-benzo[b]thiophen-7-yl)-2-methoxy-propionic acid;

(S)-2-Methoxy-3-(4-{3-[5-methyl-2-(4-trifluoromethyl-phenyl)-oxazol-4-yl]-propoxy}-naphthalen-1-yl)-propionic acid;

2Z-Ethoxy-3-{2-methyl-4-[2-(5-methyl-2-phenyl-oxazol-4-yl)-ethoxy]-phenyl}-acrylic acid;

2(S)-Ethoxy-3-{2-methyl-4-[2-(5-methyl-2-phenyl-oxazol-4-yl)ethoxy]-phenyl}-propionic acid 2Z-Ethoxy-3-{4-[2-(5-methyl-2-phenyl-oxazol-4-yl)-ethoxy]benzofuran-7-yl}-acrylic acid;

[rac]-3-{2-Hydroxy-4-[2-(5-methyl-2-phenyl-oxazol-4-yl)-ethoxy]-phenyl}-2-methoxy-propionic acid;

[rac]-2-Ethoxy-3-[2-methyl-4-(5-methyl-2-phenyl-oxazol-4-ylmethoxy)-phenyl]-propionic acid;

[rac]-2-Ethoxy-3-{4-[2-(4-isopropoxy-phenyl)-5-methyl-oxazol-4-ylmethoxy]-2-methyl-phenyl)}-propionic acid;

(2S)-3-{3,5-Dimethyl-4-[2-(5-methyl-2-phenyl-oxazol-4-yl)-ethoxy]-phenyl}-2-ethoxy-propionic acid; and (2S)-2-Ethoxy-3-{3-methoxy-4-[2-(5-methyl-2-phenyl-oxazol-4-yl)-ethoxy]-phenyl}-propionic acid;

and pharmaceutically acceptable salts thereof.

23. (S)-2-methoxy-3-{4-2-(5-methyl-2-phenyl-oxazol-4-yl)-ethoxy]-benzo[b]thiophen-7-yl}-propionic acid.

24. A pharmaceutical composition comprising a compound according to claim 1, and a pharmaceutically acceptable carrier or adjuvant.

25. The compound according to claim 1, wherein n is 1.

26. The compound according to claim 25, wherein $R^2$, $R^3$, $R^4$ and $R^6$ are independently selected from the group consisting of hydrogen, hydroxy, lower-alkenyl, halogen, lower-alkyl and lower-alkoxy, wherein at least one of $R^2$, $R^3$, $R^4$ and $R^6$ is not hydrogen.

27. The compound according to claim 26, selected from

[rac]-2-Ethoxy-3-[2-methyl-4-(5-methyl-2-phenyl-oxazol-4-ylmethoxy)-phenyl]-propionic acid; and

[rac]2-Ethoxy-3-{4-[2-(4-isopropoxy-phenyl)-5-methyl-oxazol-4-ylmethoxy]-2-methyl-phenyl}-propionic acid.

* * * * *

UNITED STATES PATENT AND TRADEMARK OFFICE
CERTIFICATE OF CORRECTION

PATENT NO.    : 6,642,389 B2
DATED         : November 4, 2003
INVENTOR(S)   : A. Binggeli et al.

It is certified that error appears in the above-identified patent and that said Letters Patent is hereby corrected as shown below:

Column 117,
Line 14, "-$(CH_2)_{2-5}$-"; should be -- -$(CH_2)_{3-5}$- --

Column 118,
Line 43, "The compound according to claim 14" should be -- The compound according to claim 12 --
Line 45, The compound according to claim 14" should be -- The compound according to claim 2 --

Signed and Sealed this

Thirteenth Day of July, 2004

JON W. DUDAS
*Acting Director of the United States Patent and Trademark Office*